US012727878B2

(12) United States Patent
Le et al.

(10) Patent No.: US 12,727,878 B2
(45) Date of Patent: Sep. 8, 2026

(54) SUTURE CLIP DEPLOYMENT DEVICES WITH SUTURE TENSIONING SYSTEMS

(71) Applicant: EDWARDS LIFESCIENCES CORPORATION, Irvine, CA (US)

(72) Inventors: Jason Thai Le, Garden Grove, CA (US); Manouchehr A. Miraki, Laguna Hills, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 352 days.

(21) Appl. No.: 18/542,484

(22) Filed: Dec. 15, 2023

(65) Prior Publication Data

US 2024/0173027 A1 May 30, 2024

Related U.S. Application Data

(63) Continuation of application No. PCT/US2022/032081, filed on Jun. 3, 2022.

(Continued)

(51) Int. Cl.

*A61B 17/04* (2006.01)
*A61B 17/00* (2006.01)

(52) U.S. Cl.

CPC .............................. *A61B 17/0487* (2013.01); *A61B 2017/00398* (2013.01); *A61B 2017/00982* (2013.01); *A61B 2017/0488* (2013.01)

(58) Field of Classification Search

CPC ...... A61B 17/0487; A61B 2017/00398; A61B 2017/00982; A61B 2017/0488;

(Continued)

(56) References Cited

U.S. PATENT DOCUMENTS 3,959,960 A * 6/1976 Santos .............. A61B 17/8861 57/22
5,634,584 A 6/1997 Okorocha et al.

(Continued)

FOREIGN PATENT DOCUMENTS

EP 0755655 A2 1/1997
EP 0755656 A2 1/1997

(Continued)

*Primary Examiner* — Phong Son H Dang
(74) *Attorney, Agent, or Firm* — Klarquist Sparkman LLP

(57) ABSTRACT

Disclosed are devices and methods for deploying securement devices onto sutures with precise and consistent tension levels in the sutures. Devices can include a handle portion having a trigger and a suture tensioning mechanism, and a shaft portion extending distally from the handle portion with at least one suture securement device positioned at a distal end portion of the shaft portion. The device can receive a suture or sutures extending through the suture securement device, across the trigger, and to the suture tensioning mechanism. Actuation of the suture tensioning mechanism gradually increases tension in the received suture until the trigger is actuated by pressure from the suture when a predetermined amount of tension is reached in the suture. Actuation of the trigger can cause the suture securement device to be deployed from the shaft portion onto the received suture with the predetermined amount of tension in the suture.

19 Claims, 102 Drawing Sheets

Related U.S. Application Data

(60) Provisional application No. 63/211,254, filed on Jun. 16, 2021.

(58) Field of Classification Search
CPC ...... A61B 2017/0496; A61B 2090/064; A61B 2090/066
See application file for complete search history.

(56) References Cited

U.S. PATENT DOCUMENTS

| | | | | |
|---|---|---|---|---|
| 6,015,428 | A | 1/2000 | Pagedas | |
| 6,626,930 | B1 | 9/2003 | Allen et al. | |
| 6,780,198 | B1 * | 8/2004 | Gregoire | A61B 17/0401 606/232 |
| 7,049,244 | B2 | 5/2006 | Becker et al. | |
| 7,083,628 | B2 | 8/2006 | Bachman | |
| 7,381,210 | B2 | 6/2008 | Zarbatany et al. | |
| 9,017,347 | B2 | 4/2015 | Oba et al. | |
| 9,055,932 | B2 | 6/2015 | Roorda | |
| 9,788,825 | B2 * | 10/2017 | Whittaker | A61B 17/0401 |
| 12,156,647 | B2 * | 12/2024 | Rogers | A61B 17/0401 |
| 2004/0204724 | A1 | 10/2004 | Kissel et al. | |
| 2005/0251209 | A1 | 11/2005 | Saadat et al. | |
| 2006/0089571 | A1 | 4/2006 | Gertner | |
| 2006/0265042 | A1 | 11/2006 | Catanese et al. | |
| 2006/0271060 | A1 * | 11/2006 | Gordon | A61B 17/0401 606/103 |
| 2006/0276871 | A1 | 12/2006 | Lamson et al. | |
| 2007/0005079 | A1 | 1/2007 | Zarbatany et al. | |
| 2007/0049970 | A1 | 3/2007 | Belef et al. | |
| 2008/0033460 | A1 * | 2/2008 | Ziniti | A61B 17/0401 606/148 |
| 2008/0154286 | A1 | 6/2008 | Abbott et al. | |
| 2008/0195145 | A1 * | 8/2008 | Bonutti | A61B 17/82 606/205 |
| 2009/0272783 | A1 | 11/2009 | Crainich et al. | |
| 2009/0326562 | A1 * | 12/2009 | White | A61B 17/8869 606/139 |
| 2012/0053599 | A1 | 3/2012 | Shikhman et al. | |
| 2012/0158044 | A1 * | 6/2012 | Jenson | A61B 17/0057 606/213 |
| 2012/0165865 | A1 | 6/2012 | Fujisaki et al. | |
| 2013/0165953 | A1 | 6/2013 | Oba et al. | |
| 2014/0031864 | A1 | 1/2014 | Jafari et al. | |
| 2015/0142021 | A1 | 5/2015 | Smith et al. | |
| 2016/0183937 | A1 | 6/2016 | Miraki et al. | |
| 2020/0281580 | A1 * | 9/2020 | Kruse | A61B 17/0401 |
| 2023/0069080 | A1 * | 3/2023 | Rao | A61B 17/04 |

FOREIGN PATENT DOCUMENTS

| | | | |
|---|---|---|---|
| EP | 1484023 | A1 | 12/2004 |
| EP | 2455001 | A2 | 5/2012 |
| EP | 2462876 | A2 | 6/2012 |
| WO | 0128455 | A1 | 4/2001 |

* cited by examiner

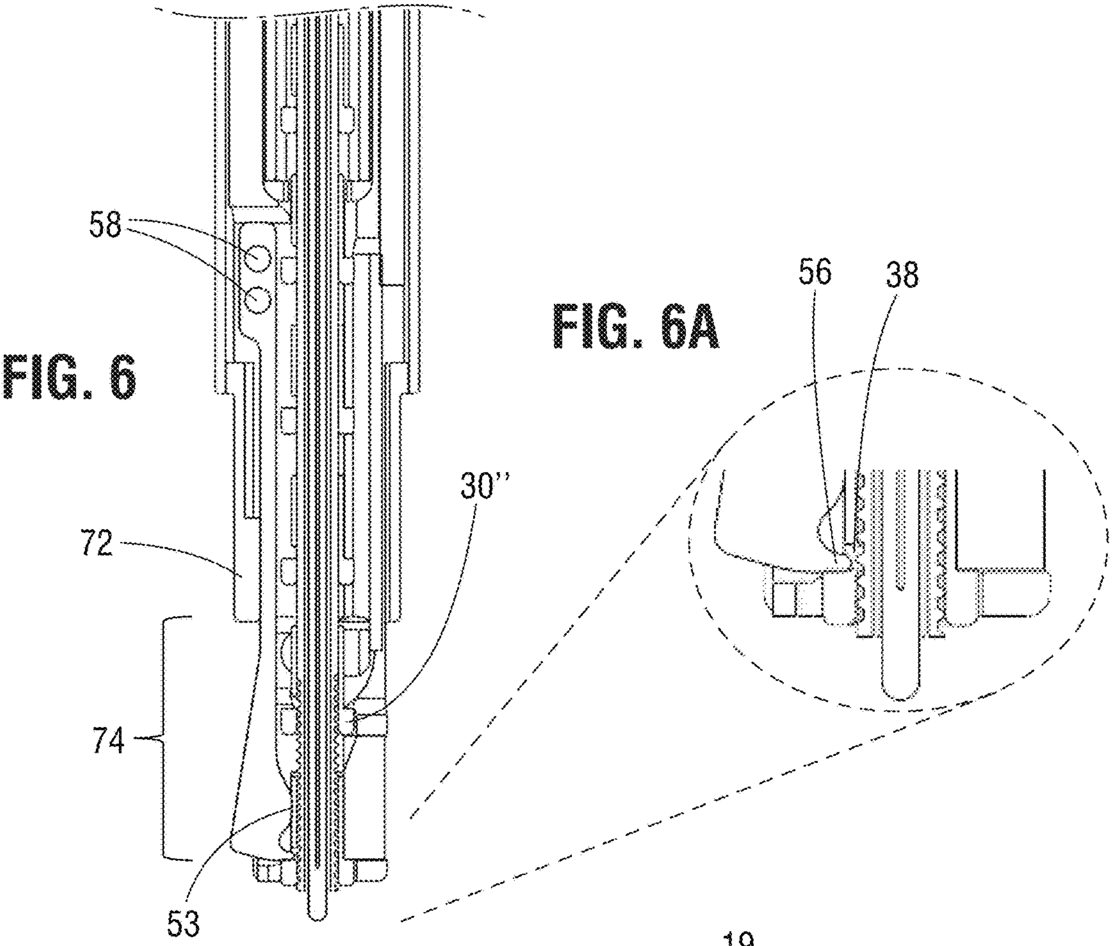
FIG. 6
FIG. 6A
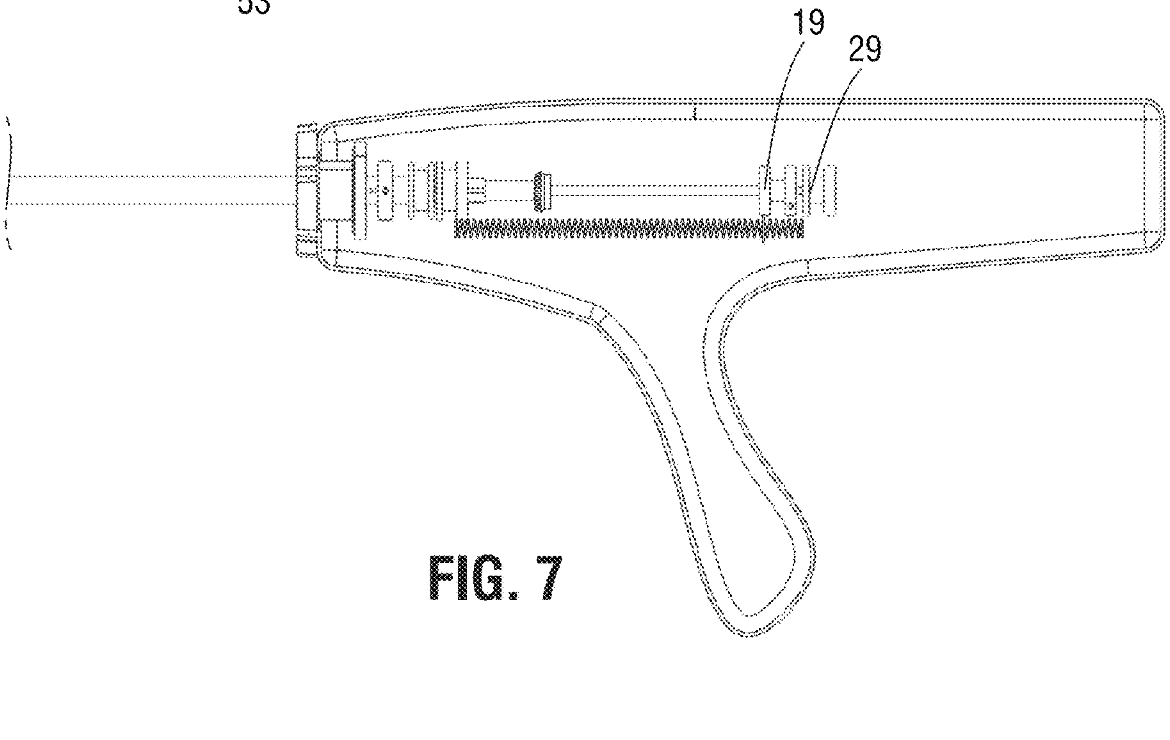
FIG. 7

FIG. 17
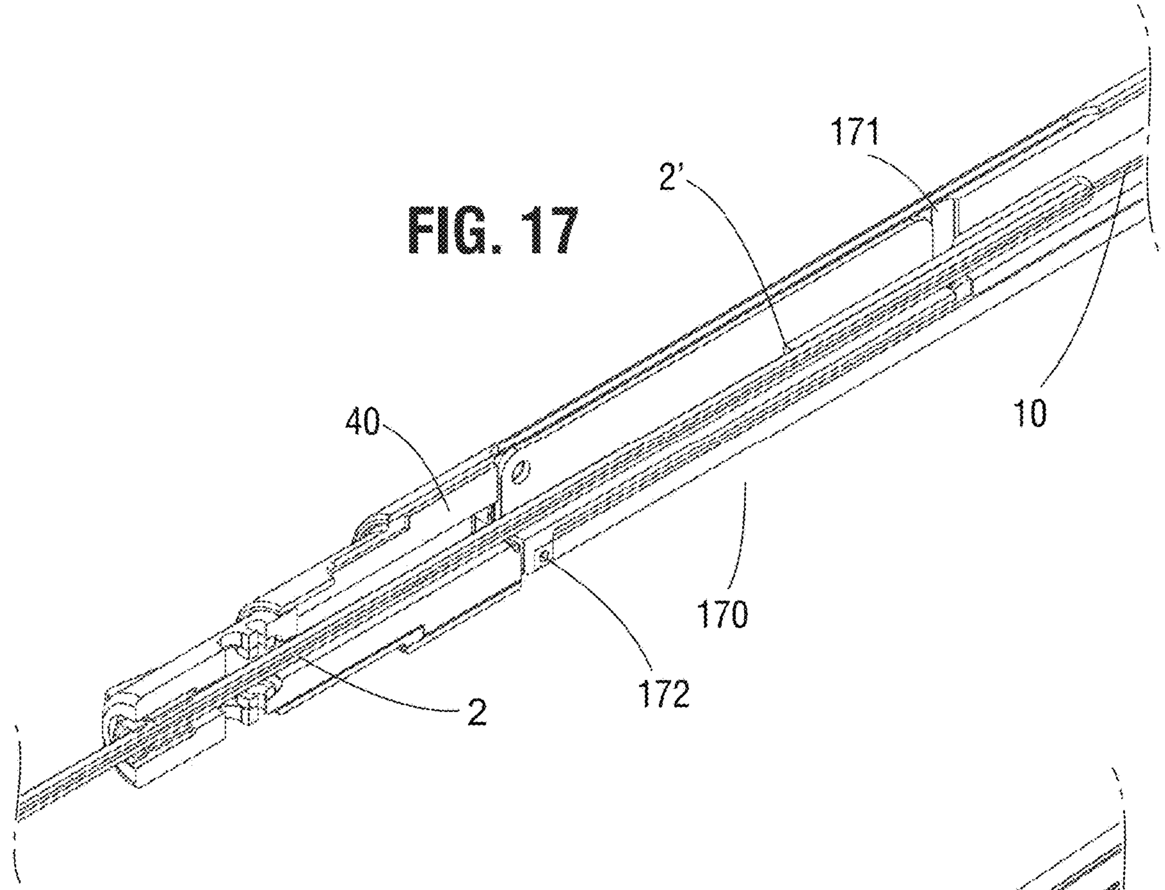
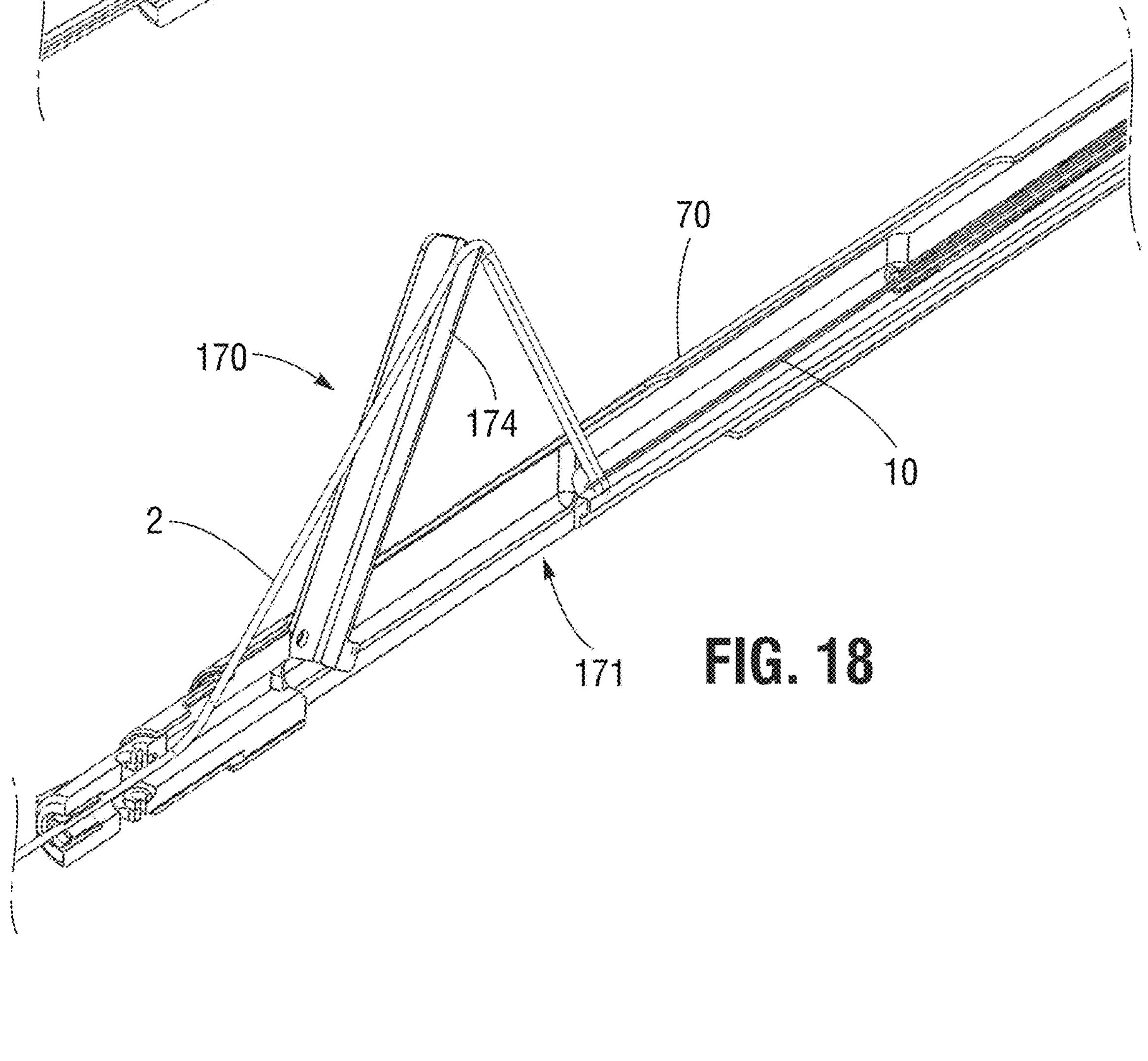
FIG. 18

FIG. 23
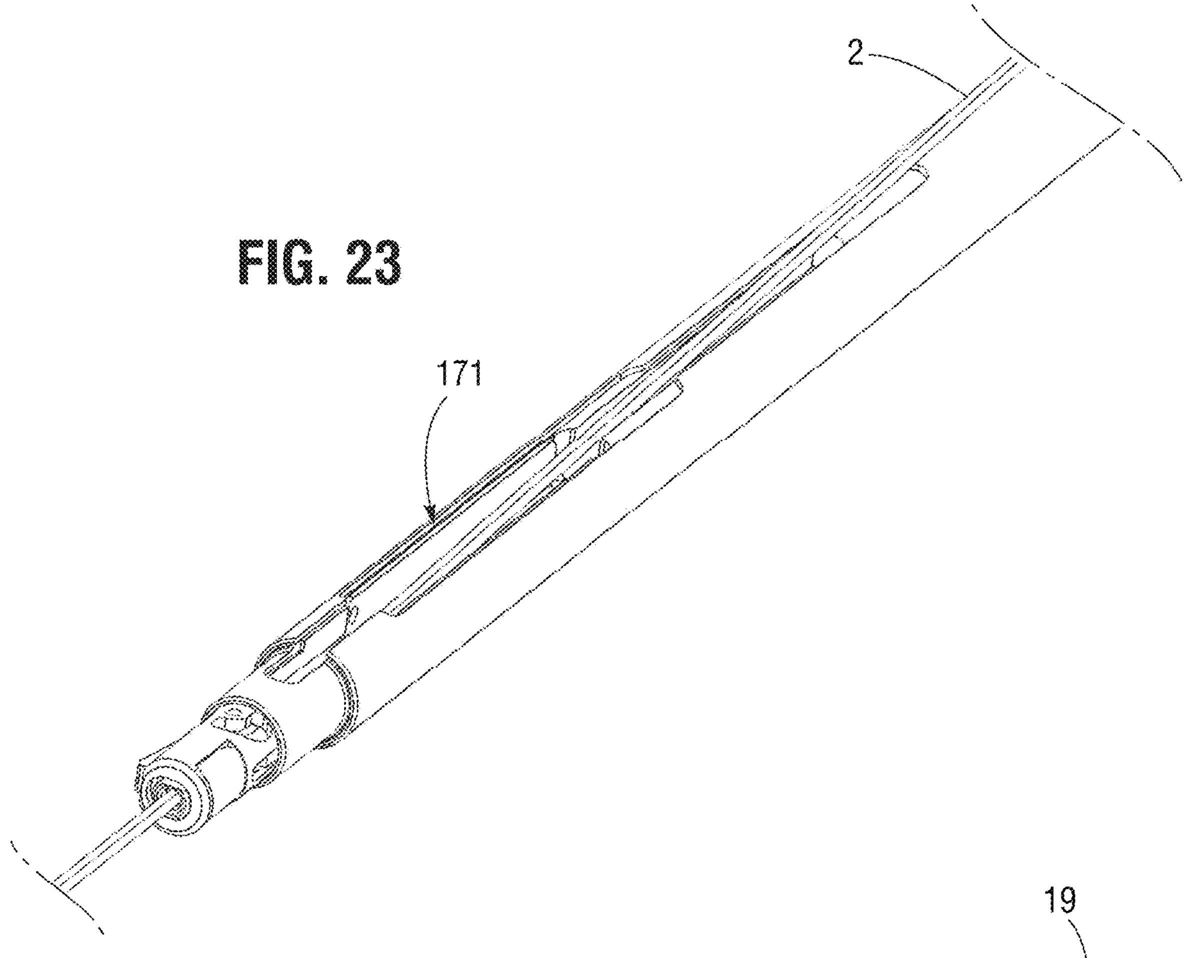
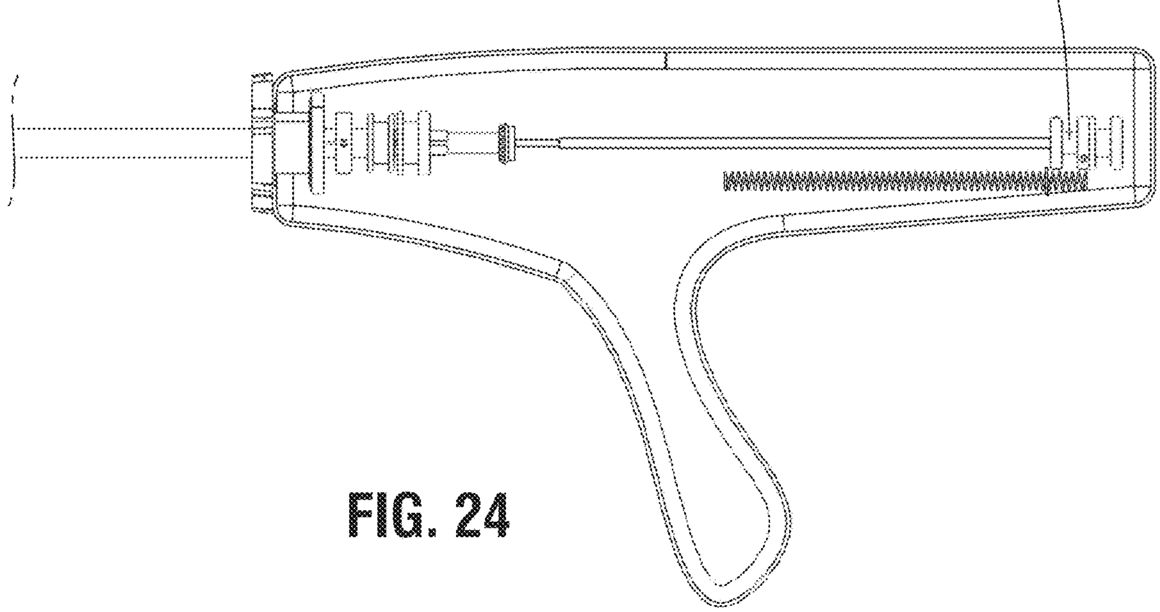
FIG. 24

FIG. 32
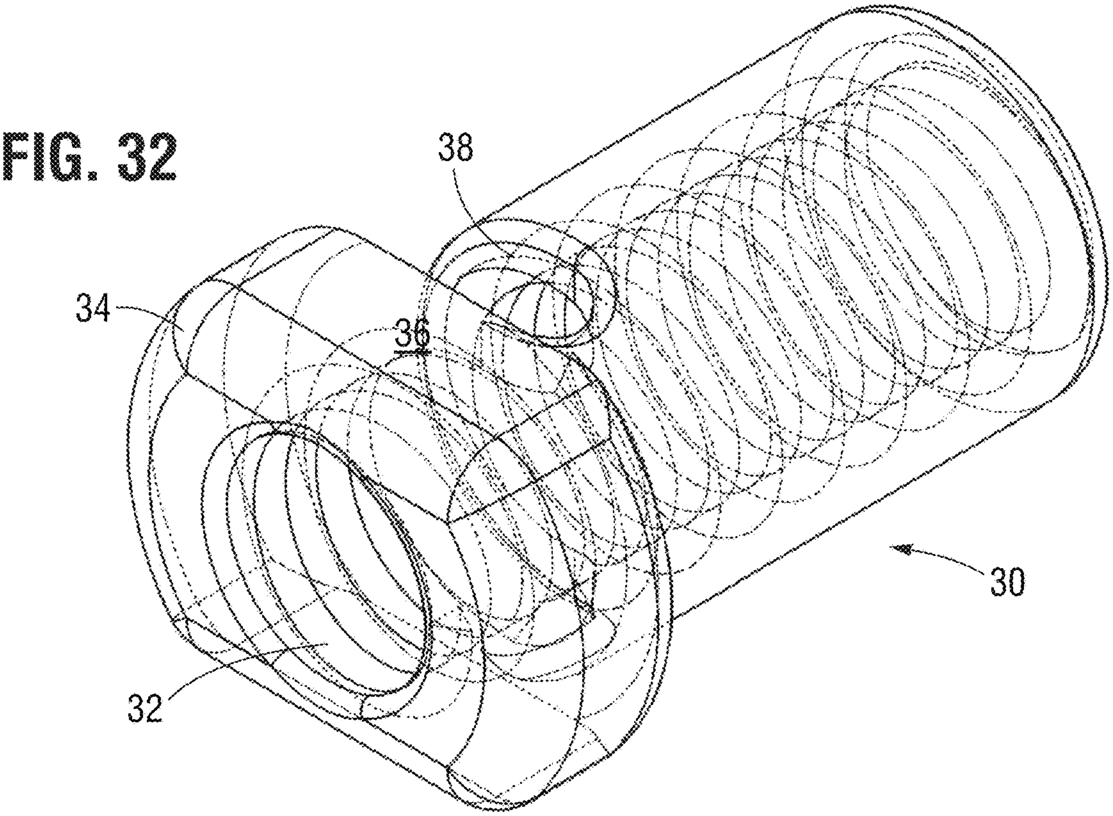
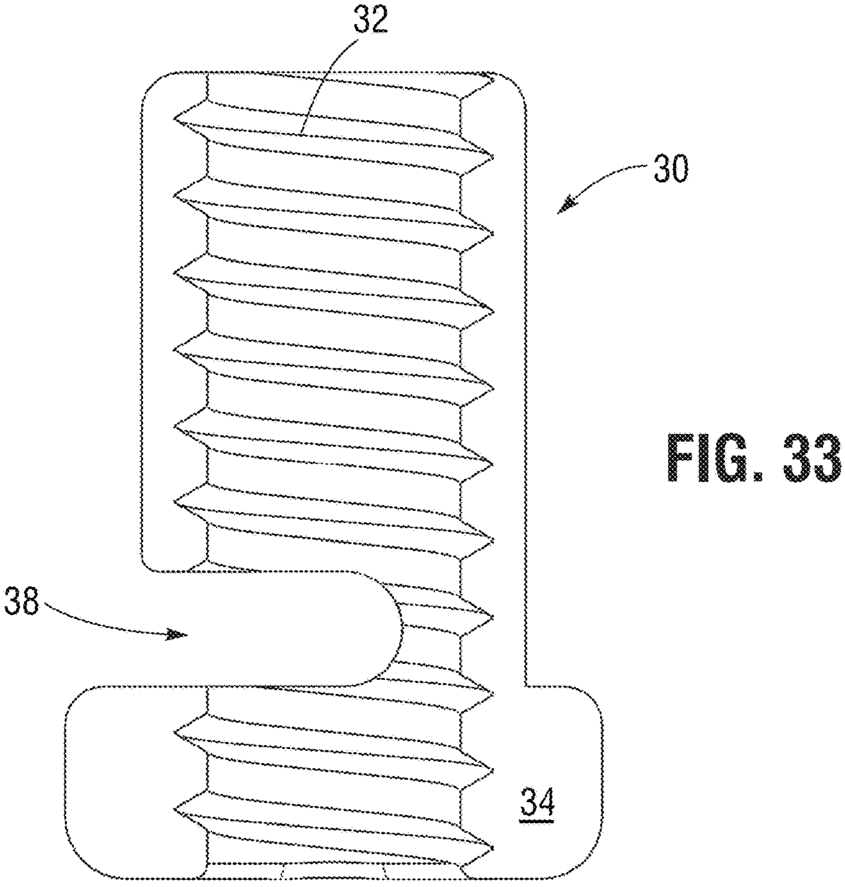
FIG. 33

Initialize
- Retract the outer tube to the limit switch.
- Retract carriage conveyor to the limit switch.
- Crimps are assumed to be properly indexed.

Load Crimp
- Advance conveyor to "CARRIAGE_LOADING" position.

Secure Crimp
- Advance conveyor to "CARRIAGE_LOADING" position.
- Advance outer tube to "HOLDING_CRIMP" position.

Unscrew Crimp
- Remove crimp carriage from crimp by "NEXT_CLIP_TURNS".
- Conveyor moves in lock step with the crimp index motor.
- Reset "CRIMP_INDEX" position.

Retract Conveyor
- Retract carriage conveyor to "CARRIAGE_IDLE" position.
- Decrement "CRIMPS_REMAINING".

Ready/ Operate Snare
- Waiting for user to press the crimp button.

Crimping
- Advance outer tube to the "FULL_CRIMP" jposition.

Cut Suture
- Wait for user to cut the suture.

Release Clip
- Retract outer tube to "JAWS_FREE" position

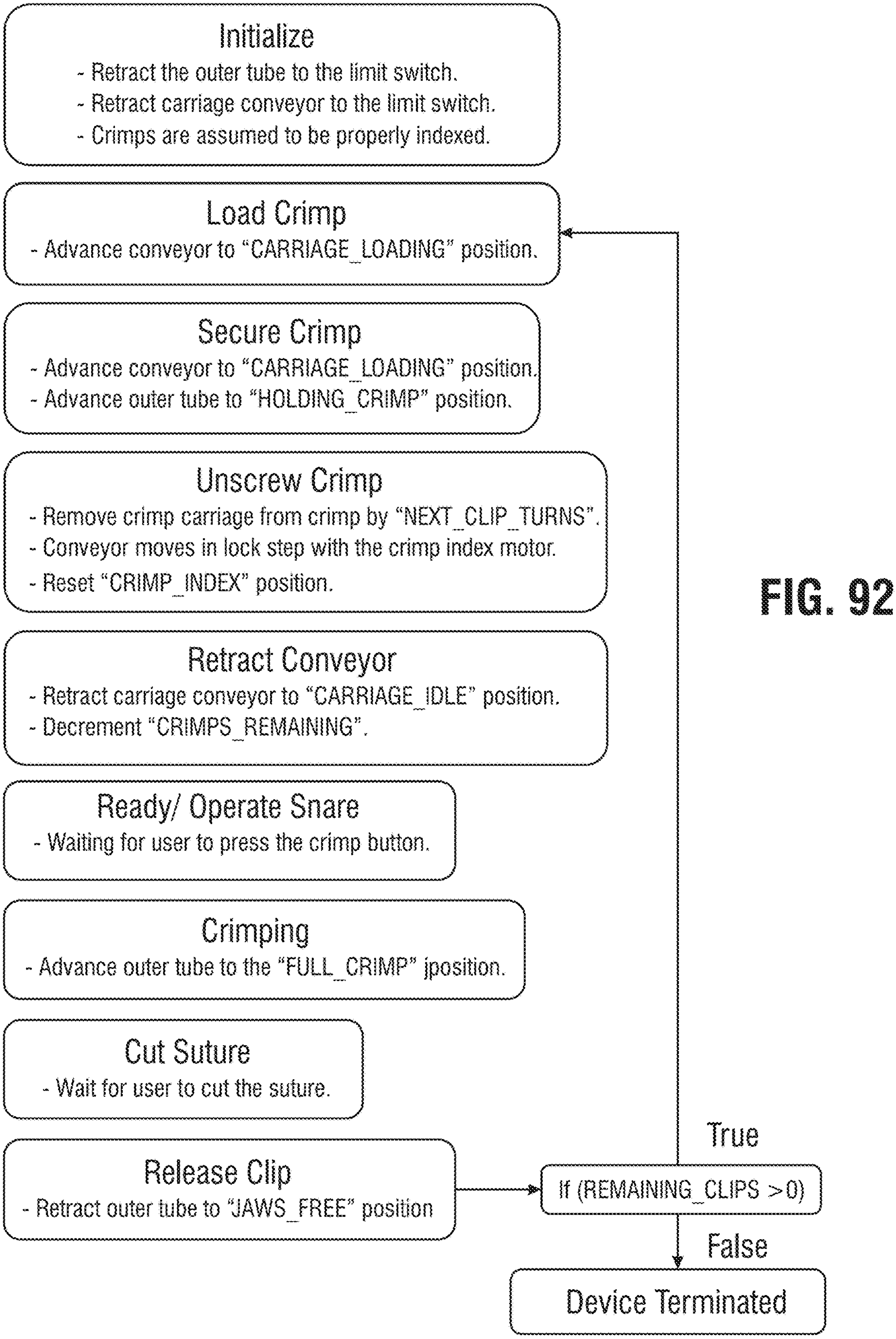

FIG. 92

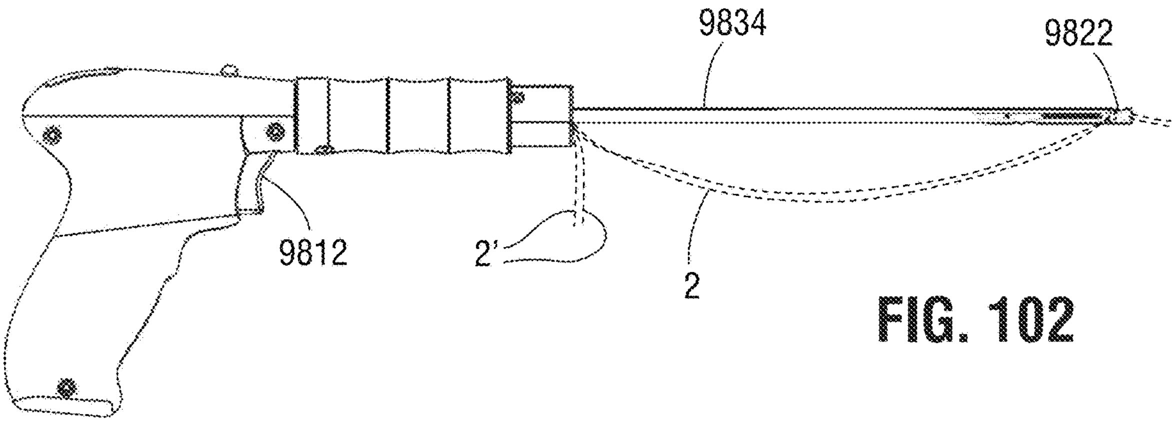

FIG. 102

Initialize
- Power the device (e.g., with press of reload button)
- Clips are loaded and properly indexed during manufacturing
- Load operational data

Grab Clip
- Retract clip pusher and grab next clip in the stack

Position Clip
- Advance clip pusher to snare-ready position

Ready/Operate Snare
- Wait for snare to return to the retracted position after a minimum of one cycle
- Wait for user to press clip securing trigger
- Upon trigger press, extend clip pusher to eject clip off rail and then to cut suture

Wait for Reload
- Trigger remains active for subsequent suture cuts
- Each additional trigger press extends clip pusher to perform additional cut
- Wait for user to press the reload button and, upon button press, ====>

If (REMAINING_CLIPS > 0)

True

False

Device Terminated

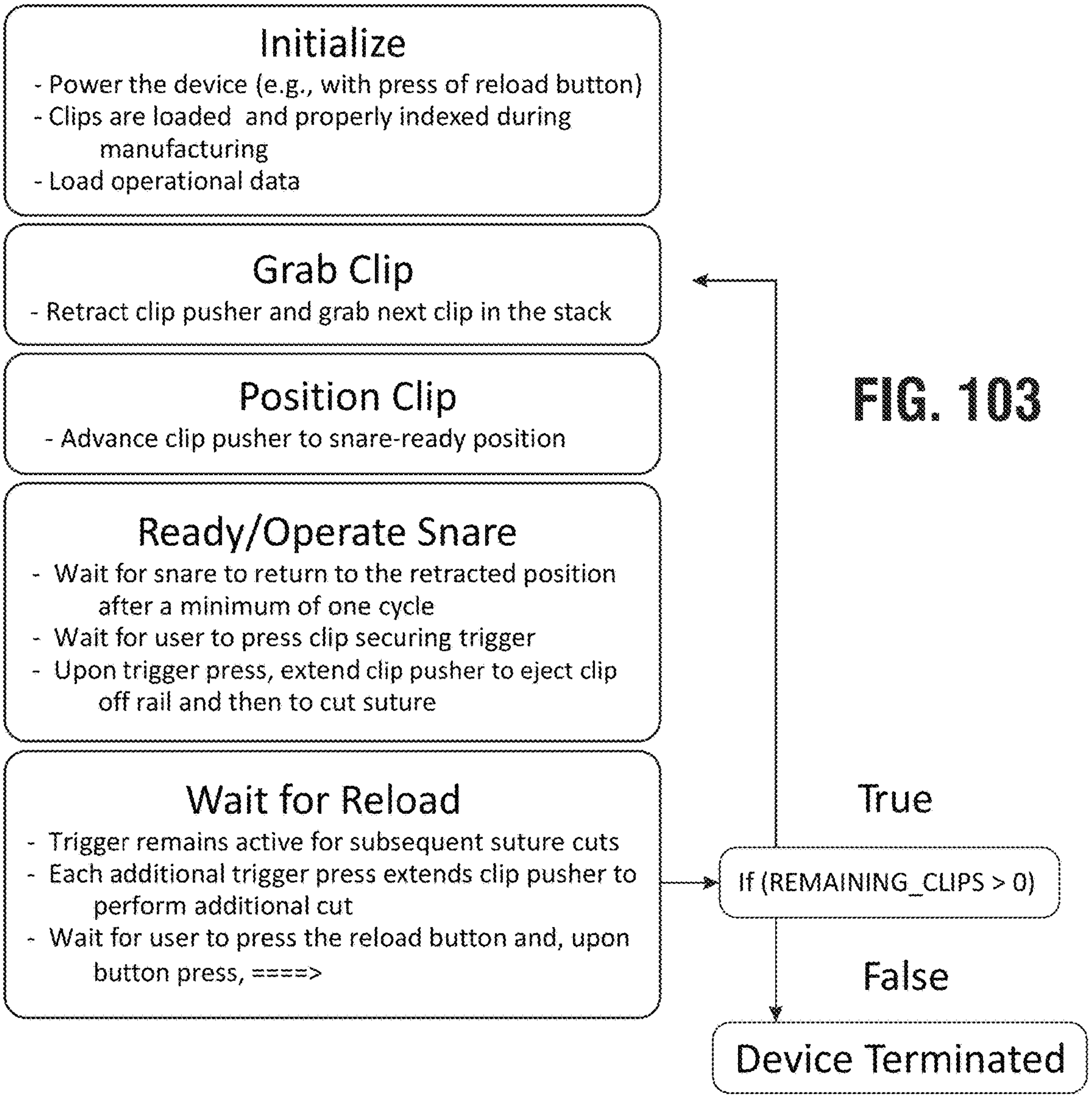

FIG. 103

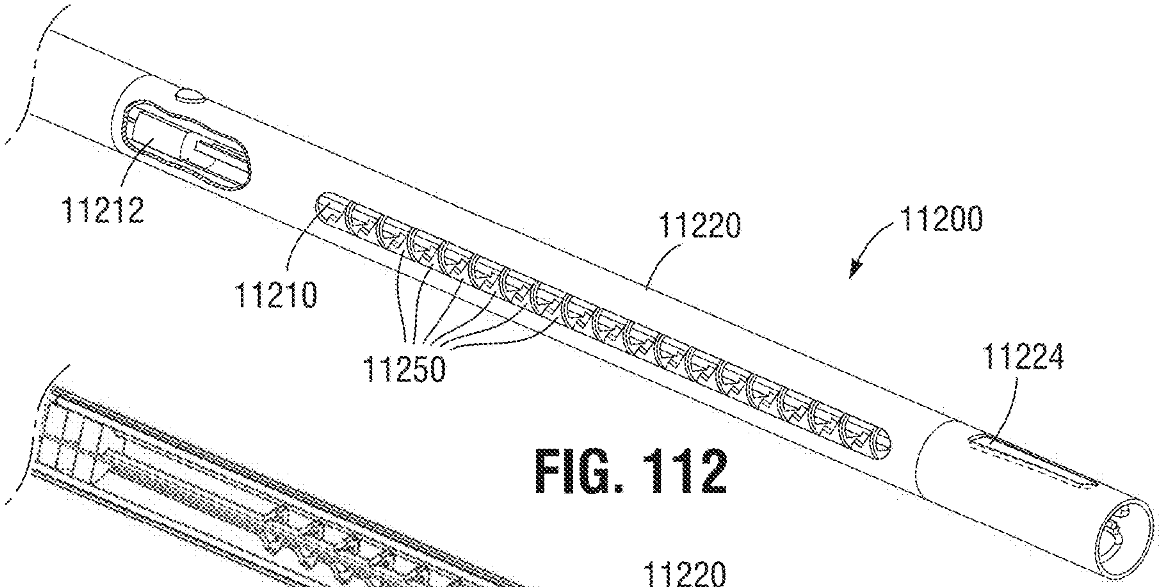
FIG. 112
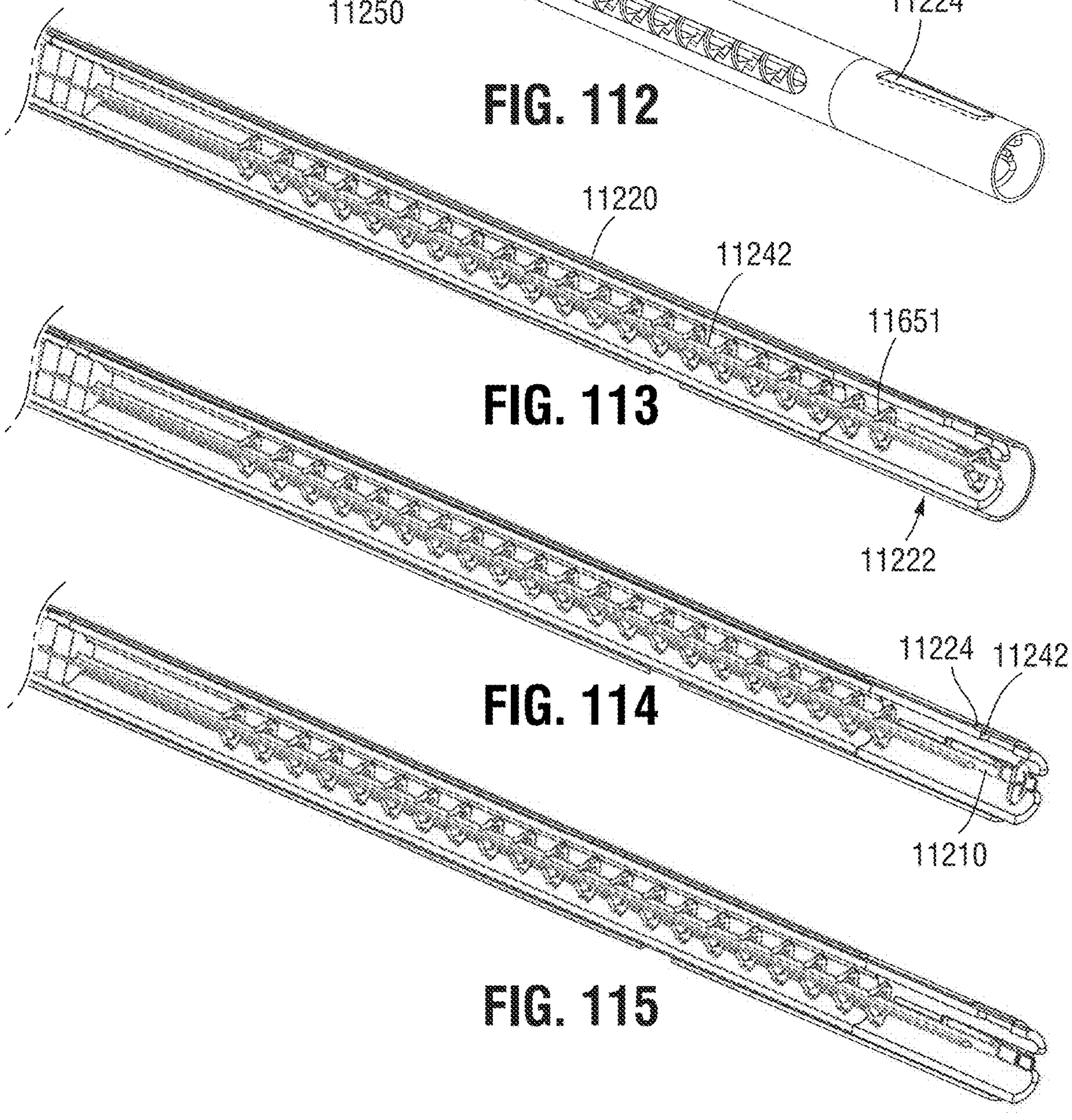
FIG. 113
FIG. 114
FIG. 115

FIG. 123
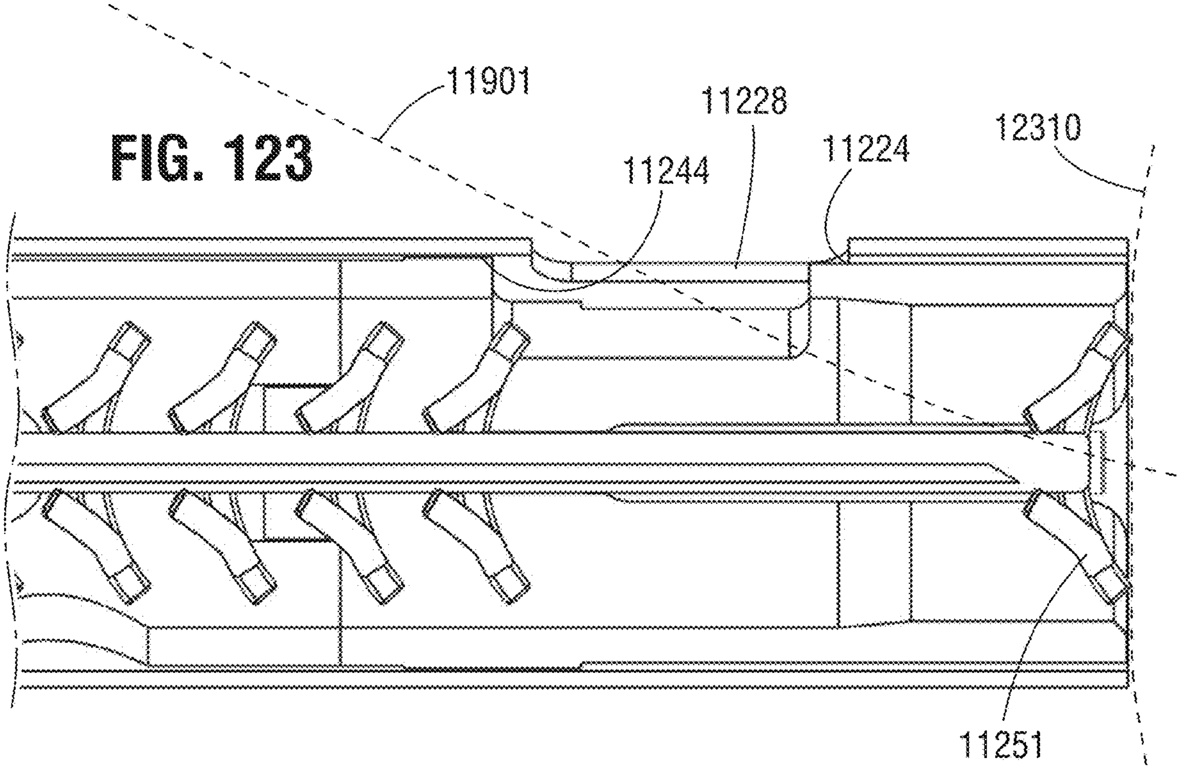
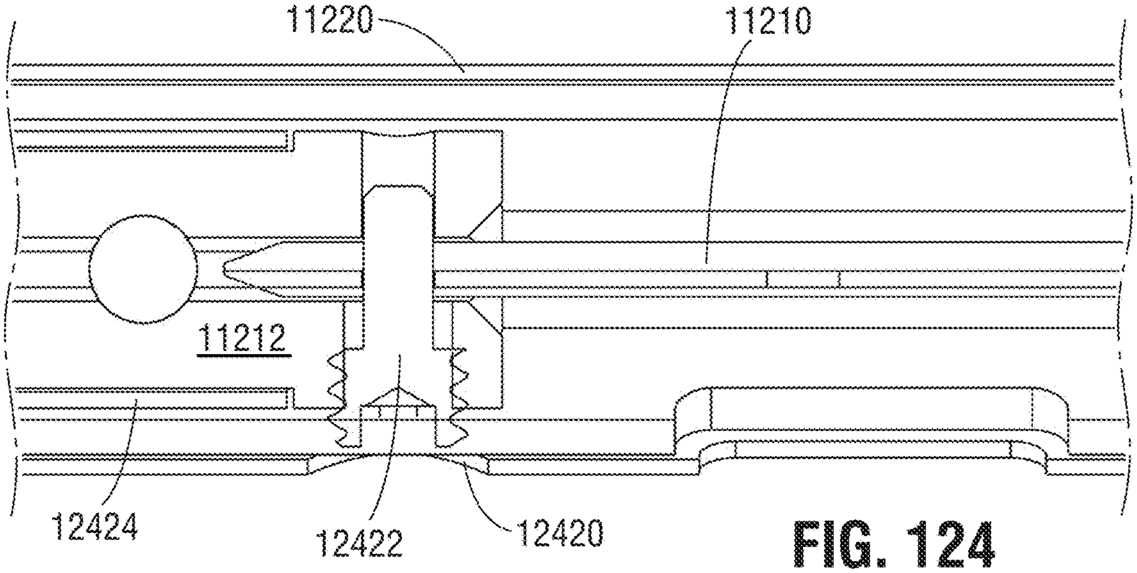
FIG. 124

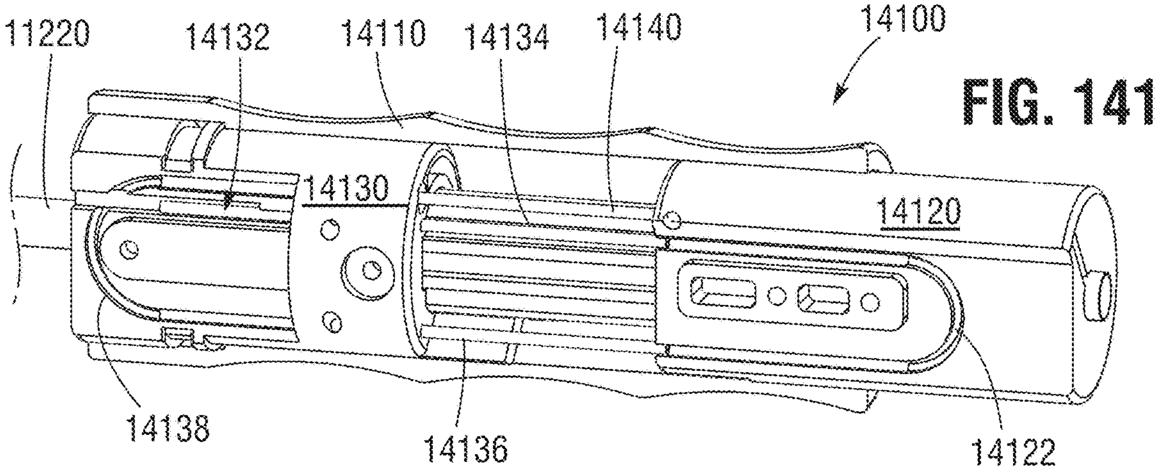
FIG. 141
FIG. 142
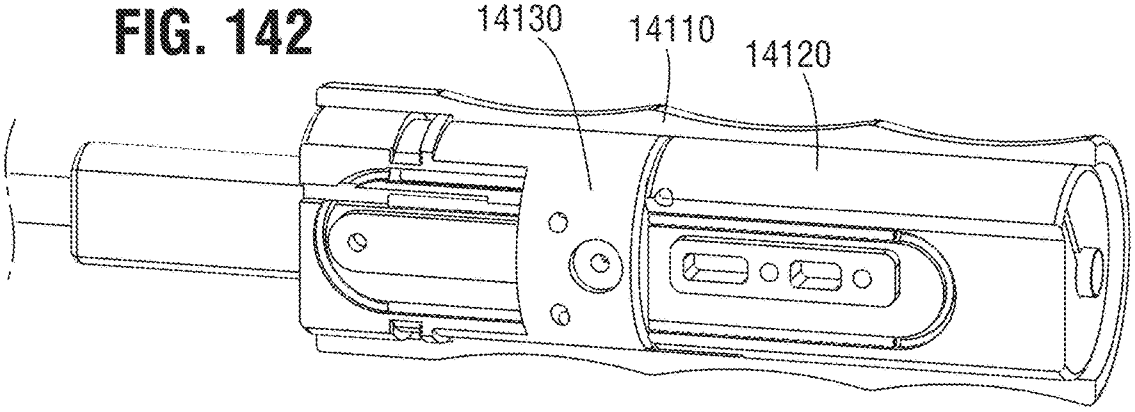
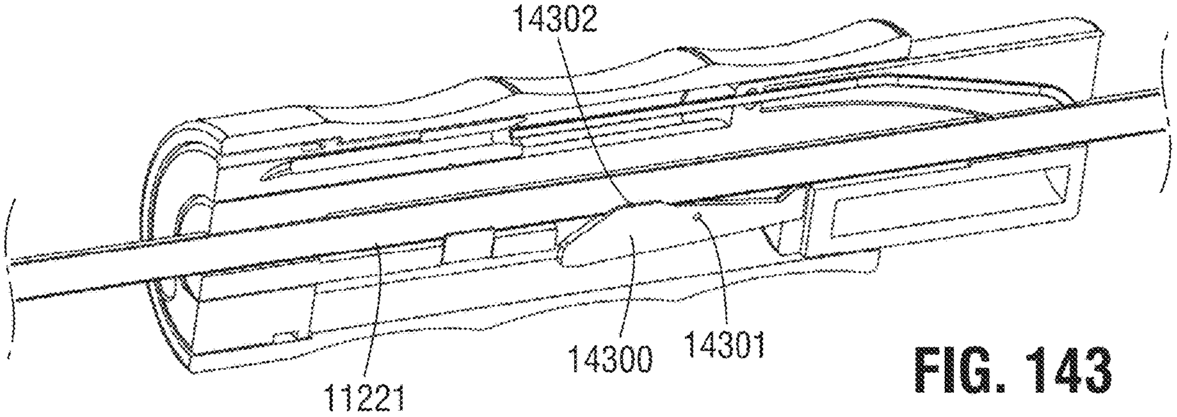
FIG. 143

14140
11228
11220
14142
11225
14304
11223
11221

14122
14120
11228
11225
11220
14142
14305
14304

14122
11228
14120
14130
11220
14600
14304
11223

11220
14302

14120
14130
14131
14303
14304
11221
14305
11225
14120
14140

14304
11223
14142
11228
14302
11225
14122
14130

14131
14303
14304
14142

15500
15520

15530
15512
15510
15514
15622
15550
15522
15612
15629
15810
15628
15550'
15664
15523
15540
15626
15560
15660
15626
15660
15610
15510

15662
15666
15650
15630
15534
15632
15521
15520

FIG. 164
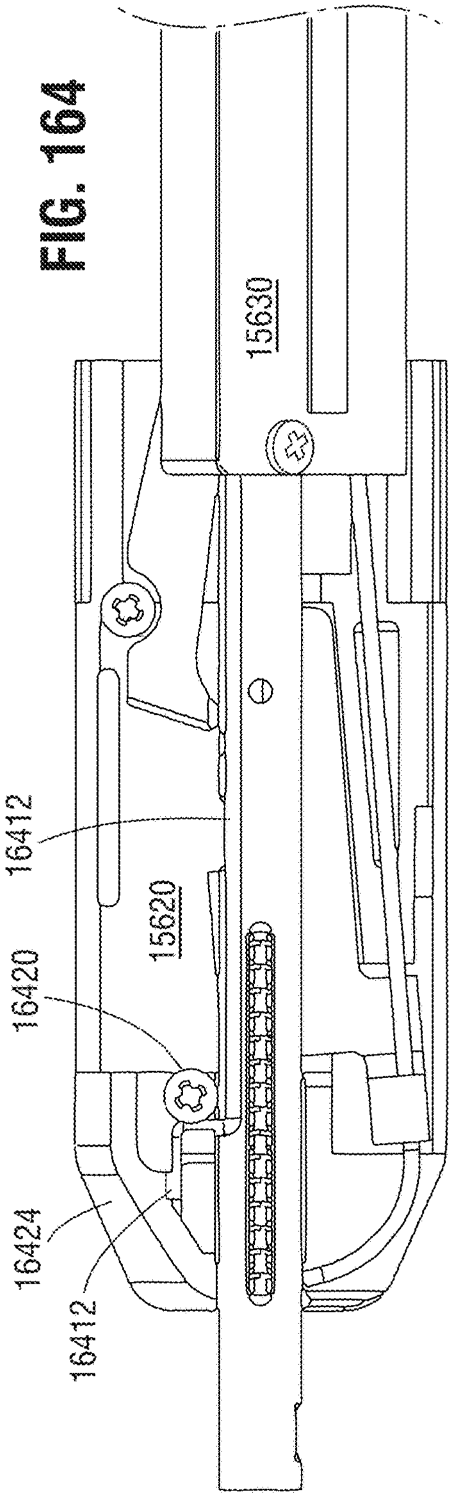
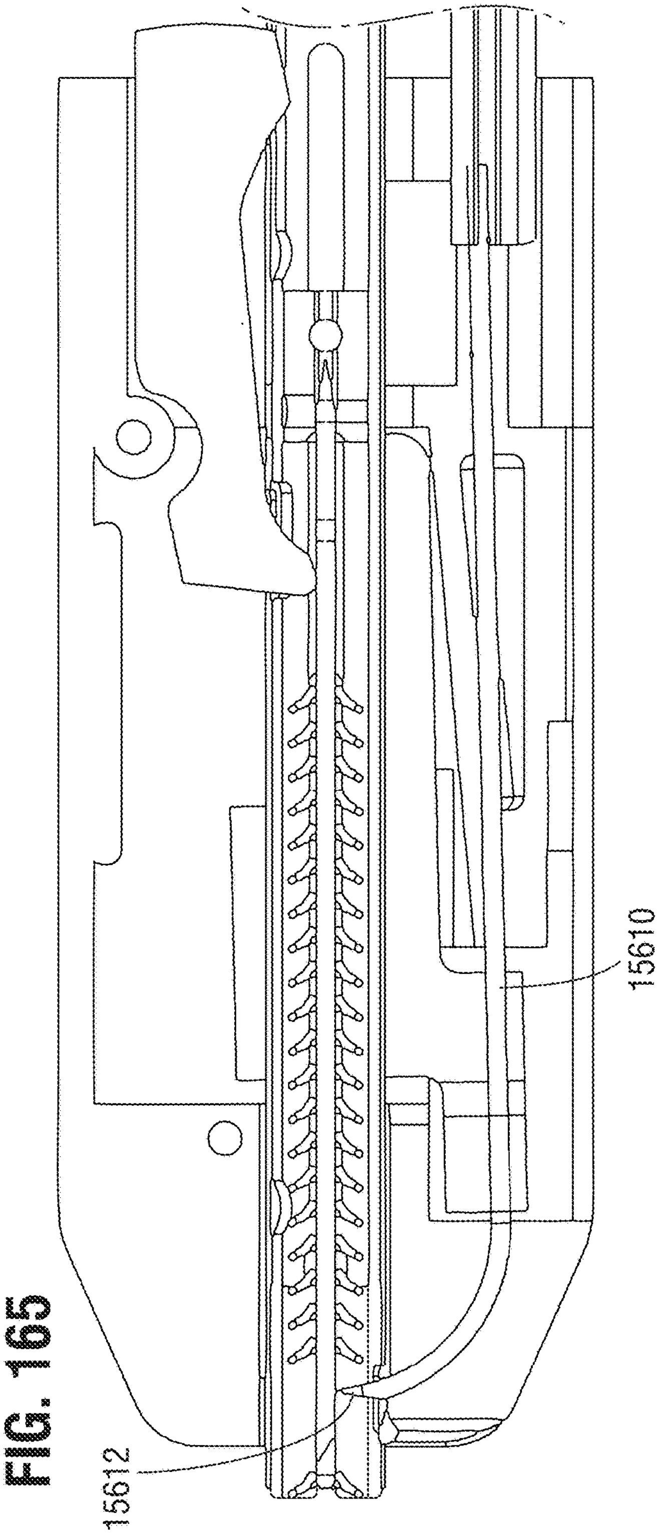
FIG. 165

SUTURE CLIP DEPLOYMENT DEVICES WITH SUTURE TENSIONING SYSTEMS

CROSS-REFERENCE TO RELATED APPLICATIONS

This application is a continuation of International Application No. PCT/US2022/032081, filed Jun. 3, 2022, which claims the benefit of U.S. Patent Application No. 63/211,254, filed Jun. 16, 2021, the entire disclosures all of which are incorporated by reference for all purposes.

FIELD

The present disclosure relates to securing cords, such as surgical sutures. The present disclosure relates to a multiple-firing securing device and methods for using and manufacturing same.

BACKGROUND

Tying sutures in surgical procedures is as old as the first stitch and knot used to close a wound. When stitching wounds, a suture, cable, cord, or other string-like object is passed through both sides of the wound and is tightened down against the wound to close the two sides together. The most common way to tighten down the cord is to tie a knot. This entails forming a loop and passing one of the free ends of the cord through the loop at least once. When the free ends of the cord are pulled away from one another, the knot reduces until there is no more room for reduction. If left alone, the knot could come loose. Therefore, techniques for forming different and varying knots have been established. In each case, the surgeon desires the knot to be tied with a sufficient tying force, referred to herein as a locking state, that, if retained after letting go of the ends of the cord, will form a stitch that holds the wound closed.

Surgical instruments can be used to replace hand-tied knots at remote sites within the body. Drawbacks of conventional surgical instruments include being limited to use with a single suture securing device (e.g., a crimp), having to reload the device for each suture, difficulty in applying the desired amount of tension in the suture when the securing device is deployed, and generating significant waste during the suture securing process, which waste must be accounted for because there exists the possibility that the waste could be lost within the patient during surgery. In an example system, a single suture crimp is loaded into the end effector and is secured for a single crimp use. To load the crimp and the snare that passes the suture through the crimp, a loading hook is passed through an end effector. The loading hook has the crimp at its distal end and is attached to a snare loop, which is threaded through the crimp. To secure the crimp between the handle and the snare loop, the snare loop is secured and held outwards as a loop by a teardrop shaped handle. After the hook is threaded into the end effector and the crimp is pressed into the distal end of the end effector, the user must remove the large, plastic handle and dispose of it properly. As such, the action of loading a reload crimp into the device generates a teardrop shaped piece of plastic waste for every single crimp. Care must be taken because there is no positive method of securing the crimp into the ready position within the crimping device. If the crimp becomes dislodged, it may not form a proper securing crimp. This may require the suture to be replaced, which may be extremely difficult. Once the snare loop is used to pull the sutures through the crimp, the snare loop must also be discarded. If during the process of passing the sutures through the crimp the sutures do not fully pass through the crimp, it is possible that the very small crimp could be dislodged from the crimping device and potentially lost within the patient. In addition, the user must manually apply the proper amount of tension on the suture while the crimp is deployed onto the suture, while can lead to variation in tension due to user error.

SUMMARY

Disclosed herein are devices for deploying multiple, successive suture securing devices onto sutures (e.g., "multi-firing" devices), and methods for using and manufacturing the same. Also disclosed herein are devices and methods for tensioning sutures in a more precise and consistent manner when placing securing devices on the sutures.

The multiple-firing securing device does can provide enough securing structures (e.g., disks, crimps) for a complete procedure to be loaded before the procedure and, therefore, do not need to be individually loaded during the procedure. The multiple-firing securing device holds a number of securing structures within the device prior to performing a procedure. During the procedure, the multiple-firing securing device automatically loads a single securing structure in a delivery position that is ready to be secured and is in a position allowing cords to pass therethrough for securing after the cords are tightened. The multiple-firing securing device provides a mechanism that passes the cords through one securing structure, placing the securing structure in a ready-to-fire position. The multiple-firing securing device provides a reliable, reusable way of passing the cords through one securing structure at a time for each of the multiple loaded securing structures. There is no waste or separate parts to account for during or after a surgical procedure.

As used herein, the multiple-firing securing device is able to be used on cords. As defined herein, the term cords is not limited to a plurality of cords, cords can be a single cord as well and, therefore, cords and cord are used interchangeably. For example, four lengths of cord can be threaded through a securing structure for securing one or more of the cords therein after the securing step occurs. Cords also are not limited to a particular type of material. The material can be made of natural fibers, man-made or synthetic fibers, plastics, and/or metals, to name a few. Cords also are not limited to a particular structure. The material can be made of twisted strands, twisted strands with a central core, or a single strand or wire, to name a few. One exemplary embodiment described herein relates to securing a surgical suture with a crimp of the multiple-firing crimp device and another exemplary embodiment described herein relates to securing a surgical suture with a disk of the multiple-firing disk device. The embodiments described herein, however, are not limited to surgical sutures, even though the example of surgical sutures is referred to or is used herein.

Traditionally, surgical sutures are cut by advancing a movable knife. One exemplary embodiment of the multiple-firing securing device uses a movable knife. Another exemplary embodiment of the multiple-firing securing device uses a fixed knife and a blunt pusher that contacts the suture and moves it to and against the fixed knife for cutting. This configuration prevents cutting from happening prematurely and allows precise control of the distance that the suture is cut from the securing device. A further exemplary embodiment of a multiple-firing securing device uses a movable inner cylinder movably housed within an outer cylinder having a window through which the cord is passed, the adjoining edges of the window and an edge of the inner cylinder forming scissors that cut the cord when the inner cylinder is moved distally past a given extent. This configuration prevents cutting from happening prematurely and allows precise control of the distance that the suture is cut from the disk.

In general, the systems and methods herein provide ways to pull cords such as surgical sutures through a set of cord securing structures, such as crimps, clips, and/or disks, all of which are used interchangeably herein. In any multi-fire applier device for fixing cords, a user must be able to pull the cords through a single securing structure where many of the securing structures are loaded in the device. In other words, the device must be a structure-threading device that can be reused during a single surgical procedure. The mechanism that pulls through the securing structure must be easy to use, have a low profile, should not produce waste during use, and significantly, should not be able to leave behind any separate parts. The challenges associated with such a device arise because the device must have a low profile in general and must be able to thread cords through a very small diameter securing structure (e.g., crimp, clip).

Many steps are undertaken in order to secure a structure onto cords with a multi-fire securing applier. First, the structure must be loaded from a magazine of multiple similar structures. Then, the cords must be threaded through that one structure that will secure the cords but not be threaded within or interfere with the other structures in the magazine. Then, the securing structure must be secured (e.g., crimped, crushed, released) onto the cords at a location that is, typically, very close to a cord-tying location (e.g., a surgical site). Finally, the device must be able to cut the cords extending out of the securing structure, dispose of the cut ends, and present a new securing structure for use next with as little user manipulation as possible.

It is beneficial to provide an automated device. In such a device, there are different moving assemblies, such as a carriage, a snare-extender, a cord lifter, a crimper or releaser, and a cutter. A handle contains automated motors, servos, and/or transmissions to carry out the functions of each of these movement assemblies. The handle is provided with a single mechanical control device for each of these assemblies or combination control devices that effect two or more functions. Alternatively, some or all of the automated actions can be replaced with mechanical systems. In any embodiment, simplicity in the entire process of installing a new structure, securing the structure at the cords, and loading another structure for repetitive cycles is important. One exemplary embodiment provides a shuttle that translates on the shaft of the device and, when positioned distally, presents a loop into which the cords to be secured are passed. This loop is referred to as a snare herein. The loop is, then, pulled back into the shuttle before the shuttle begins to move proximally. The proximal motion of the shuttle utilizes the loop to draw the cords through the securing structure and expose them to the outside of the shaft. The shuttle has a formed wire guide or channel that resides outside of the outer diameter of the device's shaft and that wire guide is able to move from outside the shaft to inside the shaft, through a window in a side of the shaft (e.g., at an upper side) m and, then, into or through a proximal end of the securing structure. When the tails of the cords are pulled through the securing structure with the shuttle, the tails are dropped off external to the shaft so that they can be grabbed by the user's hands for tensioning and subsequent securement.

In exemplary embodiments described, the snare is housed in the shuttle, which moves along the shaft attached to the handle of the securing device. If the snare is damaged during a procedure, the entirety of the shuttle containing the snare can be removed from the handle and the shaft and an entirely new shuttle from a separate, sterilized package can be used in place of the damaged shuttle.

In the exemplary embodiments, the shuttle contains various interlocks. One interlock prevents the formed wire snare from being presented until the shuttle is in a distal-most position. Another interlock prevents the shuttle from moving proximally if the snare is extended in any way. Another interlock holds the shuttle at a distal-most position for (1) extending the snare and (2) retracting the cords with movement of a shuttle saddle to position the cords in a radiused tip of the snare. Another interlock prevents the snare from moving when the cords reside in the tip and the shuttle is moving proximally to pass the cords through the crimp and thereafter present the cords outside the shaft for handling by the user.

An exemplary embodiment of the snare is formed and created from Nitinol and has a tight-radiused tip section that prevents the snare from pinching on the cords it snares while it pulls the cords through the securing device and then moves the cords to the outside of the shaft. This tight-radiused tip also ensures entry into a snare guide tube. The reservoir tip of the snare is stopped short of coming into the shuttle to form an open loop that allows the free tails of the cords to be exposed after passing through the securing device and falling free outside the shaft. The snare may be formed of any number of materials such as stainless steel, titanium, or a polymer.

Ideally, when the handle is in the middle of any of the crimping, cutting, or loading processes, the handle prevents the shuttle from moving away from the nose of the handle. In contrast, when the shuttle is advanced away from the handle, handle functions may be enabled or disabled as appropriate when the shuttle is either moving or is away from the nose.

Additional interlocks are present to enable/lock out functions in the handle based on a position of the shuttle when in its most proximal position, e.g., resting against the handle. After the shuttle is at the nose of the handle, the user can pull on the cords that run through the securing device and hang loose through a window of the shaft. When in the snaring position, the shuttle can be held by friction and/or with one or more detents or interlocks.

With the foregoing and other objects in view, there is provided, a multiple-fire securing device including a hollow outer shaft, a reloader, a rail, a reloader movement assembly, and a plurality of securing structures each defining an inner securing orifice. The reloader is longitudinally movable within the outer shaft and has a distal end shaped to temporarily contact one of the securing structures. The rail is disposed within the reloader and the plurality of securing structures are disposed on the rail. The rail has an installing location. The reloader movement assembly moves the reloader longitudinally in a distal direction to deliver a first securing structure to the installing location from a first proximal position and moves the reloader proximally away from the installing location without the first securing structure to a position in which the distal end of the reloader temporarily contacts a second one of the securing structures.

In accordance with another feature, the inner clipping orifice is an H-shaped orifice.

In accordance with a further feature, the rail has an H-shape cross-section.

In accordance with an added feature, the rail has a rectangular cross-section.

In accordance with an additional feature, the reloader movement assembly moves the reloader longitudinally further in the distal direction to remove the first securing structure from the installing location and off of the rail before moving the reloader proximally away from the installing location to the second securing structure.

In accordance with yet another feature, when at least one cord to be secured is disposed through the inner securing orifice of the first securing structure, removal of the first securing structure from the rail causes the first securing structure to secure the at least one cord within the inner securing orifice of the first securing structure.

In accordance with yet a further feature, after the reloader contacts the second securing structure, the reloader movement assembly moves the reloader longitudinally in the distal direction to deliver the second securing structure distally along the rail to the installing location.

In accordance with yet an added feature, when at least one cord to be secured is disposed through the inner securing orifice of the second securing structure, removal of the second securing structure from the rail causes the second securing structure to secure the cord within the inner securing orifice of the second securing structure.

In accordance with another feature, there is also provided a multiple-fire securing device comprising a plurality of securing structures each defining an H-shaped orifice, a hollow outer shaft having an exterior surface, an interior, and a distal end, and defining a lateral opening proximal to the distal end and communicating between the interior and the environment outside the exterior surface, a hollow inner shaft longitudinally movable within the outer shaft and having fingers extending from an intermediate point distally to define opposing structure-grasping slots shaped to temporarily grasp one of the securing structures, an H-shaped rail longitudinally disposed within the inner shaft and shaped to slidably receive thereon the plurality of securing structures, the H-shaped rail having an installing location, an inner shaft movement assembly automatically moving the inner shaft longitudinally in both distal and proximal directions and delivering one securing structure to the installing location by sliding a first securing structure longitudinally along the H-shaped rail from a first proximal position to the installing location and returning to a second proximal position without the first securing structure, and a snare movement assembly. The snare movement assembly has a snare with a snare opening and is shaped to pass through the H-shaped orifice of the first securing structure, to pass out of the interior of the outer shaft distally past the installing location, and to secure the at least one cord temporarily. The snare movement assembly moves the snare through the first securing structure past the installing location and out the distal end of the outer shaft to a snare position in which the at least one cord can be threaded through the snare opening and proximally to pull a portion of the at least one cord secured in the snare opening proximally through the first securing structure and out a side of the outer shaft through the lateral opening and present at least some of the portion of the at least one cord out through the lateral opening for access by a user.

An exemplary embodiment of the cord-securing devices and methods described herein includes a sensor associated with the device to detect and measure the amount of tying force that is being imparted by the user to the cords when tying a first knot at a location. This sensor supplies information to a display (e.g., on the handle) that shows either the amount of tying force or whether or not the amount of tying force is equal to or greater to a pre-set limit, or both. The display can take any form, such as an LCD display with graphics, an LED with yellow, green, and red display colors, or just a simple yes/no mechanical and/or electrical indicator that sufficient tying force is being applied. In this way, the user can maintain pressure against the first knot until the second knot secures the first knot. There is, accordingly, no time for loosening the first knot before the second knot secures the first knot in place with the tying force intact and leaving the first knot at the locking state. A surgeon can determine, with actual measurements or with pre-supplied data, the desired tying force for a particular cord to be tied (e.g., a surgical suture) and, during tying, to know dynamically if the cord is being tied and kept at the tying force after the cord is released.

Also disclosed are devices and methods for deploying securement devices onto sutures with precise and consistent tension levels in the sutures. Devices can include a handle portion having a trigger and a suture tensioning mechanism, and a shaft portion extending distally from the handle portion with at least one suture securement device positioned at a distal end portion of the shaft portion. The device can receive a suture or sutures extending through the suture securement device, across the trigger, and to the suture tensioning mechanism. Actuation of the suture tensioning mechanism gradually increases tension in the received suture until the trigger is actuated by pressure from the suture when a predetermined amount of tension is reached in the suture. Actuation of the trigger can cause the suture securement device to be deployed from the shaft portion onto the received suture with the predetermined amount of tension in the suture. The device can also include a peg on the side of the handle opposite from the tensioning mechanism so that the suture is routed from the peg, across the trigger, and to the tensioning mechanism in such a way that tension in the suture tends to pull the trigger.

In one example, after positioning a suture through securement device, around the trigger, and to the tensioning mechanism, the user can, for example, rotates a knob to wind the suture around a spool to gradually increase the tension in the suture until a threshold tension level is reached, which level of tension is designed to be sufficient to depress the trigger and activate a switch to cause deployment of the suture clip/securement device.

All methods disclosed herein also encompass simulations of the methods, for example, for training; testing; demonstration; or device or procedure development. Methods for treating a patient can include simulating treatment on a simulated human or non-human patient, for example, an anthropomorphic ghost. Examples of suitable simulated patients can include both an entire body, any portion of a body, or at least a portion of an organ, for example, a heart. The simulations can be physical, virtual, or any combination thereof. Examples of physical simulations can include any combination of natural or manufactured whole human or animal cadavers, portions thereof, or cadaver organs. Virtual simulations can include any combination of virtual reality, projections onto a screen or on at least a portion of a physical simulation, or other in silico elements. Some simulations can include non-visual elements, for example, auditory, tactile, or olfactory stimuli.

Although the devices and methods are illustrated and described herein as embodied in relation to particular examples, the inventive aspects of this disclosure are, nevertheless, not limited to the details shown in the provided examples because various modifications and structural changes may be made therein without departing from the spirit thereof and within the scope and range of equivalents of the claims. Additionally, well-known elements of exemplary embodiments will not be described in detail or will be omitted so as not to obscure the relevant details.

Additional advantages and other features characteristic of the present devices and methods will be set forth in the detailed description that follows and may be apparent from the detailed description or may be learned by practice of exemplary embodiments. Still other advantages may be realized by any of the instrumentalities, methods, or combinations particularly pointed out in the claims.

Other features that are considered as characteristic for the devices and methods are set forth in the appended claims. As required, detailed embodiments are disclosed herein; however, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one of ordinary skill in the art to variously employ the present devices and methods in virtually any appropriately detailed structure. Further, the terms and phrases used herein are not intended to be limiting; but rather, to provide an understandable description thereof. While the specification concludes with claims defining the features that are regarded as novel, it is believed that the devices and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present devices and methods. Advantages of embodiments will be apparent from the following detailed description of the exemplary embodiments thereof, which description should be considered in conjunction with the accompanying drawings in which:

FIG. 6 is a fragmentary, longitudinally cross-sectional view of the end effector of FIG. 1 with the crimp sub-assembly in a crimp-seated position ready for use.

FIG. 6A is a fragmentary, longitudinally cross-sectional view of an enlarged distal portion of the end effector of FIG. 6.

FIG. 7 is a fragmentary, side elevational and partially longitudinal cross-sectional view of the handle portion of FIG. 3 with the crimp sub-assembly actuators in a suture-use position corresponding to FIG. 6.

FIG. 17 is a fragmentary, longitudinally cross-sectional view of the end effector of FIGS. 14 and 15 with a cord-lifting device in a lowered position.

FIG. 18 is a fragmentary, longitudinally cross-sectional view of the end effector of FIG. 17 with the cord-lifting device in a lifted position positioning the cords for grasping by a user.

FIG. 23 is a fragmentary, perspective view of the end effector of FIG. 22.

FIG. 24 is a fragmentary, side elevational and partially longitudinal cross-sectional view of the handle of FIG. 20 with the cord-lifting device returned to the unactuated position that places the cord-lifting device in the lowered position corresponding to FIGS. 22 and 23 and with the snare actuator in the retracted position.

FIG. 32 is an enlarged perspective view of the crimp of FIG. 1.

FIG. 33 is a longitudinal cross-sectional view of the crimp of FIG. 1.

FIG. 92 is a flow chart of a process for completing a crimping procedure with a multiple-firing crimping assembly.

FIG. 102 is a right side elevational view of the multiple-clip securing device of FIG. 101 in a ready-to-fire-clip state with the snare contained within the snare assembly and the snare assembly locked in position to permit placement of a cord-retaining clip.

FIG. 103 is a flow chart of a process for performing and completing a securing procedure with a multiple-clip securing device.

FIG. 109 is a fragmentary, partially transparent, side elevational view of the distal end of the multiple-clip securing device of FIG. 108 with the clip pusher moved distally taking with it a subsequent clip and placing the subsequent clip into a clip-ready position and with one of the clip-holding fingers removed for clarity.

FIG. 110 is a fragmentary, partially transparent, side elevational view of the distal end of the multiple-clip securing device of FIG. 109 with a subsequent clip extended off a clip-holding rail and clipped to one or more cords after the cords are cut.

FIG. 111 is a fragmentary, partially transparent, side elevational view of the distal end of the multiple-clip securing device of FIG. 98 with a last clip on the clip-holding rail, a clip pusher proximal of the last clip, and with one of the clip-holding fingers removed for clarity.

FIG. 112 is a fragmentary, perspective and partially transparent view of an exemplary embodiment a distal end effector of a multiple-clip securing device with a cutting/reloading assembly in a ready-to-clip position.

FIG. 113 is a fragmentary, perspective, vertically cross-sectional view of the end effector of FIG. 112.

FIG. 114 is a fragmentary, perspective, vertically cross-sectional view of the end effector of FIG. 112 with the cutting/reloading assembly in a clip-delivered position before the first clip is ejected.

FIG. 115 is a fragmentary, perspective, vertically cross-sectional view of the end effector of FIG. 112 with the cutting/reloading assembly in a clip-delivered position after the first clip is ejected.

FIG. 116 is a fragmentary, perspective, vertically cross-sectional view of the end effector of FIG. 115 with the cutting/reloading assembly in a subsequent clip-retrieval position.

FIG. 117 is a fragmentary, perspective, vertically cross-sectional view of the end effector of FIG. 116 with the cutting/reloading assembly in a subsequent clip-retrieval position after the previous 11 clips have been ejected.

FIG. 118 is a fragmentary, perspective, vertically cross-sectional view of the end effector of FIG. 117 with the cutting/reloading assembly in a ready-to-clip position.

FIG. 119 is a fragmentary, perspective and vertically cross-sectional view of the distal end of the cutting/reloading assembly of FIG. 112.

FIG. 120 is a fragmentary, perspective and horizontally cross-sectional view of the distal end of the cutting/reloading assembly of FIG. 112.

Figure 98:
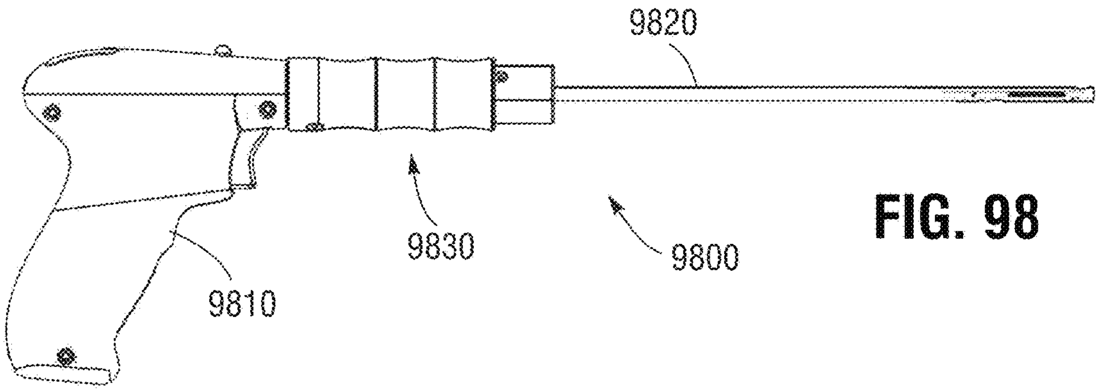
FIG. 98 is a right side elevational view of an exemplary embodiment of a multiple-clip securing device in a ready-to-use state, a snare contained within a retracted snare assembly.
Figure 121:
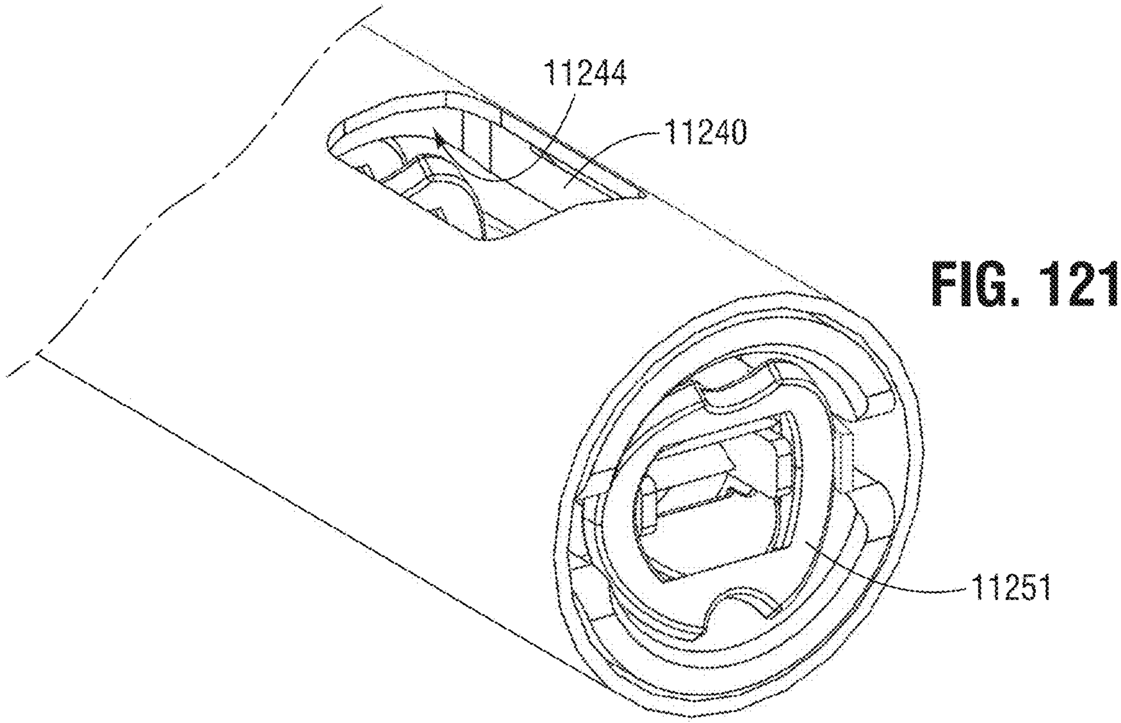

FIG. 121 is a fragmentary, enlarged, perspective view from distal of a distal end of an exemplary embodiment of a shaft of the multiple-clip securing device of FIG. 98 with a clip in a snare-ready position and with one of the clip-holding fingers removed for clarity.

Figure 122:
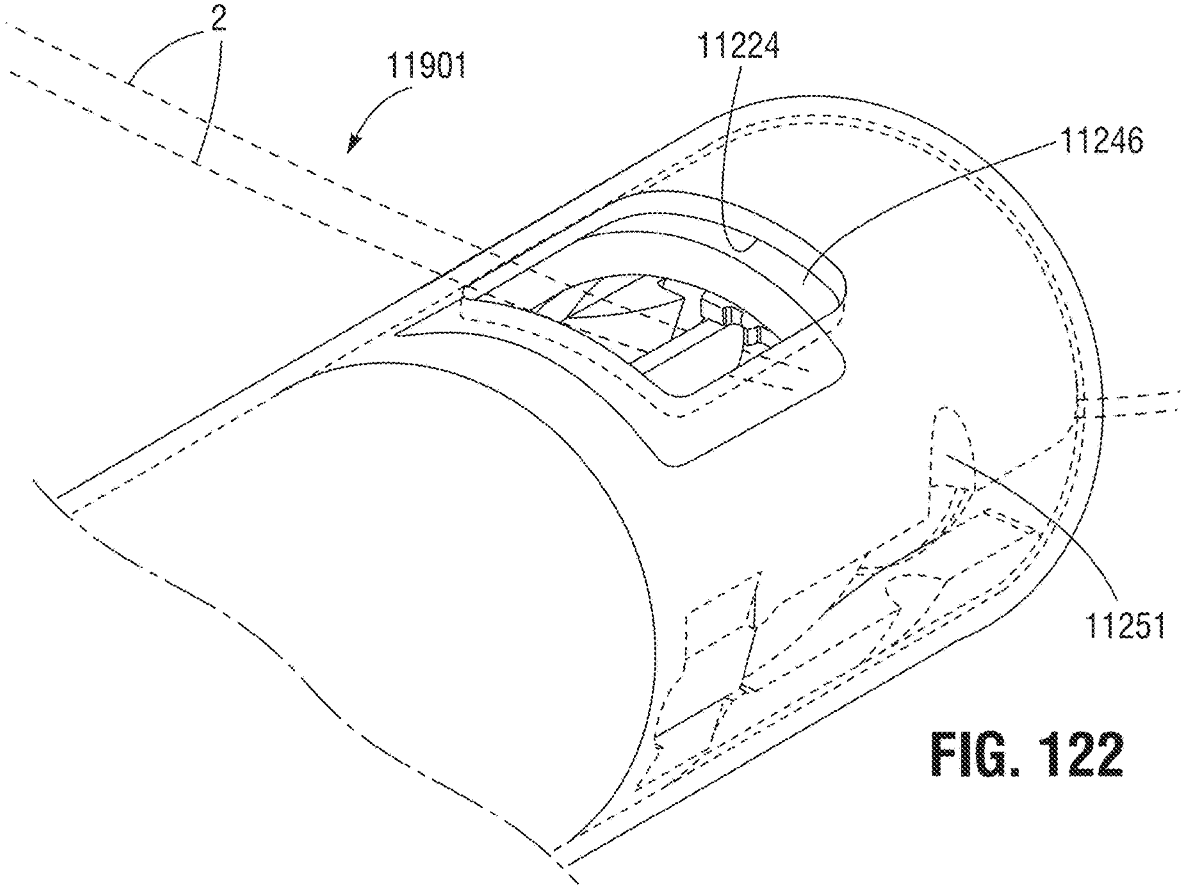

FIG. 122 is a fragmentary, enlarged, partially transparent, perspective view from proximal of the distal end of the shaft of FIG. 121 with a pair of cords, indicated in dashed lines, threaded through the clip before being clipped together to the clip and with both of the clip-holding fingers.

FIG. 123 is a fragmentary, enlarged, cross-sectional view of the distal end of the shaft of the multiple-clip securing device of FIG. 112 with the clip in a snare-ready position, a path for a cord to be clipped by the clip being indicated with a dashed line.

FIG. 124 is a fragmentary, enlarged, cross-sectional view of an intermediate portion of the shaft of the multiple-clip securing device of FIG. 112 with a set-screw holding the clip support beam within the shaft.

Figure 125:
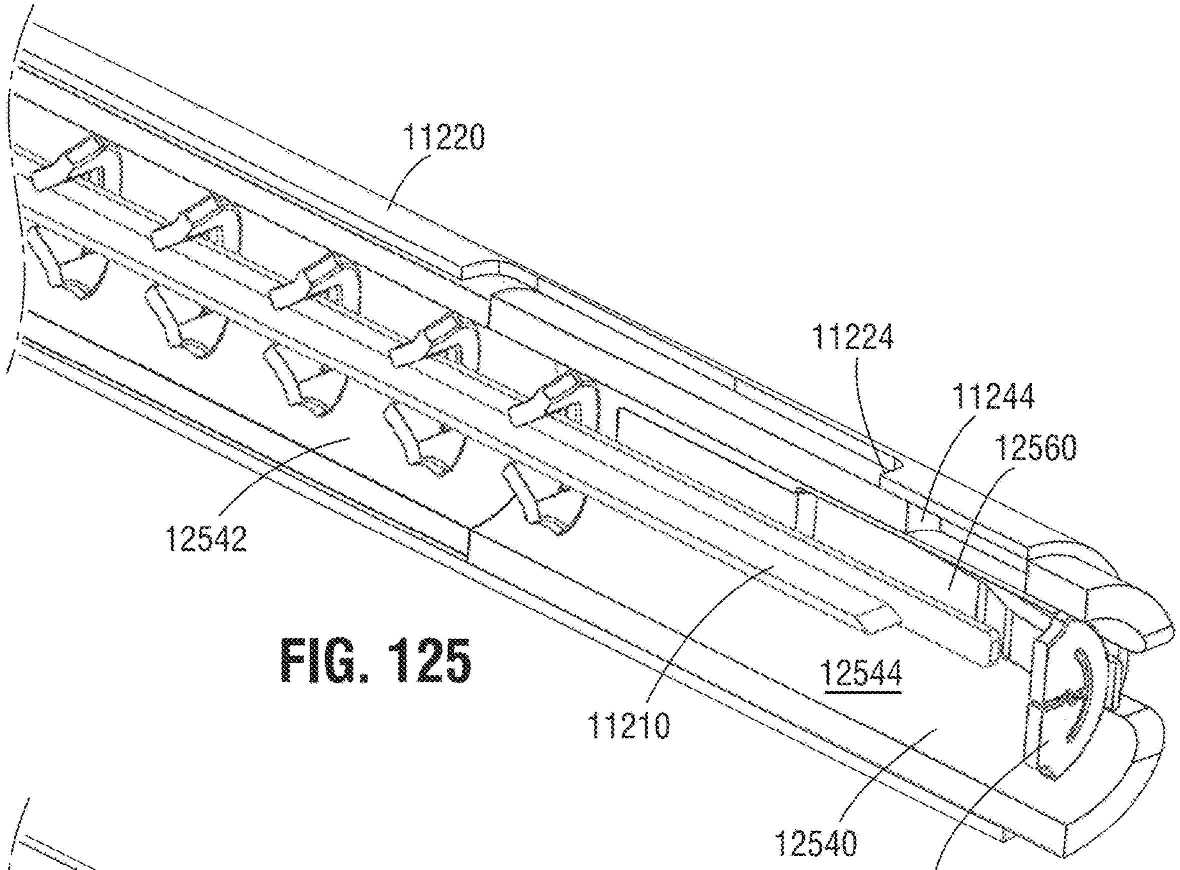

FIG. 125 is a fragmentary, perspective and vertically cross-sectional view of the distal end of the cutting/reloading assembly of FIG. 112 with the cutting/reloading assembly in a clip delivery position.

Figure 126:
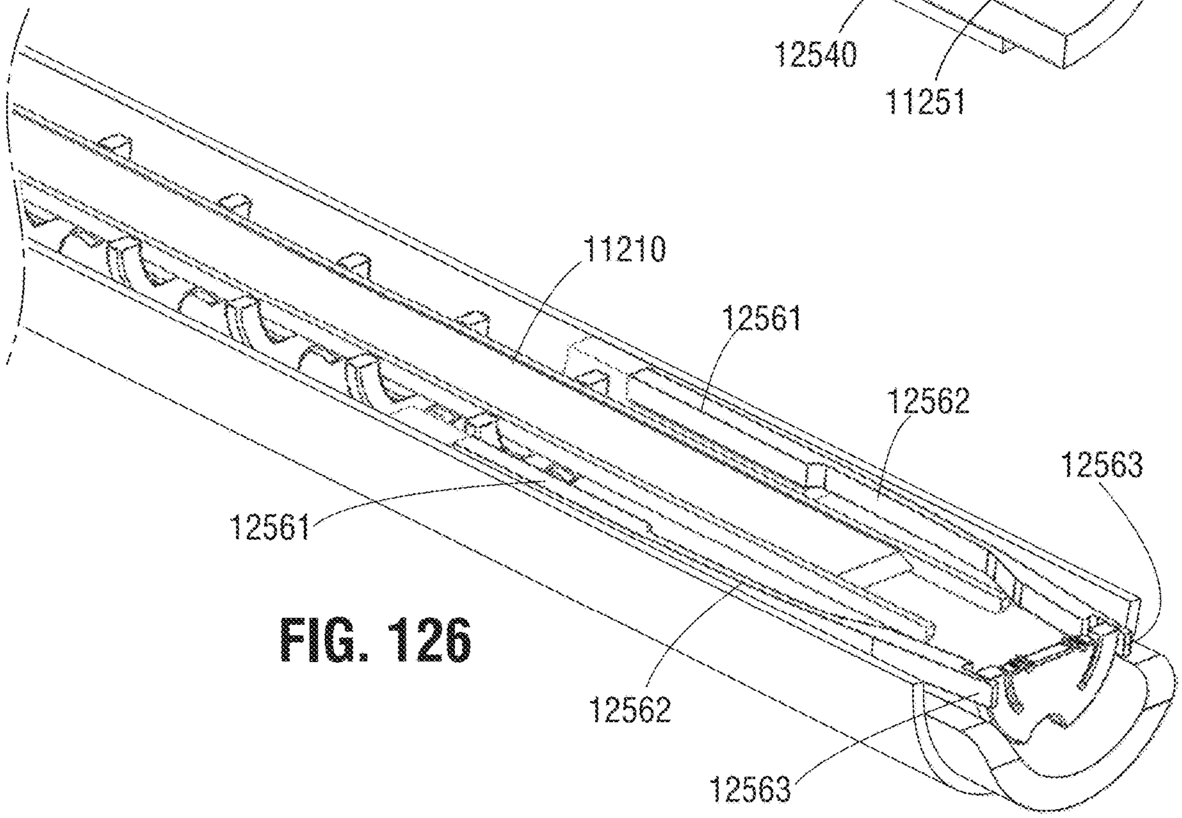

FIG. 126 is a fragmentary, perspective and horizontally cross-sectional view of the distal end of the cutting/reloading assembly of FIG. 125.

Figure 127:
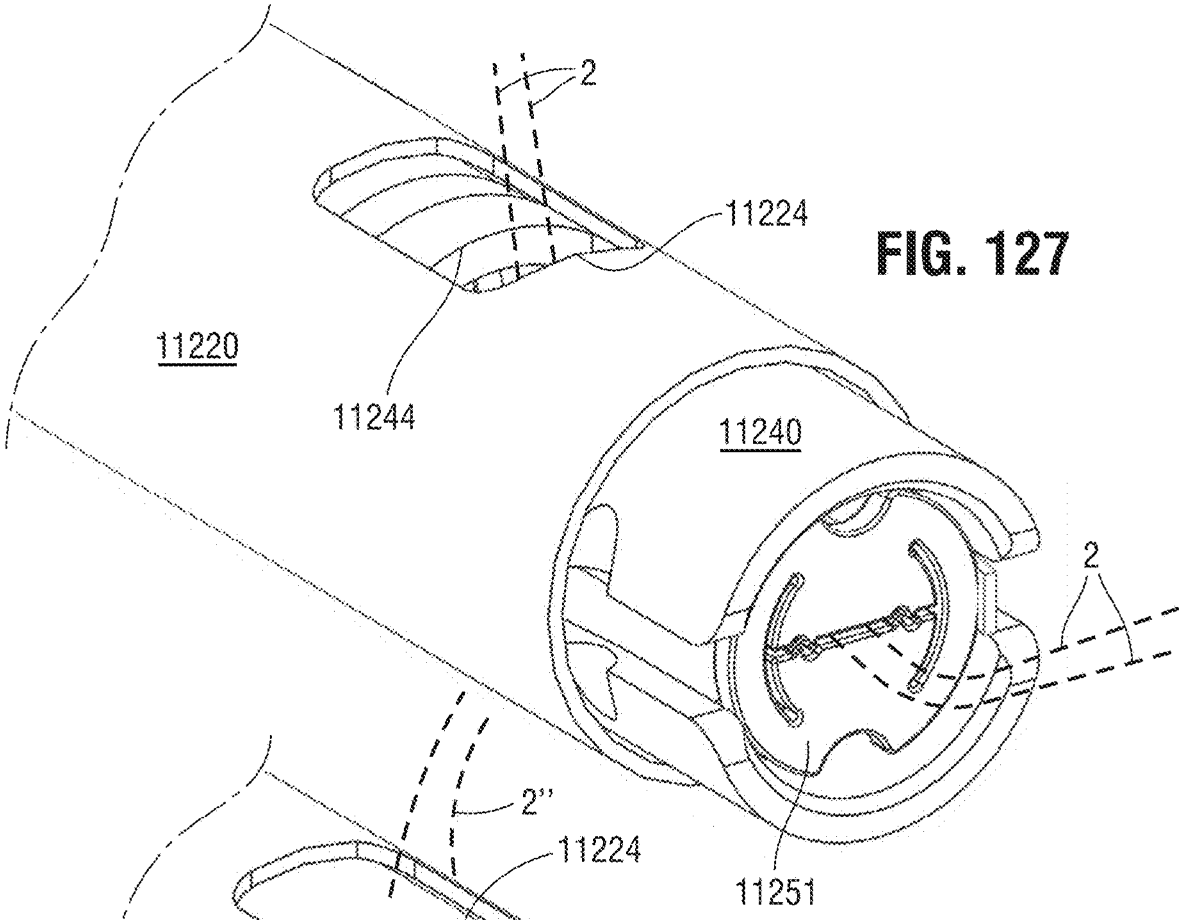

FIG. 127 is a fragmentary, enlarged, perspective view from distal of the distal end of the shaft of the multiple-clip securing device of FIG. 112 with the clip ejected from the clip guide beam, disposed within the distal end of the shaft, and clipping a pair of cords before the cords are cut and with one of the clip-holding fingers removed for clarity.

Figure 128:
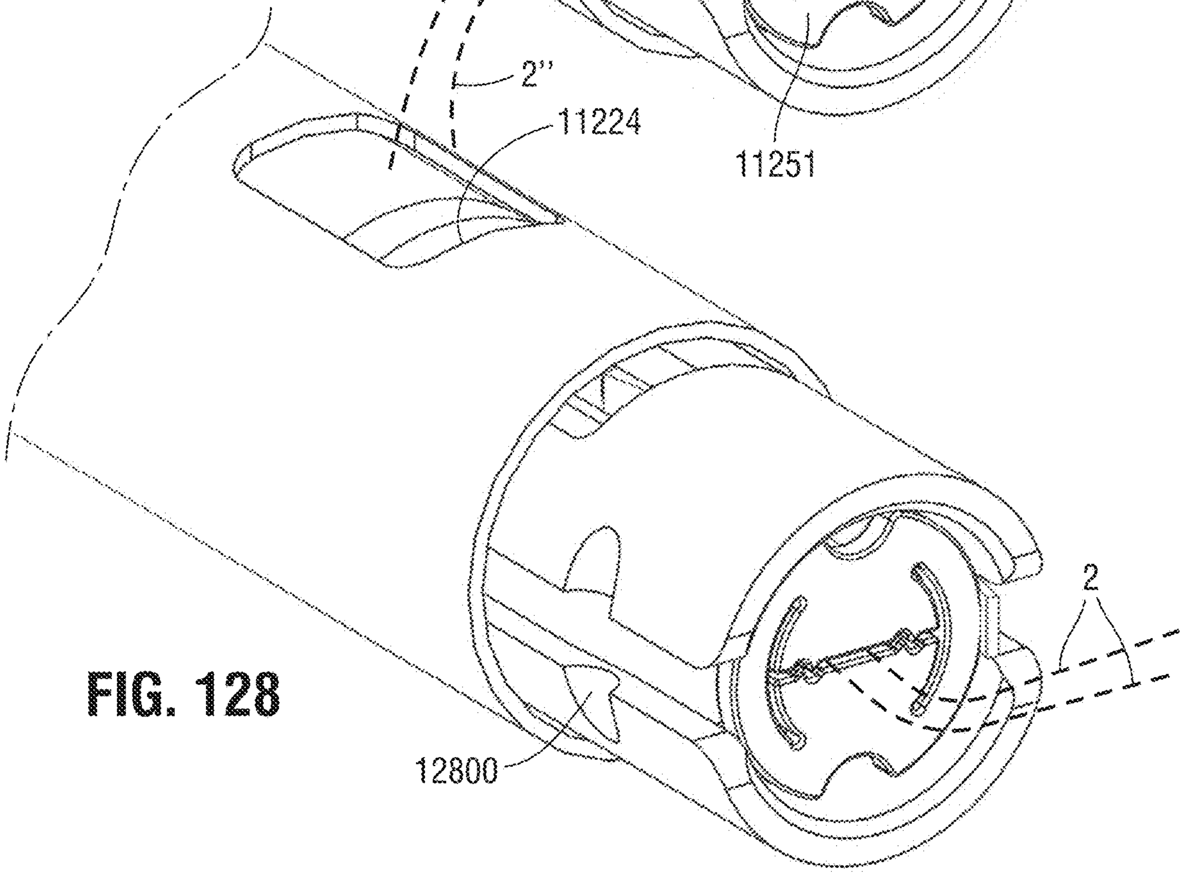

FIG. 128 is a fragmentary, enlarged, perspective view from distal of the distal end of the shaft of FIG. 127 with the clip clipped on the pair of cords after the cords are cut and before the clip exits the distal end of the shaft and with one of the clip-holding fingers removed for clarity.

Figure 129:
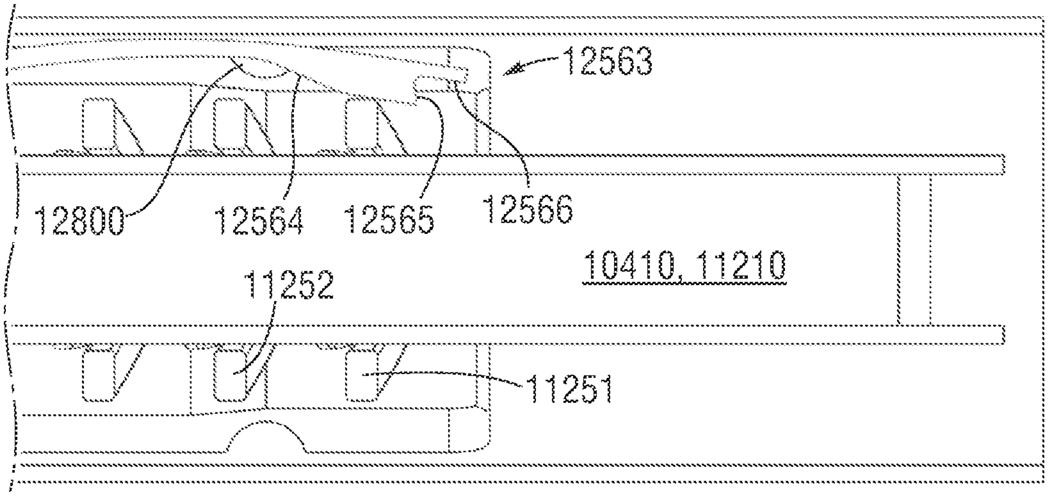

FIG. 129 is a fragmentary, enlarged, cross-sectional view of the distal portion of the shaft of the multiple-clip securing device of FIG. 112 with the clip pushing arm in a first retracted reloading position for reloading a distal-most clip on the clip-guiding rail before the distal-most clip contacts a clip-pushing face of the clip-holding finger, the clip-holding finger being cammed outwards due to an interior cam surface, and with one of the clip-holding fingers being removed for clarity.

Figure 130:
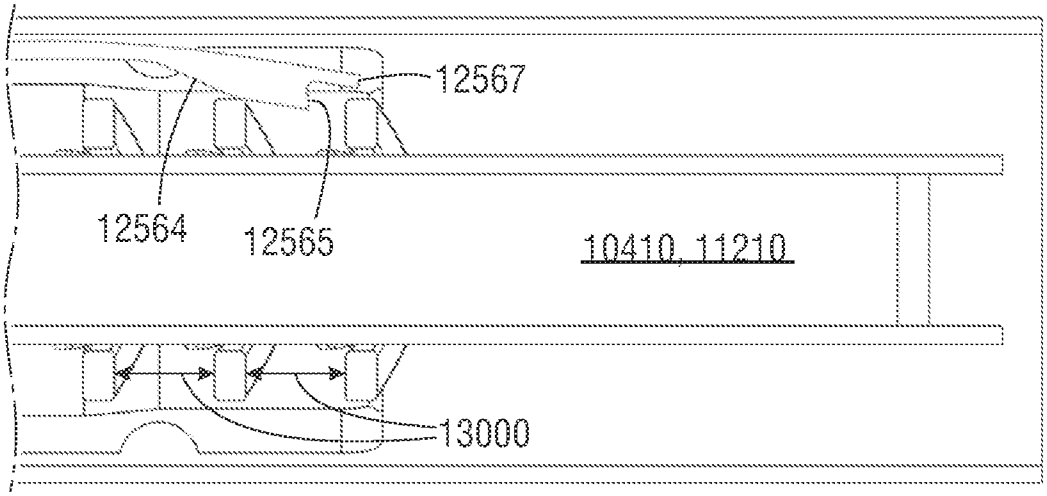

FIG. 130 is a fragmentary, enlarged, cross-sectional view of the distal portion of the shaft of the multiple-clip securing device of FIG. 112 with the clip pushing arm in a second retracted reloading position for reloading the distal-most clip with the clip-pushing face of the clip-holding finger proximal of the distal-most clip, with the cam surface resting on a second distal-most clip and being cammed outwards due to the interior cam surface to retain the fingertip outside the outer diameter of the distal-most clip, and with one of the clip-holding fingers being removed for clarity.

Figure 131:
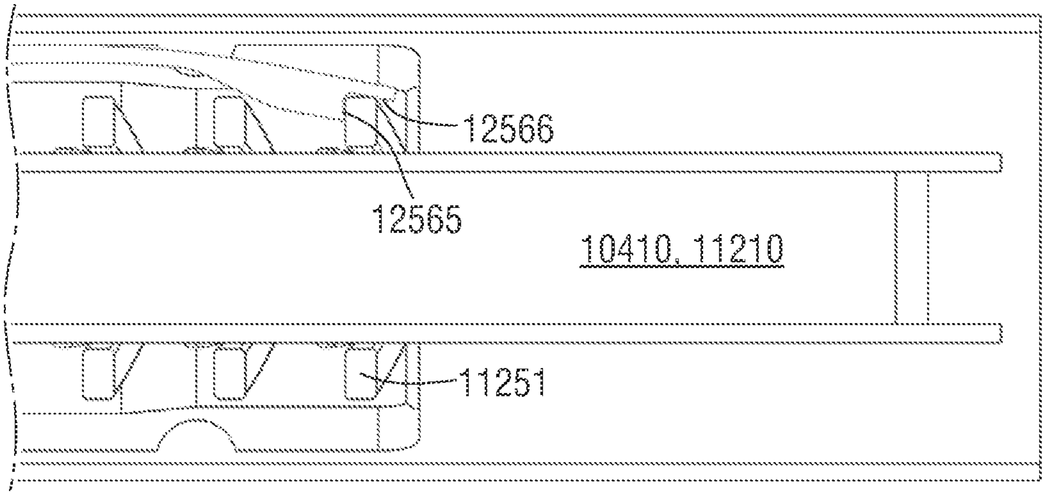

FIG. 131 is a fragmentary, enlarged, cross-sectional view of the distal portion of the shaft of the multiple-clip securing device of FIG. 112 with the clip pushing arm in a third extended reloading position for reloading the distal-most clip by contacting the clip-pushing face of the clip-holding finger with the proximal side of the distal-most clip and the interior surface of the finger tip of the clip-holding finger with the exterior surface of the distal-most clip, and with one of the clip-holding fingers being removed for clarity.

Figure 132:
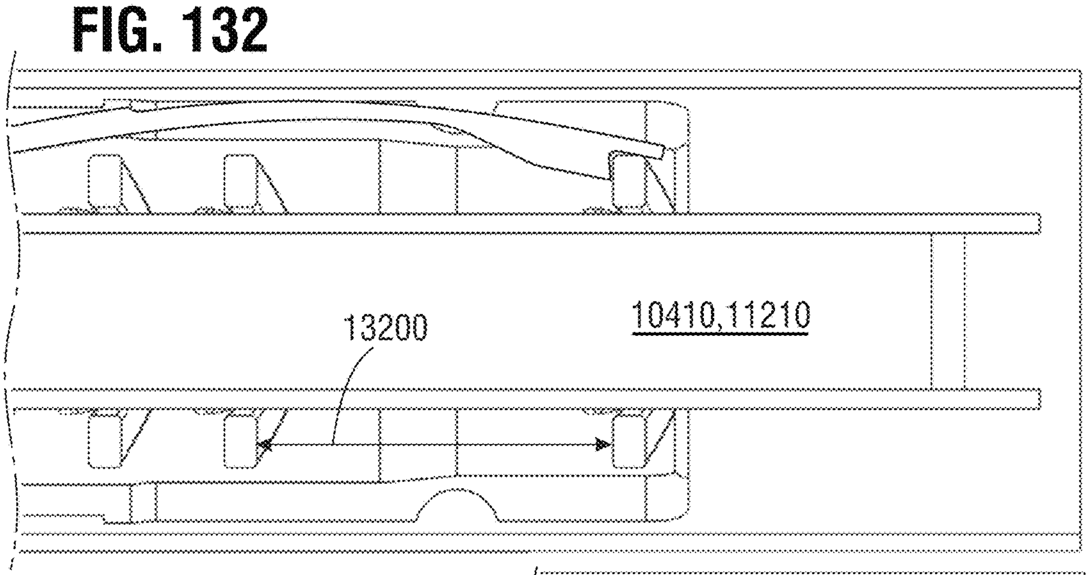

FIG. 132 is a fragmentary, enlarged, cross-sectional view of the distal portion of the shaft of the multiple-clip securing device of FIG. 112 with the clip pushing arm in a fourth extended reloading position where the distal-most clip is in an intermediate reloading position on the clip-guiding rail, and with one of the clip-holding fingers being removed for clarity.

Figure 133:
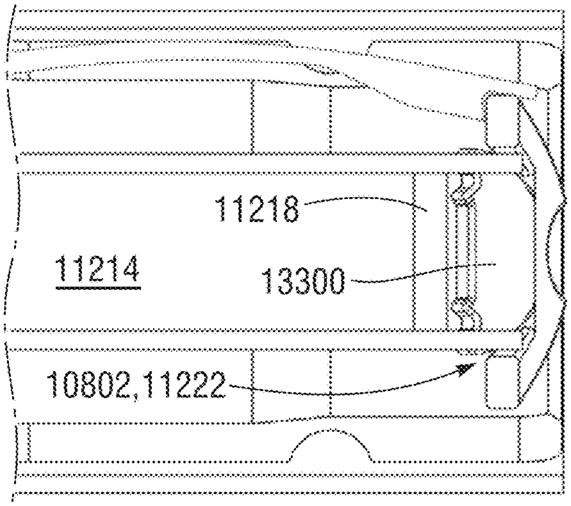

FIG. 133 is a fragmentary, enlarged, cross-sectional view of the distal portion of the shaft of the multiple-clip securing device of FIG. 112 with the clip pushing arm in the clip-loaded, ready-to-clip position, and with one of the clip-holding fingers being removed for clarity.

Figure 134:
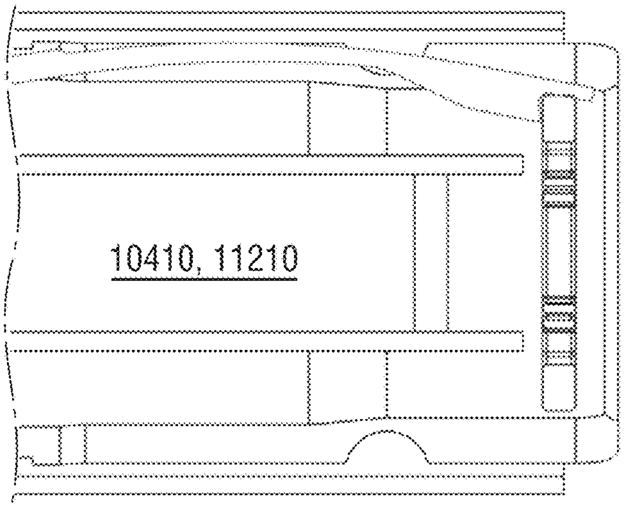

FIG. 134 is a fragmentary, enlarged, cross-sectional view of the distal portion of the shaft of the multiple-clip securing device of FIG. 112 with the clip pushing arm in a clipped position, the clip pushed off of the clip-guiding rail, before the clip exits the shaft, and with one of the clip-holding fingers being removed for clarity.

Figure 135:
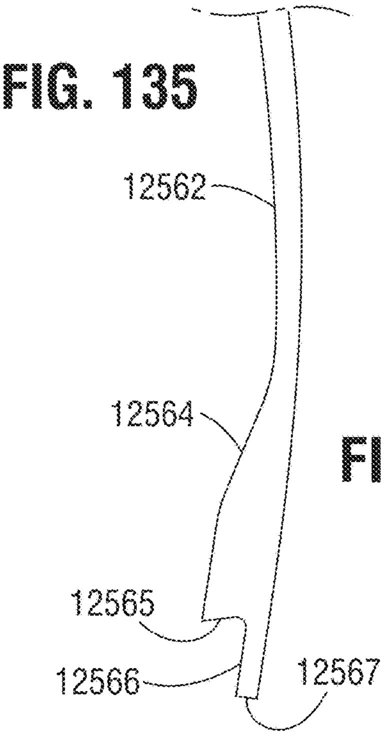

FIG. 135 is a fragmentary, enlarged, top plan view of a clip pushing arm of FIGS. 129 to 134.

Figure 136:
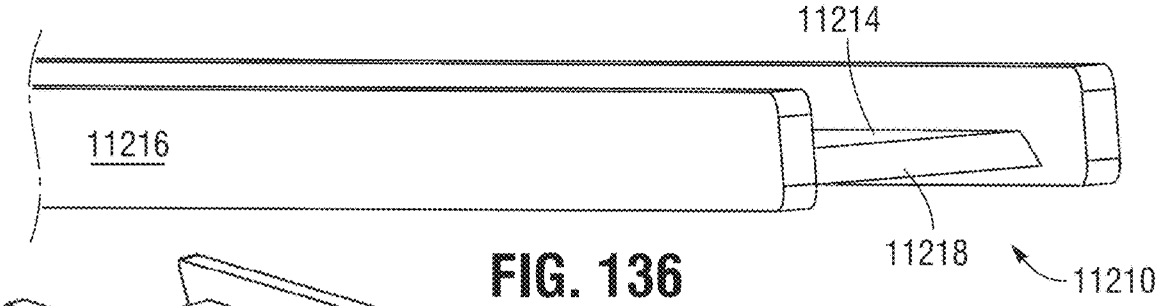

FIG. 136 is a fragmentary, enlarged, perspective view of a distal portion of the clip-holding rail of the multiple-clip securing device of FIG. 112 showing an offset of an intermediate floor between two lateral walls.

Figure 137:
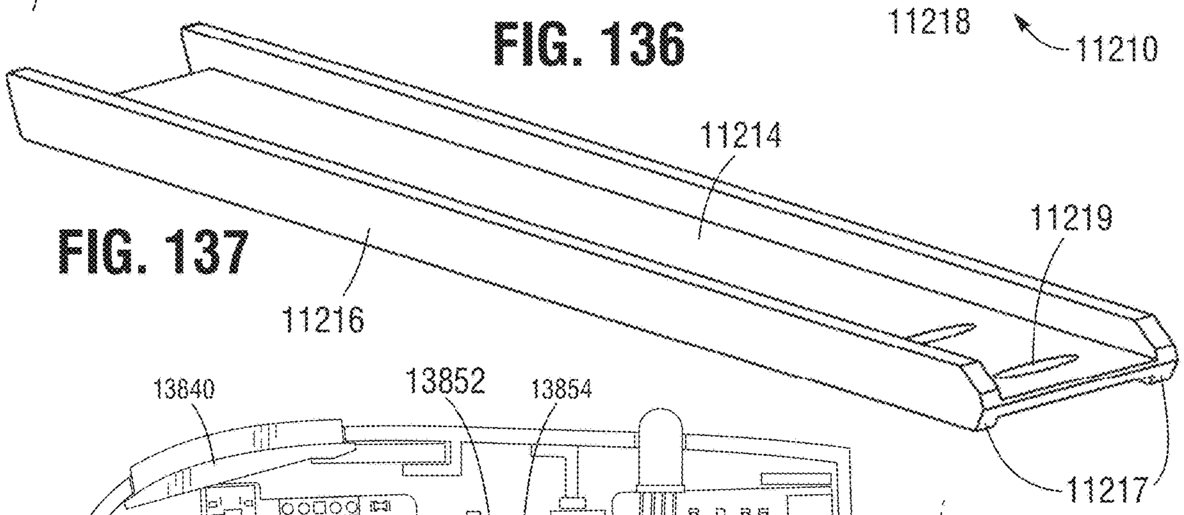

FIG. 137 is an enlarged, perspective view of from proximal of a proximal end of the clip-holding rail of the multiple-clip securing device of FIG. 112 showing the chamfers at the proximal end that enable loading the clips thereon with an initially reduced stress.

Figure 138:
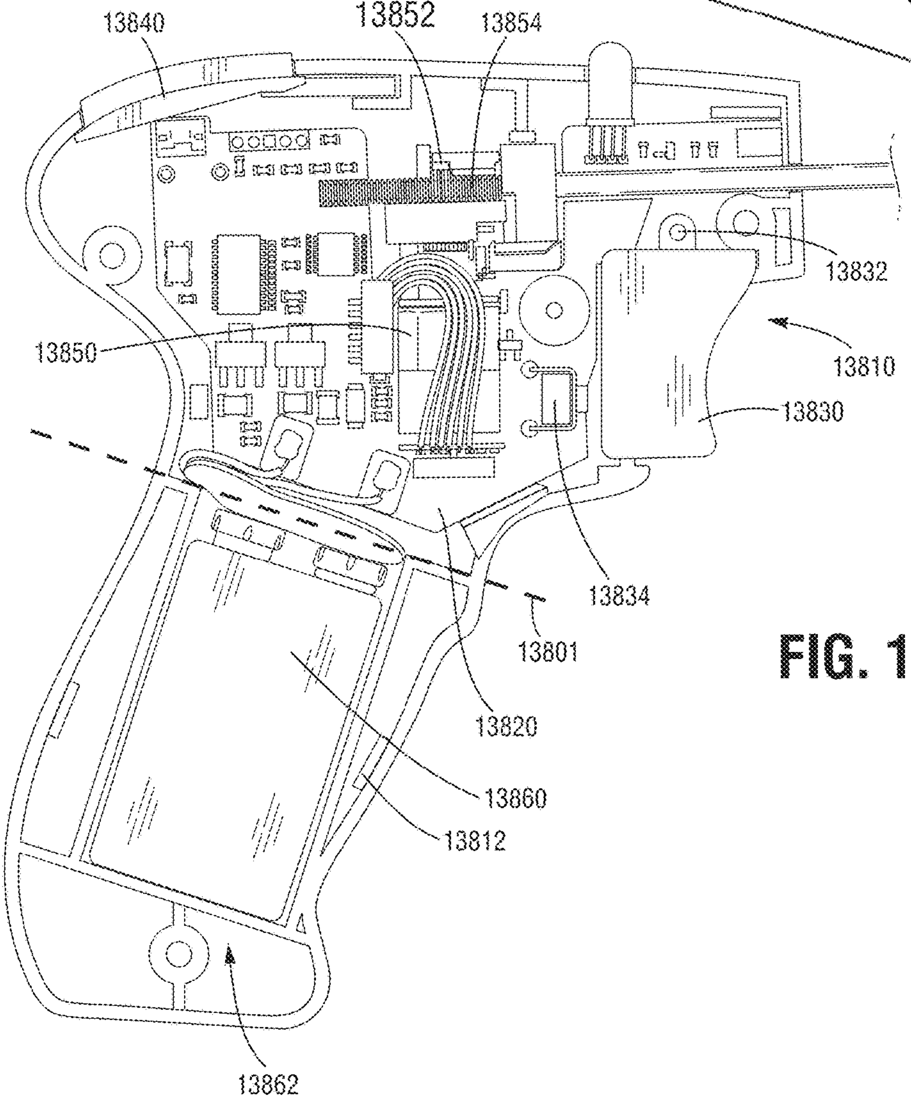

FIG. 138 is a photograph of a fragmentary side view of a handle portion of an exemplary embodiment of a multiple-clip securing device with a right cover removed to reveal a power supply, a drop-in single circuit board with side-mounted switches to minimize a footprint of the electrically powered components, a multi-colored LED display, a clip-fire switch, a reload switch, and a motor and gearbox connected to a rack and pinion.

Figure 139:
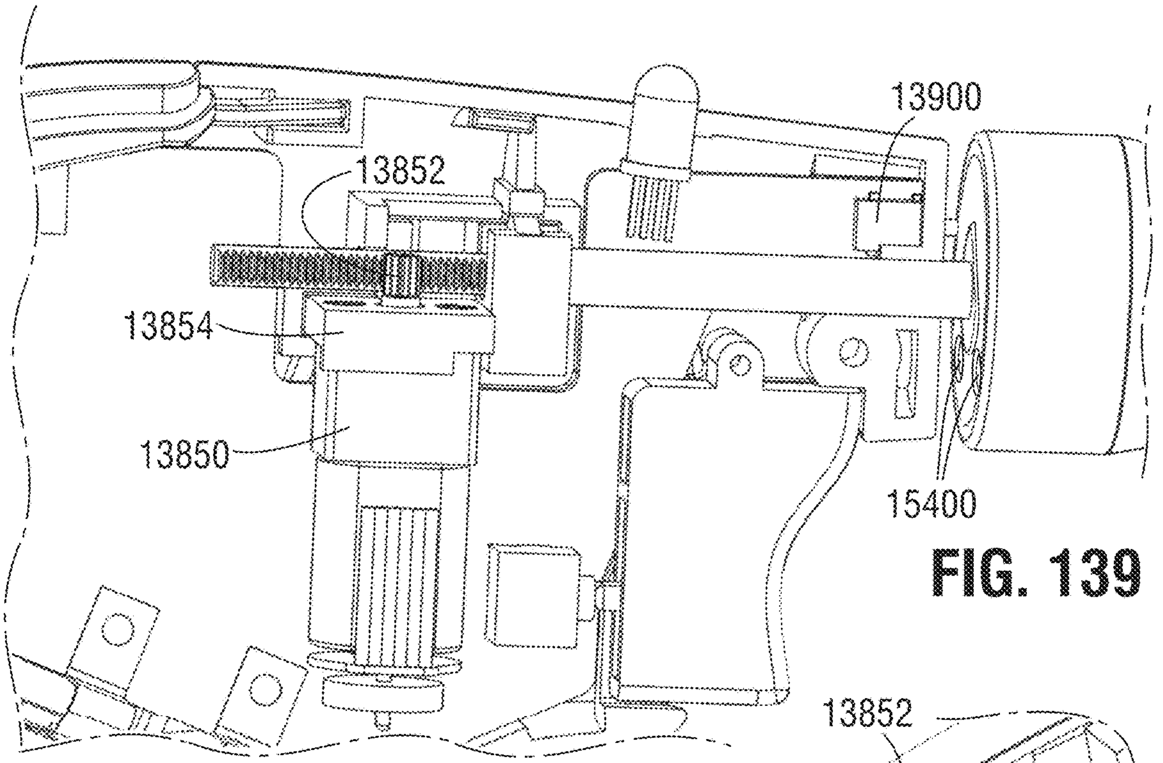

FIG. 139 is a fragmentary, side perspective view of a portion of the handle of FIG. 138.

Figure 140:
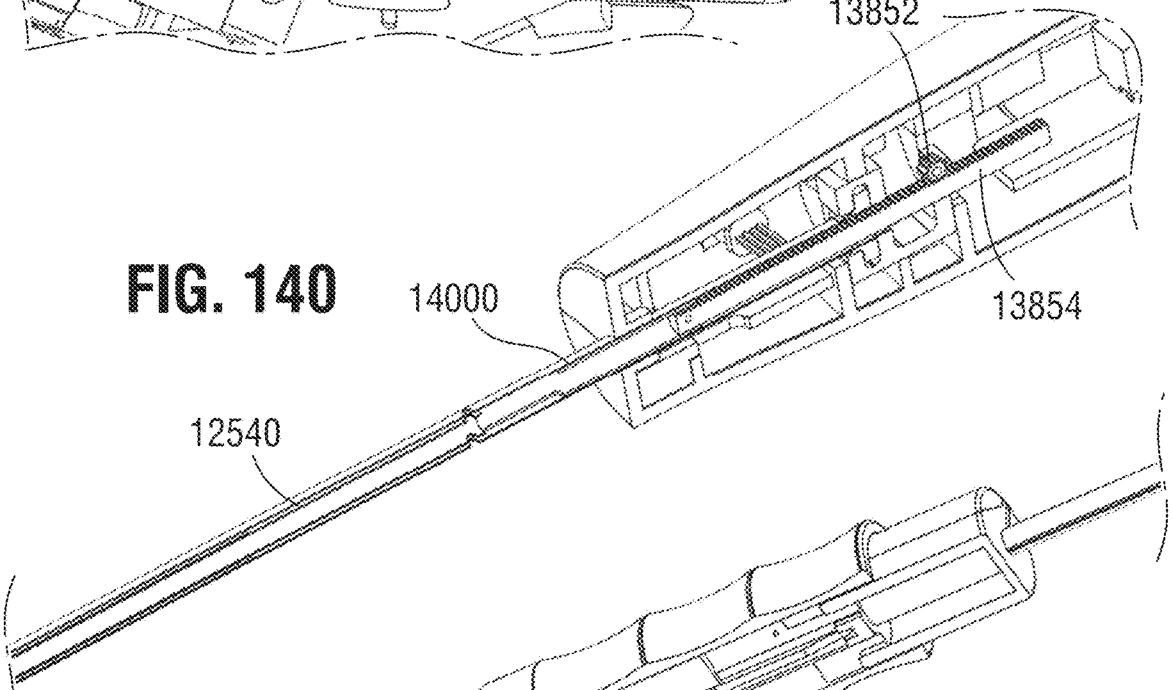

FIG. 140 is a horizontal cross-sectional view of the handle of FIGS. 138 and 139 viewed from below to reveal an outer shaft sleeve, an inner clip movement tube, and the pinion and rack connected to a proximal portion of the clip movement tube.

FIG. 141 is a fragmentary, partially vertical cross-sectional, perspective view of an exemplary embodiment of a snare assembly having a movement body in a proximal retracted position with respect to an interior body to place a snare in its most-retracted position yet still extending slightly out from a snare-guiding tube and a trombone-shaped snare guide path that, in the embodiment shown, provides an extension of the snare out from the snare-guiding tube to distance that is three times the length that the movement body traverse with respect to the interior body.

FIG. 142 is a fragmentary, partially vertical cross-sectional, perspective view of the snare assembly of FIG. 141 with the movement body in a distal position with respect to the interior body to place the snare in its distal-most extended position.

FIG. 143 is a fragmentary, vertical cross-sectional view of the snare assembly of FIG. 141 with the lockout in a first lockout state in which:

the assembly can translate along the shaft from the handle to the distal end of the shaft while the canopy of the lockout rides in a groove of the shaft to key the interior body of the snare assembly in a fixed circumferential position about the shaft; and one or more side pontoons of the lockout prevent the movement body from moving with respect to the interior body to retain the snare within the snare assembly, and with the components internal to the outer shaft tube removed for clarity.

Figure 144:
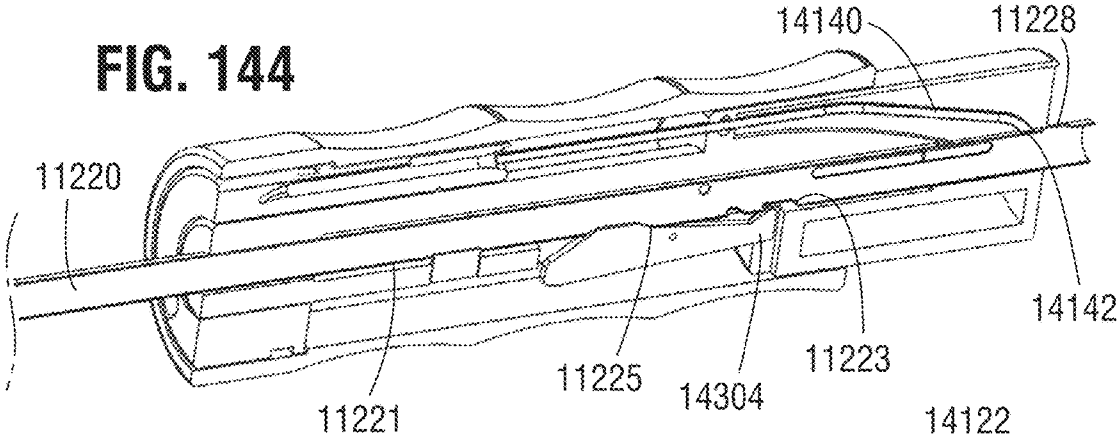

FIG. 144 is a fragmentary, vertical cross-sectional view of the snare assembly of FIG. 141 with the lockout in the first lockout state and just before a second lockout state in which the lockout pivots and a wider tail of the lockout enters a lower window of the shaft and the canopy remains within the groove of the shaft or can exit the groove, and with the components internal to the outer shaft tube removed for clarity.

Figure 145:
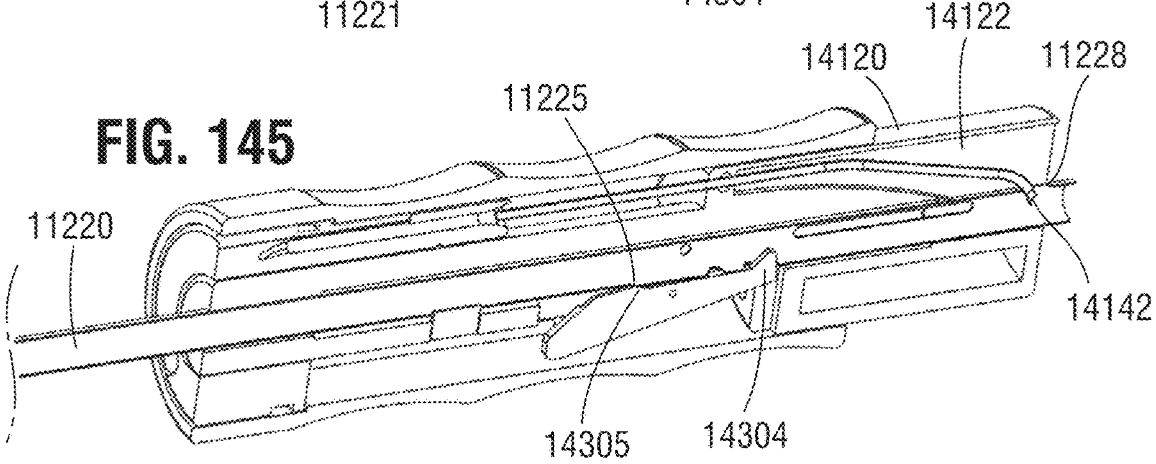

FIG. 145 is a fragmentary, vertical cross-sectional view of the snare assembly of FIG. 141 with the lockout in a second lockout state in which the lockout pivots and:

keeps the interior body circumferentially fixed, either the canopy remains within the groove or the canopy exits the groove while the tail enters the lower window of the shaft distal of the groove or both; and the side pontoons pivot down to no longer prevent the movement body from moving distally with respect to the interior body, thereby allowing the snare to exit, and with the components internal to the outer shaft tube removed for clarity.

Figure 146:
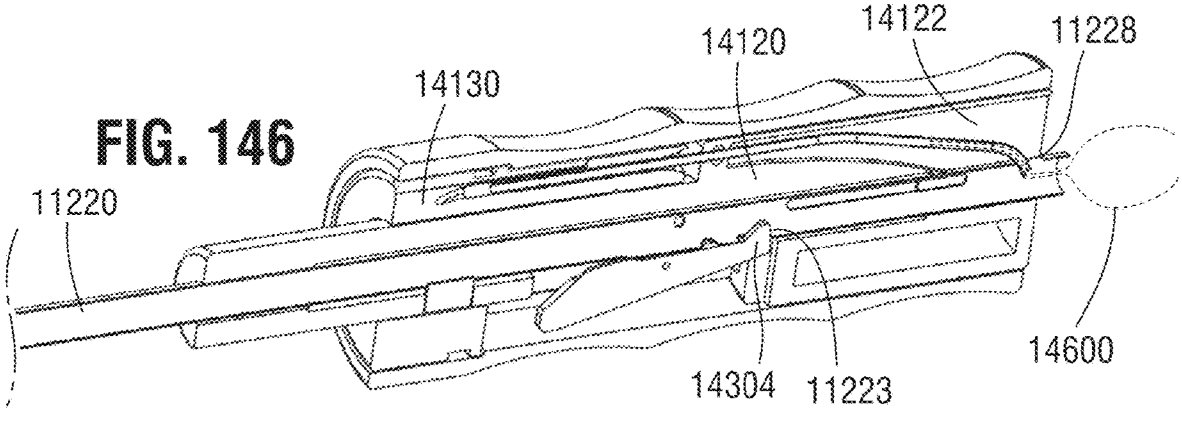

FIG. 146 is a fragmentary, vertical cross-sectional view of the snare assembly of FIG. 141 with the lockout in the second lockout state in which the movement body has moved distally with respect to the interior body and a snare exits for snaring cords to be clipped, and with the components internal to the outer shaft tube removed for clarity.

Figure 147:
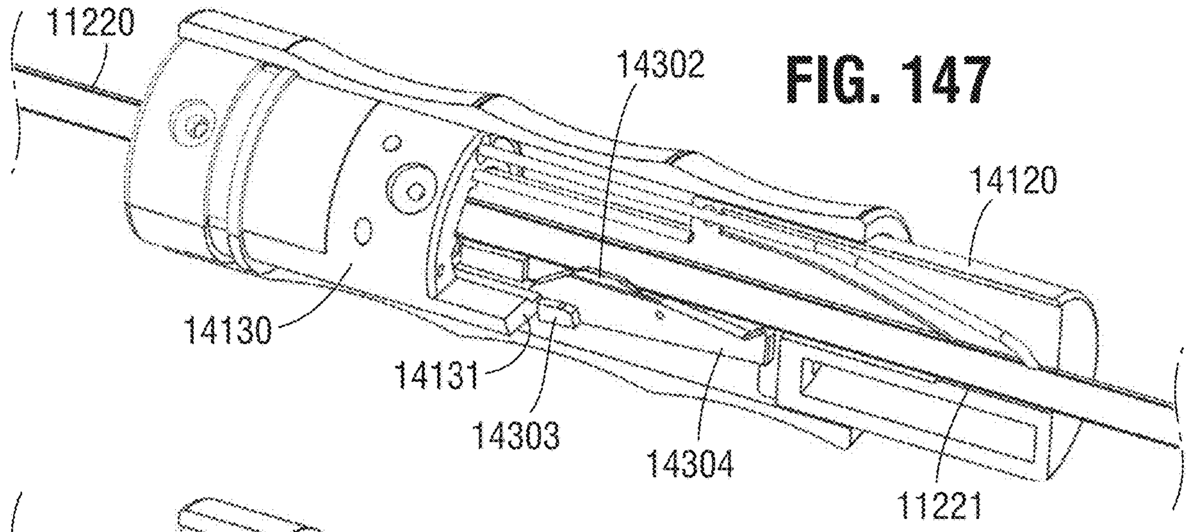

FIG. 147 is a fragmentary, partially vertical cross-sectional, perspective view of the snare assembly of FIG. 143 about the shaft with the lockout in the first lockout state, and with the components internal to the outer shaft tube removed for clarity.

Figure 148:
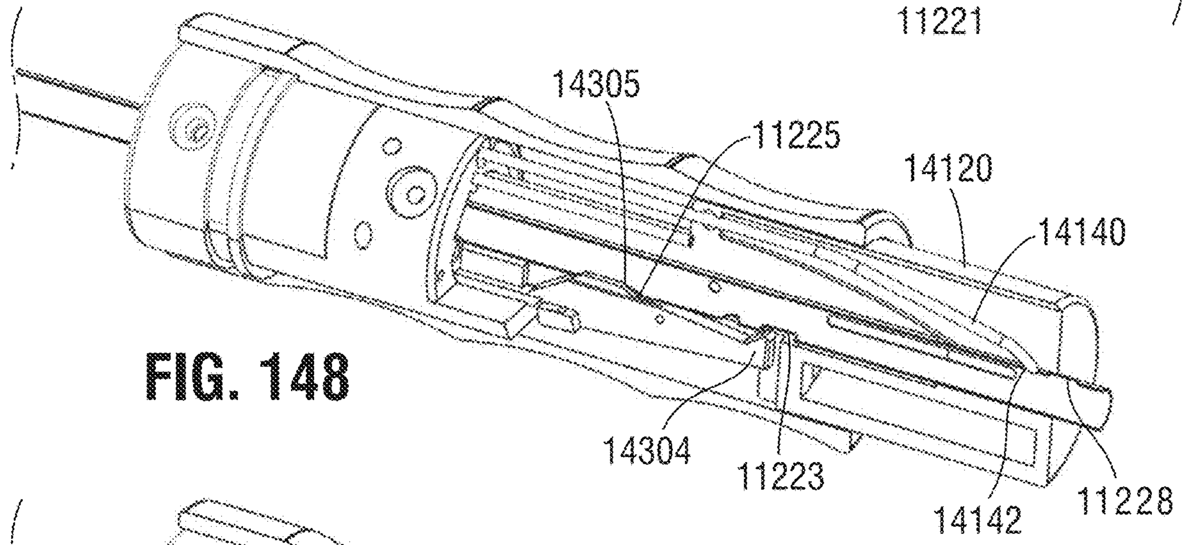

FIG. 148 is a fragmentary, partially vertical cross-sectional, perspective view of the snare assembly of FIG. 144 about the shaft with the lockout in the first lockout state, and with the components internal to the outer shaft tube removed for clarity.

Figure 149:
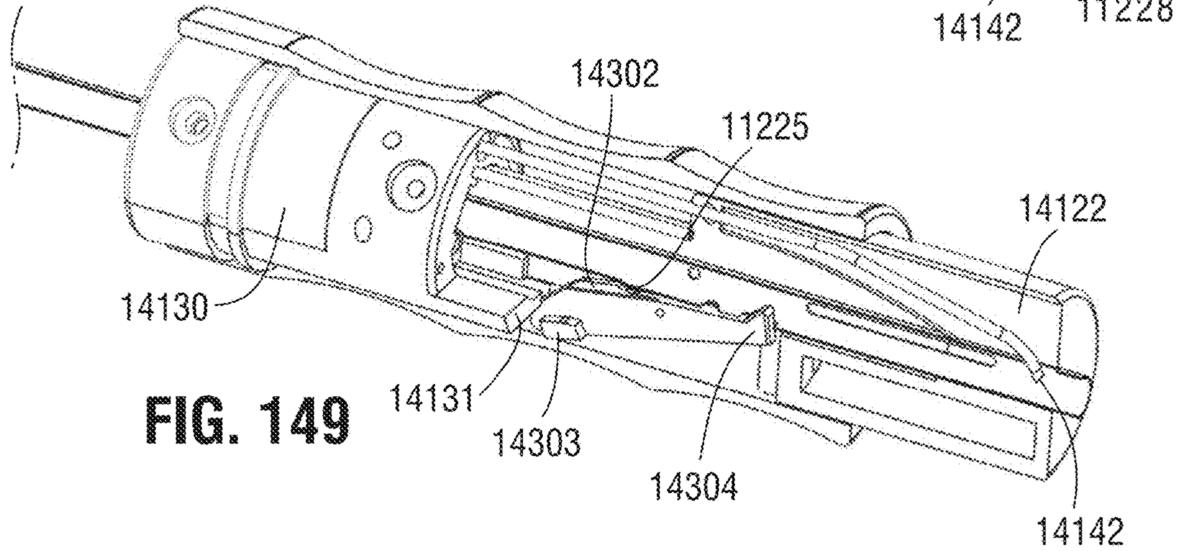

FIG. 149 is a fragmentary, partially vertical cross-sectional, perspective view of the snare assembly of FIG. 145 about the shaft with the lockout in the second lockout state in which the movement body is free to move distally and, when moved distally, secures the interior body to this distal-most position on the shaft, and with the components internal to the outer shaft tube removed for clarity.

Figure 150:
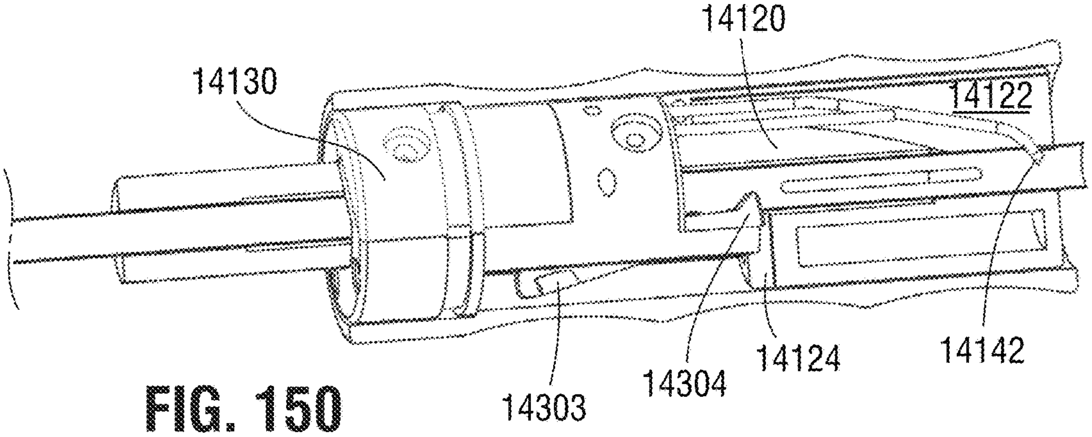

FIG. 150 is a fragmentary, partially vertical cross-sectional, perspective view of the snare assembly of FIG. 146 about the shaft with the lockout in the second lockout state, and with the components internal to the outer shaft tube removed for clarity.

Figure 151:
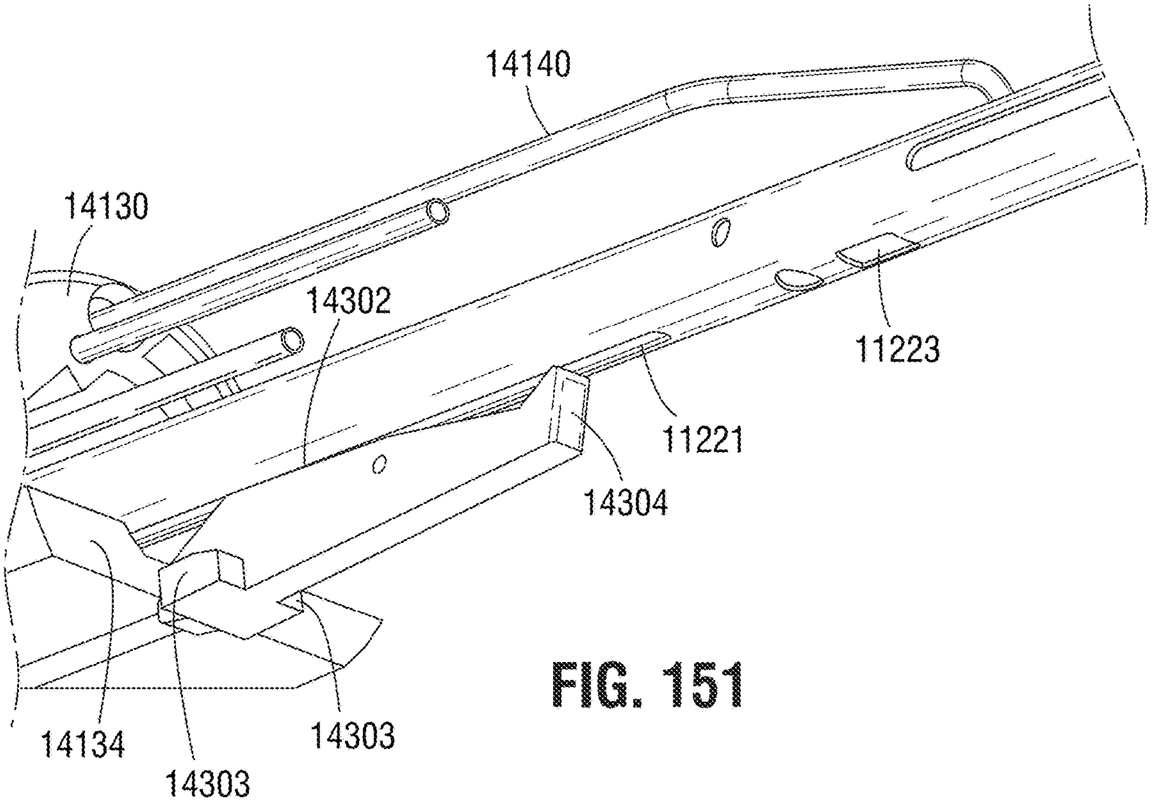

FIG. 151 is a fragmentary, enlarged, perspective view of a distal portion of the snare assembly of FIG. 141 illustrating the relative sizes of the groove and lower window of the outer shaft tube and the canopy and tail of the lockout.

Figure 152:
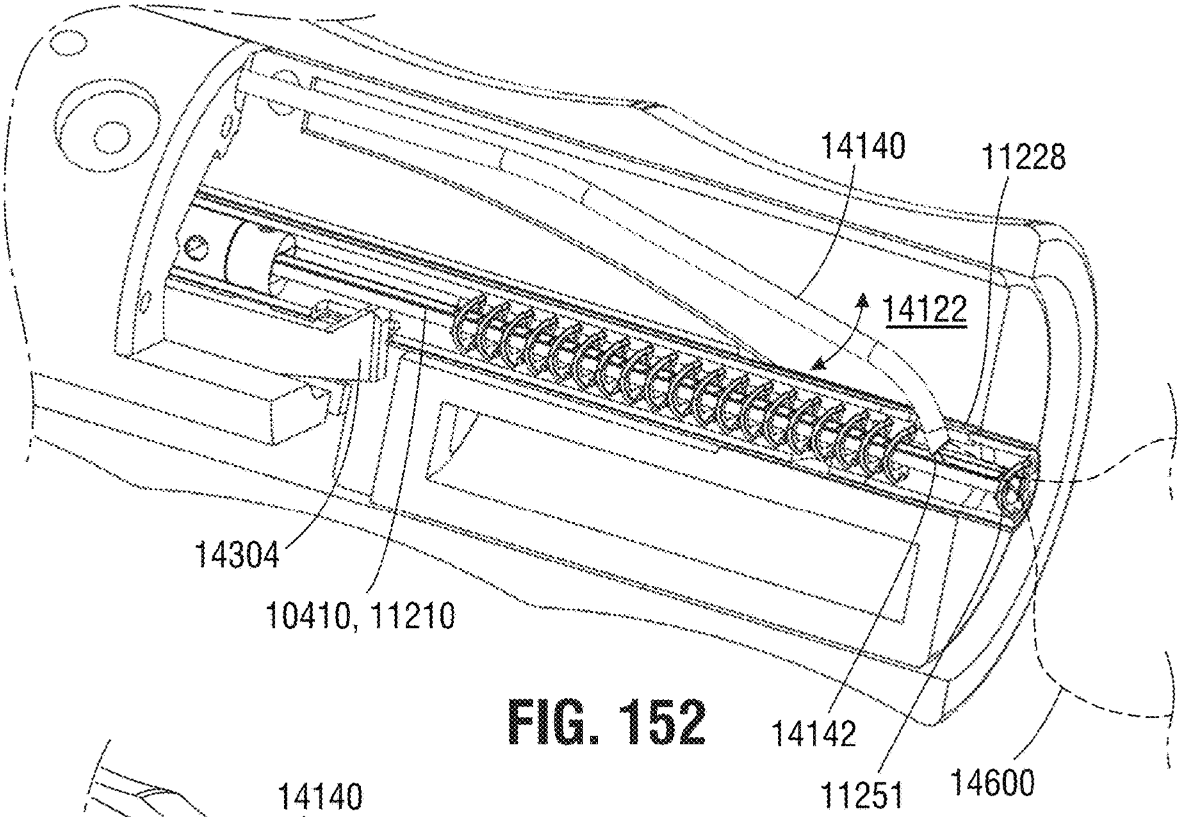

FIG. 152 is a fragmentary, enlarged, partially vertical cross-sectional, perspective view of a distal portion of the snare assembly of FIG. 146 with the lockout in the second lockout state and with the movement body in a distal position with respect to the interior body and the snare extended for snaring cords to be secured.

Figure 153:
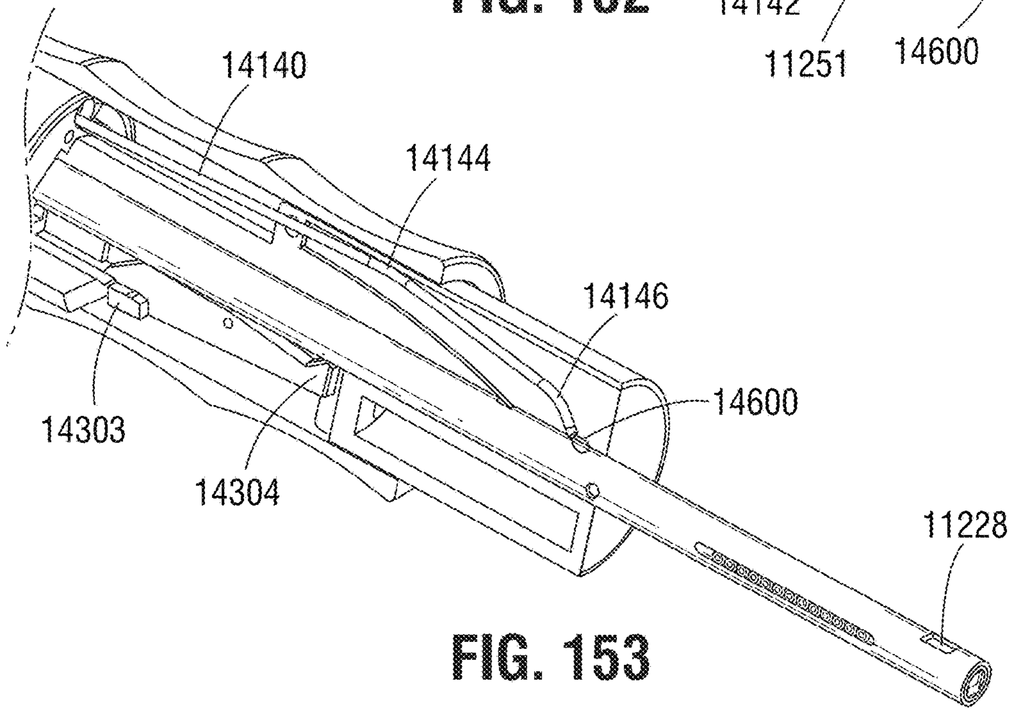

FIG. 153 is a fragmentary, partially vertical cross-sectional, perspective view of a distal portion of the snare assembly of FIG. 143 with the lockout in the first lockout state and with the movement body in a proximal retracted position with respect to the interior body and with the snare in its most-retracted position extending slightly out from the guiding tube.

Figure 154:
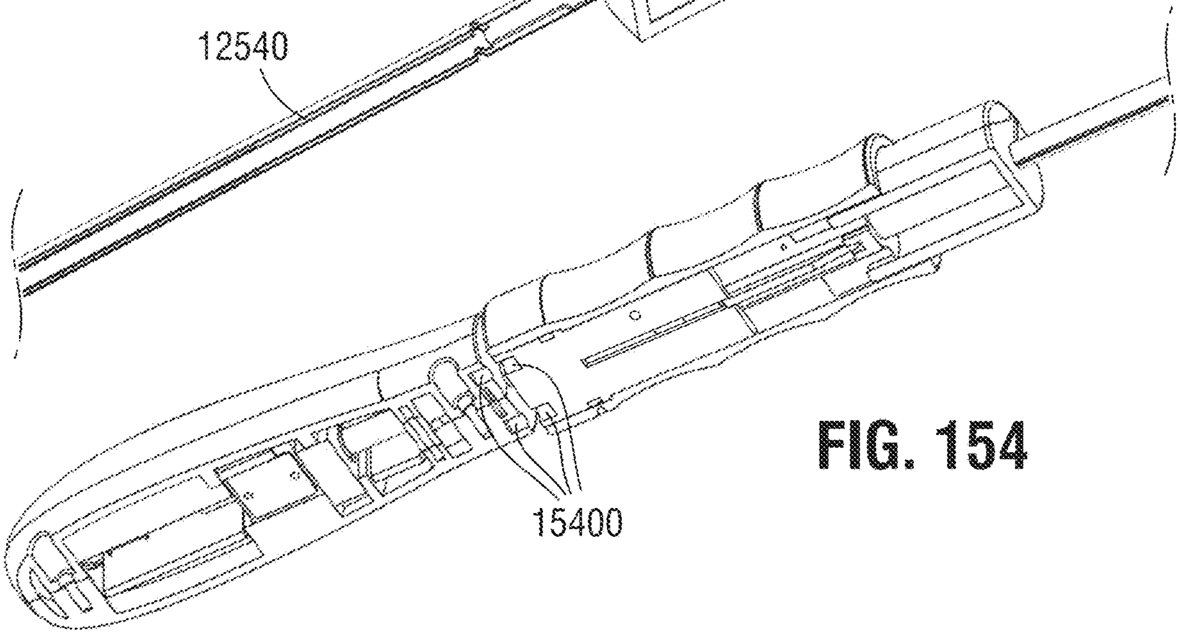

FIG. 154 is a horizontal cross-sectional view of a top portion of the handle of FIG. 98 viewed from the bottom to reveal a portion of the handle with magnet holding orifices for receiving magnets that retain the snare assembly at the handle and the snare assembly with a movable outer sleeve, magnet holding orifices for receiving magnets that retain the snare assembly at the distal end of the handle, and a lock-out subassembly including a pivoting lockout.

Figure 155:
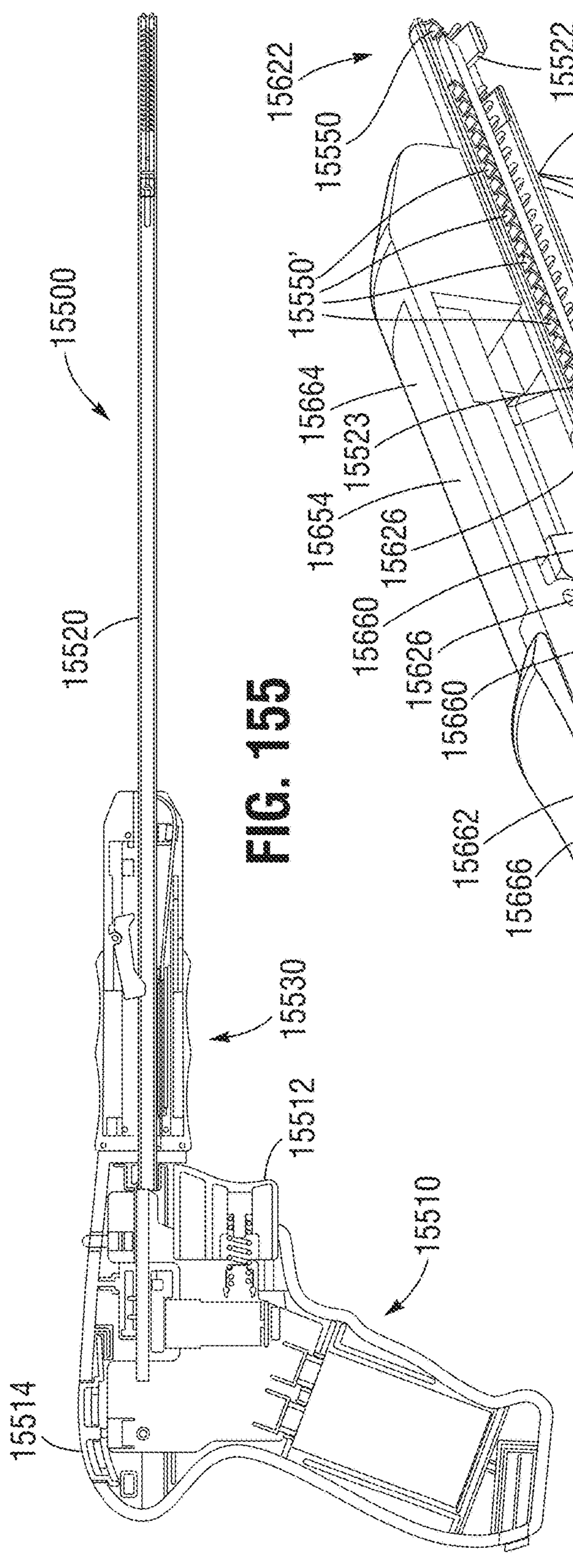

FIG. 155 is a vertical cross-sectional view of an exemplary embodiment of a multiple-clip securing device with a drop-in single circuit board with side-mounted switches to minimize a footprint of the electrically powered components, a multi-colored LED display, a clip-fire switch, a reload switch, a distal shaft, a motor and gearbox connected to a rack and pinion disposed in the shaft, and a snare assembly in a proximal-most position on the shaft.

Figure 156:
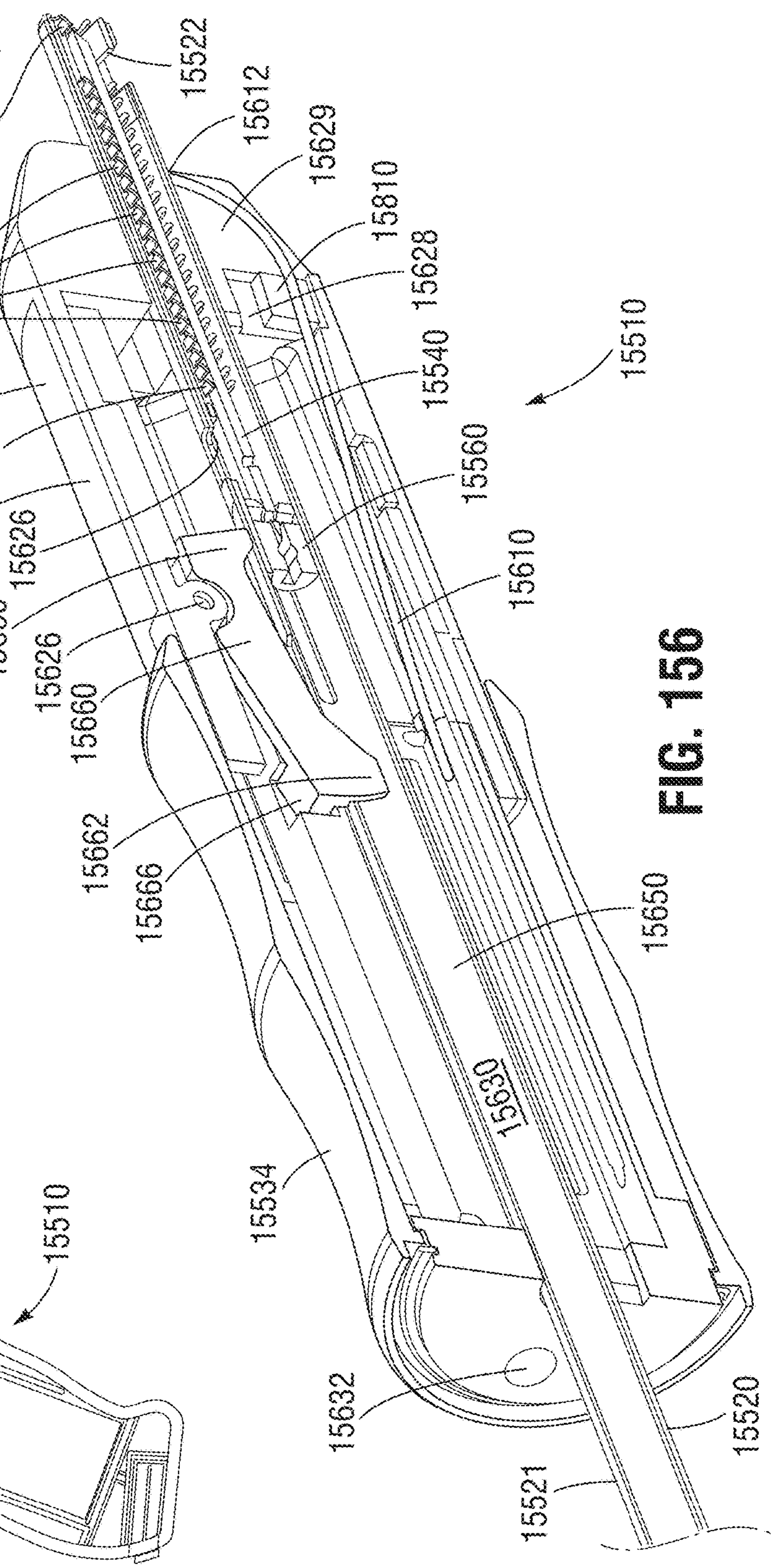

FIG. 156 is a fragmentary, enlarged, vertical cross-sectional, perspective view of the snare assembly of FIG. 155 in an intermediate position on the shaft.

Figure 157:
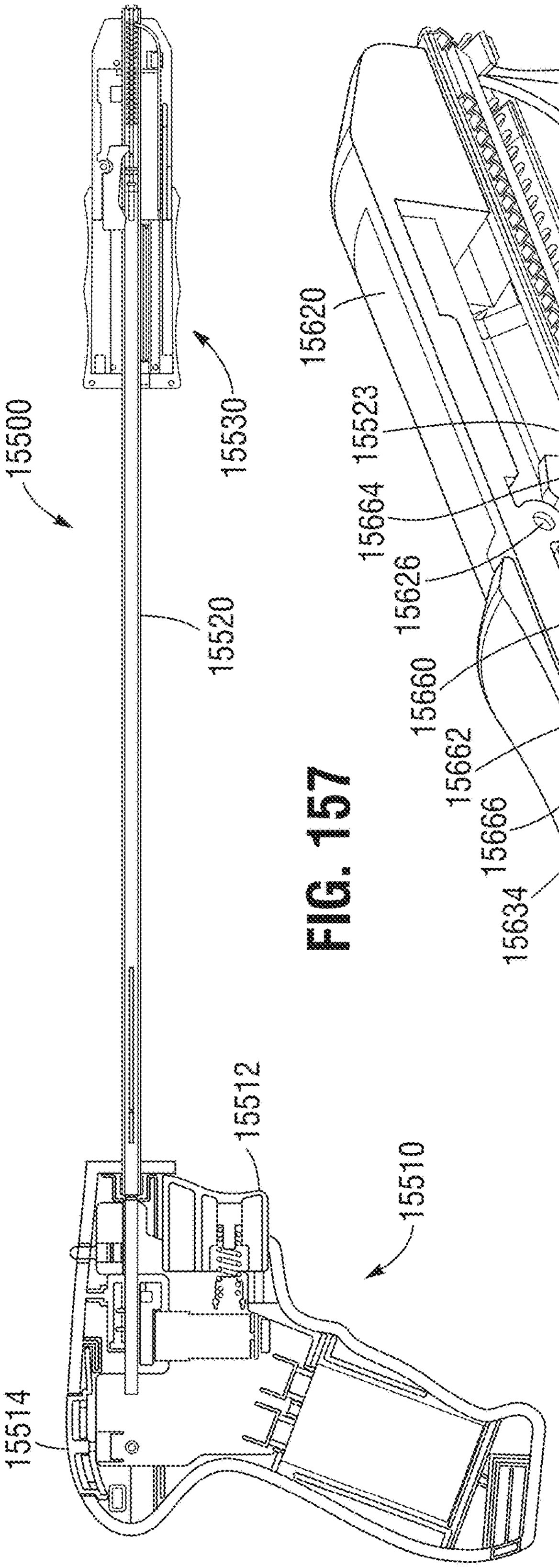

FIG. 157 is a vertical cross-sectional view of the multiple-clip securing device of FIG. 155 with the snare assembly at a distal position on the shaft before a snare is extended.

Figure 158:
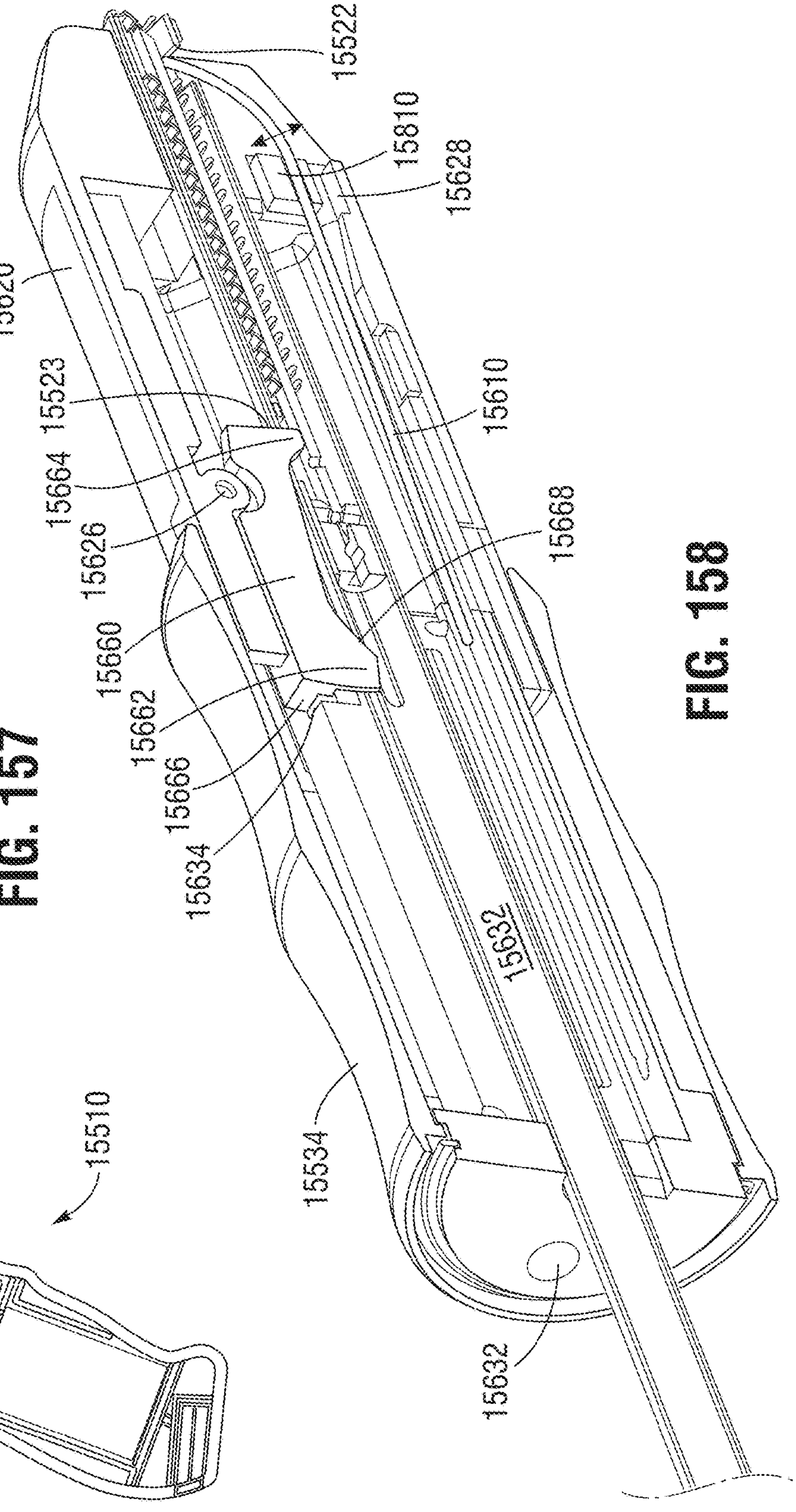

FIG. 158 is a fragmentary, enlarged, vertical cross-sectional, perspective view of the snare assembly of FIG. 157.

Figure 159:
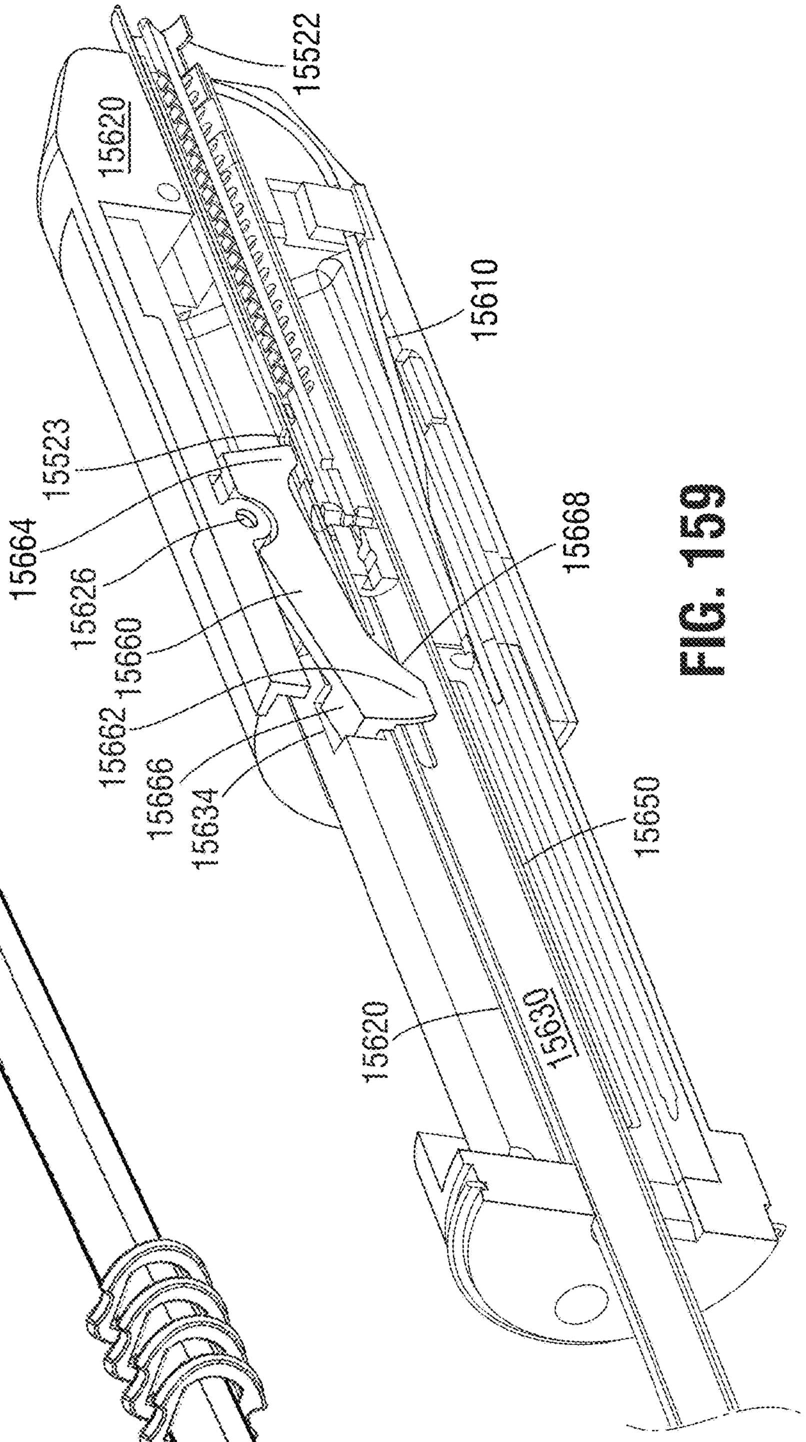

FIG. 159 is a fragmentary, enlarged, vertical cross-sectional, perspective view of the snare assembly of FIG. 158 with a snare extension handle removed.

Figure 160:
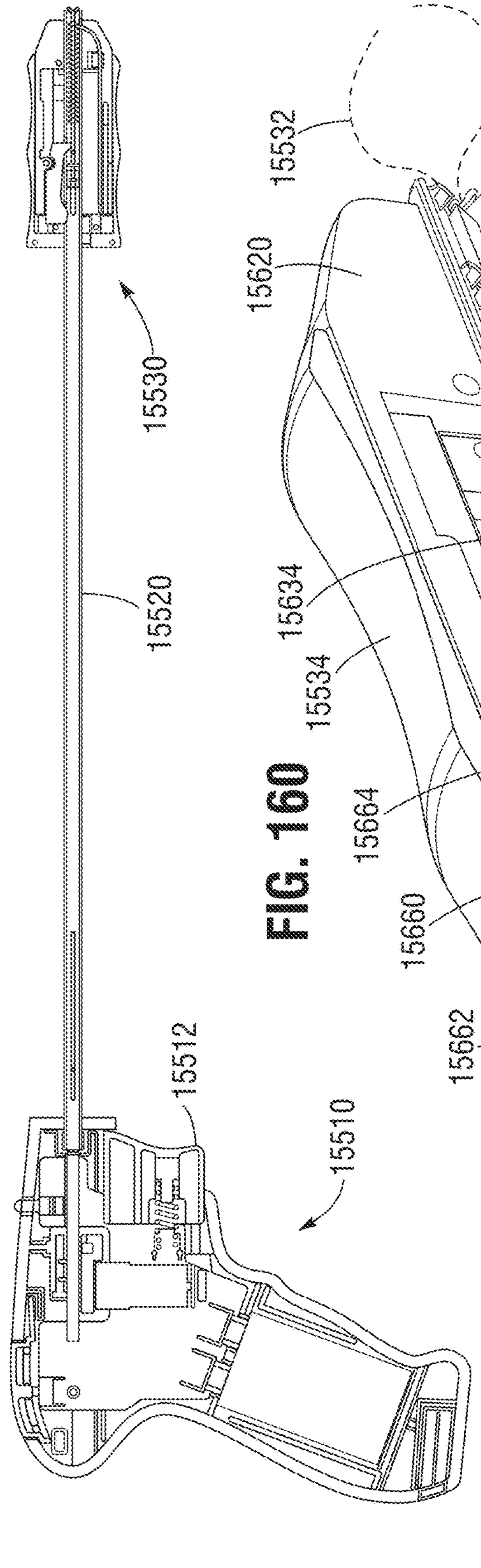

FIG. 160 is a vertical cross-sectional view of the multiple-clip securing device of FIG. 155 with the snare assembly at the distal position on the shaft in a snare extended configuration, the snare not illustrated.

Figure 161:
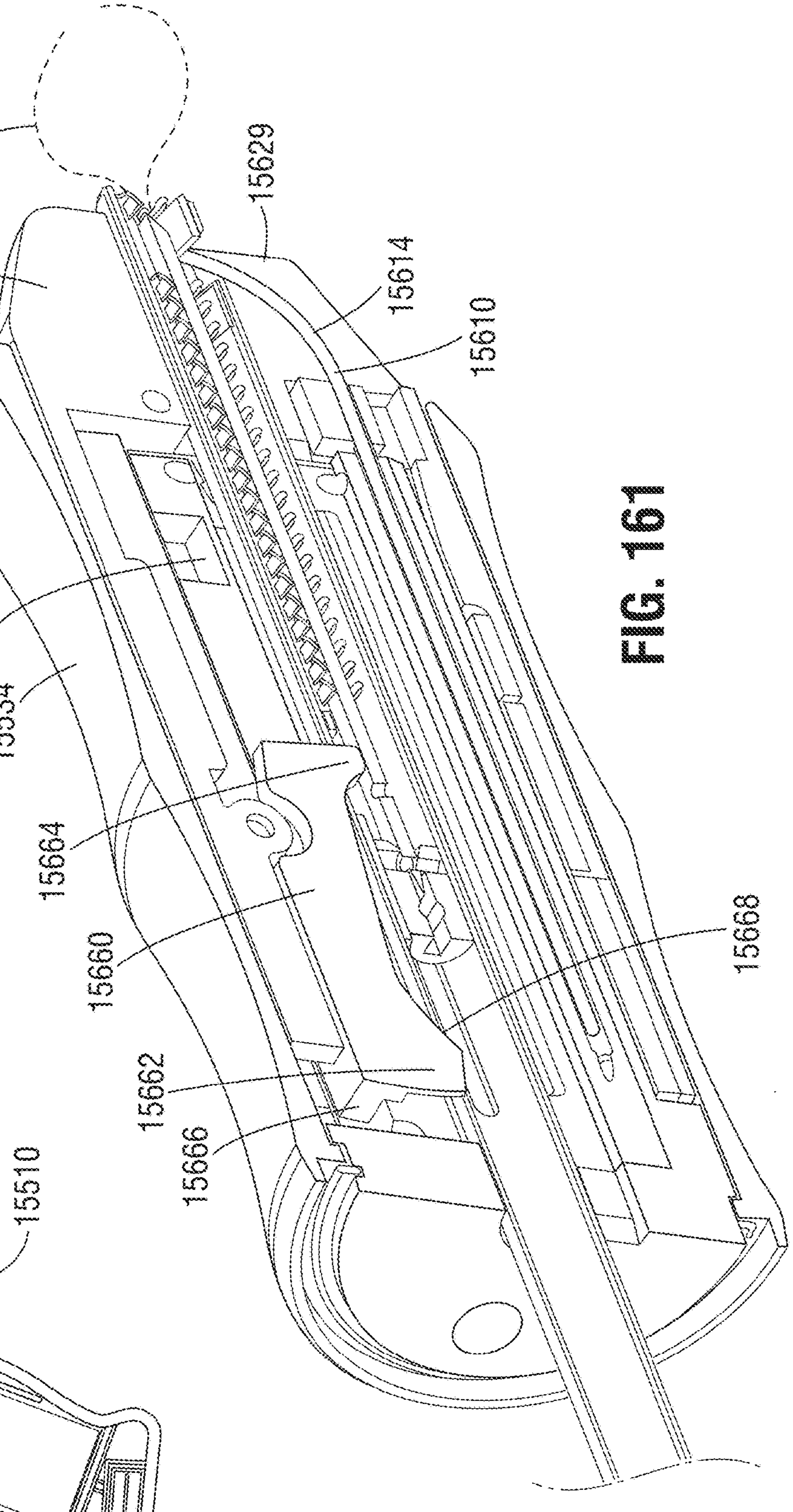

FIG. 161 is a fragmentary, enlarged, vertical cross-sectional, perspective view of the snare assembly of FIG. 160.

Figure 162:
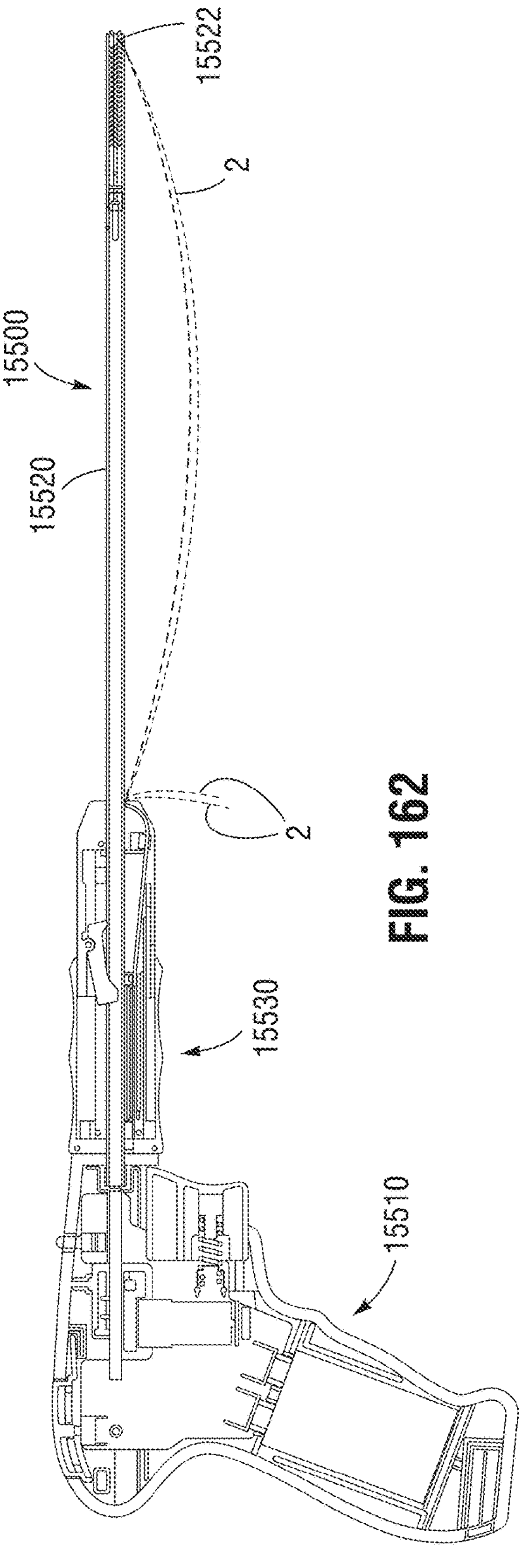

FIG. 162 is a vertical cross-sectional view of the multiple-clip securing device of FIG. 155 with the snare assembly returned to the distal-most position on the shaft in a cord-snared configuration with a snared cord draped below the shaft.

Figure 163:
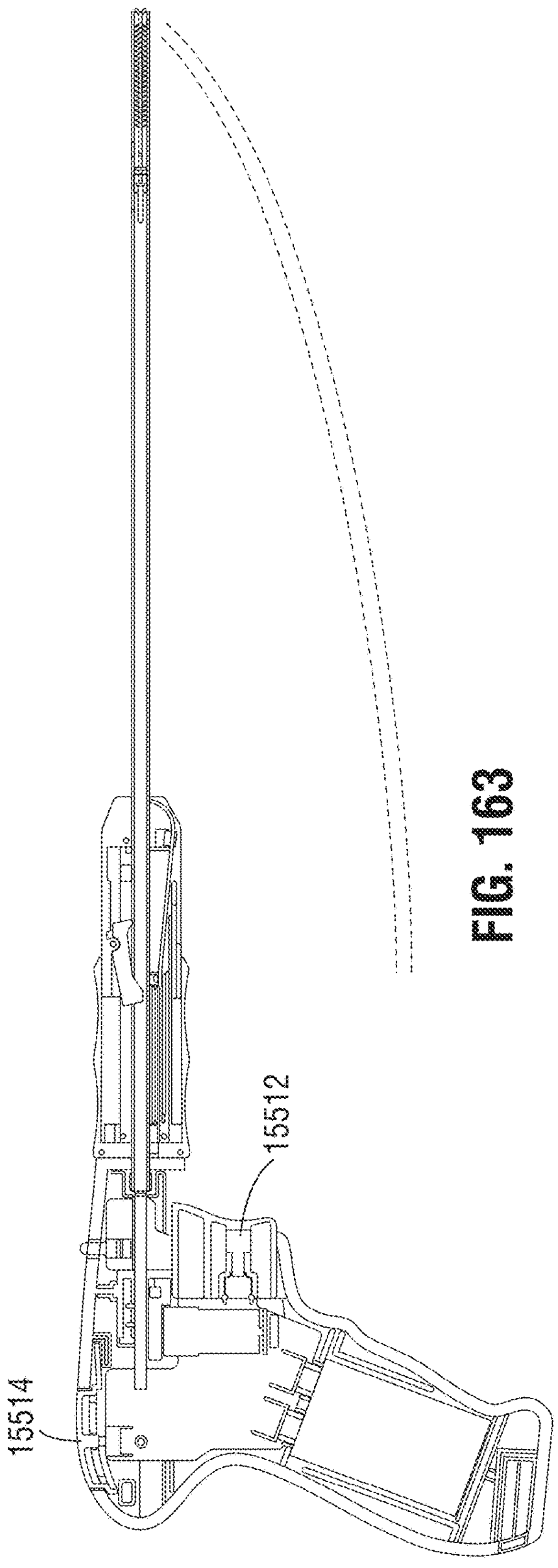

FIG. 163 is a vertical cross-sectional view of the multiple-clip securing device of FIG. 162 with the cord-securing trigger depressed to secure the cord and the cut cords falling away from below the shaft.

FIG. 164 is a fragmentary, enlarged, partially vertical cross-sectional and perspective view of the snare assembly of FIG. 156 in an intermediate position on the shaft and with the snare and snare guide tube secured to the shuttle body with a Z-bend.

FIG. 165 is a fragmentary, enlarged, vertical cross-sectional view of the snare assembly of FIG. 164 in a distal position on the shaft with the snare guiding tube extended into the shaft.

Figure 166:
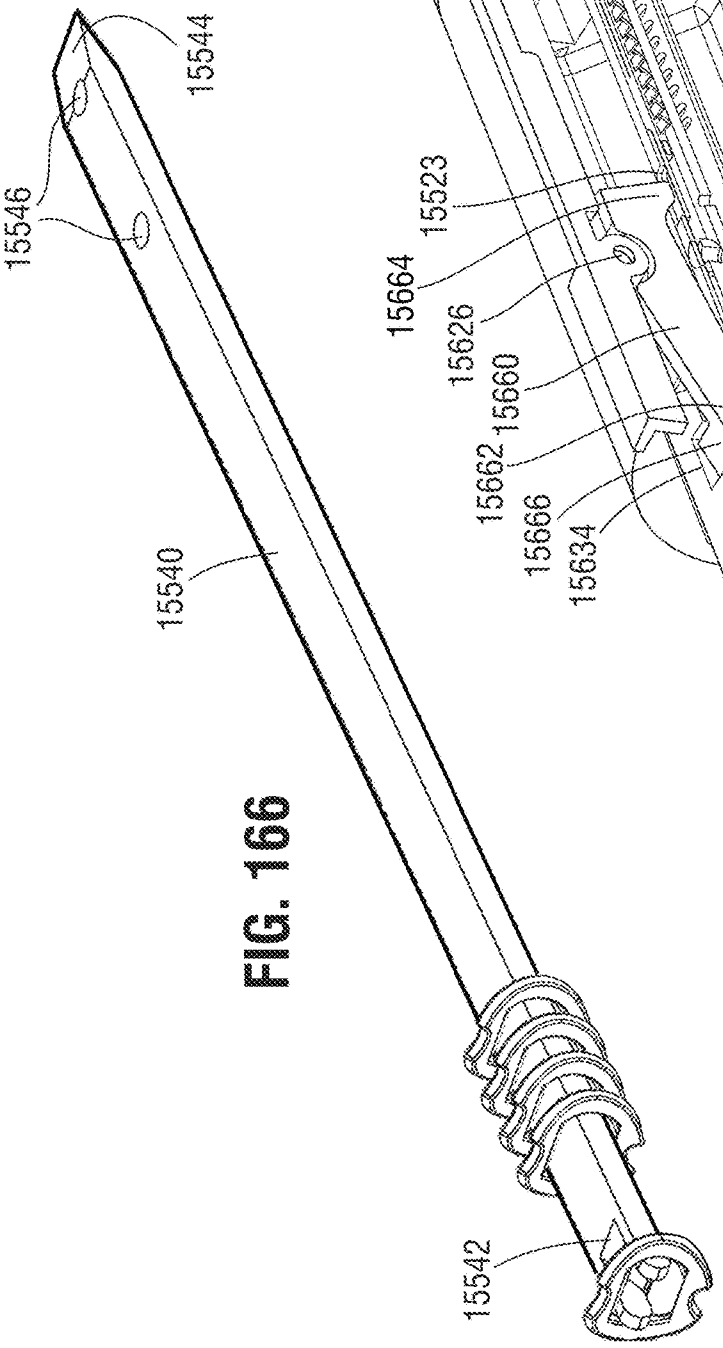

FIG. 166 is an enlarged perspective view of an exemplary embodiment of a clip-sliding rail of the multiple-clip securing device of FIG. 155 and a set of clips thereon, one in a clip-securing position.

Figure 167:
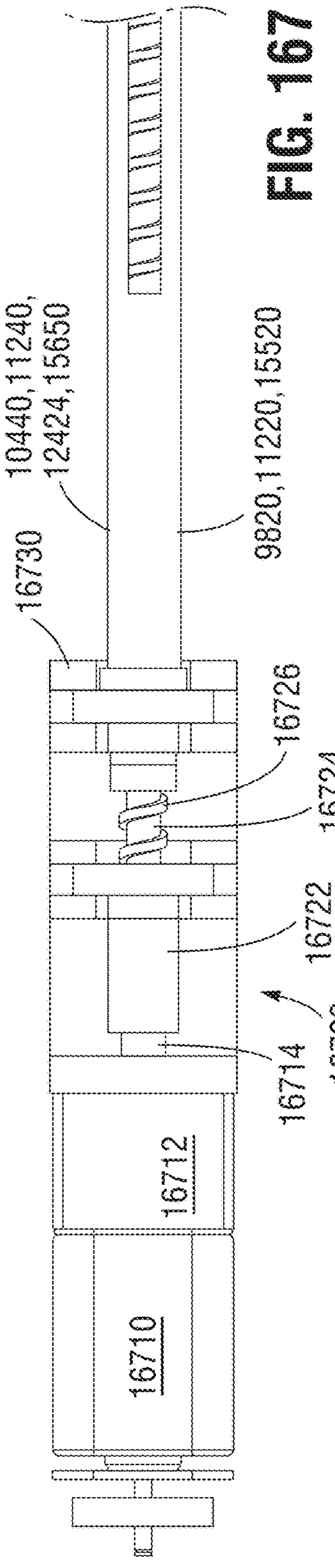

FIG. 167 is a fragmentary, side elevational and partially transparent view of a proximal securement-movement assembly of an exemplary embodiment of a multiple-fire securing device with a securement moving inner tube shaft in a retracted position and with a proximal handle not illustrated.

Figure 168:
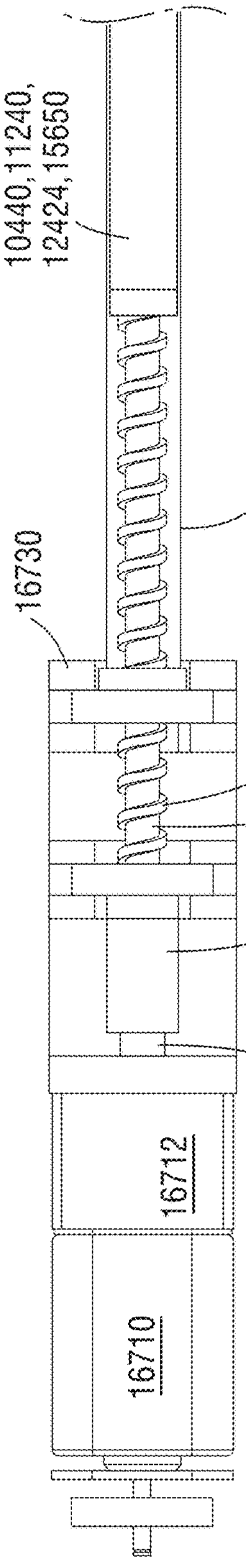

FIG. 168 is a fragmentary, side elevational and partially transparent view of the securement-movement assembly of FIG. 167 with the securement moving inner tube in an extended position.

Figure 169:
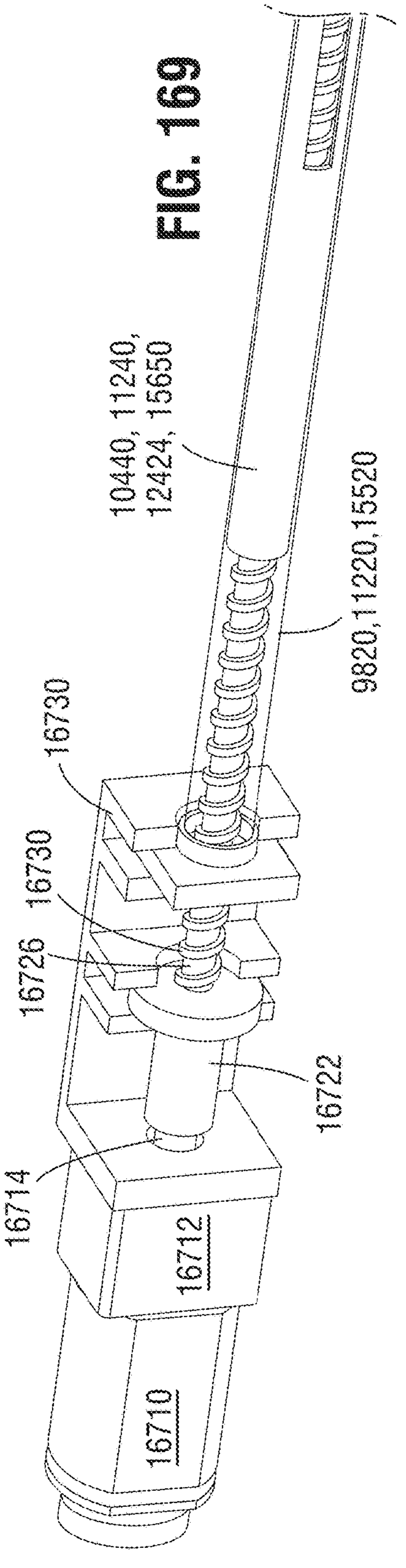

FIG. 169 is a fragmentary, perspective and partially transparent view of the securement-movement assembly of FIG. 168.

Figure 170:
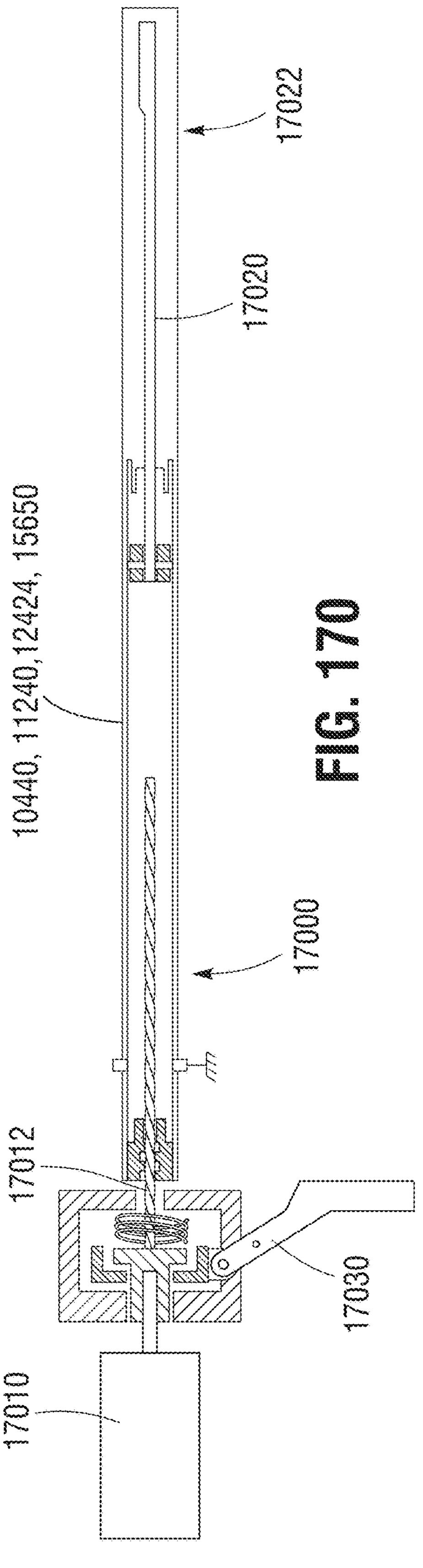
Figure 171:
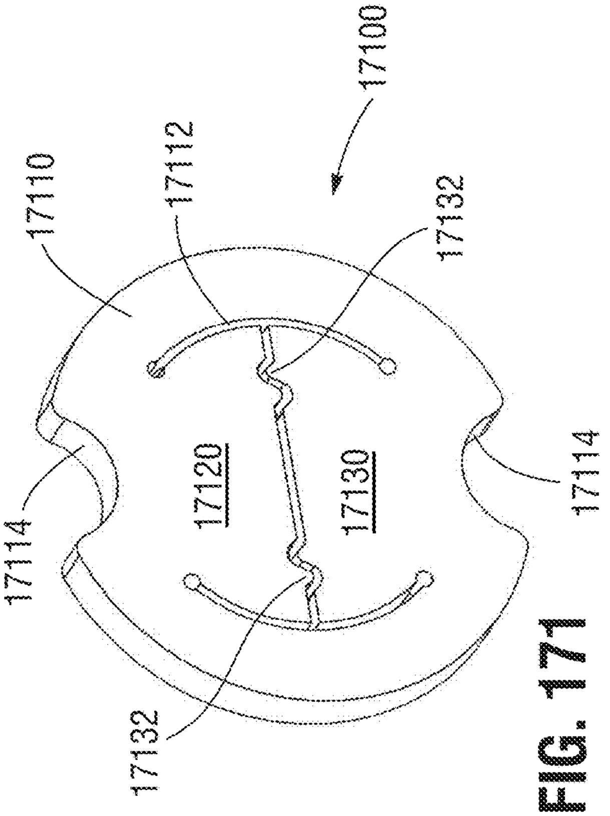

FIG. 170 is a diagrammatic, longitudinally vertical cross-sectional view of an exemplary embodiment of a multiple-firing securement device having a motor-controlled mechanism that moves the inner tube shaft to grasp various securements installed on the guide rail at successively further distances on the guide rail from the securement-installing location and a mechanical lever that moves the entire inner tube shaft assembly distal to perform cutting; and FIG. 171 is an enlarged, perspective view of an exemplary embodiment of a cord-securing clip in a steady state.

Figure 172:
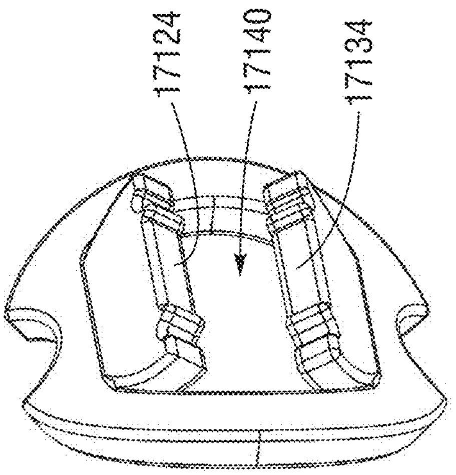

FIG. 172 is an enlarged, perspective view of the cord-securing clip of FIG. 171 in an expanded, ready-to-clip state.

Figure 173:
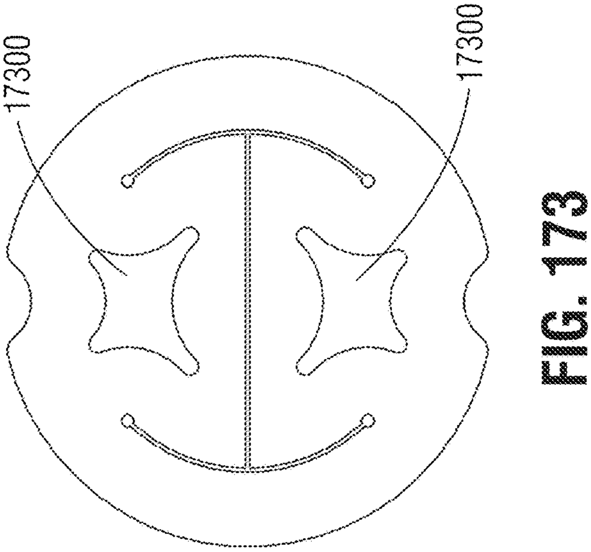

FIG. 173 is an enlarged, front elevational view of another exemplary embodiment of a cord-securing clip in a steady state.

Figure 174:
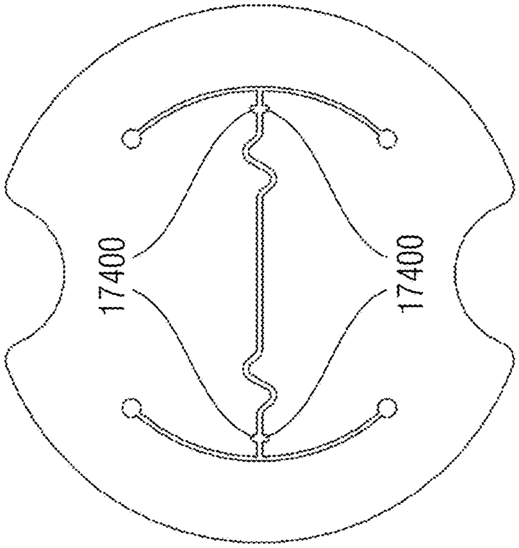

FIG. 174 is an enlarged, front elevational view of a further exemplary embodiment of a cord-securing clip in a steady state.

Figure 175:
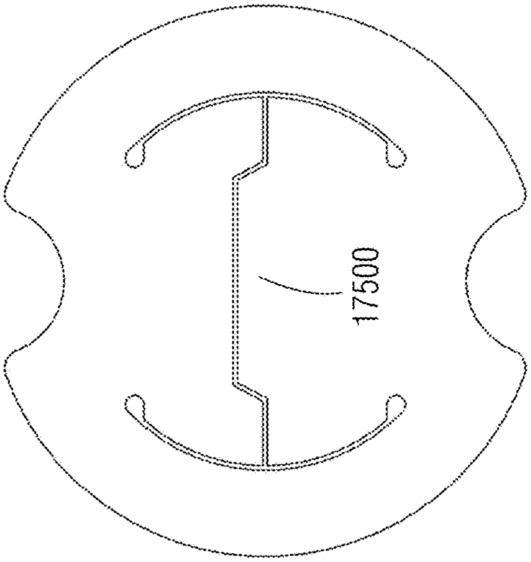

FIG. 175 is an enlarged, front elevational view of still another exemplary embodiment of a cord-securing clip in a steady state.

Figure 176:
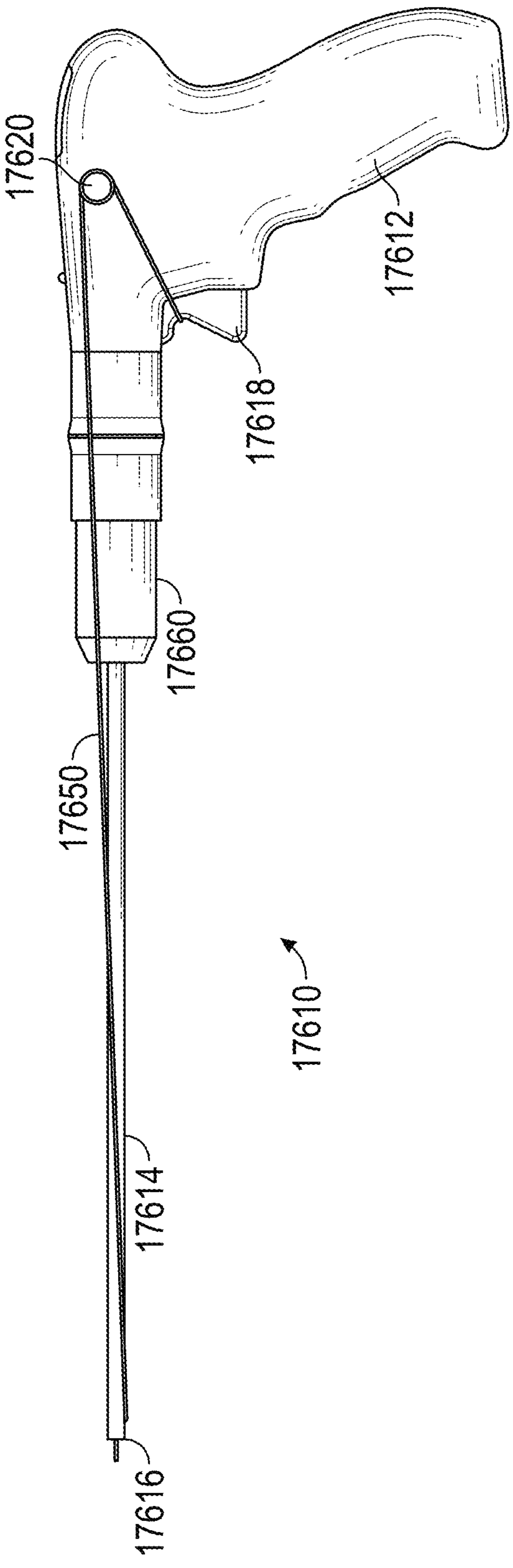

FIG. 176 is a first side view of an exemplary suture clip deployment device.

Figure 177:
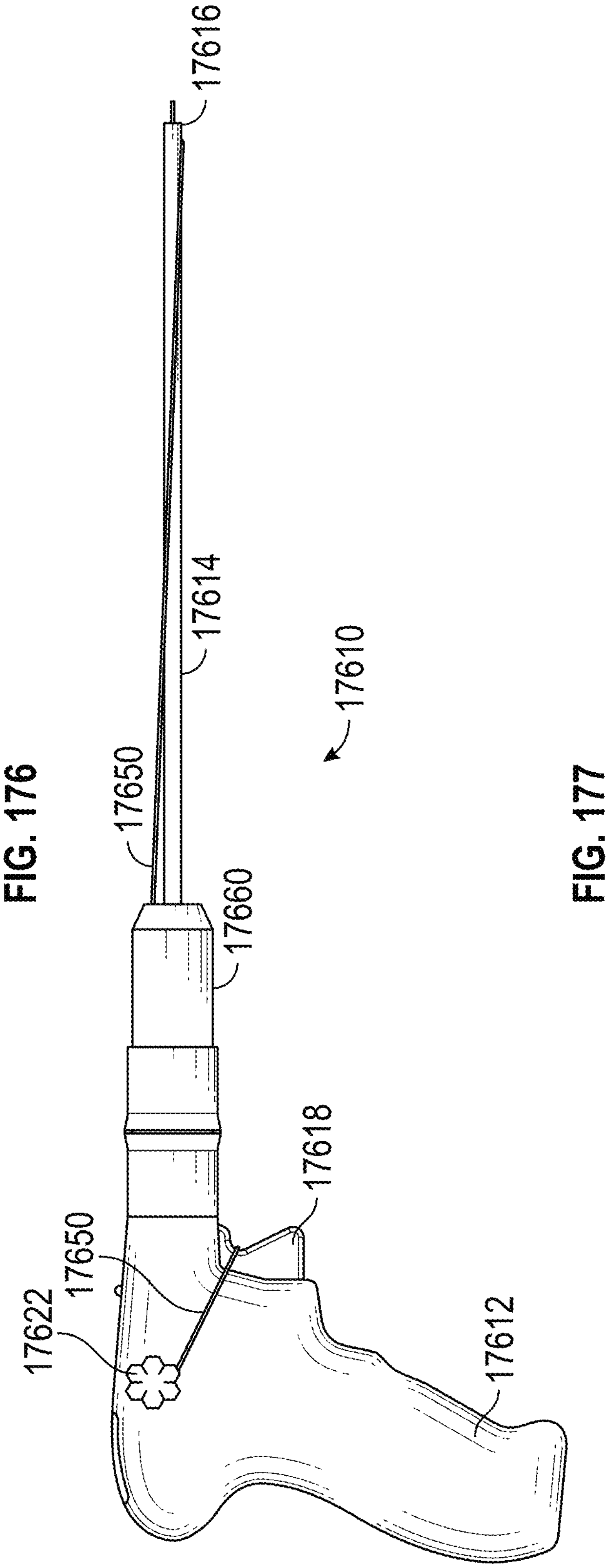

FIG. 177 is a second side view of the device of FIG. 176.

Figure 178:
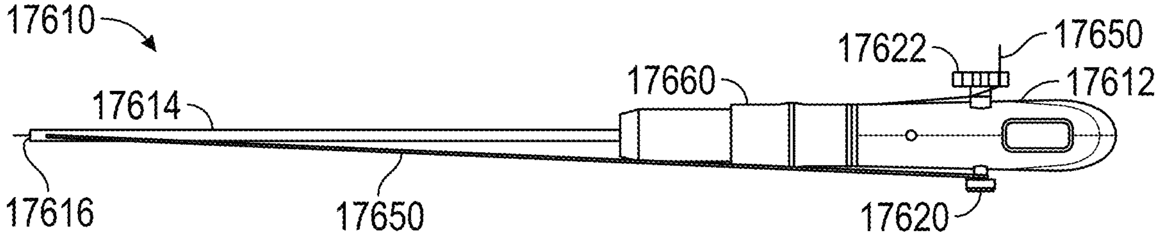

FIG. 178 is a top view of the device of FIG. 176.

Figure 179:
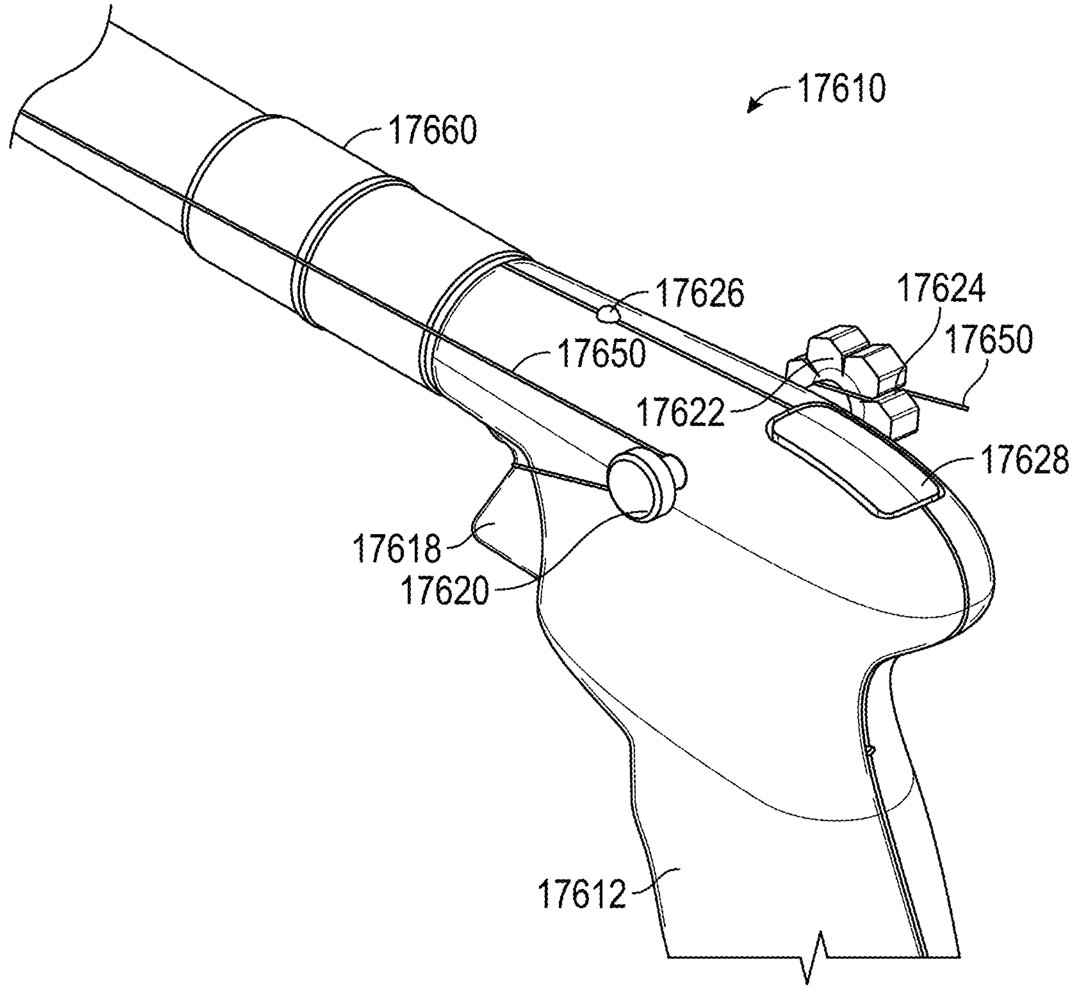

FIG. 179 is a perspective view of a handle portion of the device of FIG. 176.

Figure 180:
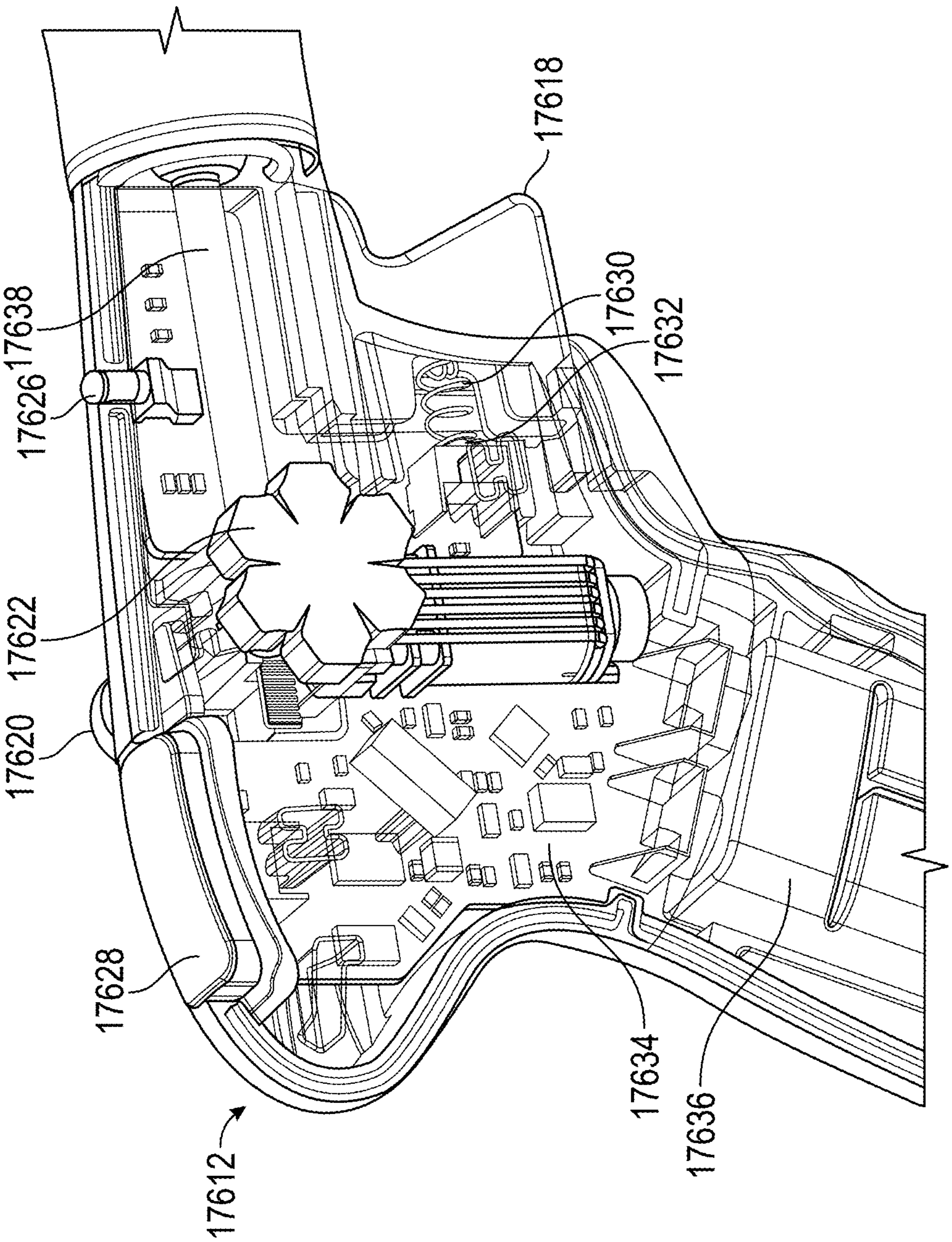

FIG. 180 is partially cut-away view of the handle portion if FIG. 179, showing internal components.

Figure 181:
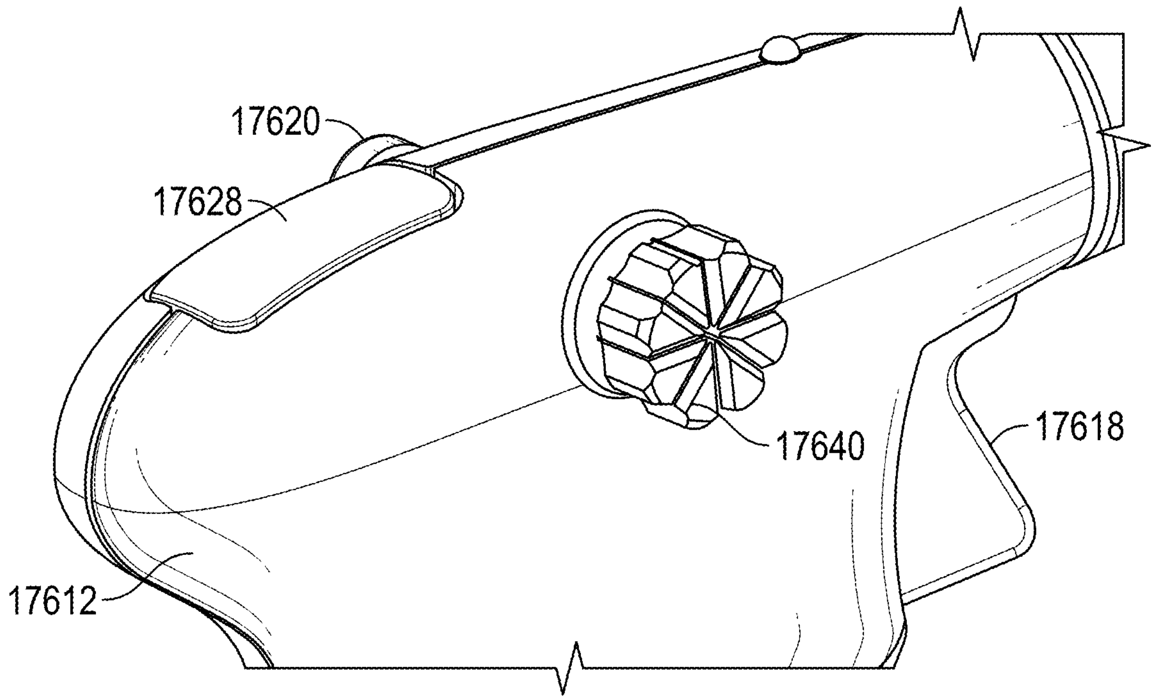

FIG. 181 shows a handle portion with an alternative suture tensioning mechanism.

Figure 182:
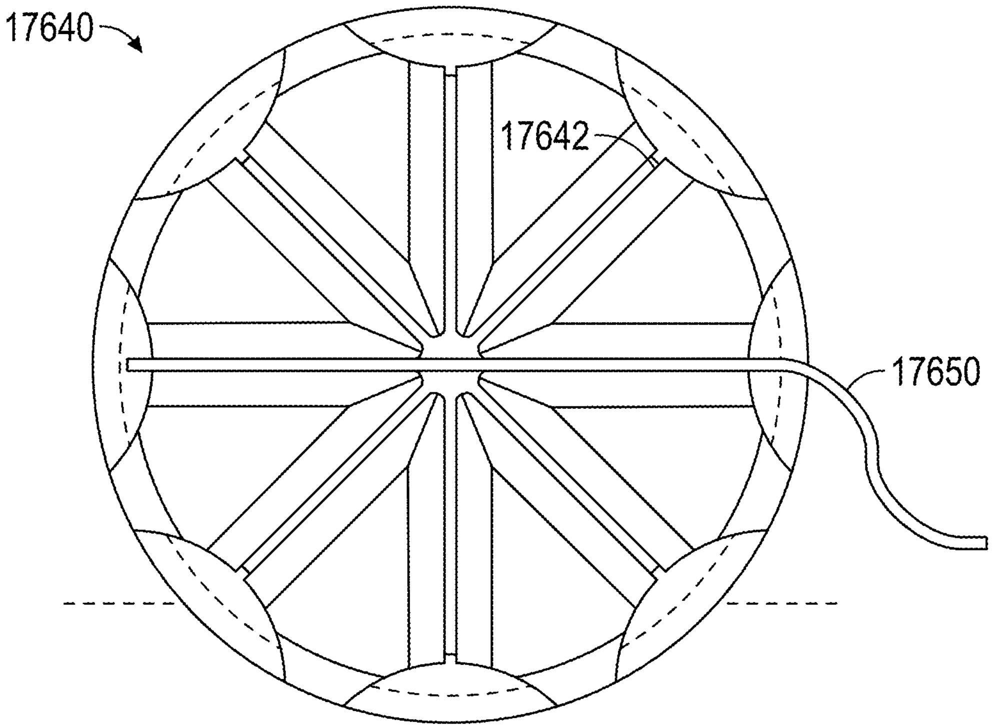

FIG. 182 is a side view of the suture tensioning mechanism of FIG. 181.

Figure 183:
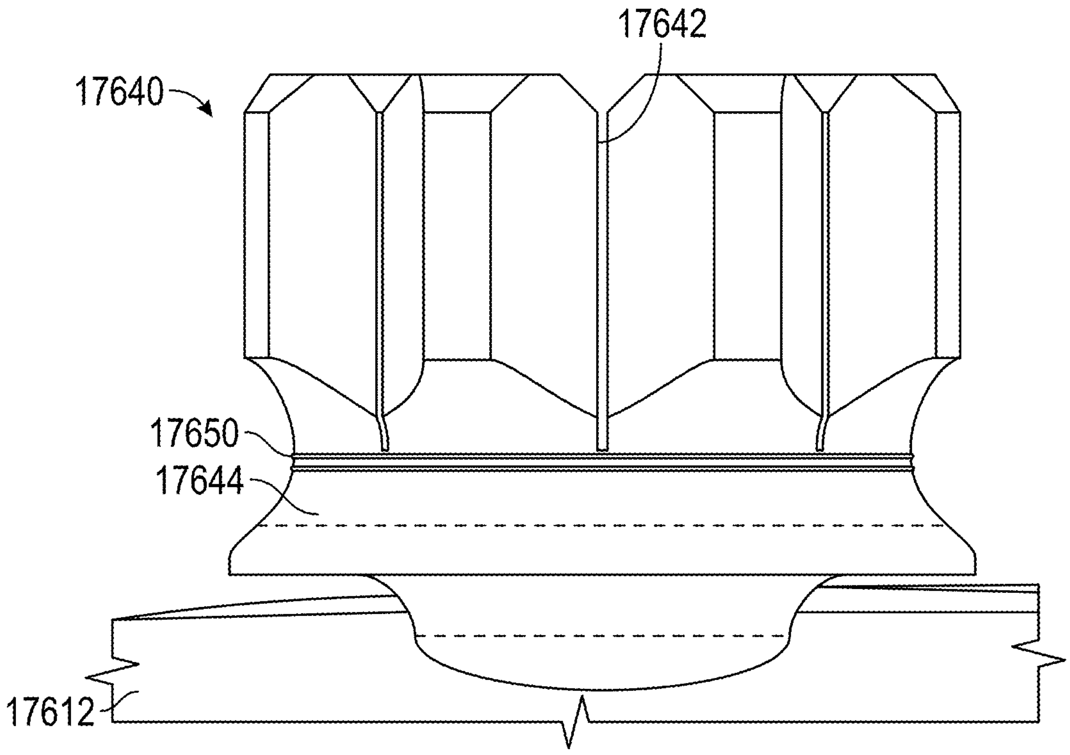

FIG. 183 is a top view of the suture tensioning mechanism of FIG. 181.

DETAILED DESCRIPTION

General Considerations

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms “a,” “an,” and “at least one” encompass one or more of the specified element. That is, if two of a particular element are present, one of these elements is also present and thus “an” element is present. The terms “a plurality of” and “plural” mean two or more of the specified element.

As used herein, the term “and/or” used between the last two of a list of elements means any one or more of the listed elements. For example, the phrase “A, B, and/or C” means “A,” “B,” “C,” “A and B,” “A and C,” “B and C,” or “A, B, and C.”

As used herein, the term “coupled” generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as “inside,” “outside,”, “top,” “down,” “interior,” “exterior,” and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an “upper” part can become a “lower” part simply by turning the object over. Nevertheless, it is still the same part and the object remains the same. As used herein, “and/or” means “and” or “or,” as well as “and” and “or.”

As used herein, with reference to the prosthetic heart valve and the delivery apparatus, “proximal” refers to a position, direction, or portion of a component that is closer to the user and/or the handle of the delivery device that is outside the patient, while “distal” refers to a position, direction, or portion of a component that is further away from the user and/or the handle of the delivery apparatus and closer to the implantation site. The terms “longitudinal” and “axial” refer to an axis extending in the proximal and distal directions, unless otherwise expressly defined. Further, the term “radial” refers to a direction that is arranged perpendicular to the axis and points along a radius from a center of an object (where the axis is positioned at the center, such as the longitudinal axis of the prosthetic valve).

Examples of the Disclosed Technology

Figure 1:
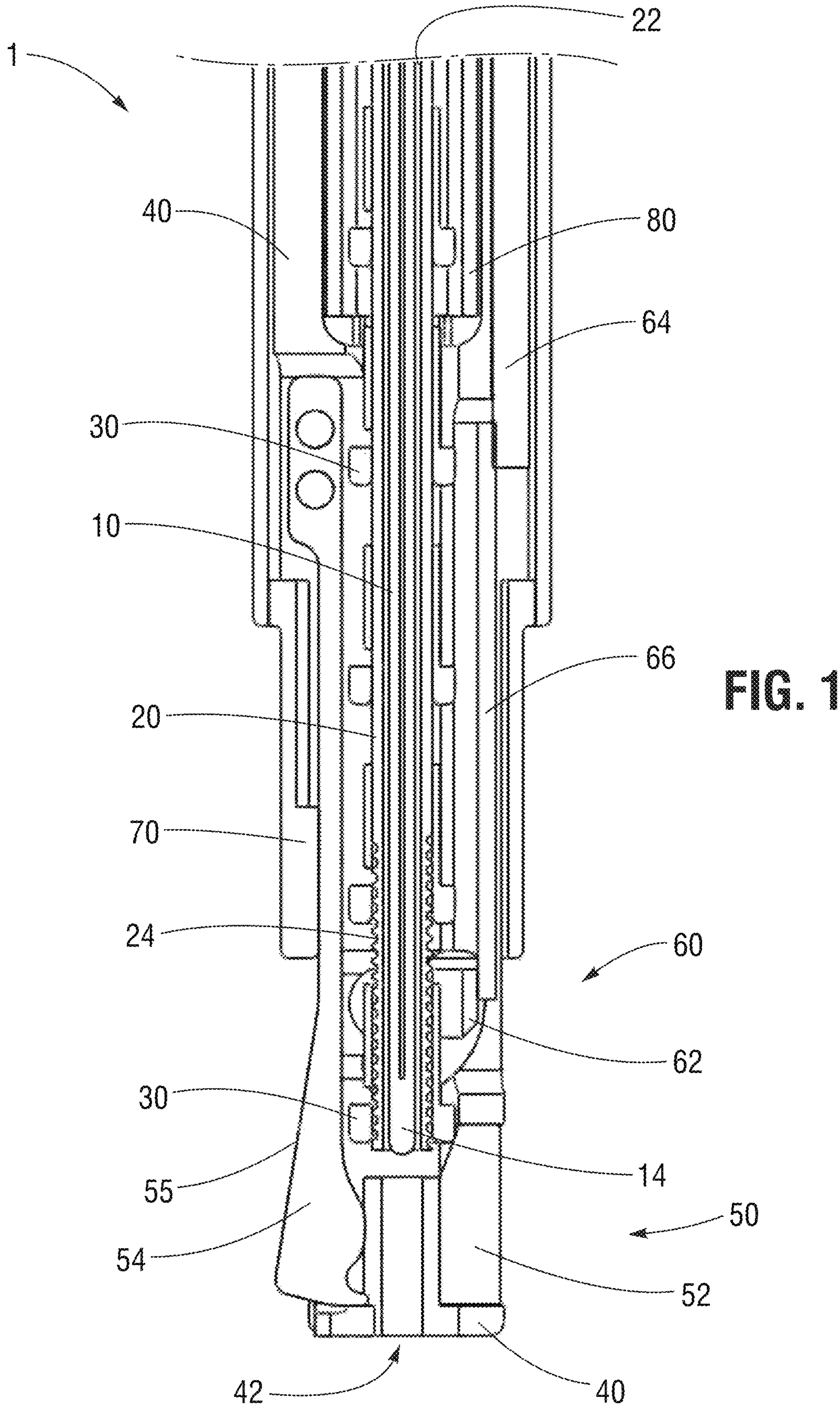
FIG. 1 is a fragmentary, longitudinal, cross-sectional view of an exemplary embodiment of an end effector for a multiple-firing crimp device with a crimp sub-assembly in a position ready to load a first crimp.
Figure 35:
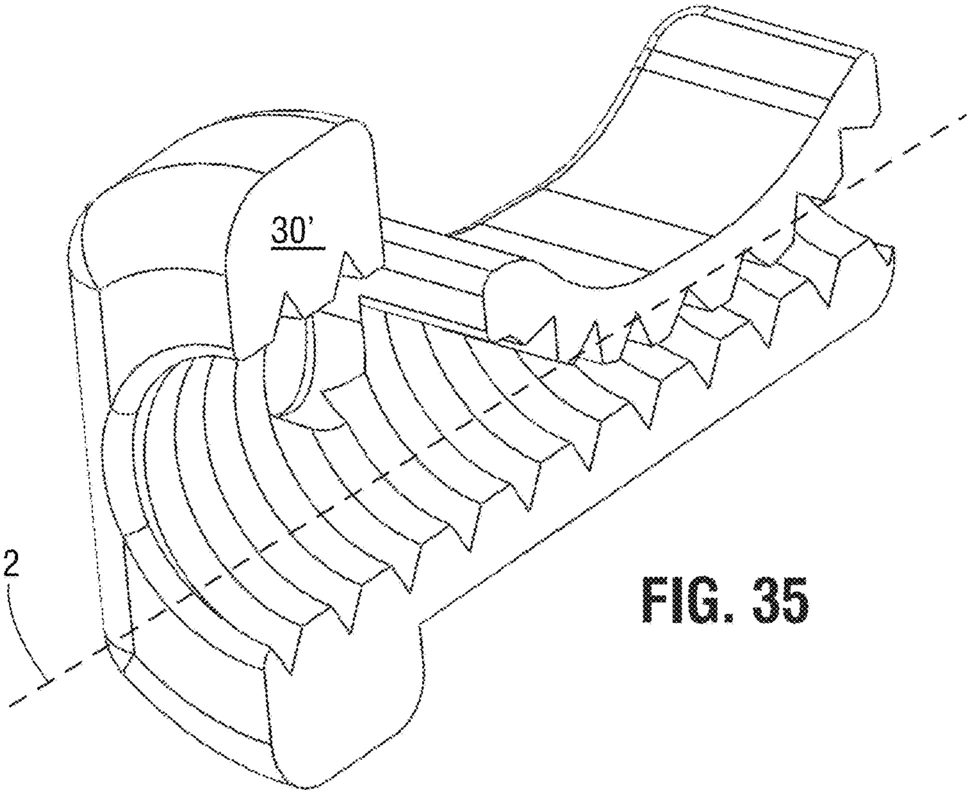
FIG. 35 is an enlarged perspective and longitudinal cross-sectional view of the crimp of FIGS. 32 and 33 after being crimped.
Figure 36:
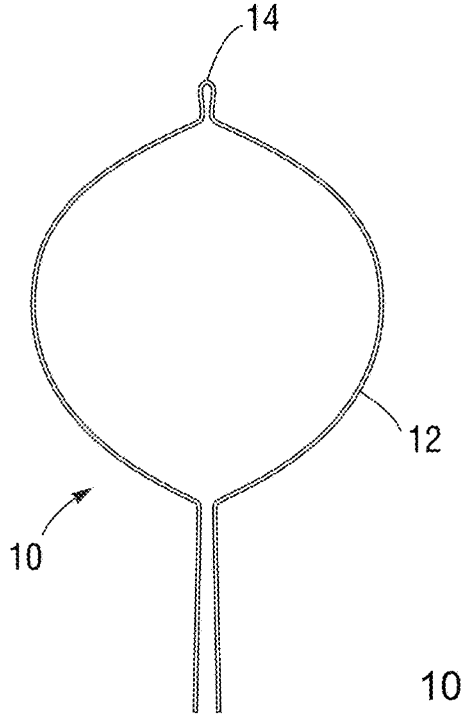
FIG. 36 is a photograph of an exemplary embodiment of a distal end of a snare with a loop and its tip expanded.

Described now are exemplary embodiments. Referring now to the figures of the drawings in detail and first, particularly to FIGS. 1 to 35, there is shown a first exemplary embodiment of a multiple-firing crimp device 1. FIG. 1 shows an end effector of the multiple-firing crimp device 1 with a crimp assembly in a position ready to load a first crimp. From the center to the exterior of the crimp assembly, the innermost structure is a snare 10. In an exemplary embodiment, the snare 10 is laser cut out of a sheet of Nitinol or is a Nitinol wire and is heat set in a snare shape. Exemplary heat-set embodiments are shown in FIGS. 36 to

38. The snare 10 has a very low profile sufficient to fit, as shown in FIG. 1, within a hollow tube having an inner diameter of approximately 0.6 mm (about 0.025"). A contained area or loop 12 is formed in the snare 10 to provide a large opening in which the user threads the cords to be connected together (e.g., ends of a surgical suture). For example, the loop 12 is approximately ovular with a major axis approximately 3 cm (about 1.25") long and a minor axis approximately 25 mm (about 1") long. The snare 10 is formed with a distal tip 14 that is described in further detail below. Herein, various snares are described and shown and are equally applicable to temporarily secure a cord or cords. Shapes of the snares described and/or shown herein are not exclusive and are not to be taken as the only shapes and/or configurations possible for snaring a cord/cords. Shapes can include closed or open loops, hooks, curves, or other shapes.

Figure 37:
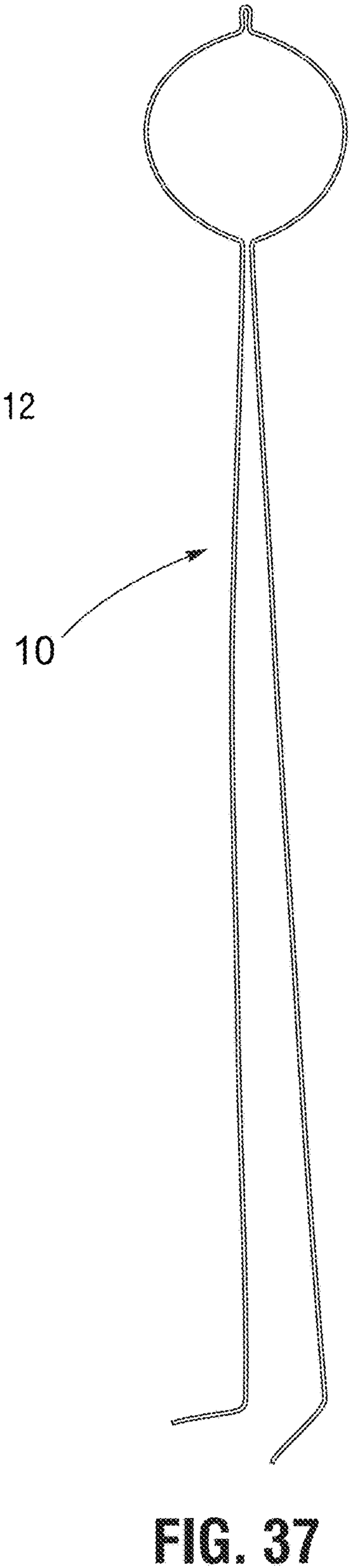
FIG. 37 is a photograph of an exemplary embodiment of a snare with a loop and its tip expanded.
Figure 38:
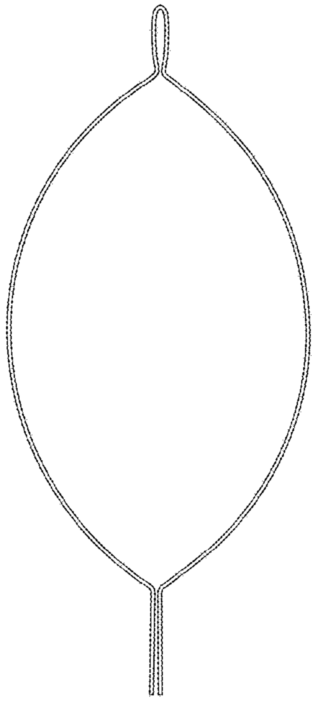
FIG. 38 is a photograph of another exemplary embodiment of a distal end of a snare with a loop and its tip expanded.

Surrounding the snare 10 is a crimp carriage 20. The crimp carriage 20 has a central lumen 22 with an inner diameter of approximately 0.6 mm (about 0.025") to house therein the snare 10. One or more of the inner surface of the central lumen 22 and the snare 10 is lubricious so that the snare 10 can move out from and back into the central lumen 22 with little friction and without catching. As the snare 10 exits the central lumen 22, the loop 12 expands and forms its heat-set shape after the entirety of the loop 12 exits the distal end of the central lumen 22 (see, e.g., FIGS. 36 to 38). The outer surface of the crimp carriage 20 has an exterior thread 24. This exterior thread 24 is described in further detail below with regard to the crimps 30 and has a shape corresponding to an interior thread 32 of each crimp 30. As such, the length of the exterior thread 24 can be as long as the crimp carriage 20 but it can also be only as long as is needed to thread the desired number of crimps 30 thereon in series. Five of the crimps 30 are illustrated as threaded onto the crimp carriage 20 in FIG. 1 but the threads are only shown diagrammatically in FIG. 1 within one crimp 30 and half of a second crimp 30 (this is done for illustration purposes only). These threads are present on the crimp carriage 20 at least for the length of all of the crimps 30 that are to be loaded on the carriage 20. Alternatively the carriage can be smooth and have the crimps stacked up on it with a retention feature disposed on the end of the carriage that prevents the crimps from falling off the end of the carriage. In such an embodiment, the crimps are biased toward the retention feature by a slide that is, itself, biased distally by a compression spring. The slide has a mechanism that only allows it to slide distally along the carriage. In this way, the crimps are advanced into position and, once the distal-most crimp is moved into the ready position, the stack of remaining crimps index forward moving the next crimp into position.

Surrounding the crimp carriage 20 at the distal end of the device is the end effector body 40, which is best seen in FIGS. 17 to 22. The end effector body 40 defines a crimp loading orifice 42 in which a crimp 30 is loaded and, when loaded, is ready for firing. FIG. 1 does not show a crimp 30 in a loaded crimping position. A crimping device 50 is disposed at the orifice 42 and, in the exemplary embodiment shown, is positioned on opposing sides of the orifice 42. More particularly, an anvil 52 is present on one side of the orifice 42 and a hammer 54 is present on the other side of the orifice 42 opposite the anvil 52. The anvil 52 can be of a different material than the end effector body 40 or it can be integral with the end effector body 40. A cutting assembly 60 is also present at the end effector body 40. The cutting assembly 60, in the exemplary embodiment shown, includes a cutter 62 that is biased in a non-cutting position (shown) by a non-illustrated spring, for example. The cutter 62 is moved (e.g., rotated) by a cutter push-rod 64, 66 that extends back to the handle 100 of the multiple-firing crimp device 1; the handle 100 is diagrammatically shown in FIG. 3, for example, and is actuated by any number of actuation mechanisms, such as a motor, a relay, a lever, and/or a rack-and-pinion. To bias at least one of the movement assemblies in a proximal direction, a bias device 3 is provided and is diagrammatically shown in the handle 100 adjacent the movement assemblies. In this example, the bias device 3 is a spring.

An outer tube 70 surrounds the end effector body 40 and surrounds at least part of the cutting assembly 60 as it moves distal and proximal with respect to the end effector body 40. Also disposed within the outer tube 70 is a suture lifter 80, which is explained in further detail below.

To explain how the multiple-firing crimp device 1 operates, reference is made to the progression of FIGS. 2 through 31. The multiple-firing crimp device 1 comes pre-loaded to the user with a number of crimps 30 on the crimp carriage 20. This number is sufficient to accomplish a particular procedure. For example, if a heart valve replacement is the procedure and there are nine, twelve, or fifteen sutures needed to fix the replacement heart valve within the native valve orifice (this assumes an even spacing on a tri-leaflet valve), then the crimp carriage 20 will be fitted with nine, twelve, or fifteen crimps 30 (e.g., six crimps 30 are shown on the crimp carriage 20 in FIG. 4).

When the multiple-firing crimp device 1 is loaded with crimps 30 and is ready to use, the movement devices of the various loading/retracting, crimping, and cutting sub-assemblies within the handle 100 will be at a first rest or start position. These assemblies are shown diagrammatically within FIGS. 3, 5, 7, 9, 11, 12, 16, 20, 24, 26, 29, and 31. Ways that each of the movement sub-assemblies can actuate the various tasks of the multiple-firing crimp device 1 include any combination of levers, motors, relays, and other mechanical structures, such as a rack-and-pinion. Thus, they are not described in further detail. Here, each of the movement sub-assemblies includes a movement spool as an exemplary structure for actuating the assembly, each of which will be identified when the particular movement assembly is referenced herein. Spools are used to allow for longitudinal translation with free rotation.

Figure 2:
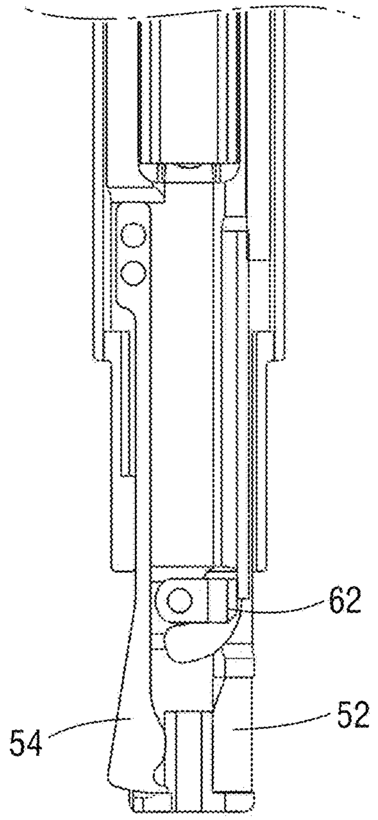
FIG. 2 is a fragmentary, longitudinal, cross-sectional view of the end effector of the multiple-firing crimp device of FIG. 1 with the crimp sub-assembly removed.
Figure 3:
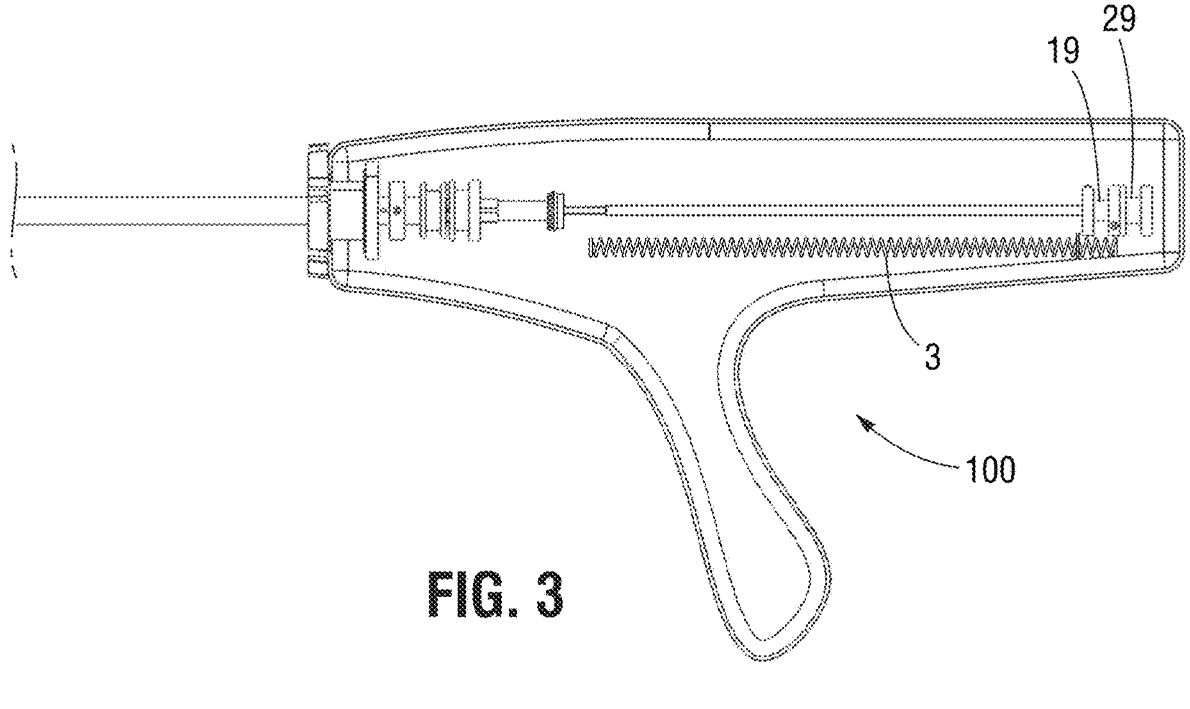
FIG. 3 is a fragmentary, side elevational and partially longitudinal cross-sectional view of an exemplary embodiment of a portion of a handle for operating the end effector of FIG. 2 with the crimp sub-assembly fully retracted.

When the multiple-firing crimp device 1 is loaded with crimps 30 prior to use, as shown in FIGS. 2 and 3, the crimp carriage 20 is retracted proximally out of the end effector body 40. Thus, the carriage spool 29 is in the furthest retracted position (e.g., proximal or closest to the user). In this state, the cutter 62 is retracted and the hammer 54 is in its steady or resting state away from the anvil 52. Significantly, no crimp 30 is loaded within the crimp orifice 42. In this state, the snare 10 is also retracted with the crimp carriage 20 and, therefore, the snare spool 19 is in the furthest retracted position as well.

Figure 4:
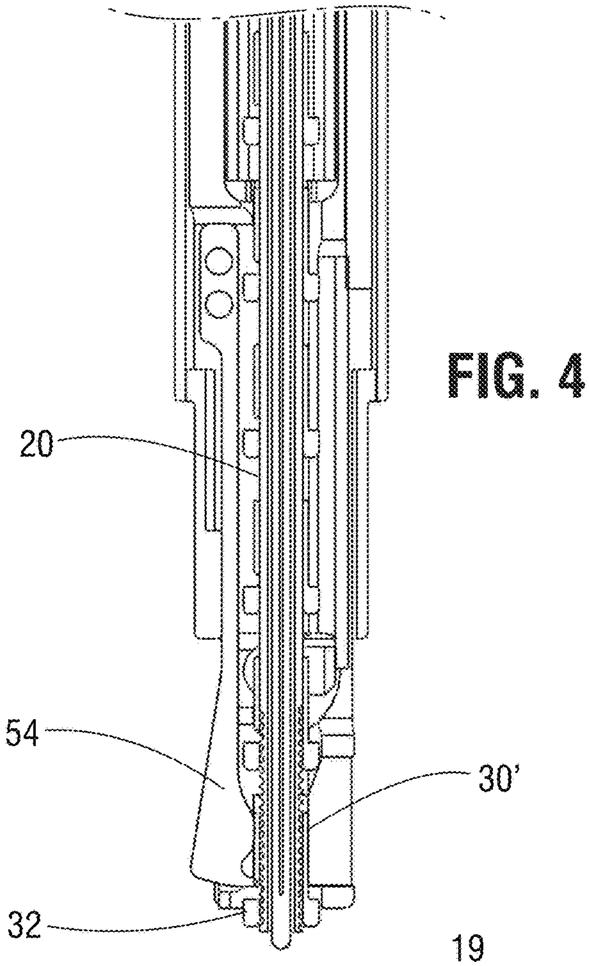
FIG. 4 is a fragmentary, longitudinal, cross-sectional view of the end effector of FIG. 1 with the crimp sub-assembly in an extended position prior to seating of a crimp.
Figure 5:
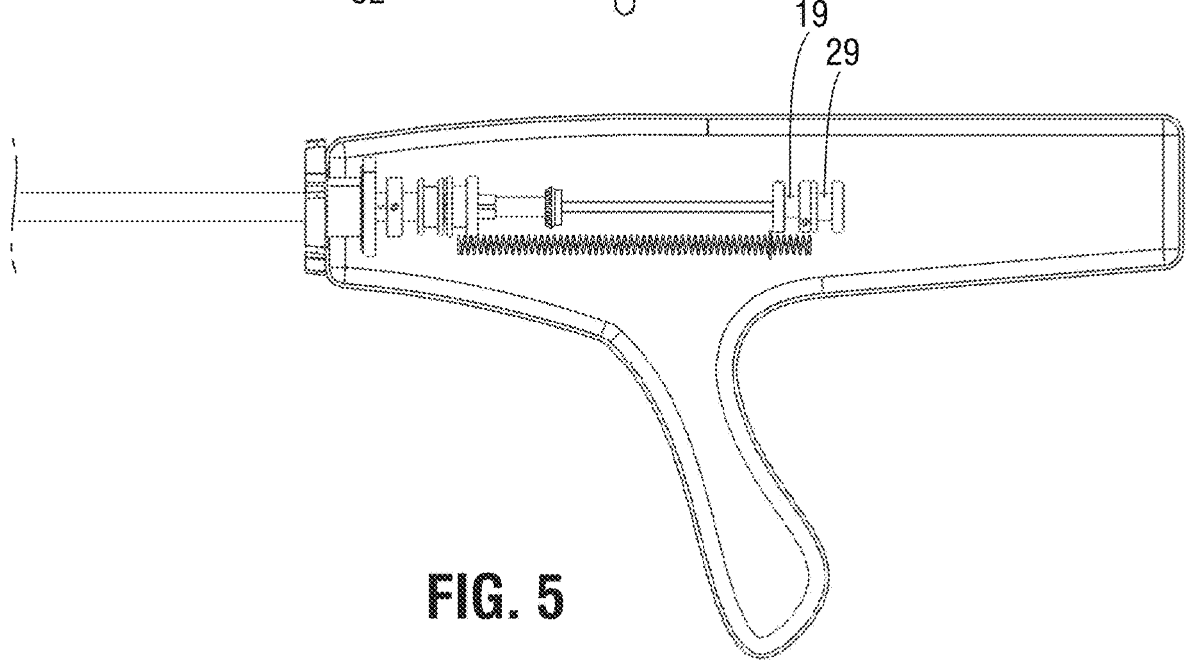
FIG. 5 is a fragmentary, side elevational and partially longitudinal cross-sectional view of the handle portion of FIG. 3 with the crimp sub-assembly actuators in a carriage-extended position corresponding to FIG. 4.

To load the multiple-firing crimp device 1 with a crimp 30 and make it ready for use, the crimp carriage 20 is extended distally. This is done by placing the carriage spool 29, along with the snare spool 19, in the position shown in FIG. 5. In this step, the snare spool 19 can be free-floating because the carriage spool 29 (having a shaft within a shaft attached to the snare spool 19) forces the snare spool 19 distally as far as the carriage spool 29 is moved. To secure the distal-most crimp 30' within the crimp orifice 42, the head 34 of the soon-to-be-loaded crimp 30' must pass the distal ends of the hammer 54 and the anvil 52, a state that is shown in FIG. 4. To describe how the crimp 30' is loaded into the crimp orifice 42 and held there, it is beneficial to first describe an exemplary embodiment of a crimp 30, which is shown in FIGS. 32 and 33. To thread the crimp 30 onto the externally threaded crimp carriage 20, the crimp 30 defines a bore having internal threads 32 corresponding to the external threads 24 of the crimp carriage 20. In this way, each crimp 30 can simply be placed in loading position at the distal end of the crimp carriage 20 and rotation of the crimp carriage 20 in a particular direction serially loads each crimp 30 thereon one after the other, as shown, for example, in FIG. 1. To prevent the crimps 30 from rotating while the crimp carriage 20 is rotating, each crimp 30 has a head 34 formed with at least one polygonal surface 36. The end effector body 40 has a corresponding shape to the polygonal surface that acts as a structure to keep each crimp 30 aligned therewithin and prevent rotation of the crimp 30. The crimp 30 has various advantageous characteristics. First, its shape delivers the highest clamp force density. Next, it presents a closed profile that houses the cord(s) therein. Finally, it is easily deformed to restrain the cord(s) therein in a reliable and secure manner.

Once the crimp carriage 20 is retracted from the crimp 30', it would, without more, rest within the crimp orifice 42 and, potentially, could fall out with movement of the multiple-firing crimp device 1. Accordingly, to positively lock the crimp 30' within the crimp orifice 42, each crimp 30 is provided with a catch 38, which can take any shape and, in the exemplary embodiment shown, is a transverse groove or cut adjacent a proximal side of the head 34 (the top side of the head 34 in the view of FIG. 33). The catch 38 can be any shape or structure and need not be the shape depicted in the figures. The catch 38 can be a hole or other depression but it can even be an extension such as a protruding boss. To effect a catch-and-securement of the crimp 30' within the crimp orifice 42, the hammer 54 is provided with a distal feature 56 having a shape that, when aligned with the catch 38, mates therewith. See, e.g., FIG. 6A. In the exemplary embodiment, the distal feature 56 is a protruding nose having a longitudinal length shorter than the longitudinal length of the catch 38. In this way, when the head 34 of the crimp 30' passes the distal feature 56 and is then retracted just slightly proximal, the distal surface of the distal feature 56 abuts the proximal surface of the head 34 and extension of the distal feature 56 into the catch prevents both proximal and distal movement. Thus, along with the polygonal surface 36, the crimp 30' is held in place in all dimensions as shown in FIGS. 6 and 6A. The distal end in FIG. 6A shows the interaction of the catch 38 and the distal feature 56 and the contact with both the distal faces of the hammer 54 and the anvil 52 to provide a proximal stop for the crimp 30'.

It is desirable to provide additional holding force on the crimp 30' to retain the crimp 30' therein. Accordingly, the hammer 54, which is shaped as a flex beam secured distally to the end effector body 40 at one or more contact points 58, has an interiorly extending section 53 that acts as a cam along the edge of the crimp 30'. As such, with the distal end 72 of the outer tube 70 preventing the intermediate portion of the hammer 54 from flexing outward, the remaining exposed portion 74 of the distal end of the hammer 54 flexes radially outward and, thereby, imparts a strong radially inward bias against the crimp 30'. The position of the crimp carriage 20 and the snare 10 in this state defines the corresponding positions of the carriage spool 20 and the snare spool 19 that are shown in FIG. 7.

Figure 8:
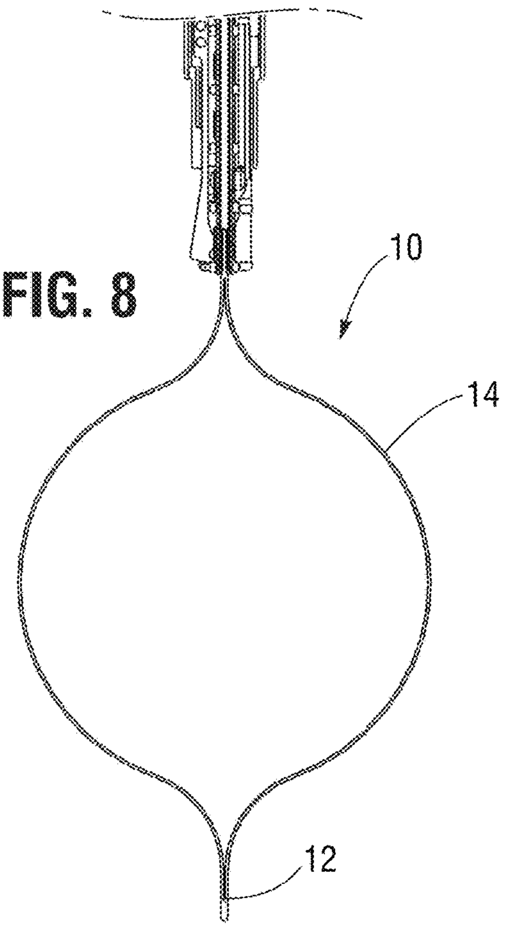
FIG. 8 is a fragmentary, longitudinally cross-sectional view of the end effector of FIG. 6 with a snare in an extended snare position ready for capturing one or more cords.
Figure 9:
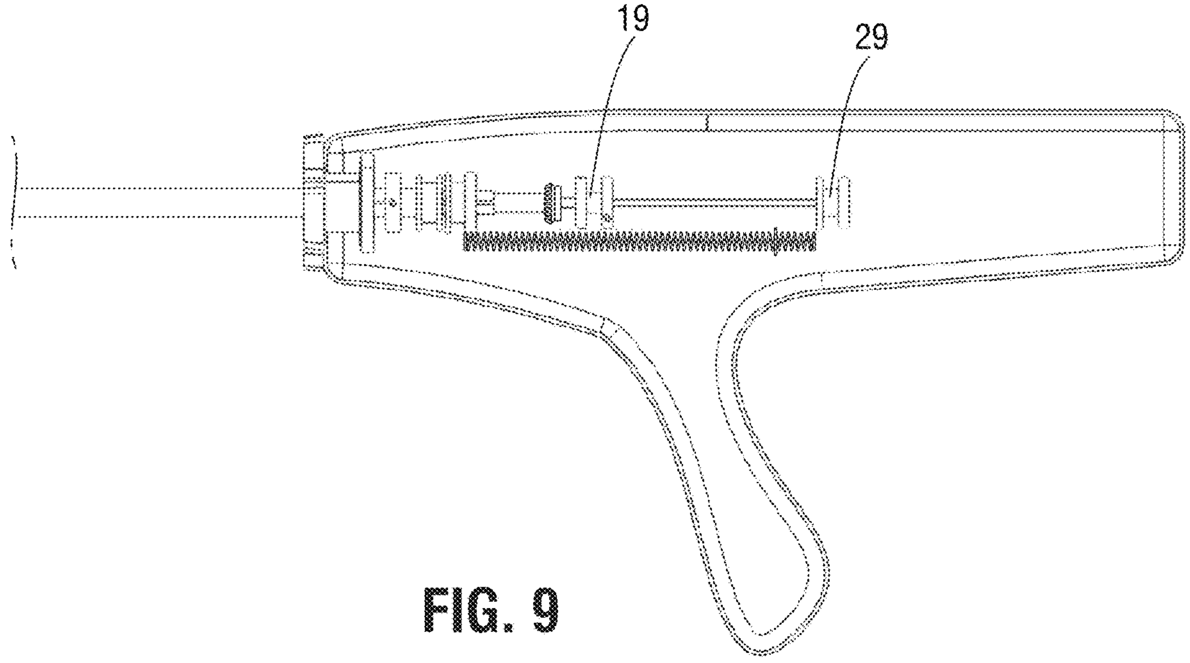
FIG. 9 is a fragmentary, side elevational and partially longitudinal cross-sectional view of the handle portion of FIG. 3 with the snare sub-assembly actuator in a snare-use position corresponding to FIG. 8.
Figure 10:
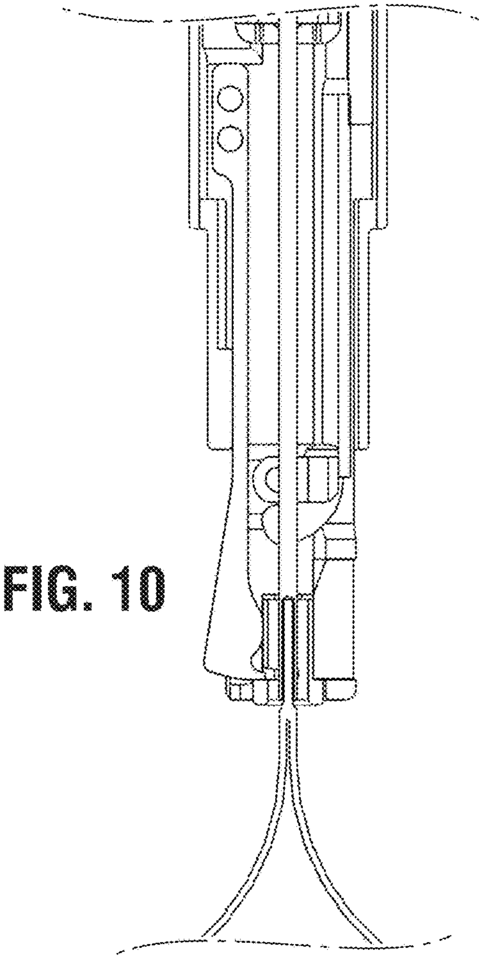
FIG. 10 is a fragmentary, longitudinally cross-sectional view of the end effector of FIG. 8 with a snare in an extended snare position ready for or capturing a suture and with the suture screw carriage disengaged from the distal-most clip and fully retracted.
Figure 11:
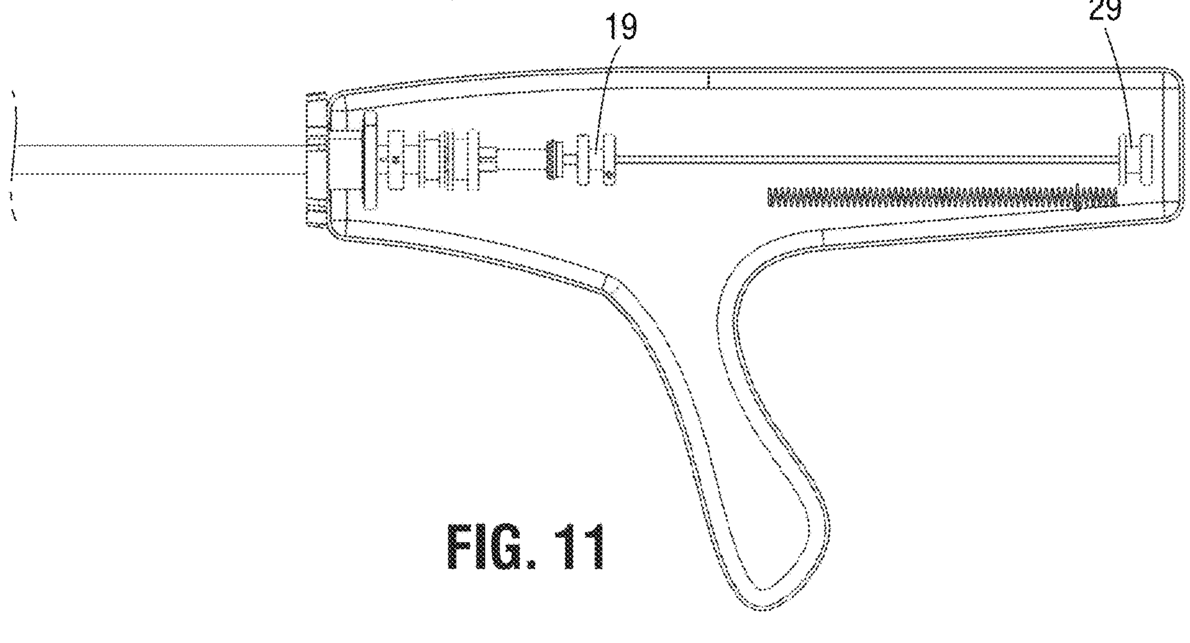
FIG. 11 is a fragmentary, side elevational and partially longitudinal cross-sectional view of the handle portion of FIG. 3 with the snare sub-assembly actuator in a snare-use position corresponding to FIG. 10 and with the suture screw carriage disengaged from the distal-most crimp and fully retracted.

Now that the crimp 30' is in position for use, in order to thread the cords into and through the hollow center of the crimp 30', the snare 10 is extended distally through the crimp 30' with the tip 14 of the snare 10 moving distally away from the distal end of the end effector body 40. As the tip 14 moves further distally, the loop 12 is permitted to open to its pre-set shape (e.g., heat-set), an example of which is shown in FIG. 8. Extension of the snare 10 occurs by moving the snare spool 19 distally away from the carriage spool 29, as shown in FIG. 9. At this point, the cords can be inserted through the loop 12 for entry into and through the crimp 30'. However, the crimp 30' is still attached to the crimp carriage 20. Accordingly, the crimp carriage 20 is rotated (by a non-illustrated device that spins the carriage spool 29, for example) to disengage the crimp 30' from the distal end of the crimp carriage 20. At the same time or either before or after, the crimp carriage 20 is moved distally out of the end effector body and is rotated further to cause the distal end thereof to move and place the previously second crimp 30" in line into the distal-most crimp position, thereby converting the second crimp 30" into the next crimp 30' to be used for the next crimping procedure. The depiction in FIG. 10 illustrates the end effector with the crimp carriage 20 entirely disengaged from the distal-most crimp 30' and retracted out of at least a portion of the end effector body 40 to not interfere with subsequent steps (even though it is shown completely out of the view of FIG. 10, this does not mean that such a distant retraction is required. It is sufficient if the carriage 20 is retracted sufficiently far enough to not interfere with subsequent steps prior to loading the next crimp 30'. The orientation of the snare and carriage movement sub-assemblies for this state is depicted with the positions of the snare spool 19 and the carriage spool 29 in FIG. 11.

Figure 12:
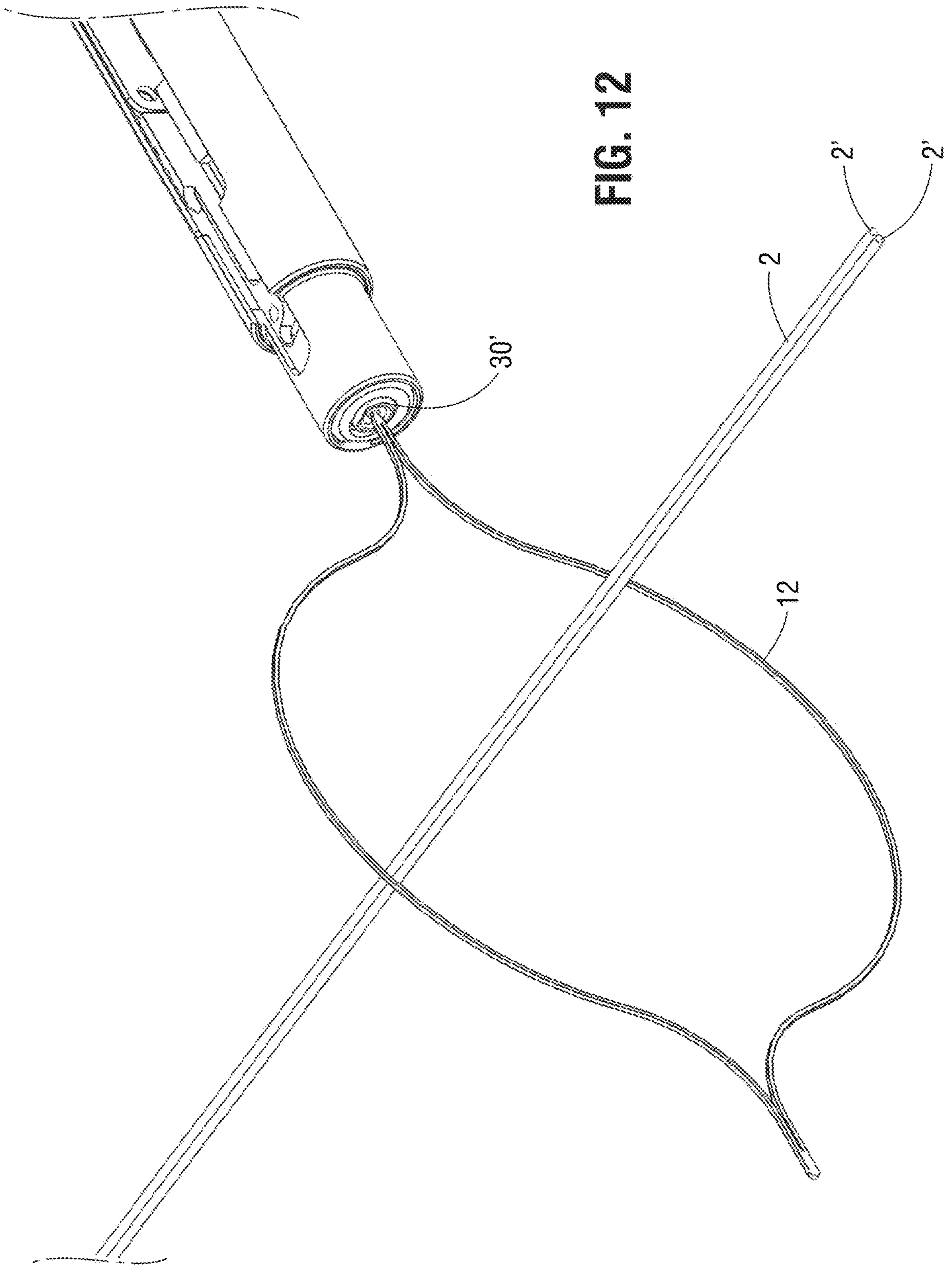
FIG. 12 is a fragmentary, perspective view of the end effector of FIGS. 8 and/or 10 with cords to be captured extended within the loop of the snare.
Figure 13:
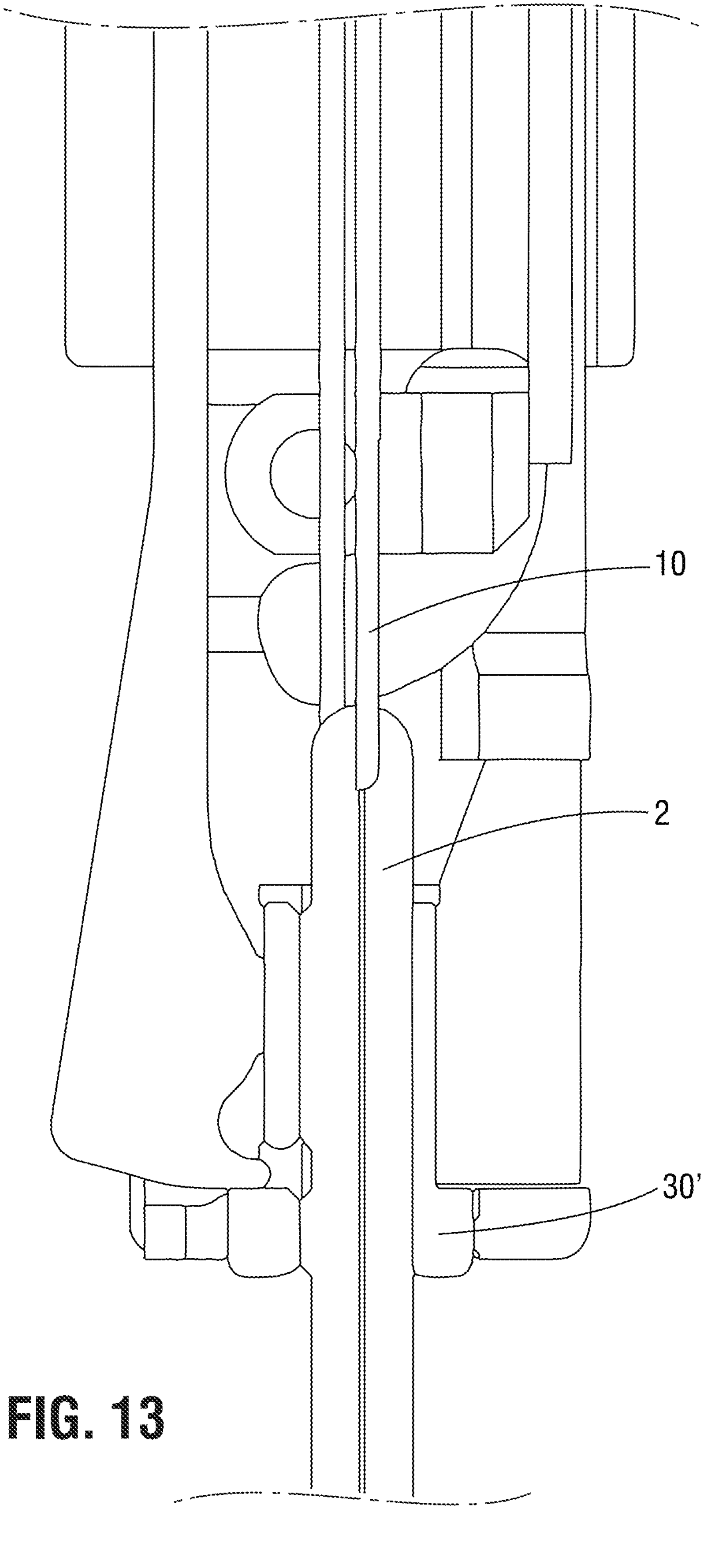
FIG. 13 is a fragmentary, longitudinally cross-sectional view of the end effector of FIG. 10 enlarged with respect to FIG. 10, with the snare in a partially retracted snare position after capturing cords and with the cords having passed partially through the crimp.
Figure 14:
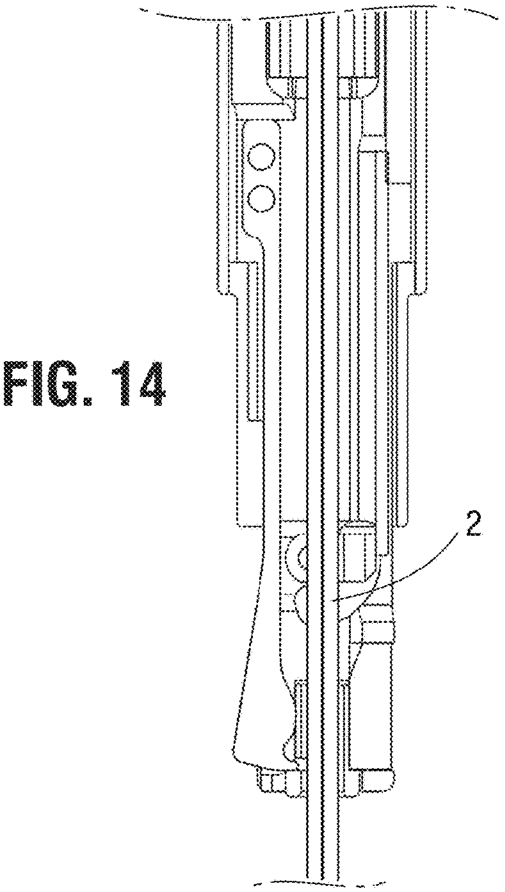
FIG. 14 is a fragmentary, longitudinally cross-sectional view of the end effector of FIG. 13 reduced with respect to FIG. 13 and with the snare in a further partially retracted snare position after capturing the cords.
Figure 15:
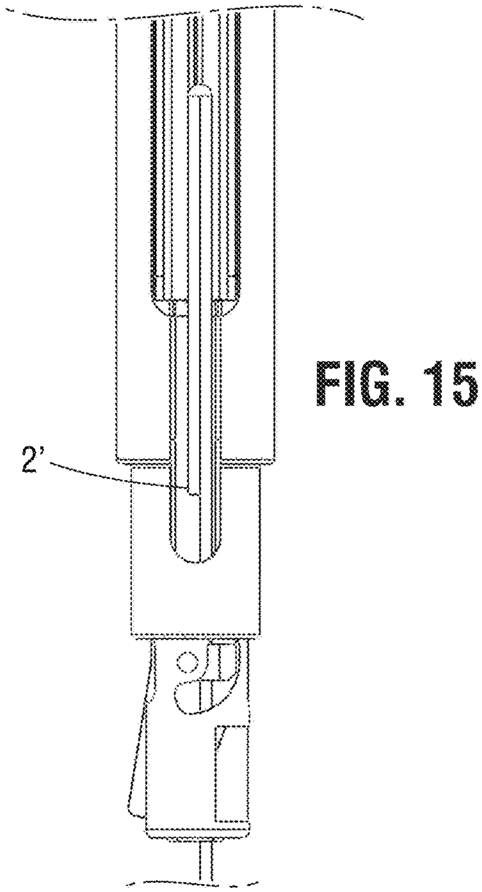
FIG. 15 is a fragmentary, side elevational view of the end effector of FIG. 14.
Figure 16:
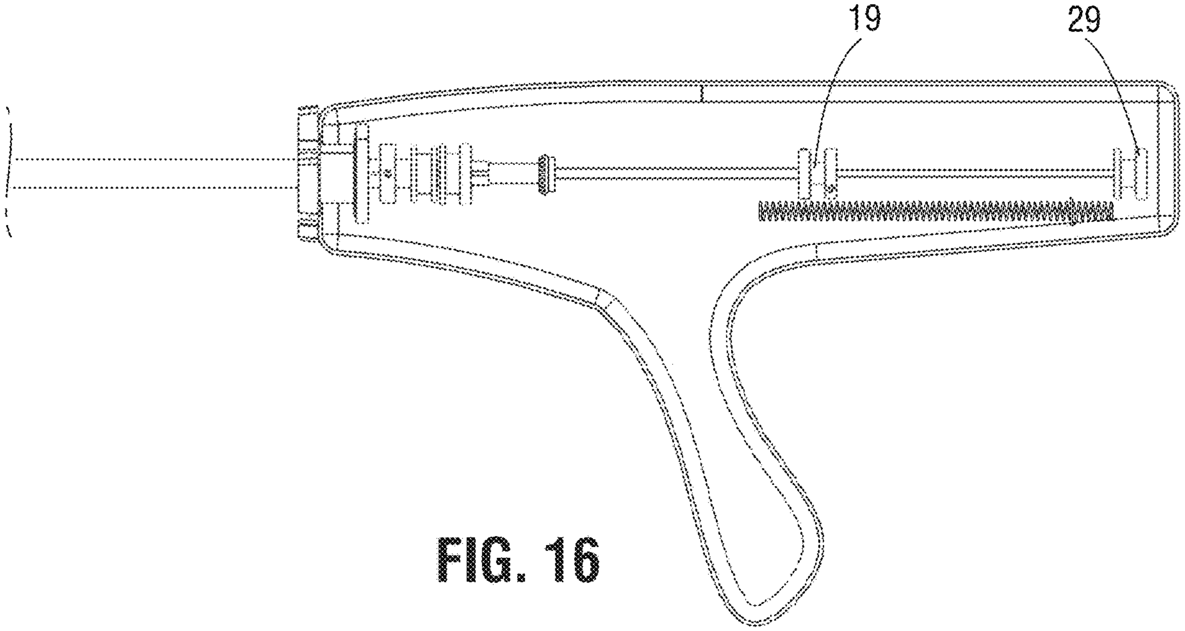
FIG. 16 is a fragmentary, side elevational and partially longitudinal cross-sectional view of the handle of FIG. 11 with the snare sub-assembly actuator further retracted than the position of the snare corresponding to FIG. 12.

In the example of FIG. 12, the free ends 2' of a looped cord 2 are passed through the loop 12 (from the left to the right in the drawing). At this point, the cords 2 are ready to be threaded through the crimp 30'. The snare 10 is drawn proximally to catch the cords 2 within the loop 12 and then in the tip 14, which, in an exemplary embodiment, forms a small extension area of the interior of the loop 12 in which the cords 2 are moved as the loop closes and moves proximally. As the proximal end of the loop 12 is drawn proximally into the crimp 30', the loop 12 compresses flat, as in the orientation of FIG. 6, and the cords 2 are, then, folded in half and reside within the interior of the tip 14. Further proximal movement draws the cords 2 through the crimp 30' as depicted in FIG. 13. The looped ends of the cords 2 in the tip 14 are drawn in further proximally into the device as shown in FIG. 14 until the free ends 2' of the cords 2. enter the end effector body 40, as shown in FIGS. 15 and 17. The orientation of the snare and carriage movement sub-assemblies for this state is depicted with the positions of the snare spool 19 and the carriage spool 29 in FIG. 16.

Now that the cords 2 are through the crimp 30' and the ends 2' are pulled sufficiently far enough into the shaft of the device, the process for presenting these ends 2' to the user begins.

Figure 19:
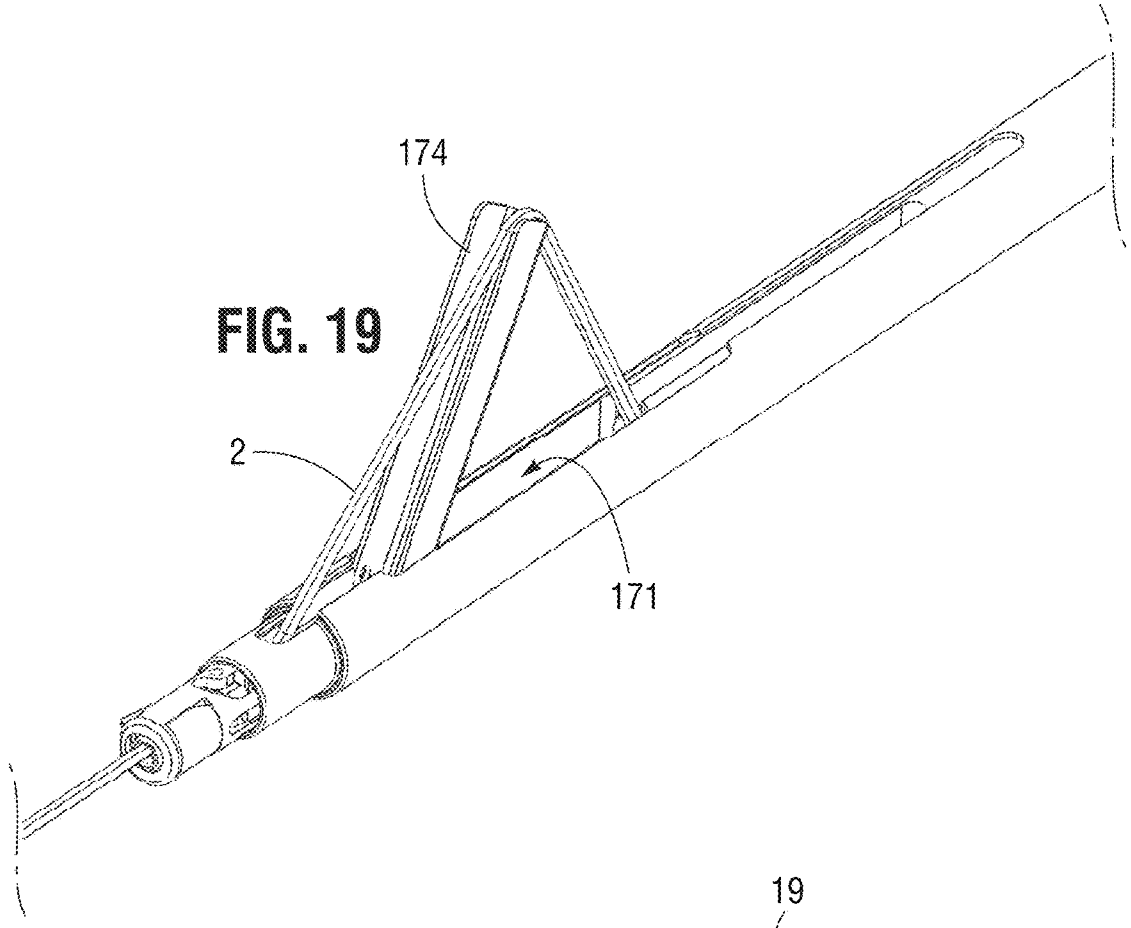
FIG. 19 is a fragmentary, perspective view of the end effector of FIG. 18.
Figure 20:
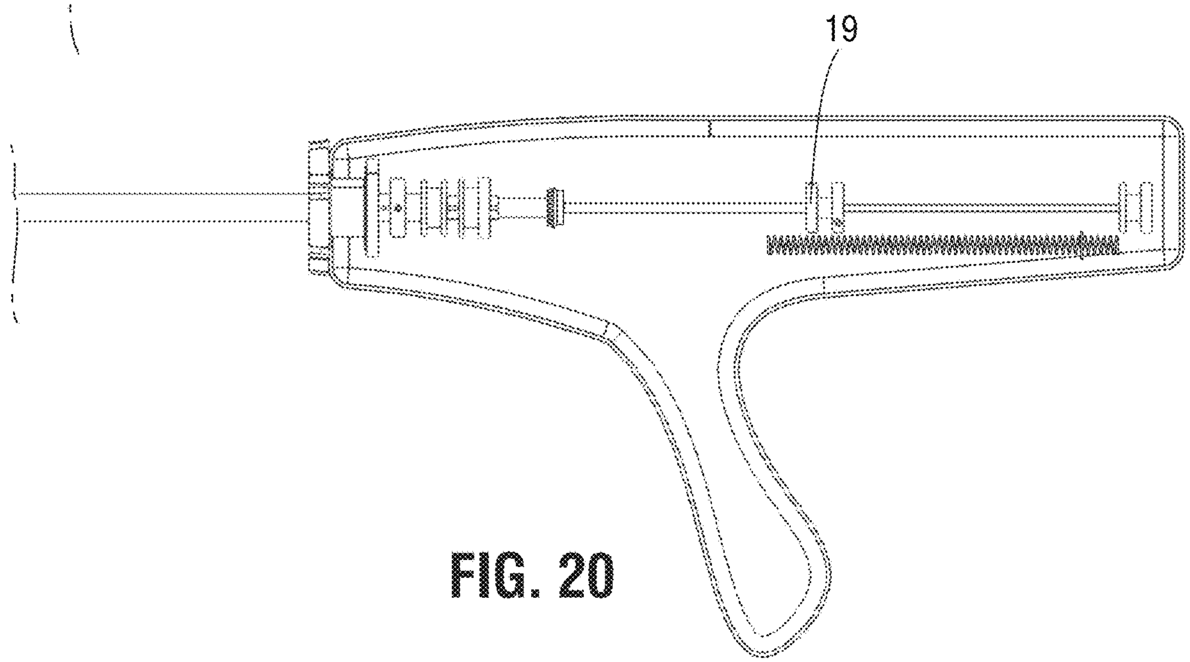
FIG. 20 is a fragmentary, side elevational and partially longitudinal cross-sectional view of the handle of FIG. 16 with the cord-lifting device actuated to position the cord lifter to the position corresponding to FIGS. 18 and 19.
Figure 21:
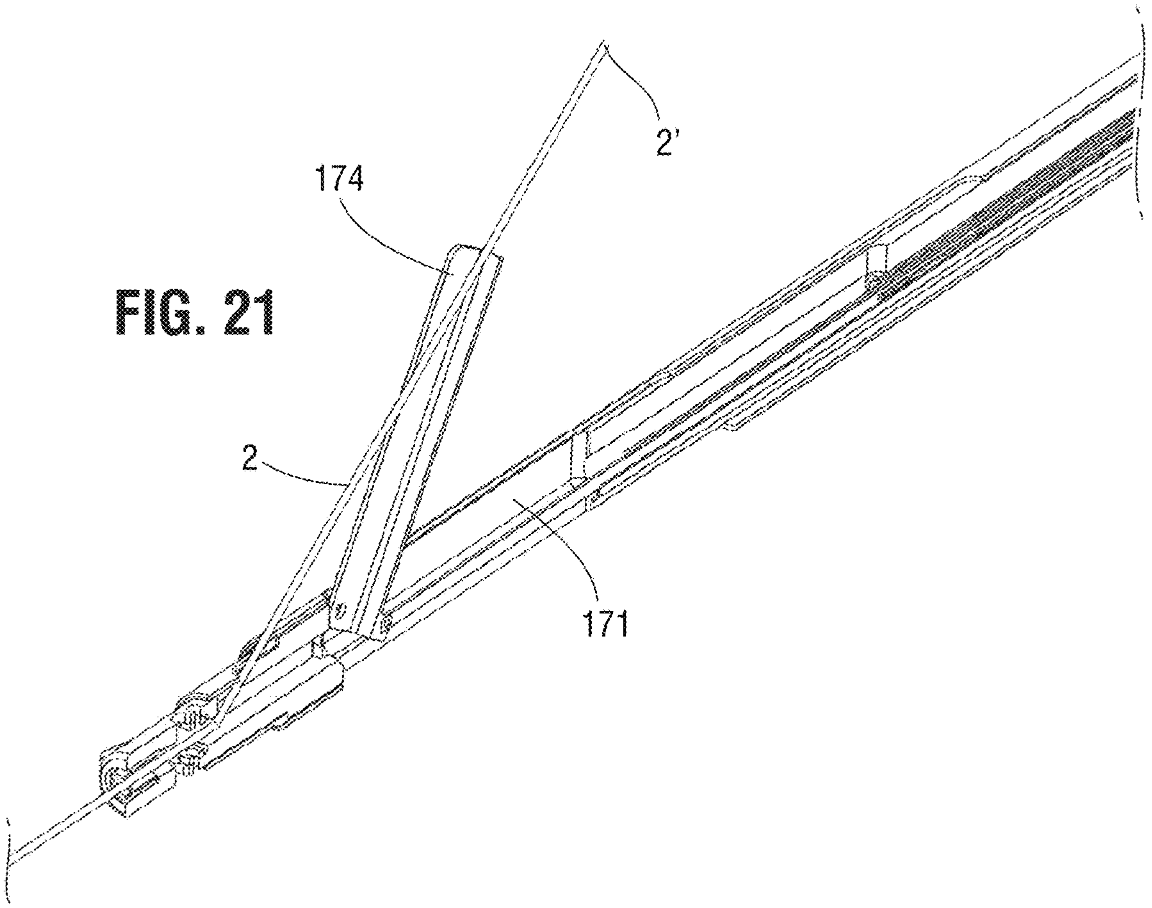
FIG. 21 is a fragmentary, longitudinally cross-sectional view of the end effector of FIG. 19 with the cord-lifting device in a lifted position, with the suture grasped by a user, and with the snare in the partially retracted position.

FIGS. 17 to 24 illustrate this process with an exemplary embodiment of a cord-lifting device 170, which is one possible way to present the ends 2' to a user. The cord-lifting device 170 is fastened to the end effector body 40 at a pivot 172 so that the cord-lifting device 170 is able to pivot away from the central axis of the outer tube 70. With this pivot 172, when the cord-lifting device 170 is actuated, the cord-lifting plate 174 pivots to lift the cords 2 out of the outer tube 70 through a window or lateral opening 171, as shown in FIG. 18. The lifting can be effected with any mechanism, for example, a push rod extending from the handle 100 and attached in an intermediate position of the cord-lifting plate 174 or extending adjacent the pivot 172 to connect to a lever that lifts the cord-lifting plate 174 when either pushed or pulled. This actuation device is not depicted for drawing clarity. At this point, the snare 10 still grasps the cords 2. Accordingly, either the snare 10 can move distally to keep retention of the cords 2, as shown in FIG. 18, or the snare 10 can remain in place and, as the cord-lifting device 170 lifts the cords 2 outwards, either the length of the cords 2 distal of the crimp 30' are pulled into the crimp 30' or the ends 2' of the cords 2 are caused to shorten their distance from the tip 14 of the snare 10. FIG. 19 illustrates the lifted cords 2 still attached to the snare 10 and the cord-lifting device 170 lifted. FIG. 20 illustrates the positions of the various movement sub-assemblies for this state.

Figure 22:
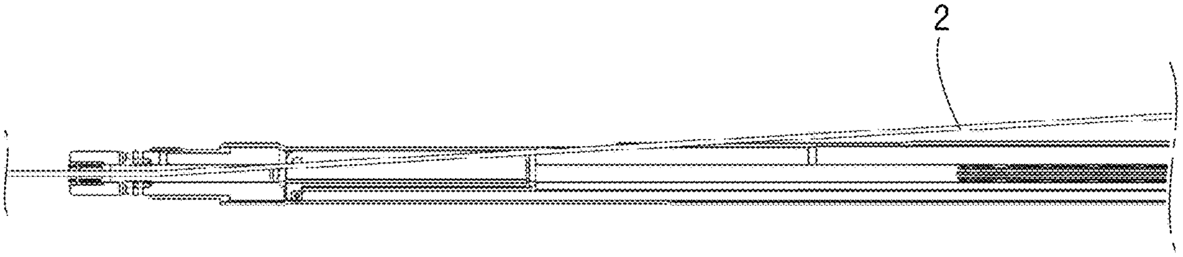
FIG. 22 is a fragmentary, longitudinally cross-sectional view of the end effector of FIG. 21 with the cord-lifting device in a lowered position, with the cords grasped by a user at an acute angle with the longitudinal axis of the end effector, and with the snare in a retracted position.

As the snare 10 is pulled further distally, the ends 2' of the cords 2 become freed therefrom and now rest outside the outer tube 70 of the device. The user can, therefore, grasp these ends 2' and, after the cord-lifting device 170 is lowered, can pull them taut as shown in FIGS. 22 and 23. At this point, the snare 10 can be retracted in the device as shown in FIG. 24 by the position of the snare spool 19. Now, the crimp 30' can be installed/crimped/deformed on the cords 2.

Movement of the distal end of the device with respect to the opposite ends of the cords 2 held by the user (not illustrated but to the lower left of FIG. 23) will depend on the location that the user desires to fix the crimp 30'. If the current location is sufficient, then crimping will occur with the length of the cords shown to the lower left of FIG. 23 remaining as is. However, if the distance from the opposite ends of the cords 2 is desired to be short, then the user will move the device distally along the cords 2 while holding onto the free ends 2' and keeping them taut. If, for example, the cords 2 are surgical sutures and the opposite ends of the cords 2 are fixed at a surgical location, and if the surgeon wishes to have the crimp 30' be applied as close to the surgical location as possible, then the top of the head 34 of the crimp 30' will be moved along the sutures distally and up against the surgical site. When there, with tension on the sutures, the surgeon can fix the crimp 30' at a location closest to the surgical site.

Figure 25:
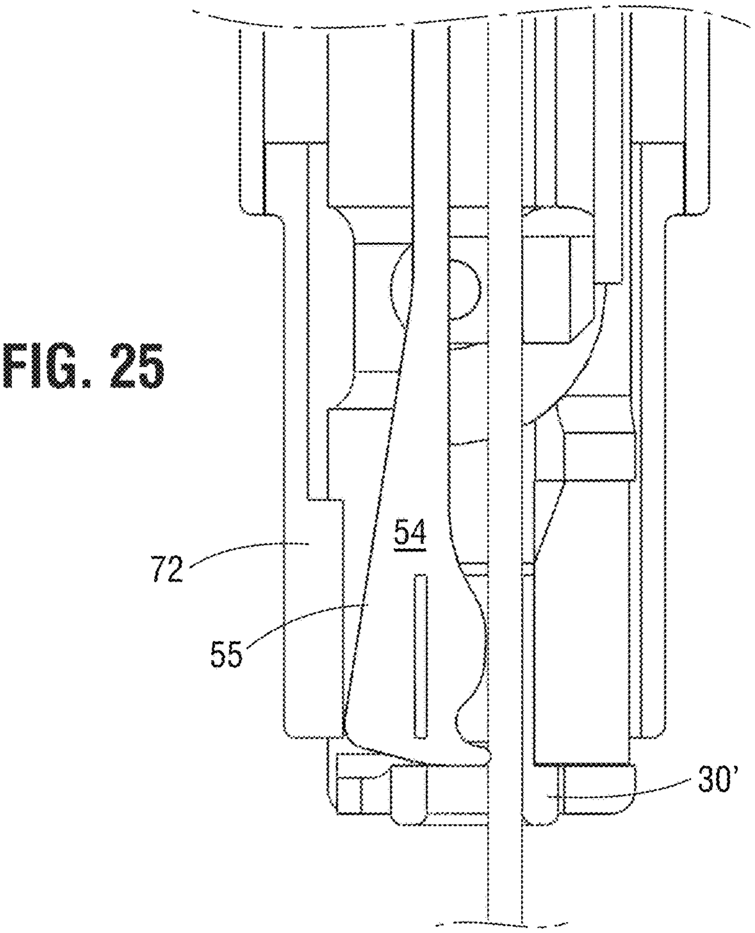
FIG. 25 is a fragmentary, longitudinally cross-sectional view of the end effector of FIG. 23 enlarged with respect to FIG. 23 and with the outer tube partially extended to move the hammer radially inwards and thereby crimp the crimp to the cords therewithin.
Figure 26:
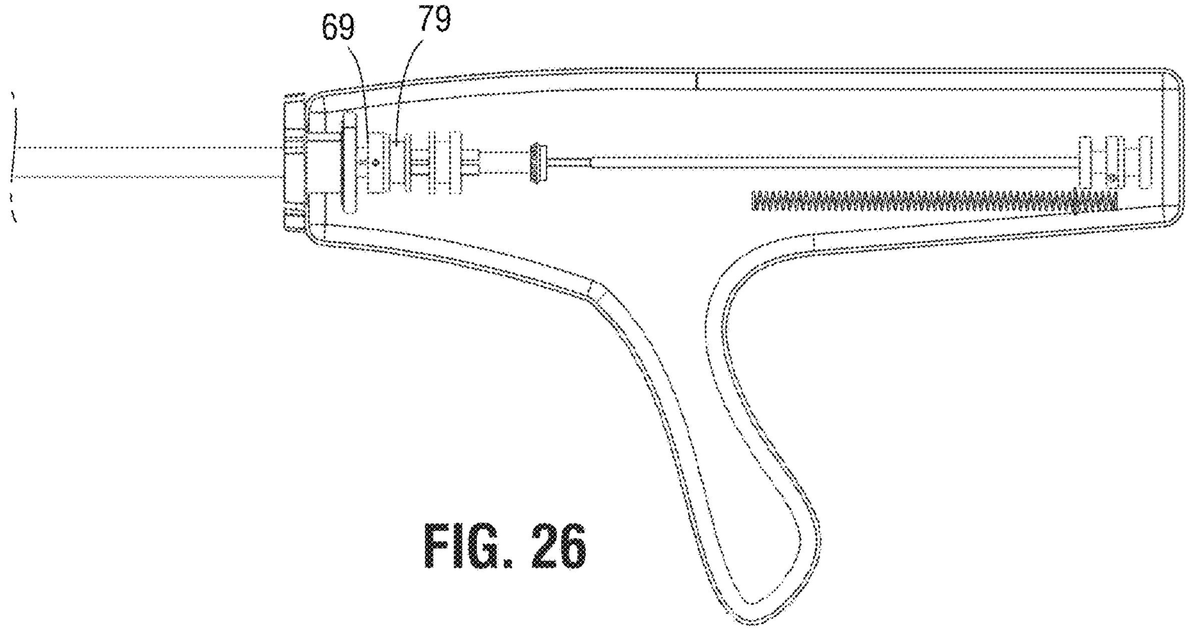
FIG. 26 is a fragmentary, side elevational and partially longitudinal cross-sectional view of the handle of FIG. 24 with the outer tube extended distally into the position corresponding to FIG. 25.
Figure 27:
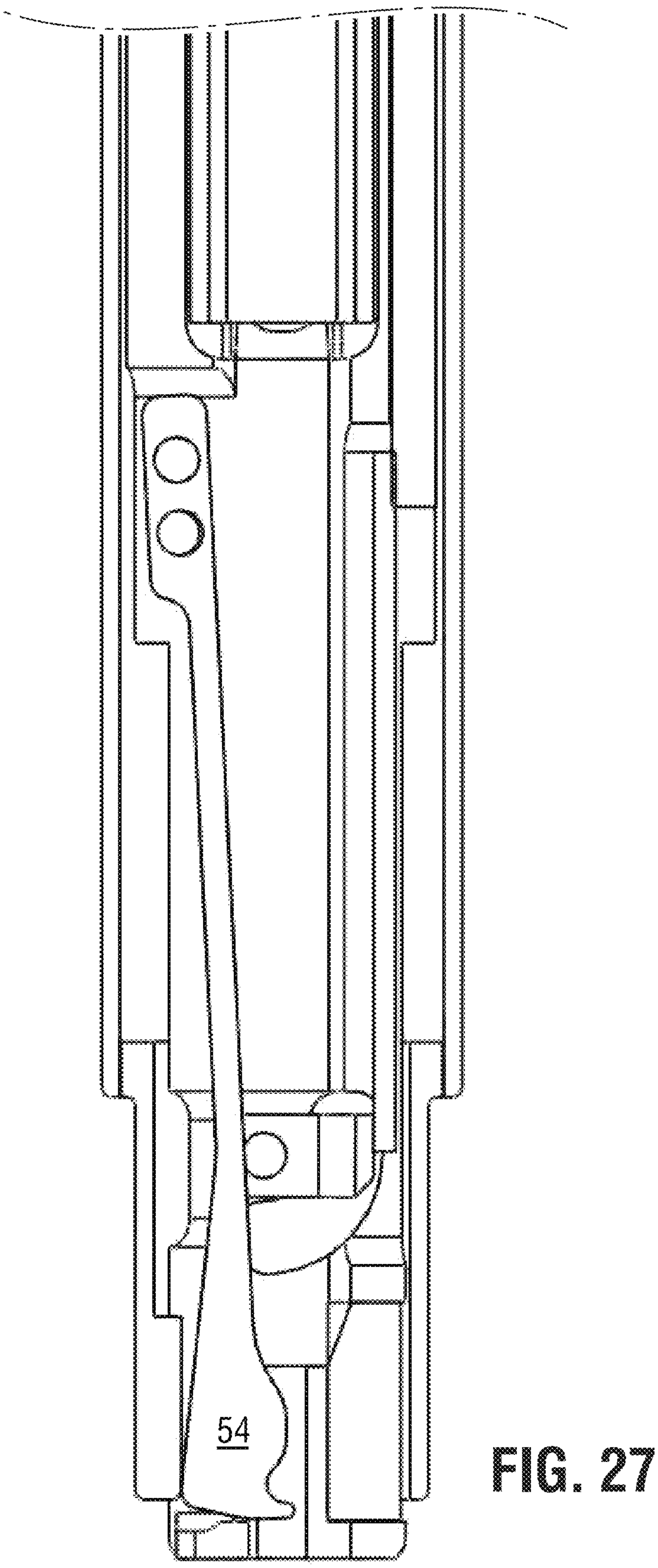
FIG. 27 is fragmentary, longitudinally cross-sectional view of the end effector of FIG. 25 with the crimp and cords removed.
Figure 28:
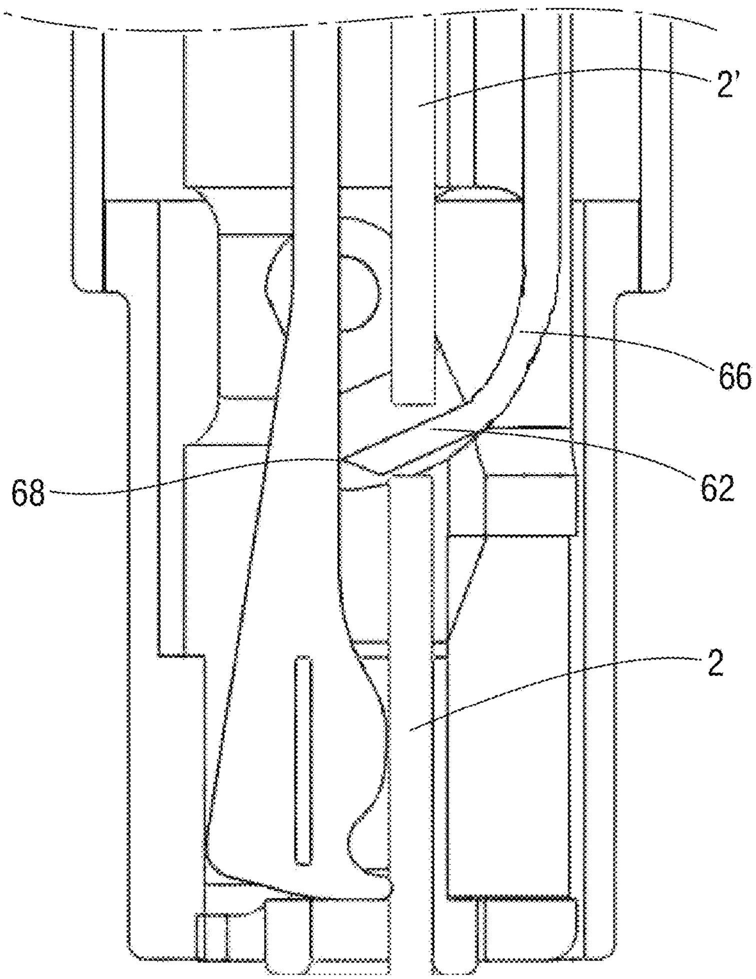
FIG. 28 is fragmentary, longitudinally cross-sectional view of the end effector of FIG. 25 with the cutter actuator fully extended to move the cutting blade and thereby cut the cords.
Figure 29:
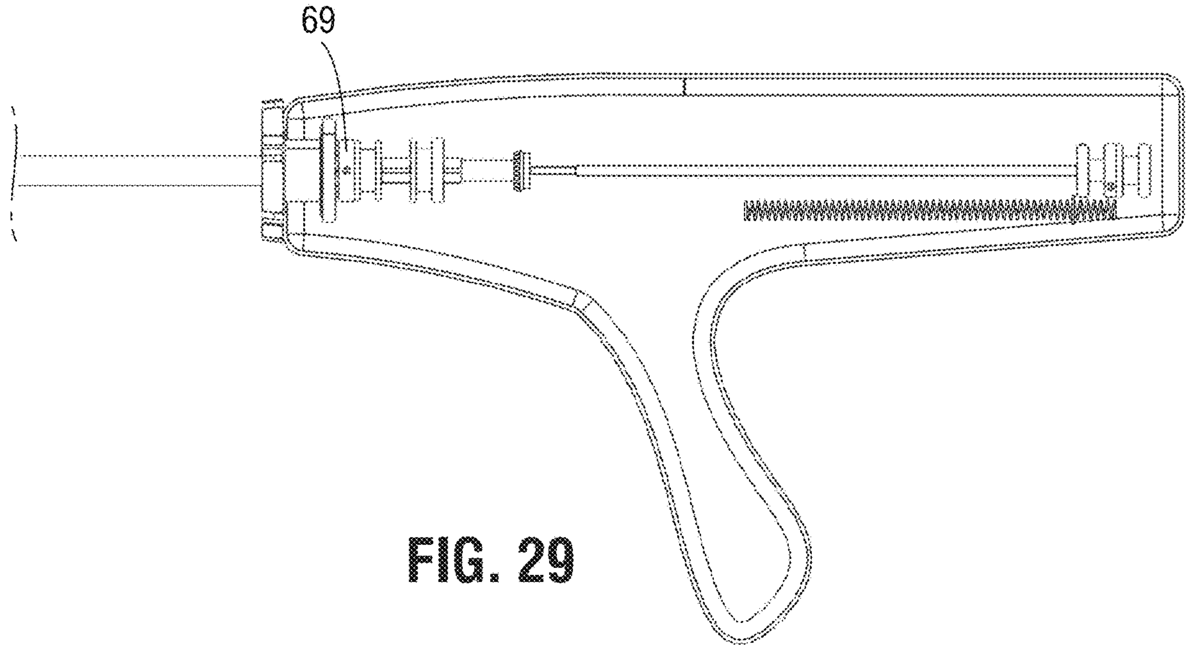
FIG. 29 is a fragmentary, side elevational and partially longitudinal cross-sectional view of the handle of FIG. 26 with the cutter actuator fully extended distally into the position corresponding to FIG. 28 to thereby cut the captured cords.
Figure 30:
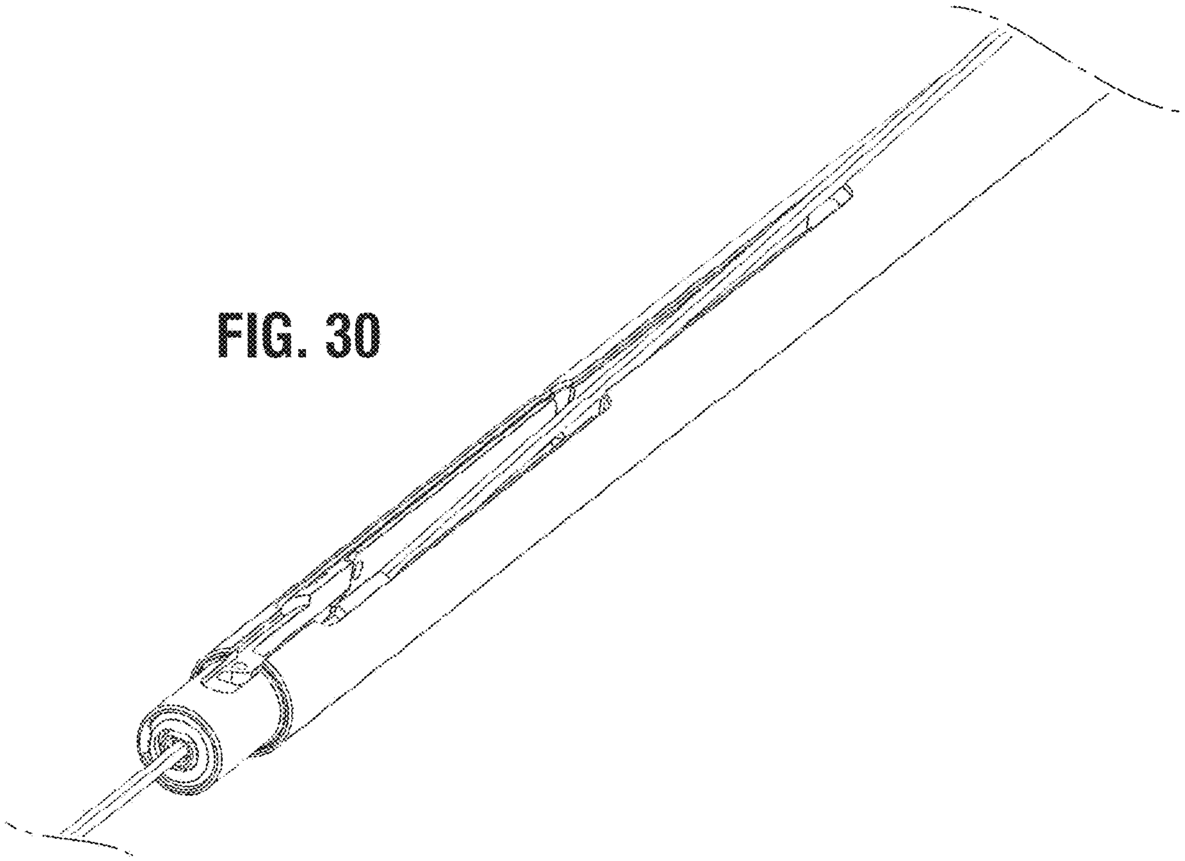
FIG. 30 is a fragmentary, perspective view of the end effector of FIG. 25.
Figure 31:
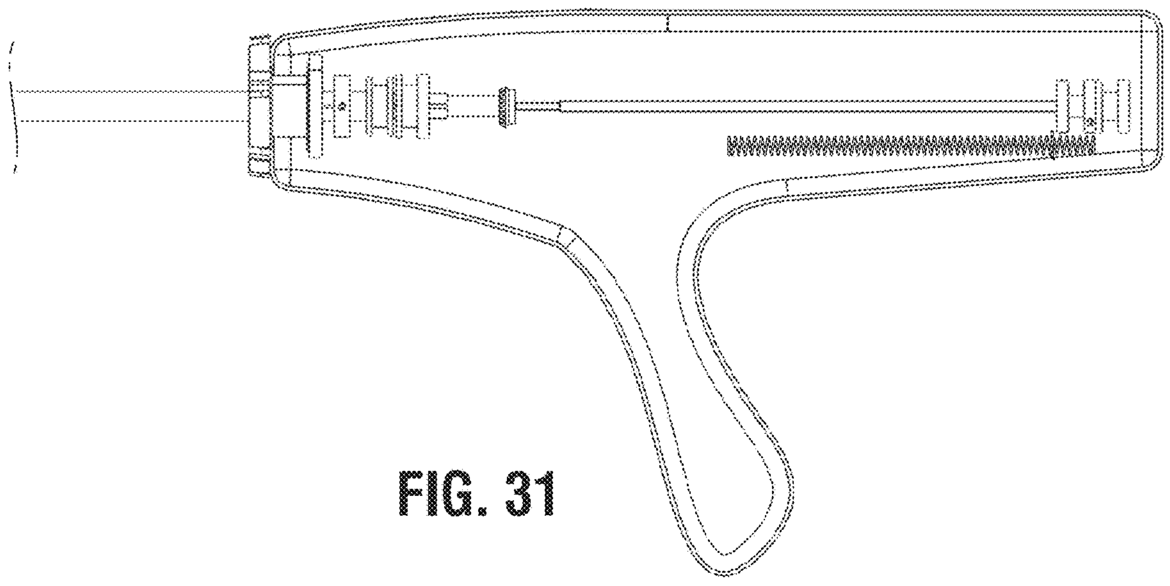
FIG. 31 is a fragmentary, side elevational and partially longitudinal cross-sectional view of the handle of FIG. 29 with the cutter and crimping actuators retracted proximally to release the crimped crimp and with the crimp sub-assembly ready to reload a new crimp into the end effector.
Figure 34:
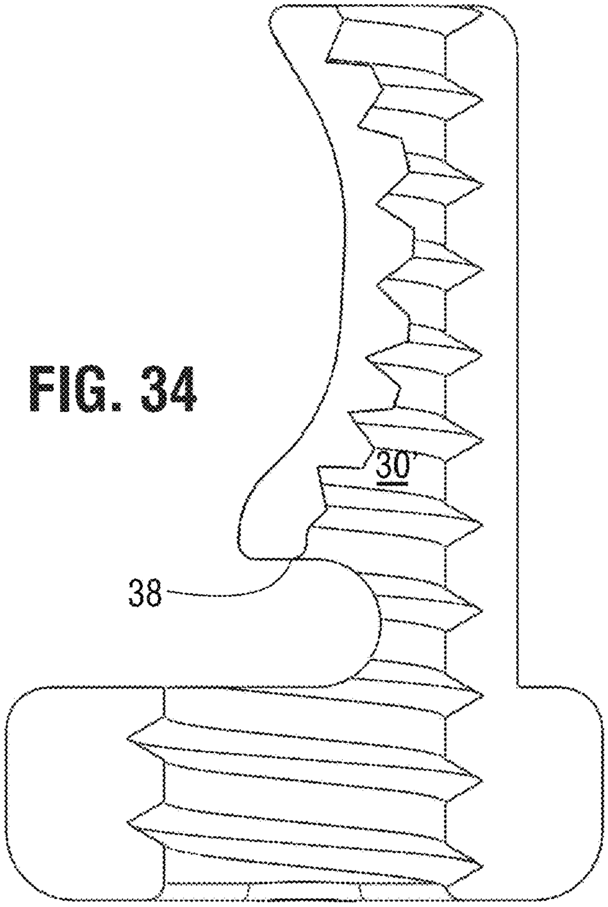
FIG. 34 is an enlarged perspective view of the crimp of FIGS. 33 and 34 after being crimped.

Crimping occurs by moving the outer tube 70 distally, which is indicated in FIG. 26 by the distal movement of the crimp spool 79. As the distance for crimping the crimp 30' is very short, the crimp spool 79 needs to only move a short distance distally. This movement can be caused manually by a lever, a toggle, or a button, for example, or by an electrical motor, such as a stepper motor. Crimping occurs by the outer surface 55 of the hammer 54 acting as a cam profile with the distal end of the outer tube 70. As the outer tube 70 moves distally parallel to the longitudinal axis of the device, the rising cam surface with respect to the outer tube 70 causes the hammer 54 to press inwards against the crimp 30' with a force sufficient to deform the crimp 30' and fix it to the cords 2, as shown in FIGS. 25, 34, and 35. In this state, the crimp 30' is crimped and, thereby, fixed to the cords 2 therewithin (shown diagrammatically with the dashed line in FIG. 35). For ease of visualization, FIG. 27 illustrates the hammer 54 in the crimping position without the crimp 30' present.

It is noted that the internal threads 32 of the crimp 30' provide additional friction and holding power when crimped onto the cords 2. The internal threads of the crimp can be adjusted to not be full depth threads. The threads also can be adjusted to optimize the ID of the crimp for clearance to pass the cords and snare as well as to present a less damaging but still gripping surface to the cords upon crimping. The catch 38 also provides crimp relief and length reduction for when the crimp 30' is squeezed. The distal-most section of the crimp 30' remains undistorted to provide a smooth transitional surface that the cords 2 can follow to prevent high stress that might damage the cords 2.

After crimping occurs, the lengths of the cords 2 on the proximal side of the fixed crimp 30' are to be trimmed off. The cutting assembly 60 described above is able to cut the cords 2 with a cutter pushrod having a relatively stiff proximal portion 64 and a relatively flexible distal portion 66 that is able to bend as the pivoting blade 62 moves (see, for example, FIG. 28). As such, cutting of the cords 2 occurs when an actuator at the handle 100 causes the proximal portion 64 to move distally. This, in turn, causes the distal portion 66 to move distally and, because it is fixed to the proximal side of the blade 62, causes the blade 62 to move about its pivot point and allow the cutting edge 68 to sever the cords 2. As the blade 62 is only required to move a very short distance, the distance that the cutting rod 64, 66 needs to move is also very short and is illustrated by the relative positions of the cutting spool 69 in FIGS. 26 and 29. It is noted that the outer tube 70 and tube spool 79 also move along with the cutting spool 69, but this movement is optional. In order to assure cutting is complete and the device is unobstructed for use of the next crimp 30, the cutting movement assembly is biased proximally (e.g., with a spring) to automatically retract the knife 62 after a cut is complete.

This cutting configuration of the cutter assembly 60 is merely one exemplary embodiment. Another embodiment can include a pusher that cuts the cords 2 by pressing the cords 2 against a fixed blade as described in further detail below. A further embodiment can have the knife cut against a cut block or stop. Yet another embodiment can apply electric current to the knife and allow it to cut as a hot wire. In any case, it is desirable to have the knife cut close to location of the crimped crimp 30' to reduce the remaining length of the cords 2 extending from the end of the crimp 30 opposite the head 34.

Like the cutting movement assembly, the movement assembly for the outer tube 70 is biased proximally (e.g., with a spring, even the same spring as the cutting movement assembly) to automatically retract the outer tube 70 after a crimp 30' fixation is complete. In this way, the hammer 54 is allowed to spring back to its ready-to-crimp position when the outer tube 70 is disengaged.

Figure 39:
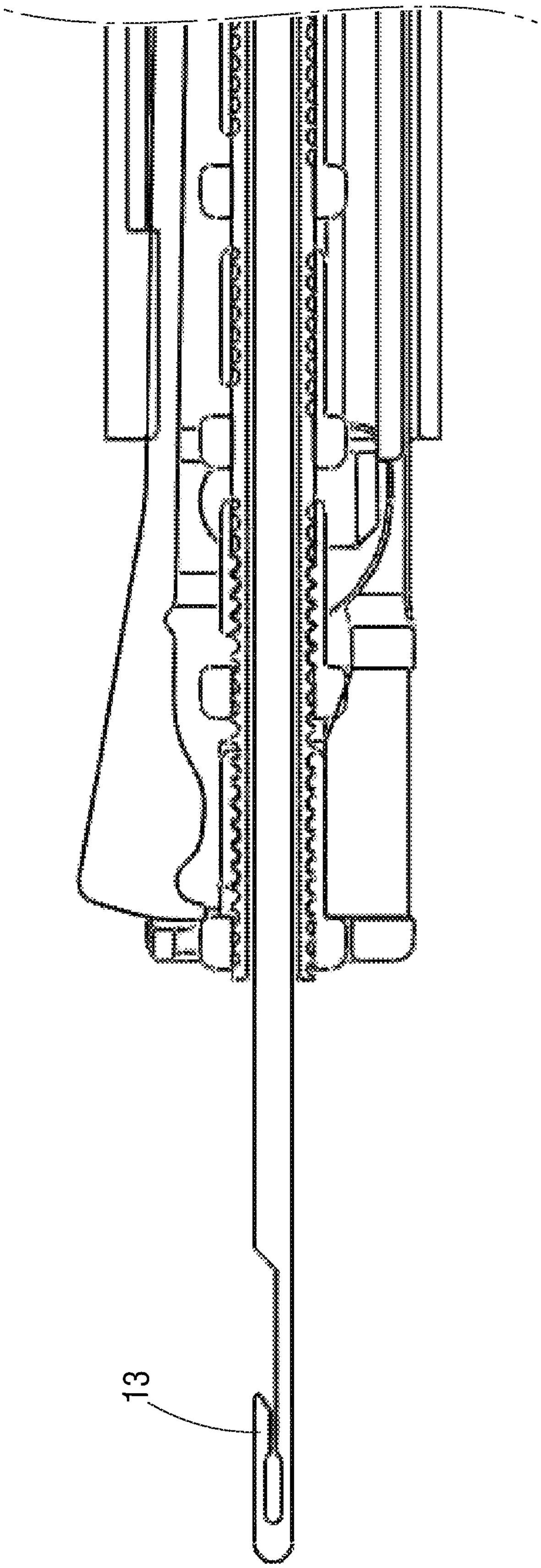
FIG. 39 is a fragmentary, longitudinally cross-sectional view of an exemplary embodiment of an alternative end effector to the device shown in FIGS. 1 to 31 and similar to FIG. 8, wherein the snare is replaced with a distal hook that hooks the cords and draws them into the assembly for securing with a loaded crimp, this embodiment allowing the user to thread the crimp with a single hand that is holding the device's handle.
Figure 40:
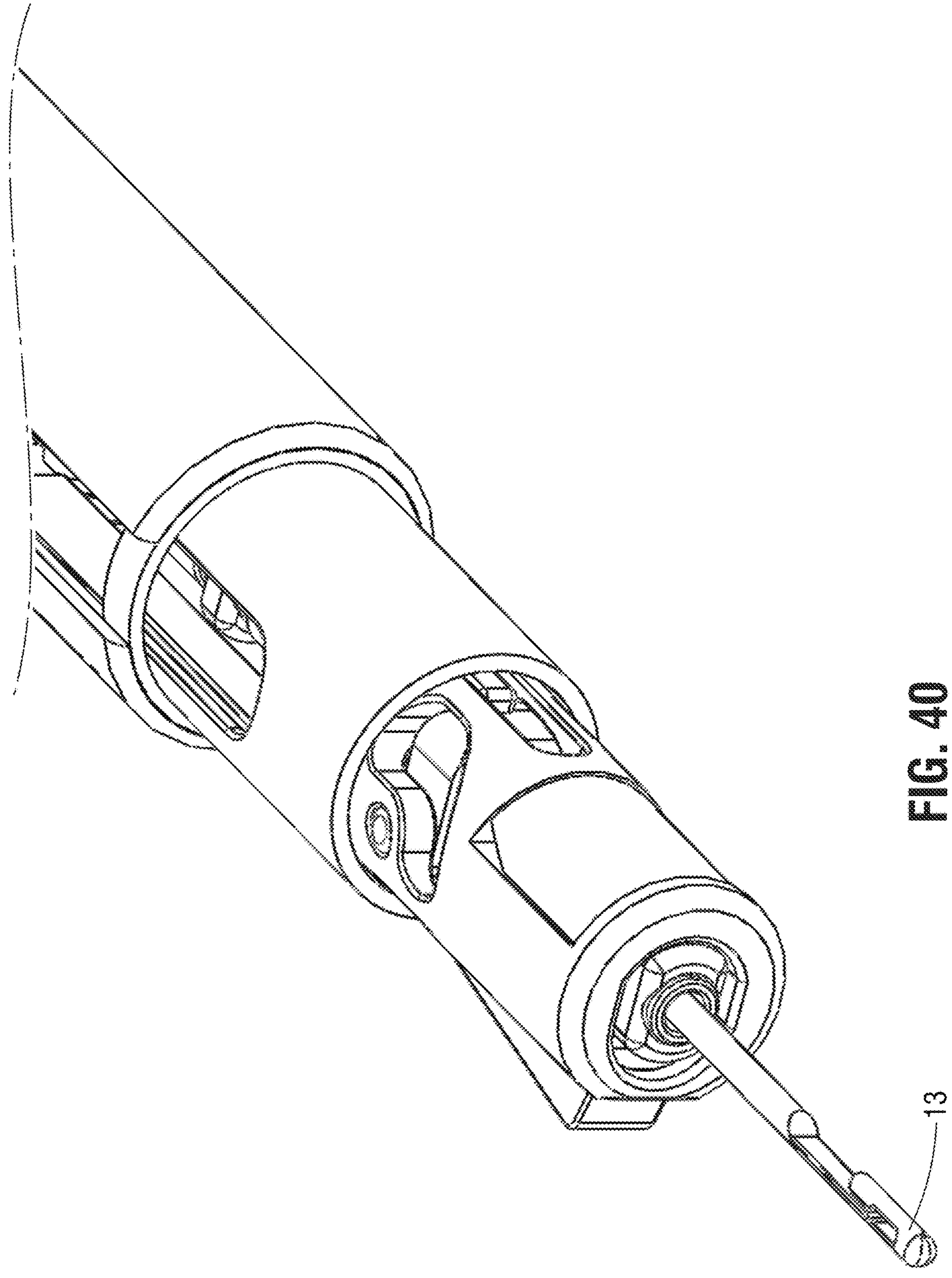
FIG. 40 is a fragmentary, enlarged perspective view of the end effector of FIG. 39.
Figure 41:
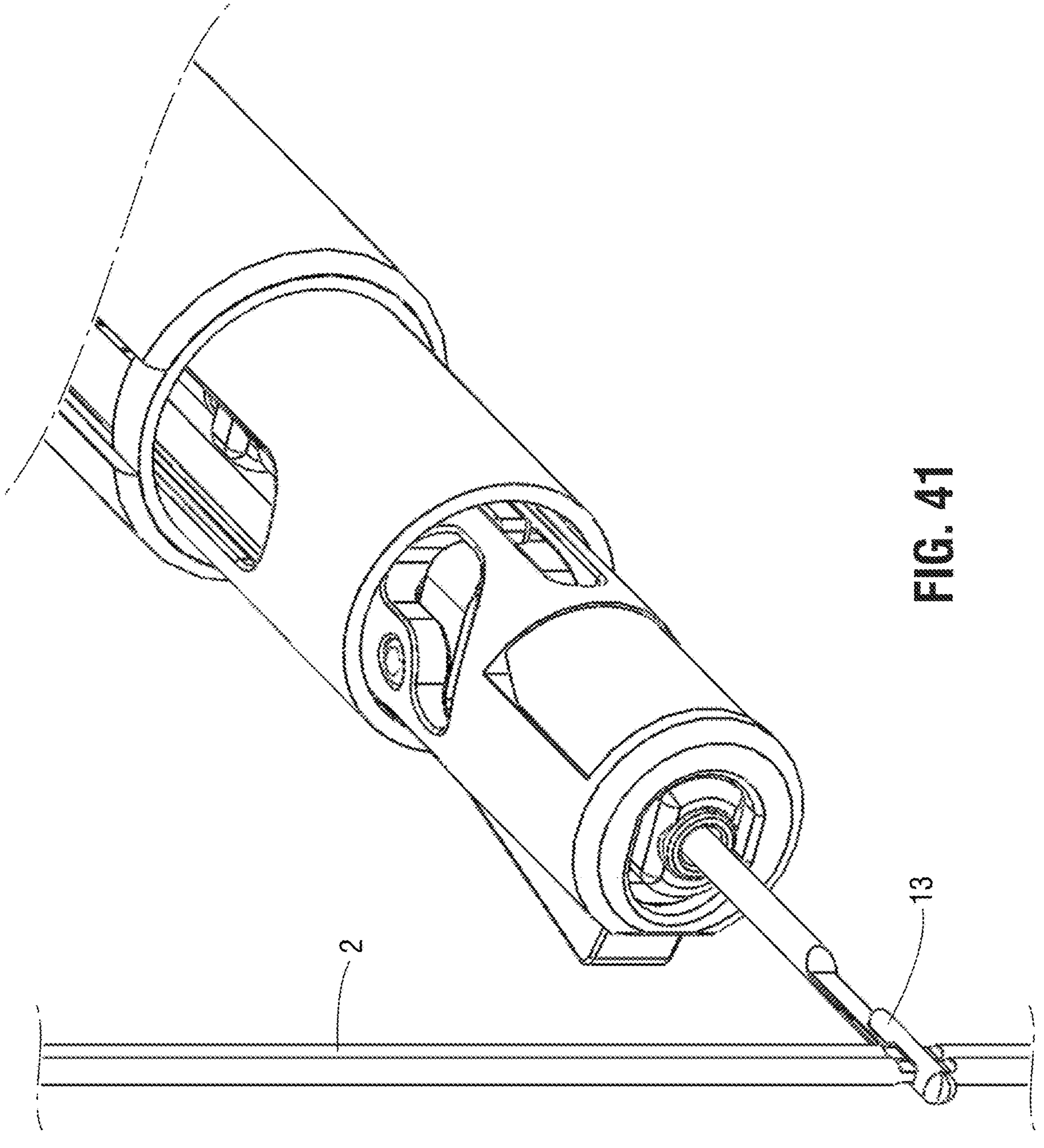
FIG. 41 is a fragmentary, enlarged perspective view of the end effector of FIG. 40 with the hook holding two leads of a suture.

An alternative to the loop 12 of the snare 10 is a hook needle configuration shown in FIGS. 39 to 41. Instead of the loop 12, the snare 10 has a hook 13 that is able to catch and hold the cords 2 as shown in FIG. 41. Like the loop 12, the hook 13 is pulled proximally until the ends 2' of the cords 2 release from the hook 13 and become loose for presentation to a user. The presentation can include the cord-lifting device 170, for example.

Another exemplary embodiment of a multiple-firing crimp device 200 is illustrated in FIGS. 42 to 56. In this multiple-firing crimp device 200, the crimp carriage 20 and the crimps 30 along with their respective movement sub-assemblies can be similar or identical to the previous embodiments described and shown. Thus, where identical structures are present, the same reference numerals may be used herein. Different structures, in contrast, have numbers with a prefix of two hundred. In the embodiment of FIGS. 42 to 56, the movement devices for placing and operating the snare 10 are included within a shuttle 280 that is movably displaced along the outer tube 270. In order to keep the shuttle 280 rotationally aligned in one orientation about the outer tube 270, the shuttle 280 and the outer tube 270 contain an alignment structure that can take many forms.

Figure 57:
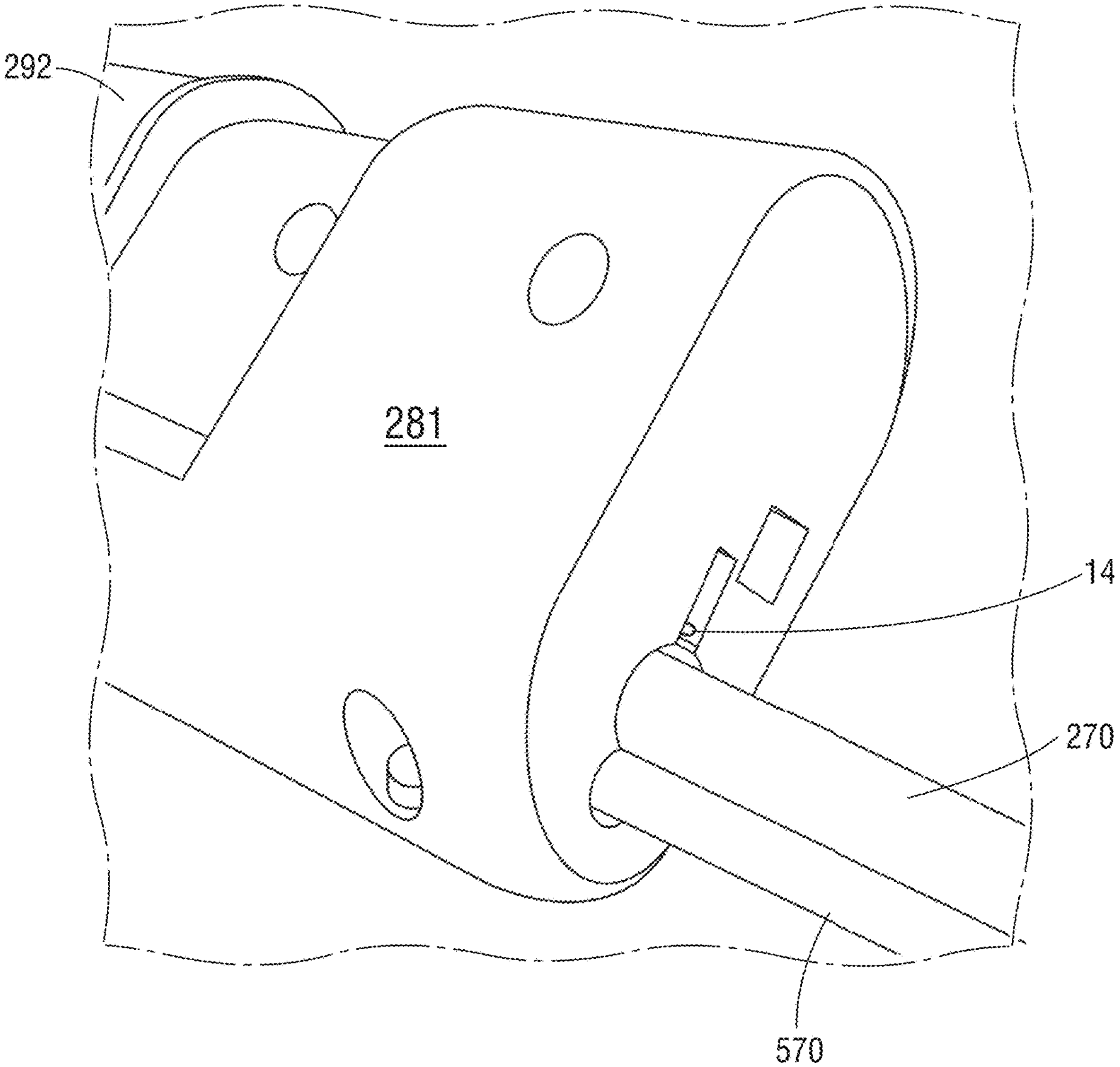
FIG. 57 is a photograph of a fragmentary, perspective view of an exemplary embodiment of a shuttle for the multiple-firing crimp device of FIG. 42

One possible form is a tongue-and-groove in which one of the shuttle 280 and the outer tube 270 has the groove and the other has the tongue. A further alignment device can attach a secondary tube or rod 570 to the bottom of the outer tube 270 and form a rail upon which a corresponding longitudinal orifice in the shuttle 280 slidably resides. In such a configuration, the cross-section of the outer tube 270 and rail can take the shape of an "8" (as shown in FIG. 57). The rail can have a different diameter than the diameter of the outer tube 270, for example, it can be smaller. Alternatively the outer tube 270 can have a non-round profile such as an oval or a hexagon. It is noted that all of the features of the handle 100 need not be illustrated and, therefore, only a diagrammatic portion of the handle 100 is shown.

The process for completing a crimp installation is described and/or shown in the transition from FIGS. 42 through 56, in which the various parts are introduced. The steps of loading the crimp 30' into the end effector body 240 and then withdrawing the crimp carriage 20 proximally for crimping is not repeated or shown here for the sake of brevity. In these figures, the crimp 30' has already been set into the end effector body 240 and is ready to be used and crimped on cords 2.

Figure 42:
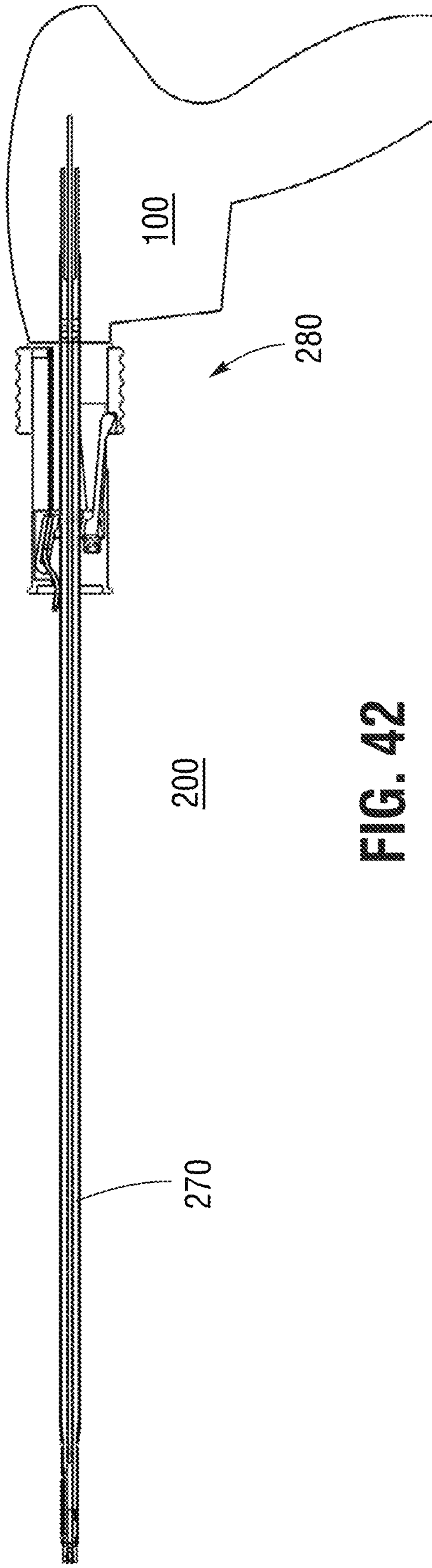
FIG. 42 is a fragmentary, longitudinally cross-sectional view of an exemplary embodiment of a multiple-firing crimp device having an end effector with a manually actuated crimp sub-assembly in a position with a first crimp loaded for use.
Figure 43:
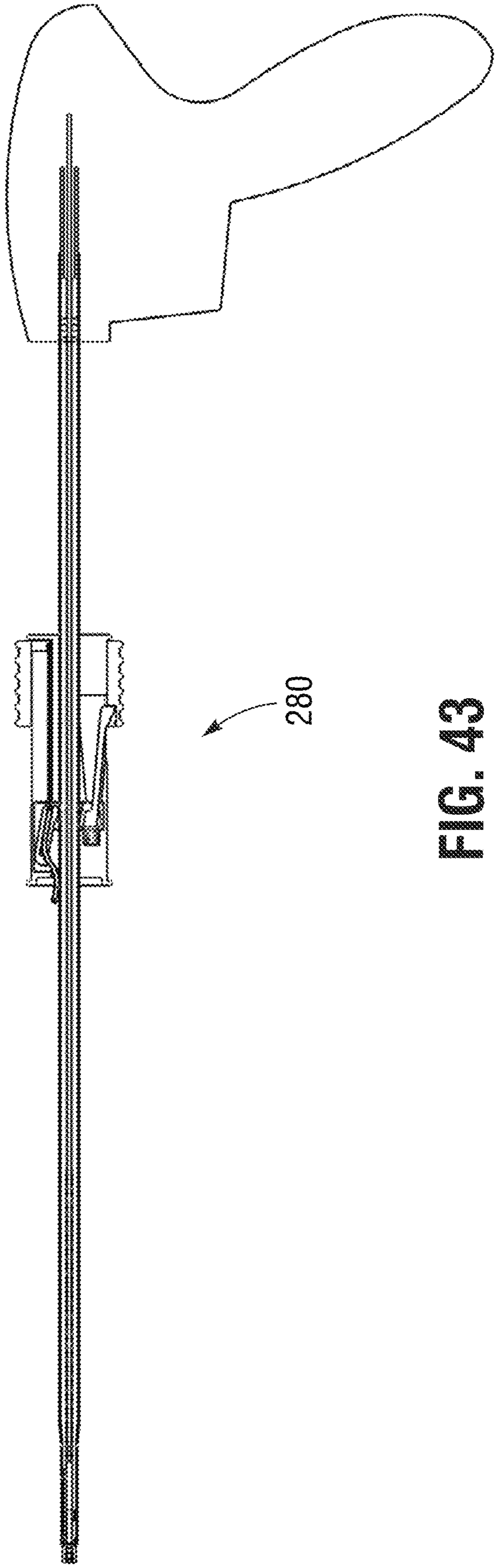
FIG. 43 is a fragmentary, longitudinally cross-sectional view of the multiple-firing crimp device of FIG. 42 with the manually actuated crimp sub-assembly in a partial snare-movement position toward the first crimp.

In FIG. 42, the manually actuated shuttle 280 is in a fully retracted position, in which position the steps of loading the crimp 30' into the end effector body 240 and then withdrawing the crimp carriage 20 proximally occurs. Accordingly, the first crimp 30' is in a position for use. FIG. 43 illustrates the shuttle 280 moving distally towards the end effector body 240. In both the fully retracted and intermediate positions almost to the distal end of the outer tube 270 (see FIGS. 44 to 48), a snare-extension tube 212 resides outside the outer tube 270.

Figure 44:
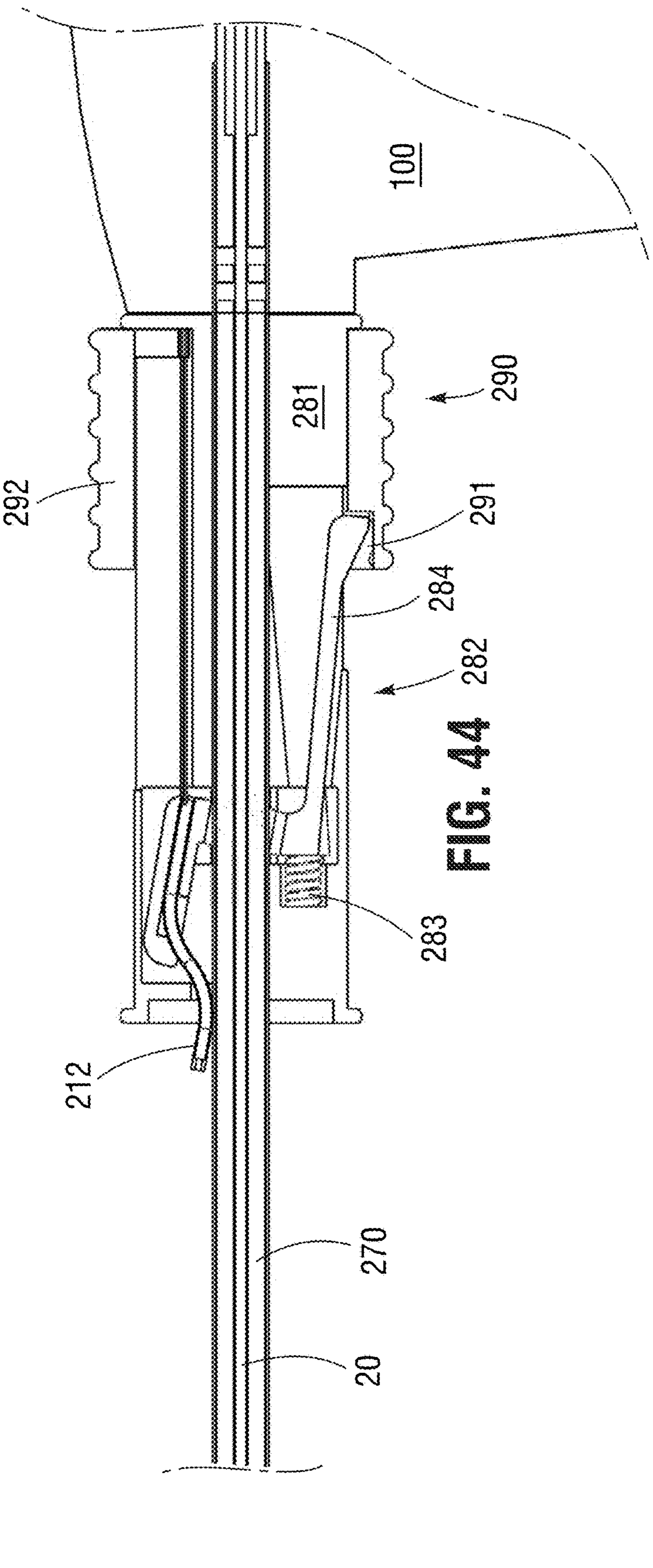
FIG. 44 is a fragmentary, enlarged, longitudinally cross-sectional view of the multiple-firing crimp device of FIG. 42.
Figure 45:
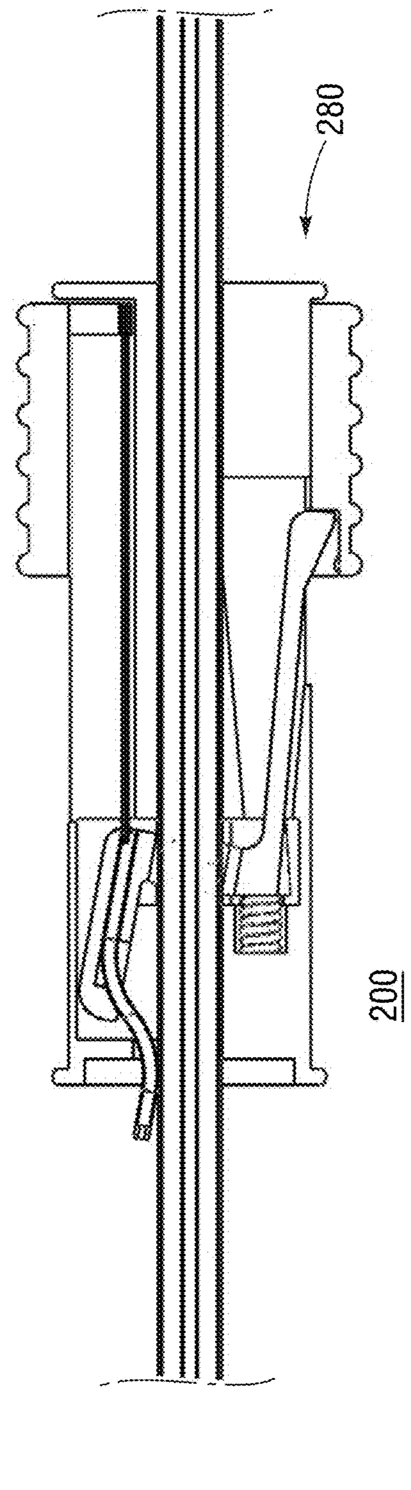
FIG. 45 is a fragmentary, enlarged, longitudinally cross-sectional view of the multiple-firing crimp device of FIG. 43.

The shuttle 280 includes a snare-aligning assembly 282 and a snare-movement assembly 290, both of which are illustrated, for example, in FIG. 44. The snare-aligning assembly 282 pivots the snare-extension tube 212 into and out of alignment with the central axis of the outer tube 270 so that the distal end of the snare-extension tube 212 can be placed adjacent or even enter the longitudinal cavity of the crimp 30' from the proximal side and, thereby, allow extension of the snare 210 directly through the crimp 30'. The pivot of the snare-aligning assembly 282 is disposed approximately at the midpoint of a vertical height of the shuttle body 281 and, because the outer tube 270 is present in these figures, the pivot is obscured from view. The pivoting action can be seen in the transition from FIGS. 48 to 49. The snare-aligning assembly 282 is biased with a force from a bias device 283 that presses the snare-extension tube 212 downwards against the outer surface of the outer tube 270. In this manner, the outer surface of the outer tube 270 acts as a cam surface to the snare-extension tube 212.

Additionally, the snare-aligning assembly 282 also has a lock-out arm 284 extending proximally from the bias device 283 and residing in a pocket 291 of the snare-movement assembly 290. The lock-out arm 284 has a proximal surface that opposes the distal-facing interior surface of the pocket 291 and, when the proximal end of the lock-out arm 284 is disposed in the pocket 291, the proximal surface prevents distal longitudinal movement of a snare-extender slide 292 until the lock-out arm 284 exits the pocket 291. In this manner, until the snare-aligning assembly 282 is able to pivot the snare-extension tube 212 into alignment with the crimp 30', the snare-extender slide 292 is longitudinally fixed from moving distally.

Figure 46:
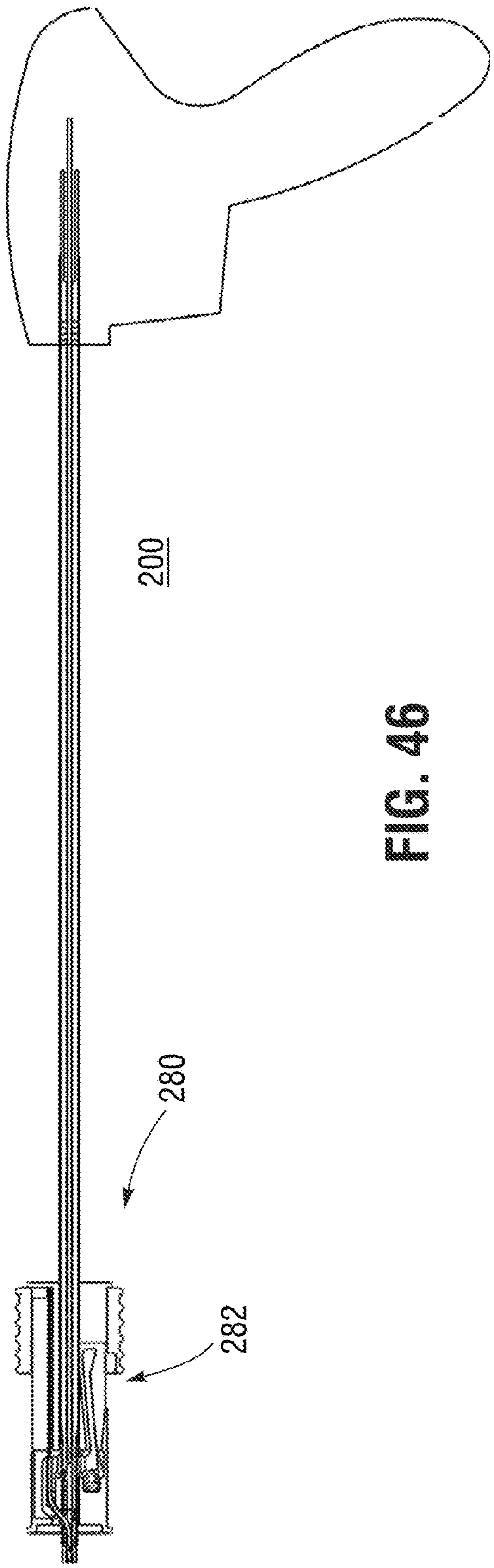
FIG. 46 is a fragmentary, longitudinally cross-sectional view of the multiple-firing crimp device of FIG. 42 with the manually actuated crimp sub-assembly lowering the snare guide tube into the snare guide tube loading track and axially aligning with the center of the first crimp.
Figure 47:
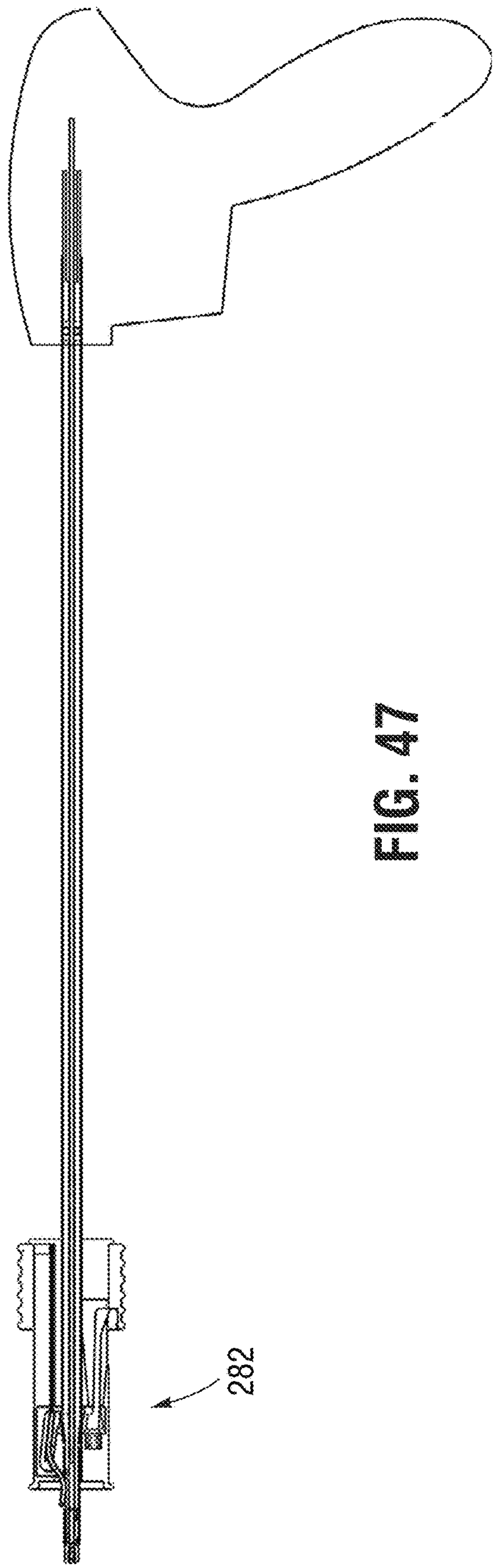
FIG. 47 is a fragmentary, longitudinally cross-sectional view of the multiple-firing crimp device of FIG. 42 with the manually actuated crimp sub-assembly inserting the snare guide tube up to the center of the first crimp for receiving therein the snare, the lowering of the snare guide tube unlocking the snare assembly for distal movement.
Figure 48:
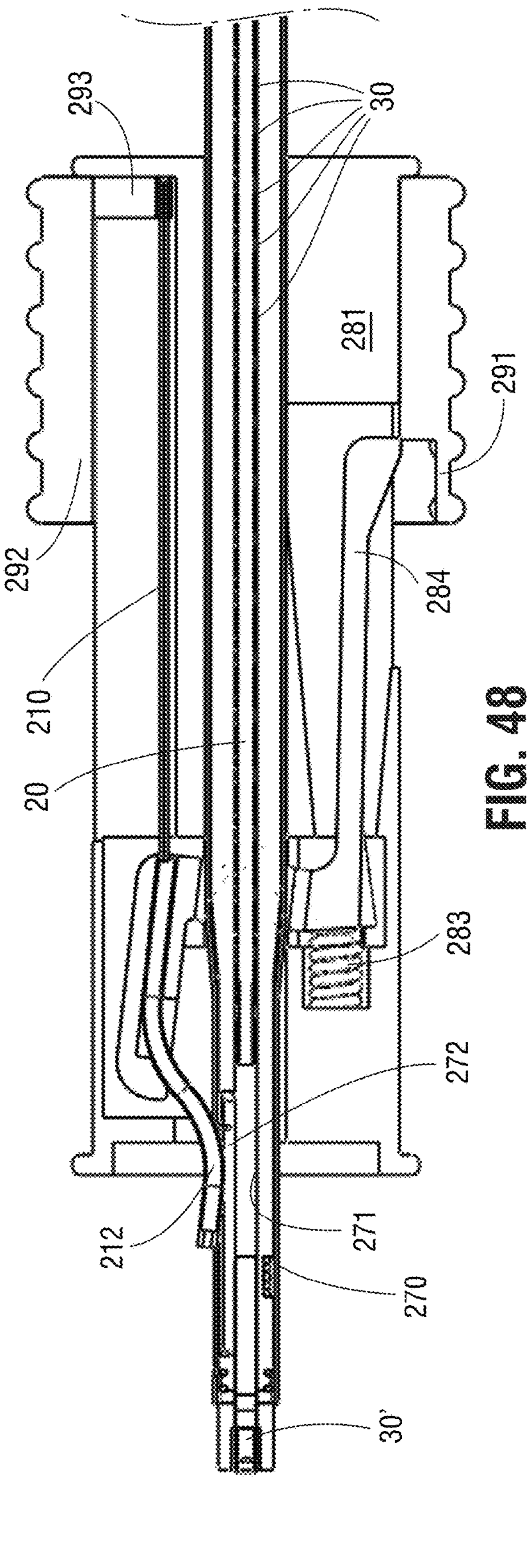
FIG. 48 is a fragmentary, enlarged, longitudinally cross-sectional view of the multiple-firing crimp device of FIG. 46.
Figure 49:
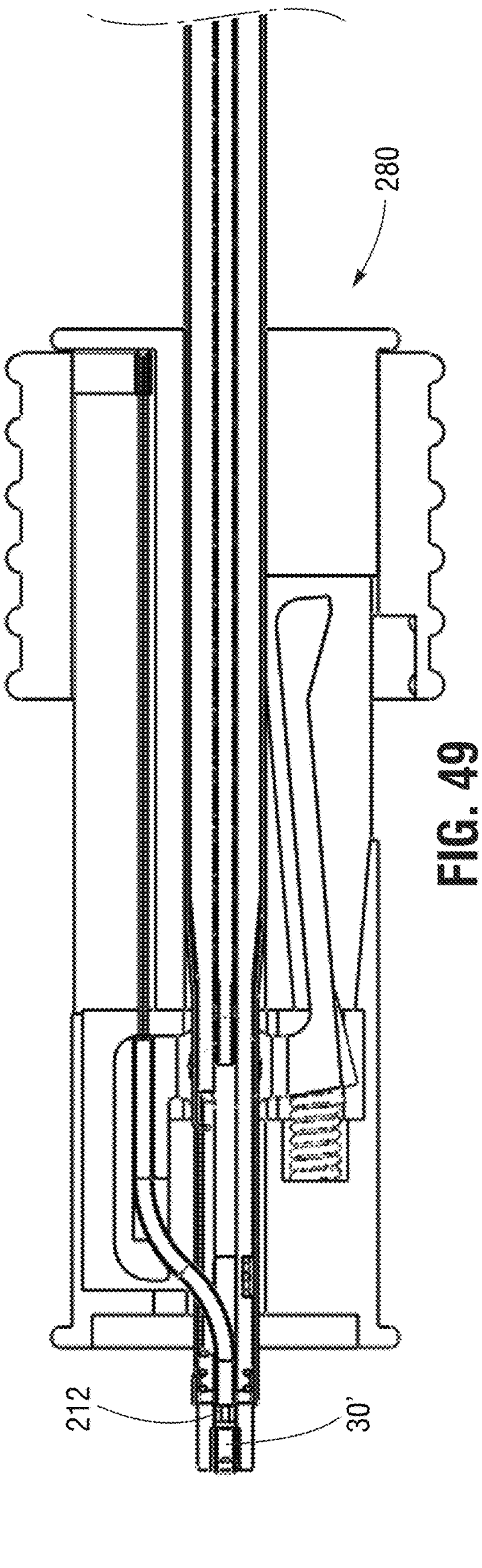
FIG. 49 is a fragmentary, enlarged, longitudinally cross-sectional view of the multiple-firing crimp device of FIG. 47.
Figure 50:
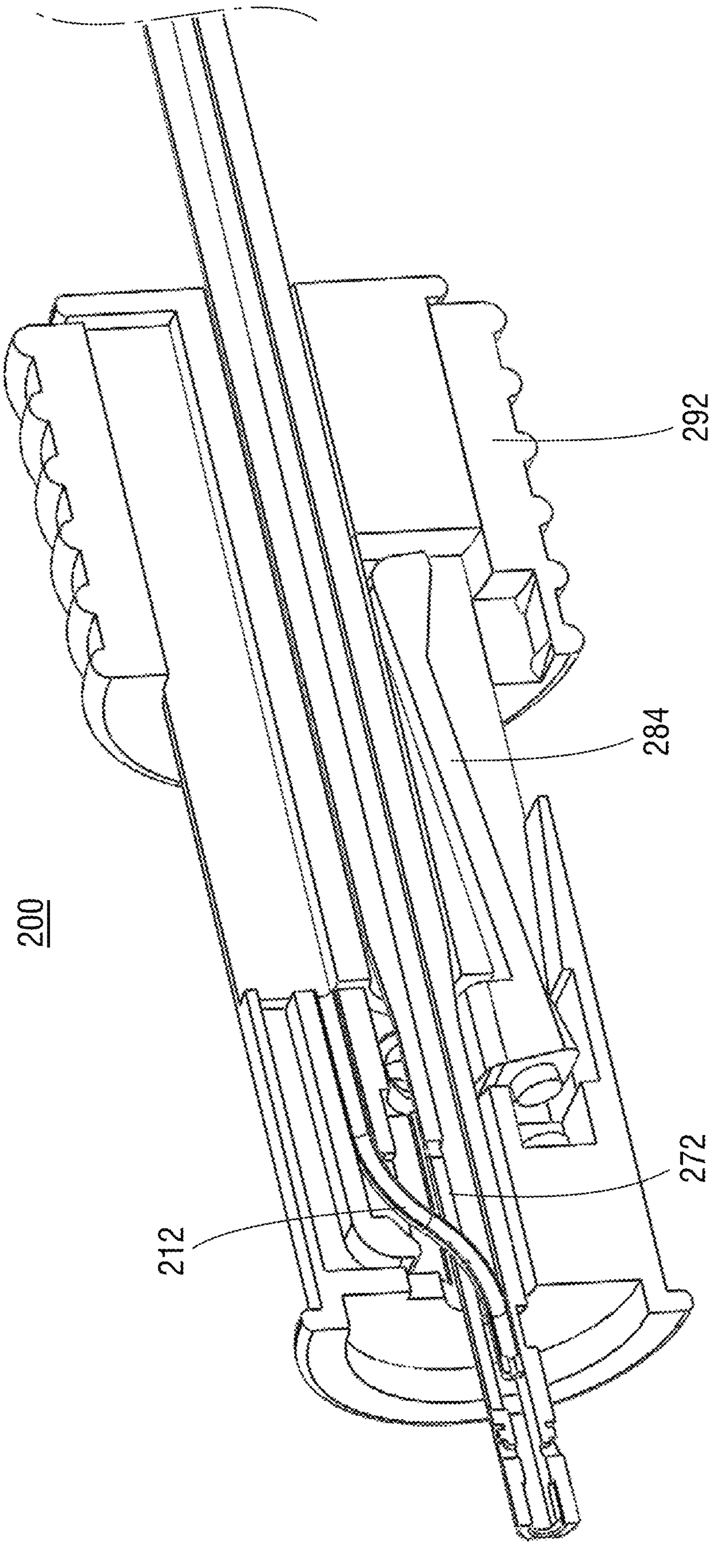
FIG. 50 is a fragmentary, enlarged, partially longitudinally cross-sectional view of the multiple-firing crimp device of FIG. 47.

FIGS. 46 and 47 illustrate the longitudinal positions of the shuttle 280 on the outer tube 270 at which the pivoting movement of the snare-aligning assembly 282 is made possible, which movement unlocks the snare-extender slide 292. FIGS. 48 and 49 are close-up views of the shuttle 280 in its respective positions in FIGS. 46 and 47. Movement of the snare-extension tube 212 is dependent upon the exterior surface of the outer tube 270. Accordingly, to allow the distal end of the snare-extension tube 212 to align with the lumen in which the crimp carriage 20 travels, the outer tube 270 has a longitudinal slot 272. The shape of the slot 272 acts as a track to guide and insert the distal end of the snare-extension tube 212 up to or into the proximal end of the crimp 30'. As such, when the shuttle 280 passes the position on the outer tube 270 shown in FIG. 48, the snare-extension tube 212 enters the slot 272 and drops against and into the inner carriage lumen 271 of the outer tube 270, as shown in FIGS. 49 and 50. When this dropping movement occurs, the pivot of the snare-aligning assembly 282 is complete and the lock-out arm 284 no longer impedes distal movement of the snare-extender slide 292. In this state, the distal opening of the snare-extension tube 212 is axially aligned with the center of the crimp 30'.

Also revealed in detail in FIGS. 48 and 49 is the crimp carriage 20 carrying a set of crimps 30. In these views, eighteen crimps 30 are illustrated. This number, however, is only exemplary and the number can be as little or as great as desired dependent upon the procedure being carried out. In these figures, the carriage lumen 271 has the polygonal shape to keep the crimps 30 aligned but this keying feature is not illustrated.

With the snare-extender slide 292 unlocked for distal movement, extension of the snare is now made possible. The snare 210 is different from the above embodiments in that the distal end is no longer connected to the handle 100. Here, in contrast, the snare 210 is connected, at its proximal end, to a tab 293 that is fixed to or integral with the snare-extender slide 292. As such, the longitudinal length of the snare 210 (or its movement shaft) is significantly shorter than those in the previous embodiments. In this manner, when the snare-extender slide 292 moves distally, the snare 210 also moves distally. In these figures, the distal portion of the snare with the loop 12 and the tip 14 are within the snare-extension tube 212 but are hidden for clarity. As the snare 210 is relatively flexible and could possibly buckle when pushed distally out of the snare-extension tube 212, a non-illustrated support tube (typically polymer based) surrounds the proximal portion of the snare 210 within the shuttle body 281. This support tube can be attached to or be integral with the snare-extender slide 292. The length of the support tube should be such that the distal end of the support tube is not able to be freed from the proximal end of the snare-extension tube 212, thus keeping the two always aligned and preventing exit of the snare 210 from either.

Figure 51:
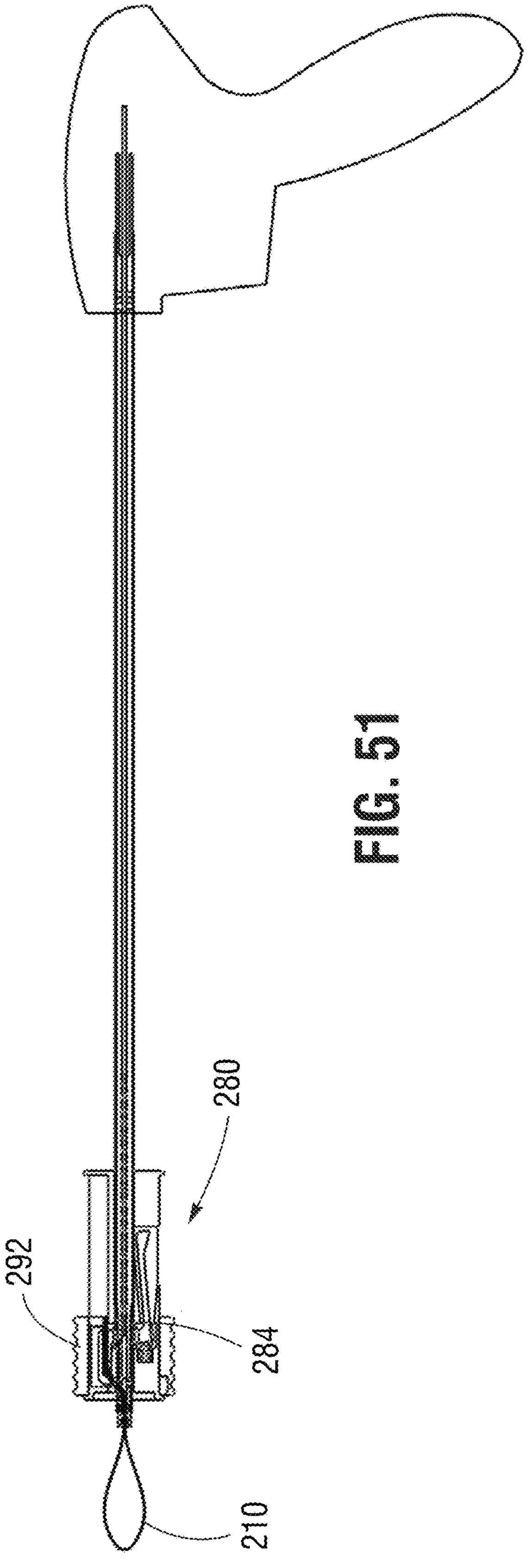
FIG. 51 is a fragmentary, longitudinally cross-sectional view of the multiple-firing crimp device of FIG. 42 with the manually actuated crimp sub-assembly extending the snare through the snare guide tube and through and out from the first crimp for receiving therein the cords to be snared, movement of the outer body being locked and only permitting movement of the snare assembly for snare movement.
Figure 52:
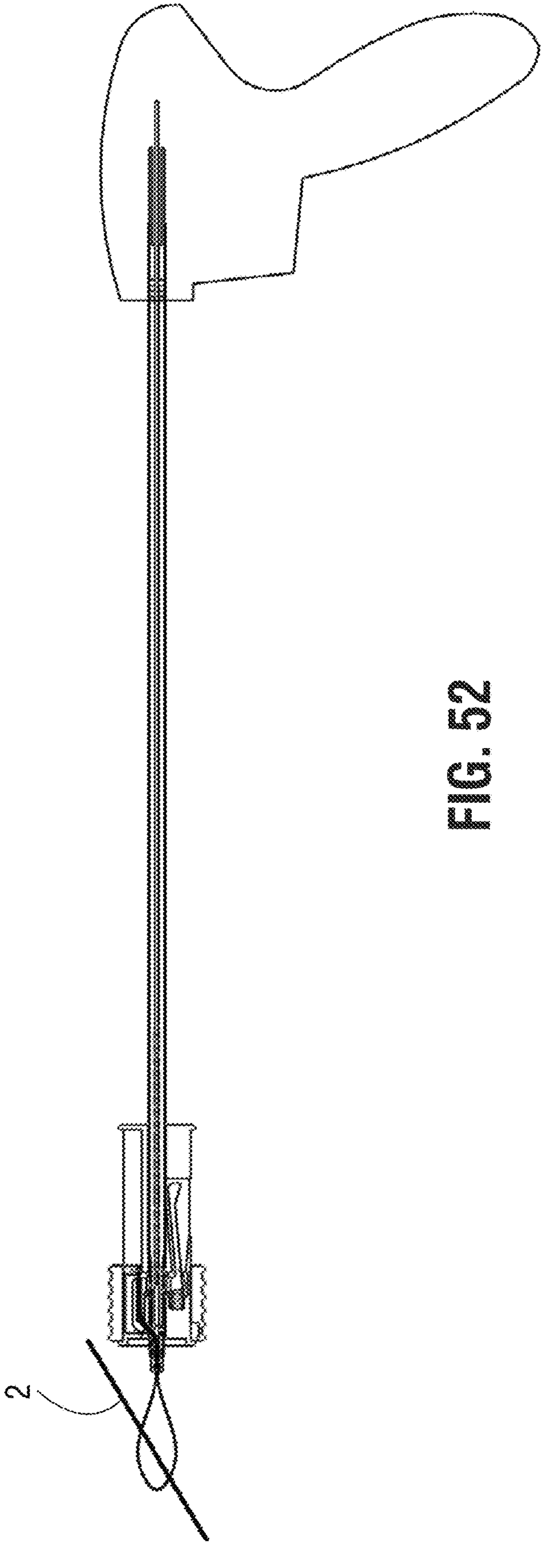
FIG. 52 is a fragmentary, longitudinally cross-sectional view of the multiple-firing crimp device of FIG. 51 with cords in the snare.
Figure 53:
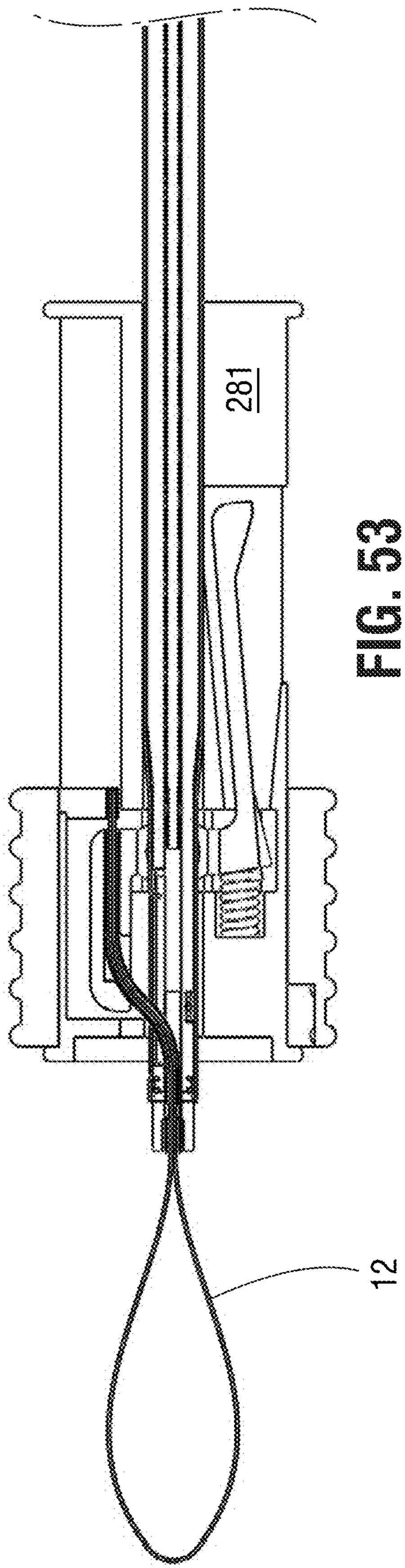
FIG. 53 is a fragmentary, enlarged, longitudinally cross-sectional view of the multiple-firing crimp device of FIG. 51.
Figure 54:
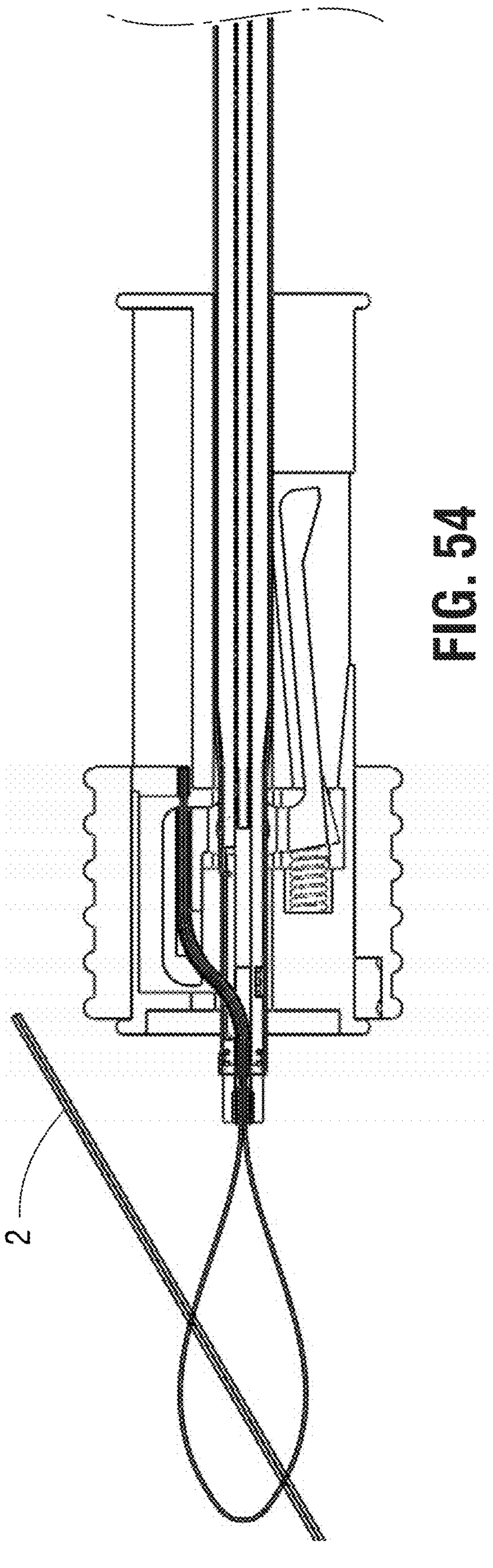
FIG. 54 is a fragmentary, enlarged, longitudinally cross-sectional view of the multiple-firing crimp device of FIG. 52.
Figure 55:
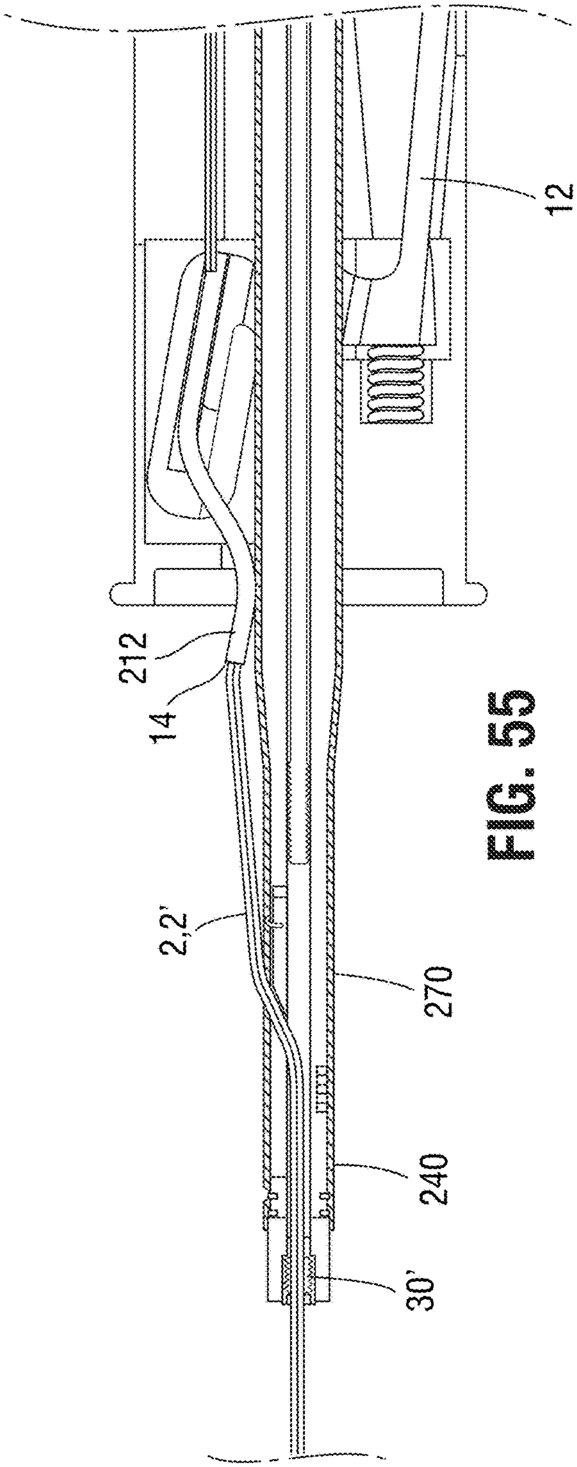
FIG. 55 is a fragmentary, enlarged, longitudinally cross-sectional view of the multiple-firing crimp device of FIG. 42 with the manually actuated crimp sub-assembly having retracted the snare and the cords along with the snare guide tube out from the distal end of the shaft assembly and having pulled the cords through the first crimp, movement of the outer body being free in the proximal direction and movement of the snare assembly being free to retract the snared cords.
Figure 56:
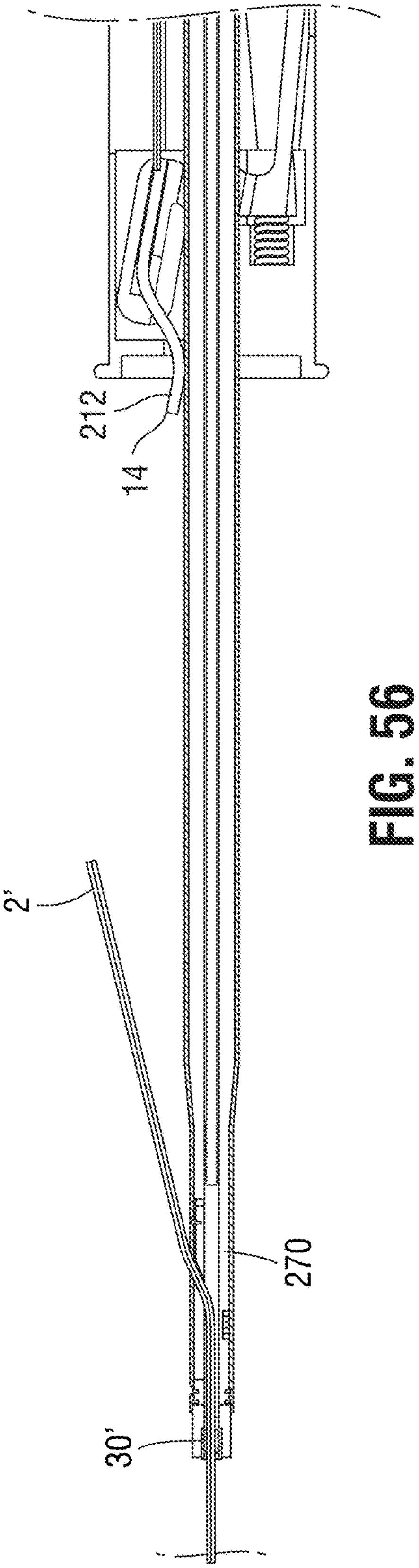
FIG. 56 is a fragmentary, enlarged, longitudinally cross-sectional view of the multiple-firing crimp device of FIG. 42 with the manually actuated crimp sub-assembly having completely retracted the snare from the cords to allow a user to manually pull the free ends of the previously snared suture tight and to place the crimp adjacent to the loop of the cords where crimping is to take place after the user pulls tightly on the cords to place the distal end of the device at the cord-tying location.

The snare 210 can now be extended, as shown in FIGS. 51 and 53. As the snare-extender slide 292 moves distally, the distal end of the snare 210 emerges from inside the crimp 30' and finally exits to the environment distal of the shuttle 280 so that the loop 12 opens to define an area into which the cords 2 are inserted, as shown in FIGS. 52 and 54. In FIGS. 51 to 54, the tip 14 of the snare 210 is not illustrated for clarity.

It is undesirable for the shuttle 280 to move longitudinally in any way while the snare 210 is moving distally from the position shown in FIGS. 49 and 50. Accordingly, movement of the shuttle body 281 is locked when the snare-extender slide 292 moves. Such a movement prevention device is not illustrated in FIGS. 42 to 56, but there is one shown in FIG. 60, in which a spring clip 590 engages an opening in the shaft 270 (or 570) when the shuttle is in its distal-most, snare-extending position. The motion of the spring clip 590 into the opening frees the snare-extender slide 292, allowing it to now move distally while simultaneously locking the shuttle 280 in the snare-extending position.

Once the cords 2 are inserted into the exposed and expanded loop 12 of the snare 10, retraction of the cords 2 through the center of the crimp 30' is now possible. To effect this retraction, the user moves the snare-extender slide 292 proximally, in which position all but the tip 14 of the snare 210 is retracted back into the shuttle body 281, as shown in FIGS. 57 and 153. The orientation of the tip 14 while the snare-extender slide 292 is in it proximal-most position is illustrated in FIGS. 57 and 153. At this point, a portion or all of the free ends of the cords 2 are still within the end effector body 240 or are distal of the crimp 30' while the cords 2 are threaded through the tip 14. Now that the snare-extender slide 292 is proximal, proximal movement of the shuttle body 281 becomes possible given the fact that the spring clip 590 is free to flex back to its home position outside the opening in the shaft 270, 570 (because the interlock holding the shuttle body 281 has disengaged). The user continues retraction of the shuttle 280 with the snare and the coupled cords 2 proximally until the free ends 2' pass entirely through the crimp 30', exit the shaft through slot 272, completely shorten, and finally exit the tip 14, as is shown in the transition from FIG. 55 to FIG. 56.

At this point, the user is presented with the free ends 2' outside the outer tube 270 and is now able to manually pull the free ends 2' of the previously snared cords 2 tight and place the crimp 30' adjacent to the distal loop of the cords 2 (not illustrated but to the left of FIG. 56) where crimping is to take place. While pulling tightly on the free ends 2' of the cords 2, the user can place the distal end of the device where the crimp 30' is being held at a cord-fixing location. Actuation devices of the handle 100 (as described above) cause the crimp 30' to compress on and fix the cords 2 together and, thereafter or simultaneously, also cut the cords 2 just proximal of the crimped crimp 30'. The shuttle 280 is moved to its start position shown in FIGS. 42 and 44, thereby placing the device in a position to load the next crimp 30" into the crimp orifice 42.

The snare 10 is secured at its proximal end to the snare-extender slide 292 (e.g., at tab 293) positioned adjacent the proximal end of the shuttle 280. Because the travel distance of the snare-extender slide 292 is greater than or equal to the length of the snare that is to extend outward from the shuttle 280 in the distal direction, the shuttle 280 must have a longitudinal length that is dependent upon and is at least as long as the length of that snare. In other words, the extension of the snare 10 by the snare-extender slide 292 is 1:1. If the length of the shuttle 280 requires it to have significant weight or to have a length that is greater than is needed, it would be desirable to provide an assembly that permits a greater than 1:1 ratio and reduces the longitudinal length and/or weight.

Figure 58:
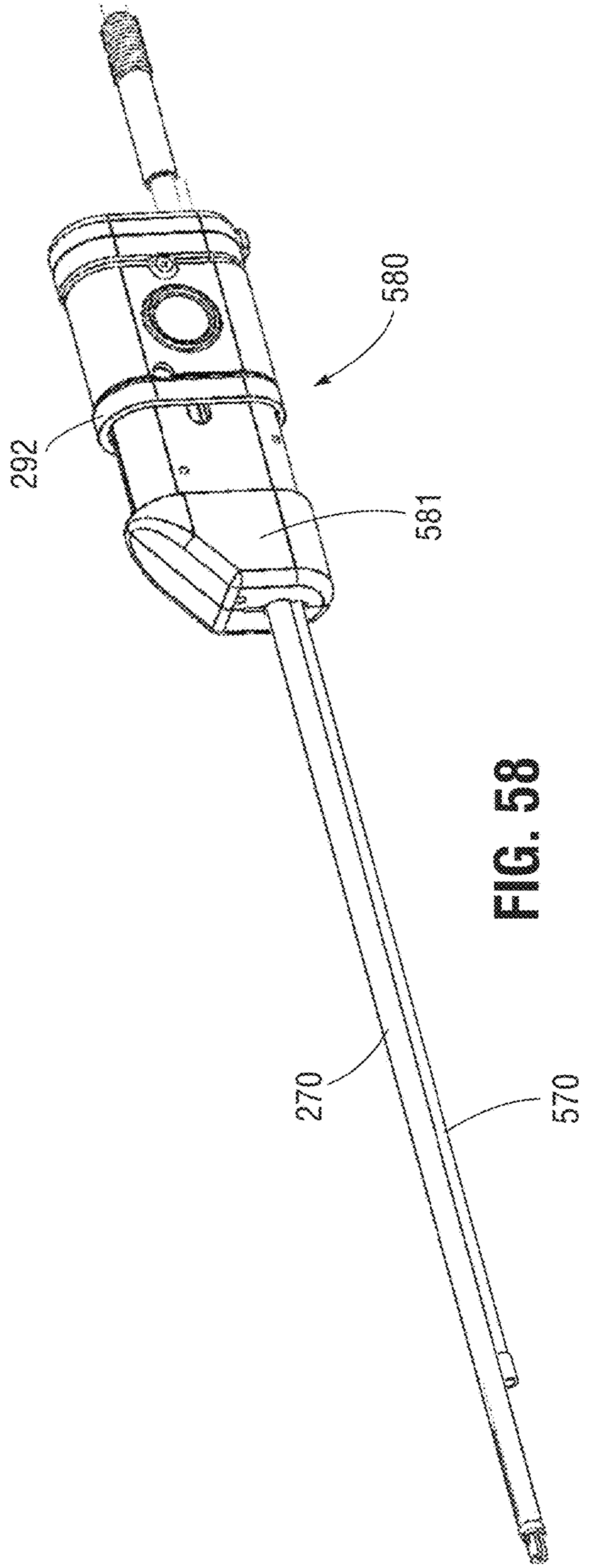
FIG. 58 is a fragmentary, perspective view of an exemplary embodiment of a multiple-firing crimp device having an end effector with a manually actuated crimp sub-assembly in a position with a first crimp loaded for use, with a shuttle in a ready to use state, and with a handle removed.

In the embodiments of FIGS. 58 to 74, the movement devices for placing and operating the snare 10 are included within a shuttle 580 that is movably displaced along the outer tube 270. This shuttle 580 is able to be shorter and lighter than the shuttle 280. To keep the shuttle 580 rotationally aligned in one orientation about the outer tube 270, the shuttle 580 and the outer tube 270 contain an alignment structure that can take many forms. One possible form is a tongue-and-groove in which one of the shuttle 580 and the outer tube 270 has the groove and the other has a tongue. A further alignment device can attach a secondary tube or rod 570 to the bottom of the outer tube 270 and form a rail upon which a corresponding longitudinal orifice in the shuttle 580 slidably resides. In such a configuration, as shown in FIG. 58, the cross-section of the outer tube 270 and the rail 570 takes the shape of an "8". As above, the rail 570 can have a different diameter than the diameter of the outer tube 270, for example, it can be smaller. It is noted here that all of the features of the handle 100 need not be illustrated here and, therefore, the handle 100 is omitted.

The shuttle 580 depicted in FIGS. 58 to 74 provides a snare extension to slide movement length in a ratio that is greater than 1:1 and, at the same time, reduces the longitudinal length and weight of the shuttle 580. These features are provided by removing the longitudinal tube fixed to the snare-movement slide and replacing it with a rack-and-pinion snare-movement assembly having the snare wrapped around a snare discharge spool. In this shuttle 580 for the multiple-firing crimp devices herein, the crimp carriage 20 and the crimps 30 along with their respective movement sub-assemblies can be similar or identical to the previous embodiments described and shown. Thus, where identical structures are present, the same reference numerals will be used herein. Different structures, in contrast, will have numbers with a prefix of five hundred.

Figure 59:
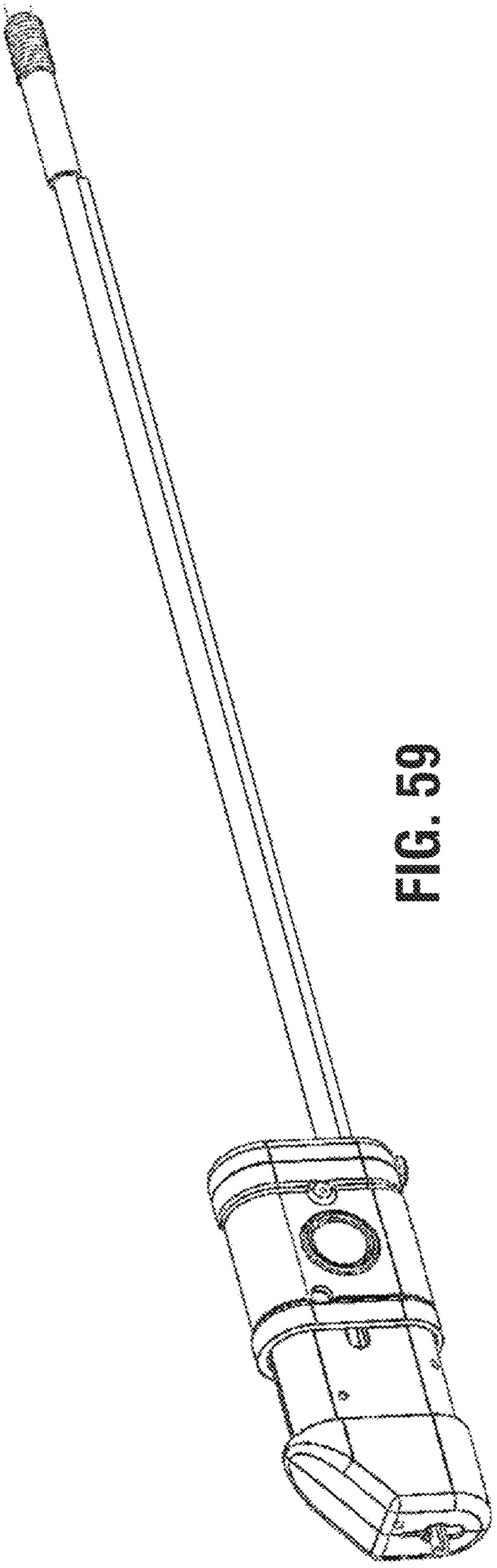
FIG. 59 is a fragmentary, perspective view of the multiple-firing crimp device of FIG. 58 with the manually actuated crimp sub-assembly with the shuttle in a snare-movement position.
Figure 60:
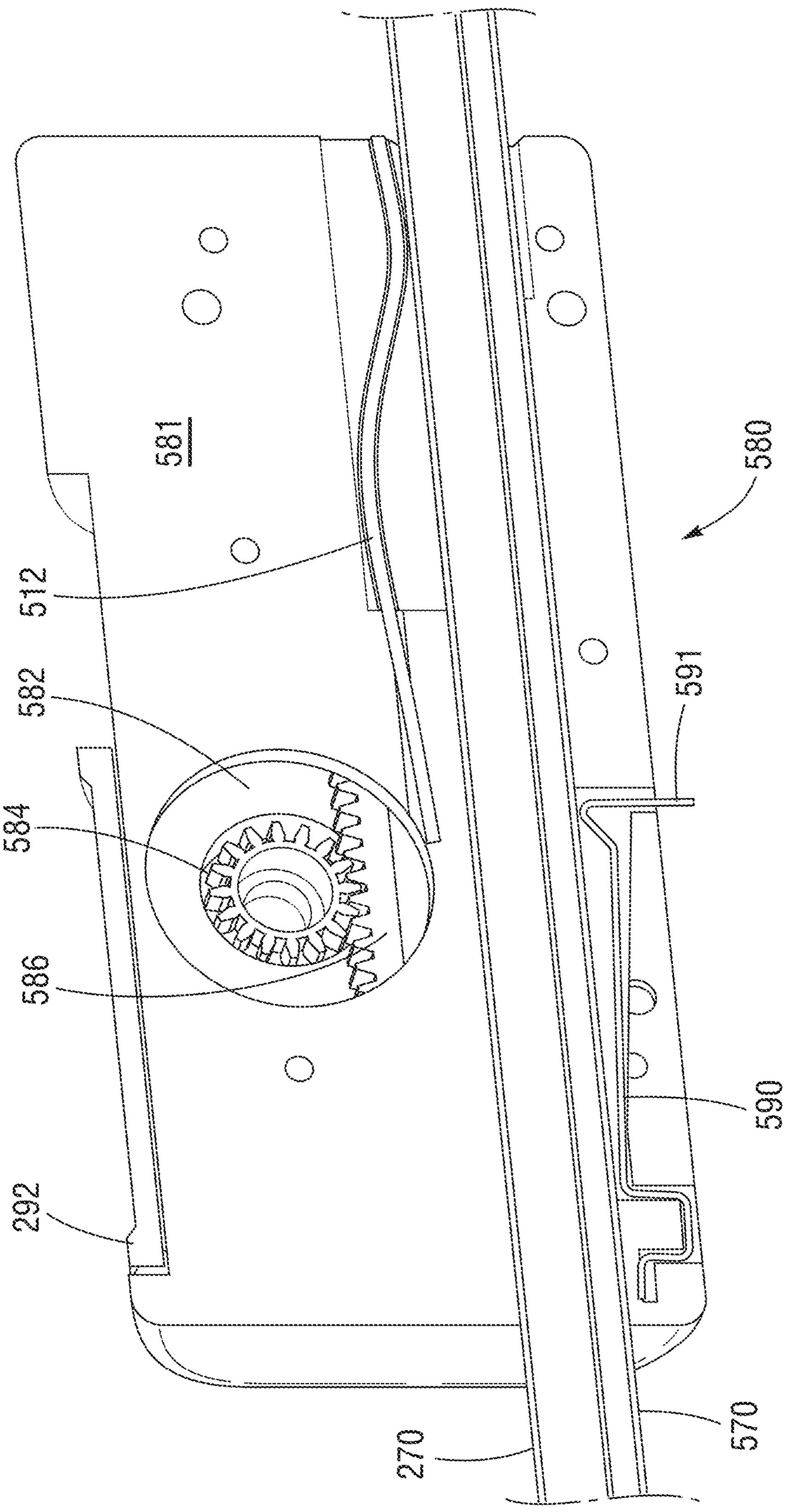
FIG. 60 is a fragmentary, enlarged, longitudinally cross-sectional view of the multiple-firing crimp device of FIG. 58 with the shuttle in an intermediate position between the handle and the crimp and with a snare scroll removed.
Figure 61:
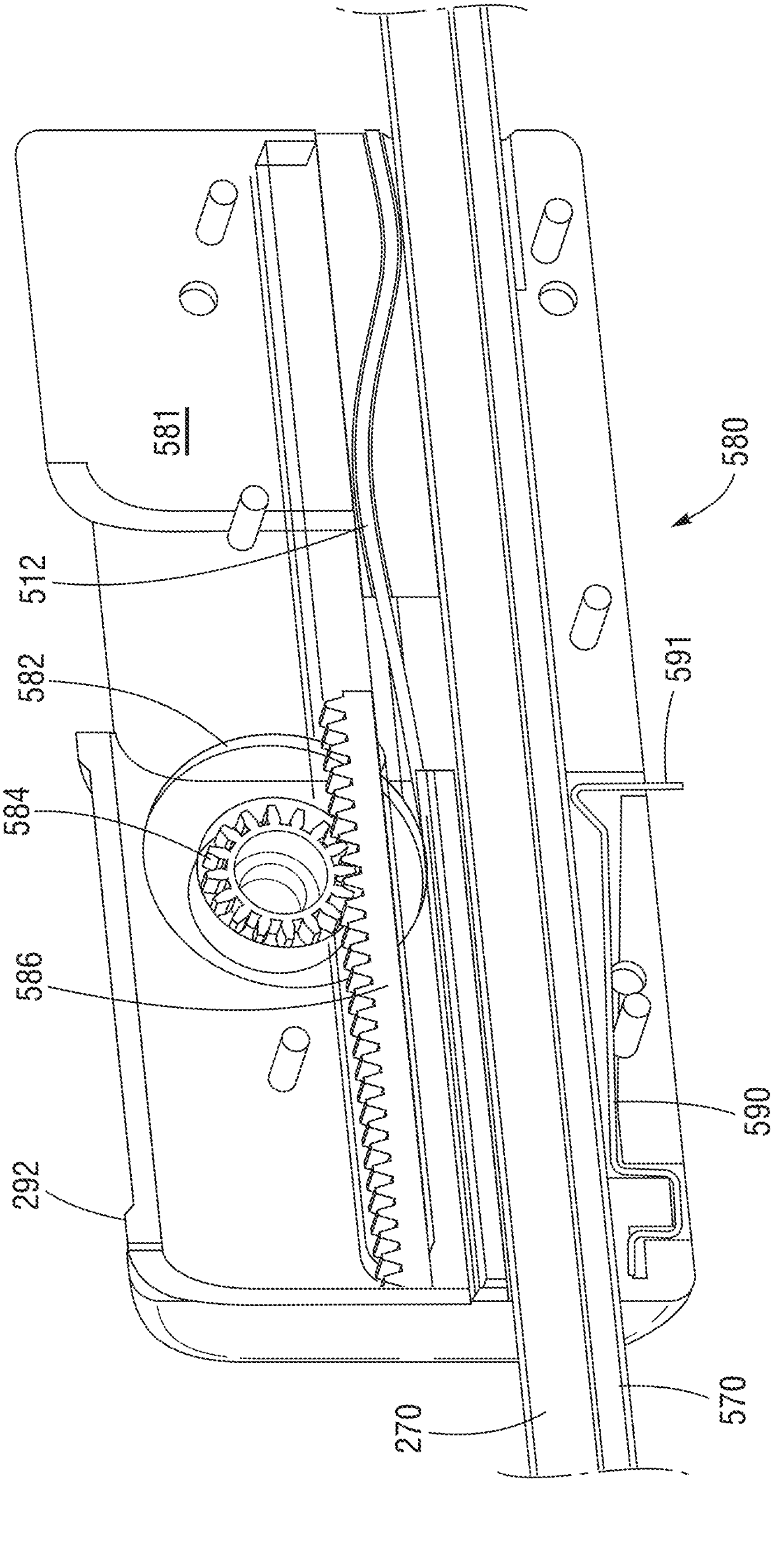
FIG. 61 is a fragmentary, enlarged, partially transparent, longitudinally cross-sectional view of the multiple-firing crimp device of FIG. 58 with the shuttle in an intermediate position between the handle and the crimp and with the snare scroll removed.
Figure 62:
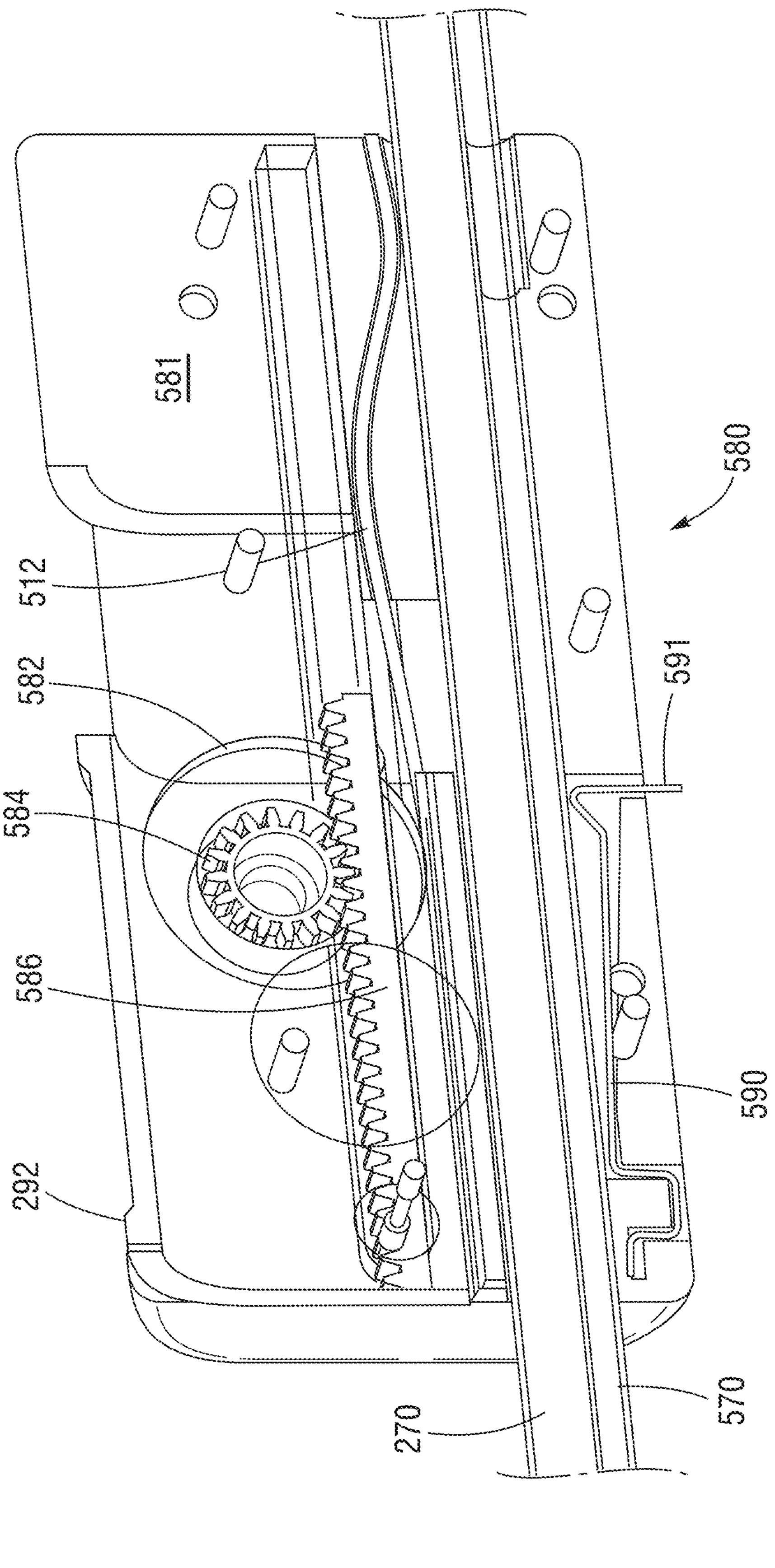
FIG. 62 is a fragmentary, enlarged, transparent, longitudinally cross-sectional view of the multiple-firing crimp device of FIG. 58 with the shuttle in an intermediate position between the handle and the crimp and with the snare scroll removed.
Figure 63:
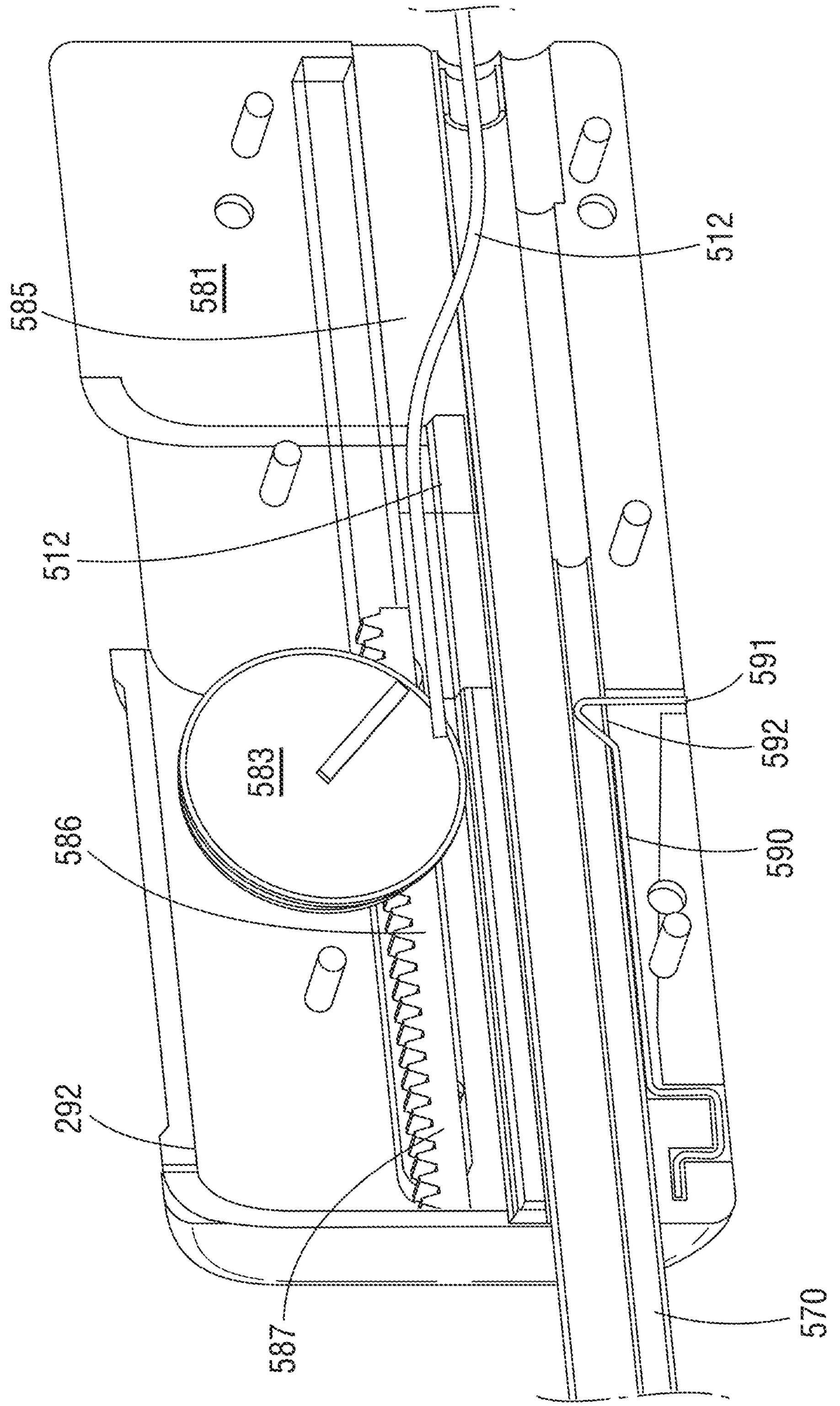
FIG. 63 is a fragmentary, enlarged, partially transparent, longitudinally cross-sectional view of the multiple-firing crimp device of FIG. 59 with the shuttle in a snare-movement position.
Figure 64:
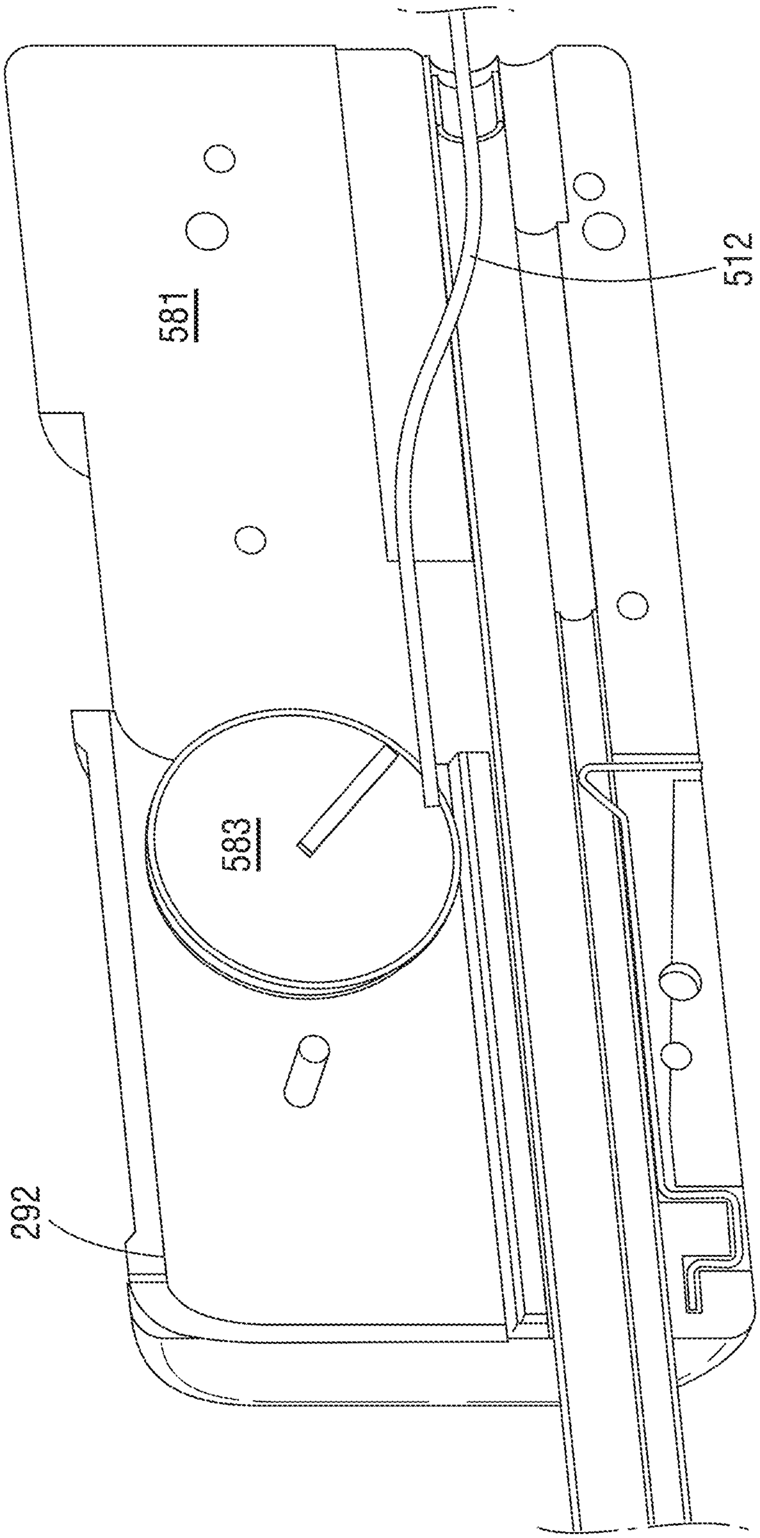
FIG. 64 is a fragmentary, enlarged, longitudinally cross-sectional view of the multiple-firing crimp device of FIG. 59 with the shuttle in the snare-movement position.
Figure 65:
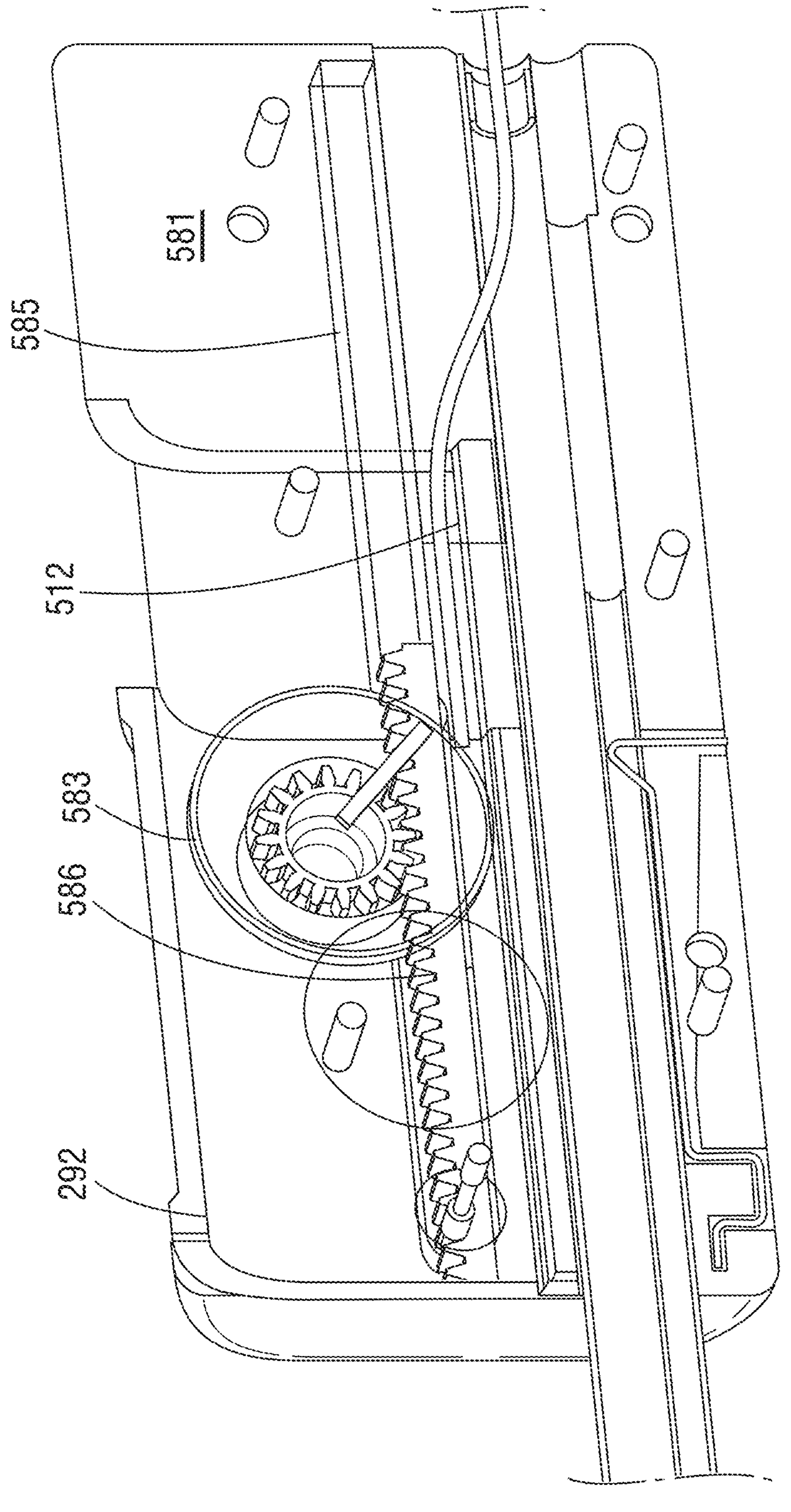
FIG. 65 is a fragmentary, enlarged, transparent, longitudinally cross-sectional view of the multiple-firing crimp device of FIG. 59 with the shuttle in the snare-movement position.
Figure 66:
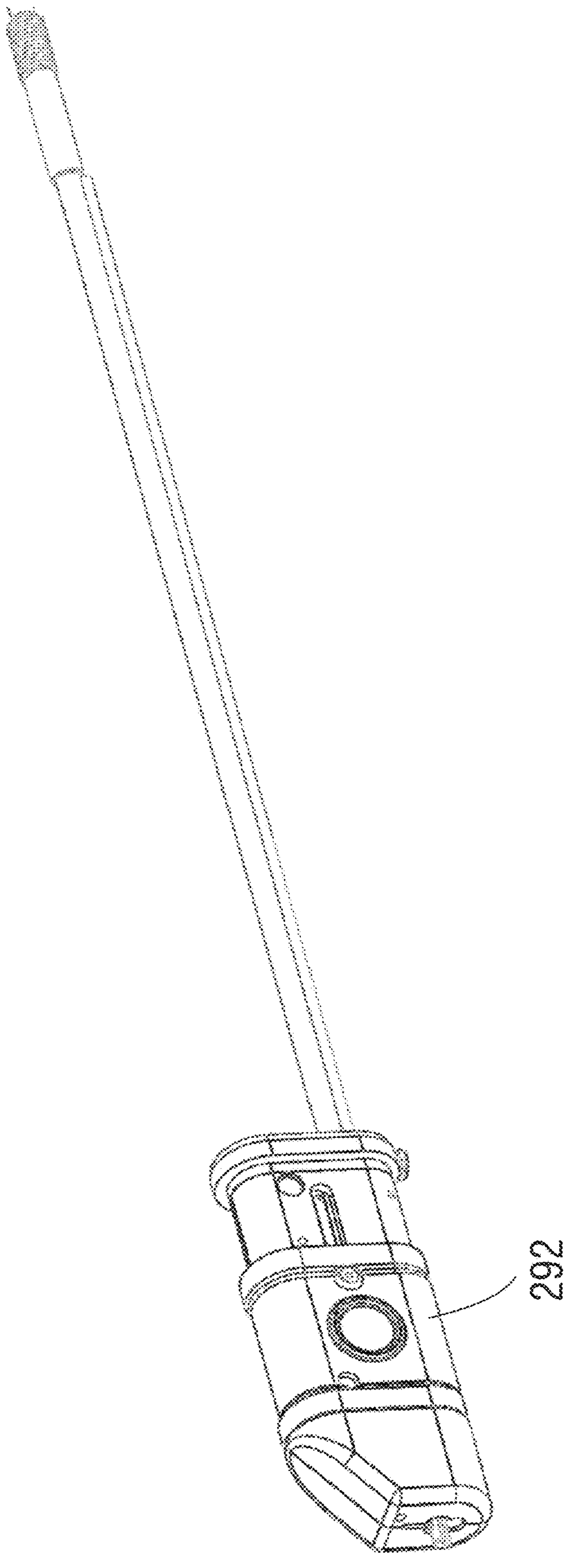
FIG. 66 is a fragmentary, perspective view of the multiple-firing crimp device of FIG. 58 with the manually actuated crimp sub-assembly with the shuttle in a snare-extended position.
Figure 67:
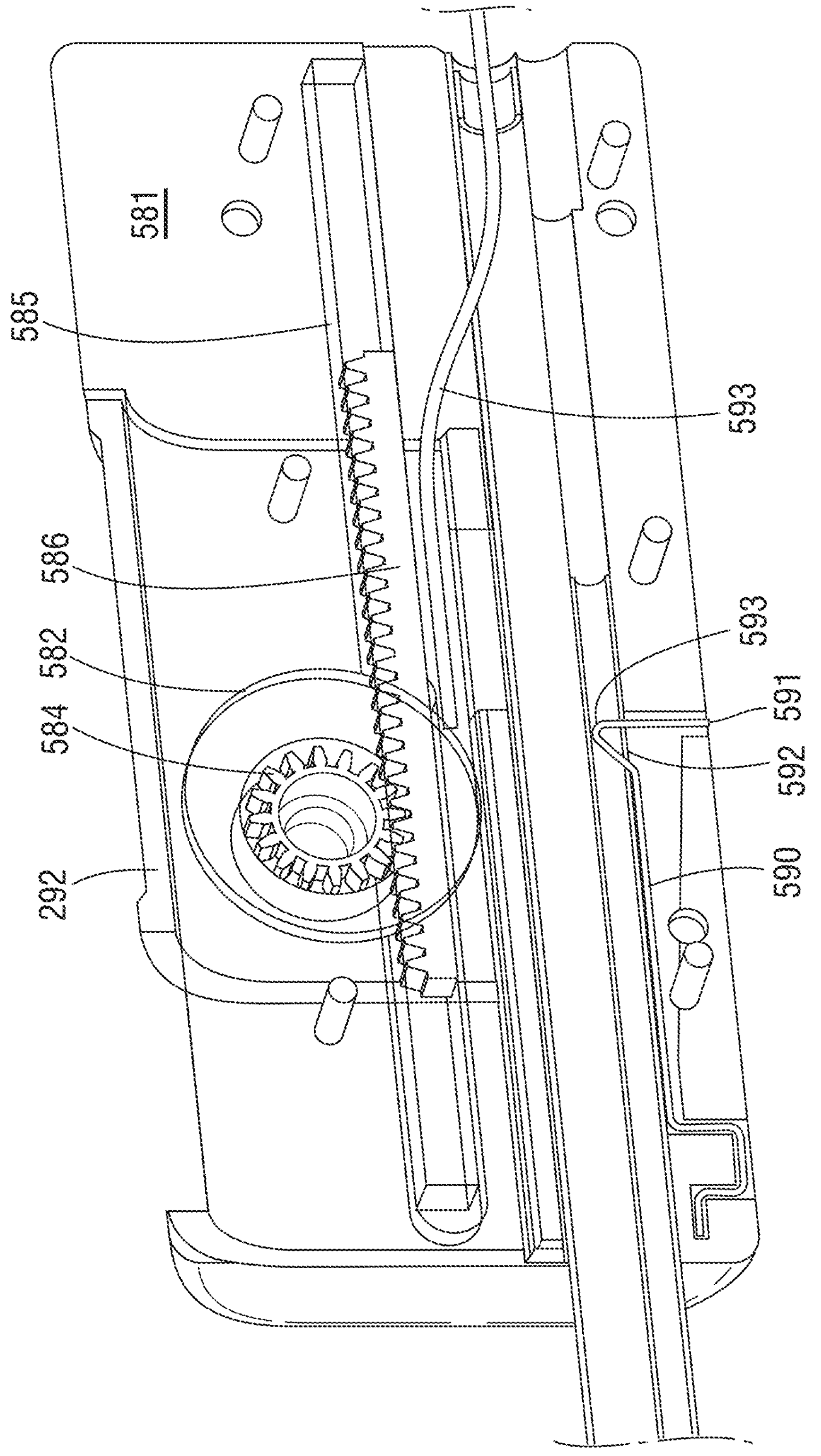
FIG. 67 is a fragmentary, enlarged, partially transparent, longitudinally cross-sectional view of the multiple-firing crimp device of FIG. 66 with the shuttle in the snare-extended position.
Figure 68:
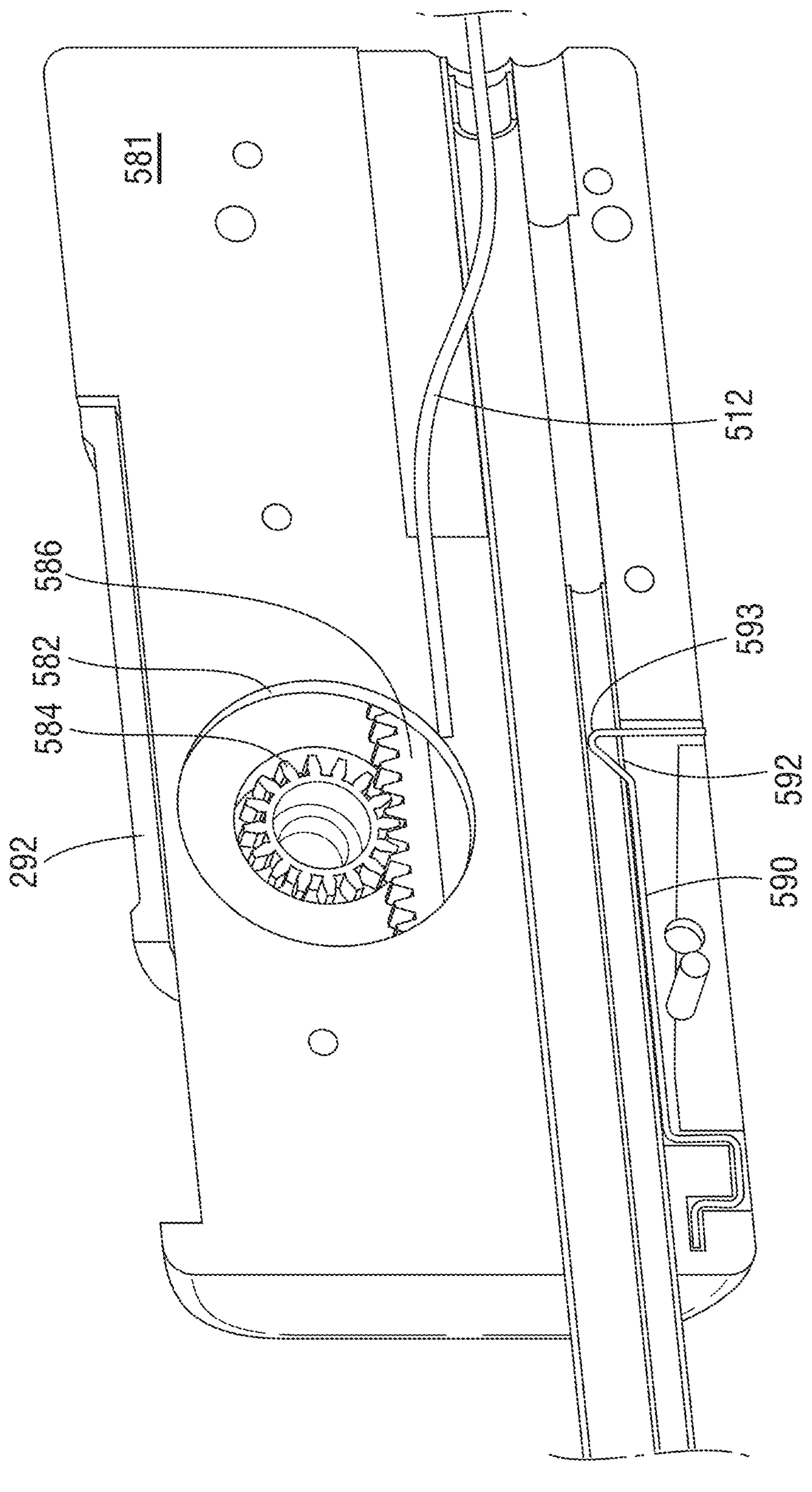
FIG. 68 is a fragmentary, enlarged, longitudinally cross-sectional view of the multiple-firing crimp device of FIG. 66 with the shuttle in the snare-extended position.
Figure 69:
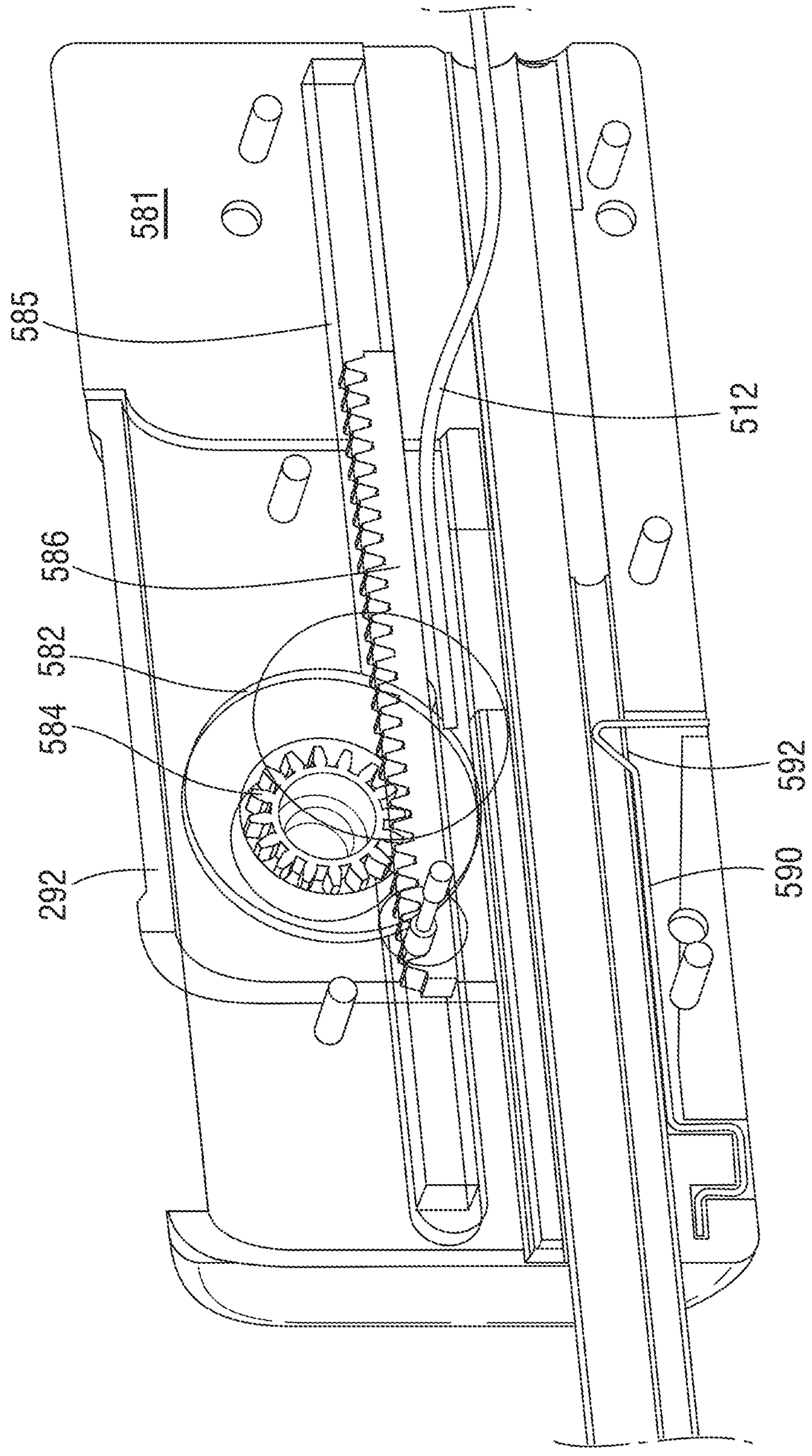
FIG. 69 is a fragmentary, enlarged, transparent, longitudinally cross-sectional view of the multiple-firing crimp device of FIG. 66 with the shuttle in the snare-extended position.
Figure 70:
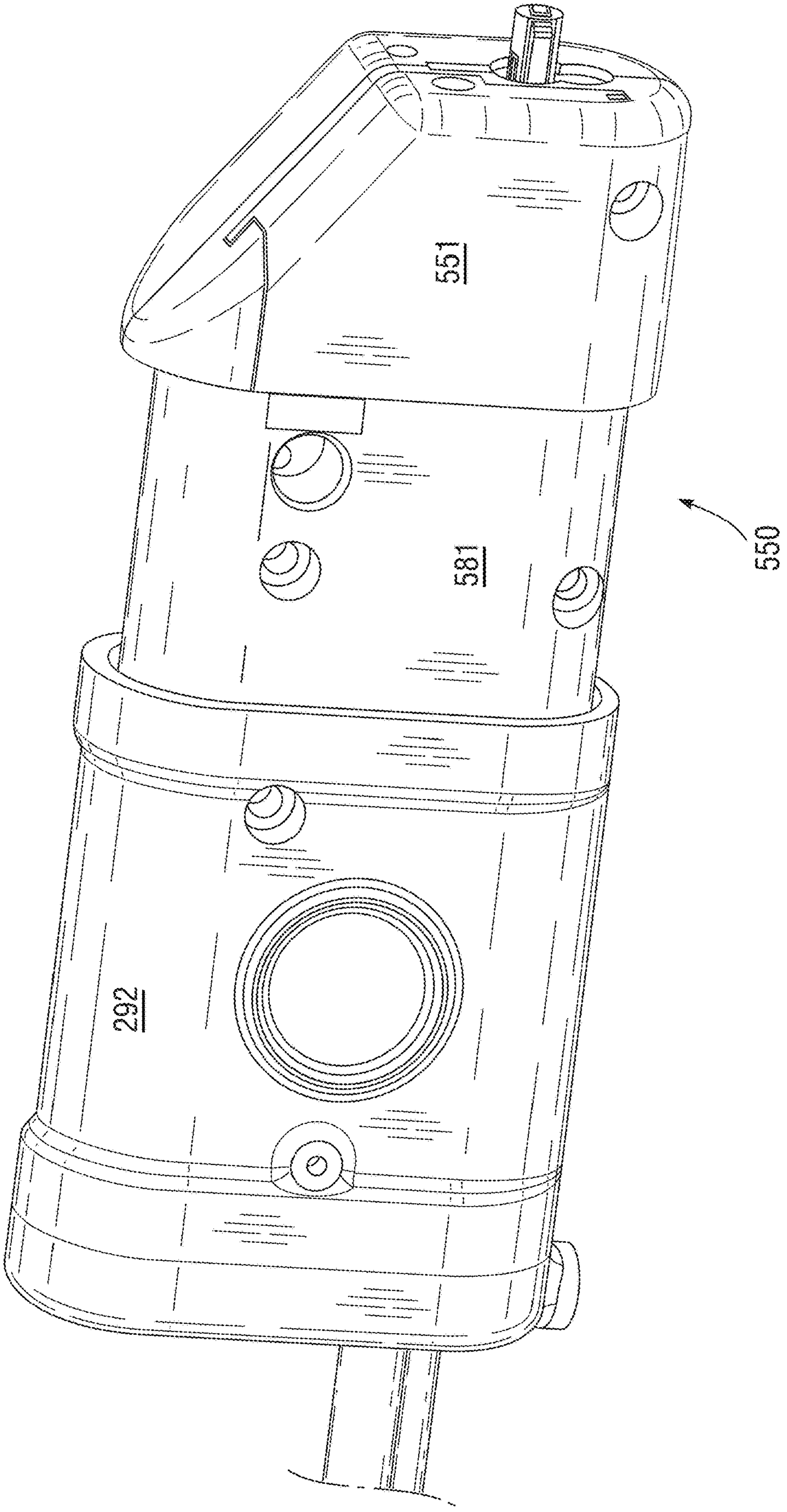
FIG. 70 is a fragmentary, perspective view of an exemplary embodiment of a distal end of a multiple-firing crimp device having a distal headlight assembly in an off state and an end effector with a manually actuated crimp sub-assembly in a position with a first crimp loaded for use and with a shuttle in a ready to use state.
Figure 71:
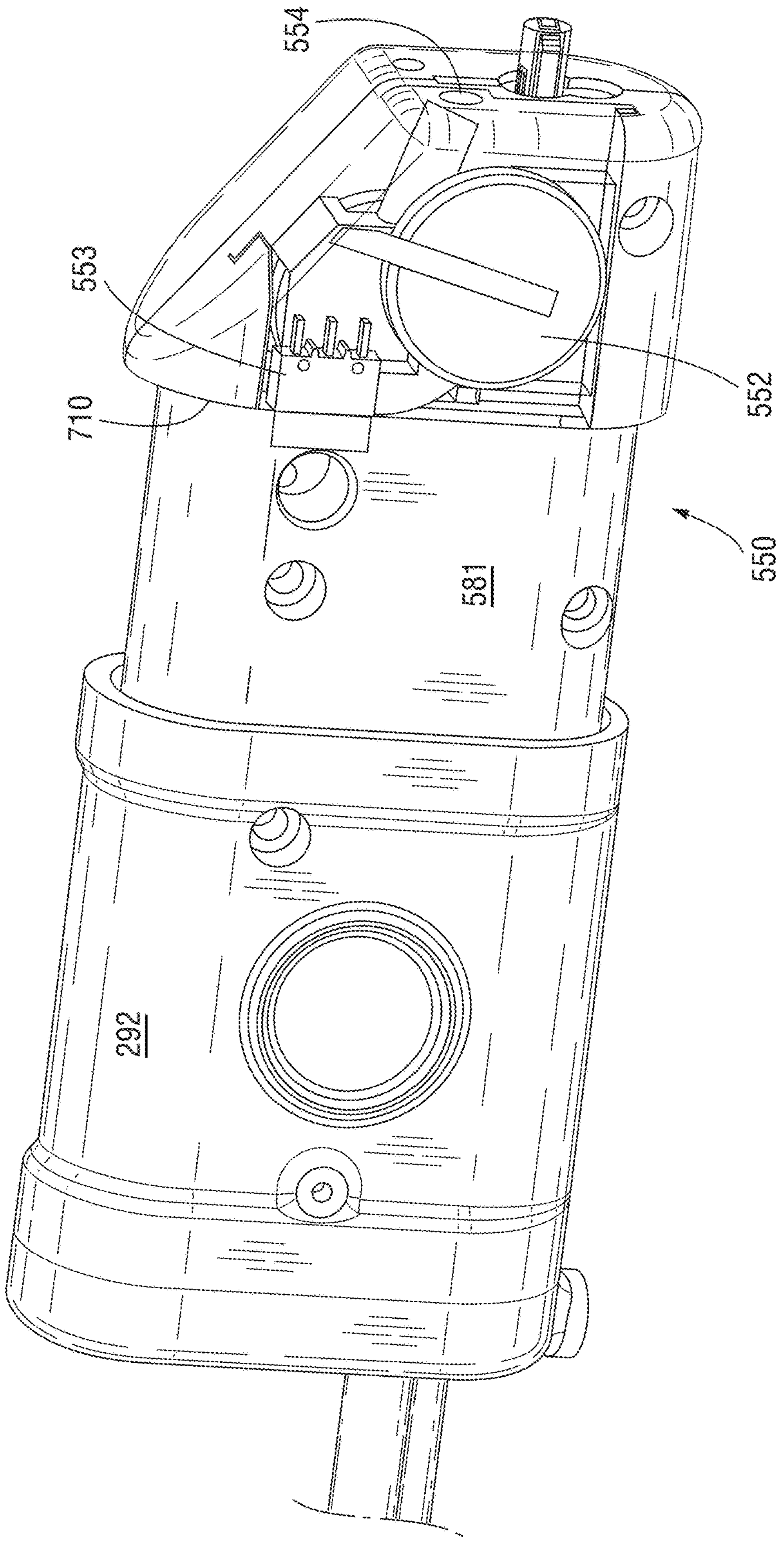
FIG. 71 is a fragmentary, partially transparent, perspective view of the multiple-firing crimp device of FIG. 70.
Figure 72:
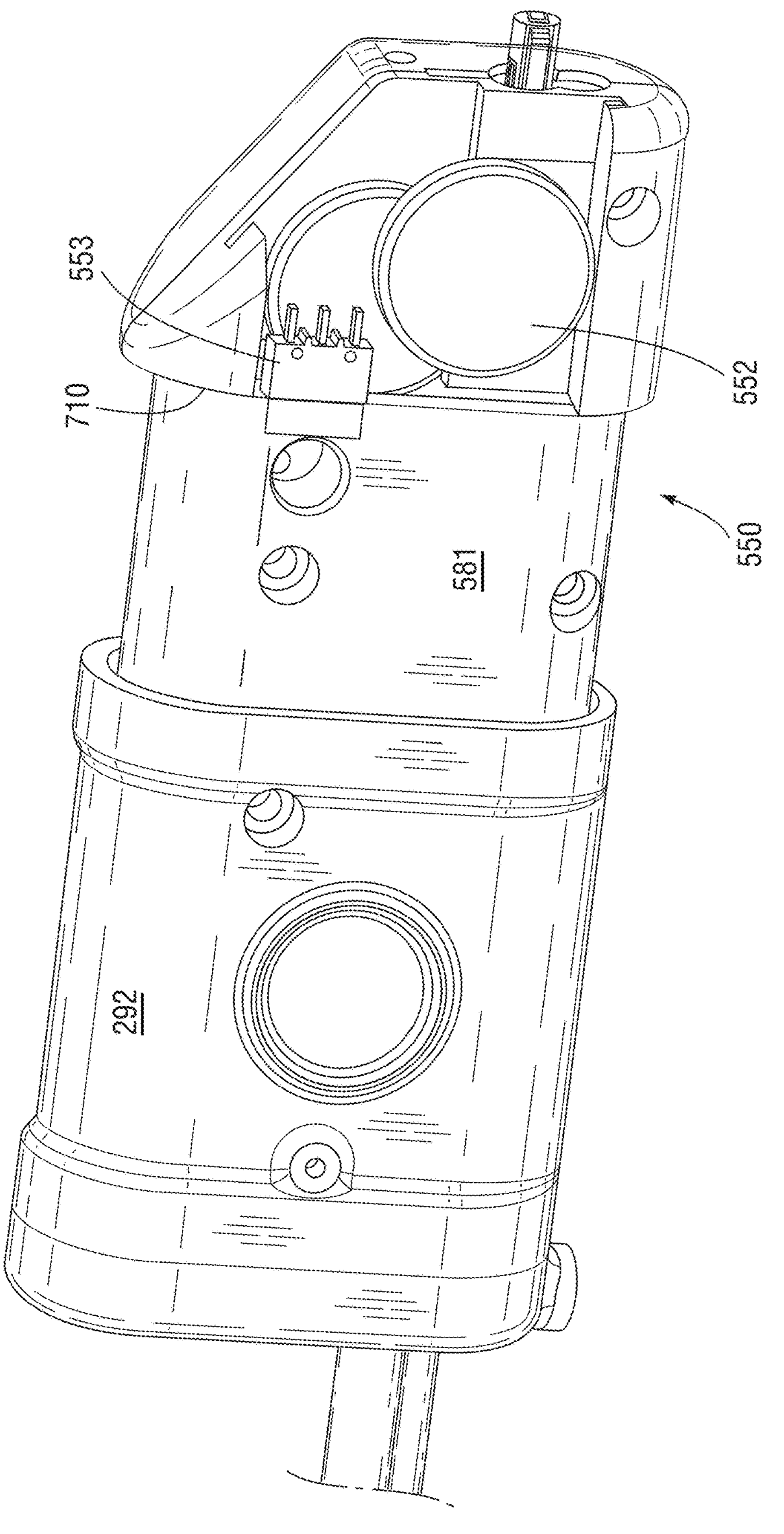
FIG. 72 is a fragmentary, perspective view of the multiple-firing crimp device of FIG. 70 with a headlight cover removed.
Figure 73:
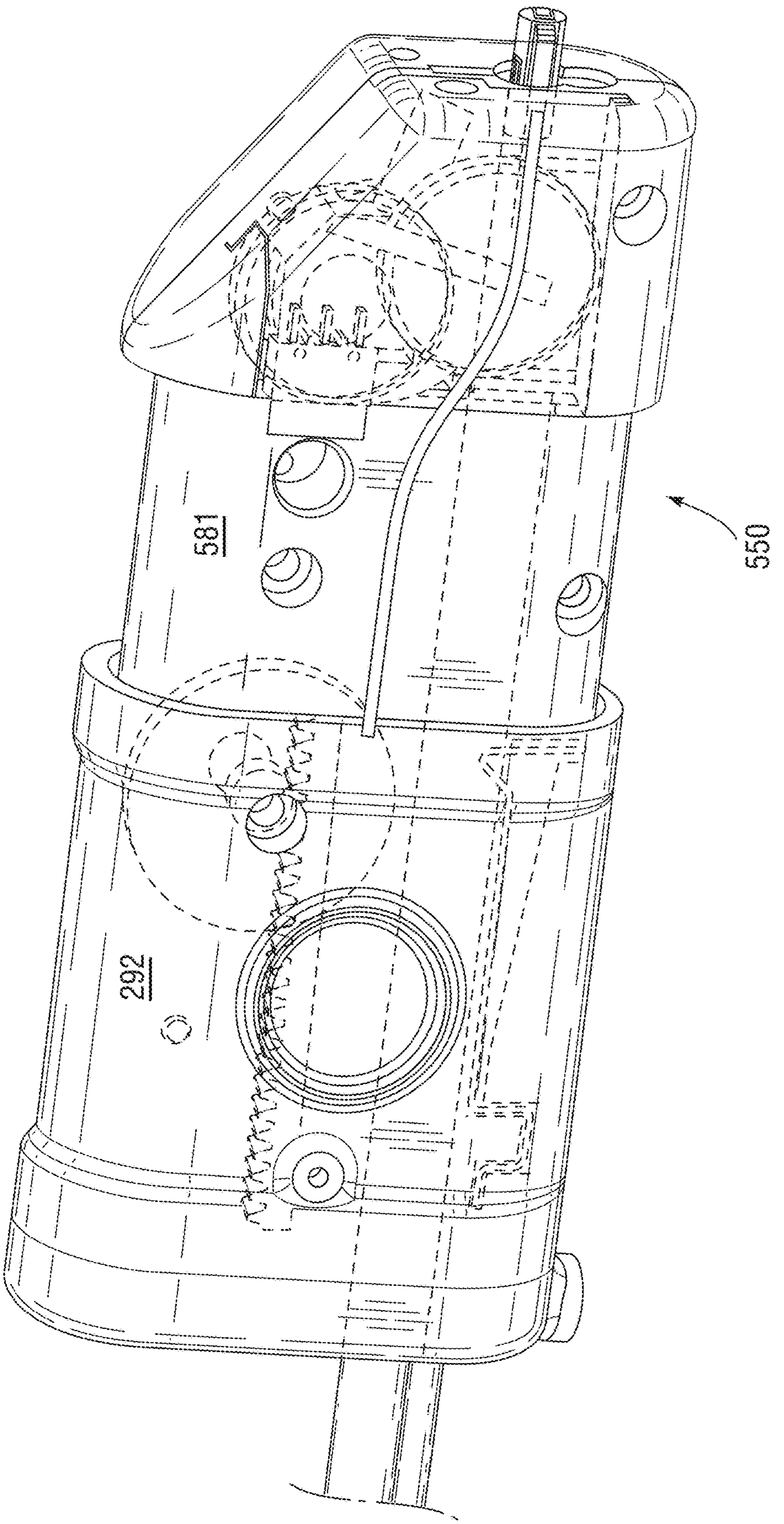
FIG. 73 is a fragmentary, transparent, perspective view of the multiple-firing crimp device of FIG. 70.

FIGS. 58 and 59, respectively, depict the shuttle translating from a retracted position against the handle 100 to an extended position where the snare-extension tube 512 drops into the slot 272 of the outer tube 270. FIGS. 60 to 62 illustrate the shuttle 580 in a state where the snare-extension tube 512 has not reached the slot 272 and, therefore, still remains against the outer surface of the outer tube 270. In comparison, FIGS. 63 to 65 illustrate the shuttle 580 in a state where the snare-extension tube 512 has dropped into the slot 272 and is ready to extend the snare within the outer tube 270 through the crimp 30' (which is not illustrated here). All of the steps for aligning the snare-extension tube 512 are the same as above and, therefore, the details of which are not repeated here.

The body 581 defines an interior snare spool cavity 582 in which a snare spool 583 and a pinion 584 rotatably reside. The snare spool 583 is rotationally fixed to the pinion 584 so that rotation of the pinion 584 results in a corresponding rotation of the snare spool 583. The snare spool 583 is illustrated in cross-section in FIG. 63. The body 581 also defines an interior rack cavity 585 in which a rack 586 resides for longitudinal movement within the rack cavity 585. A distal end of the rack 586 is fixed to the snare-extender slide 292, for example, it is pinned thereto at point 587. The snare 10, which is not illustrated in FIGS. 59 to 68 for purposes of clarity, has a proximal end that is pinned to the snare spool 583. In an exemplary embodiment of the snare spool 583 in FIG. 63, the snare spool 583 has a radial bore extending radially inwards from a spool outer contact surface. The distal end of the snare 10 is positioned inside the bore and is fixed there, for example, with a set screw or pin. The snare 10 is then wound around the snare spool 583 (e.g., counterclockwise with respect to FIG. 63) on the spool contact surface and is threaded into the snare-extension tube 512. The spool sides are raised to have a diameter greater than a diameter of the spool contact surface to keep the snare 10 from sliding off the snare spool 583 laterally.

With such a configuration, as the snare-extender slide 292 is moved distally by the user, the rack 586 moves distally as well, thereby rotating the pinion 584 and the snare spool 583. Because the diameter of the pinion 584 is smaller than the diameter of the snare spool 583, the pinion 584 acts as a speed increasing gear to enable a larger movement of the snare spool 583 and, thereby, a length of the snare 10 that is wound about the snare spool 583. In particular, the overall length of the snare 10 is set to position the tip 14 just outside the distal end of the snare-extension tube 512 when the snare-extender slide 292 and the rack 586 are in their proximal-most, unactuated position (shown in FIG. 63). This tip 14 position is shown, for example, in FIG. 57. As the rack 586 moves distally, the snare spool 583 unwinds the snare 10 (e.g., in a counterclockwise direction with regard to FIG. 63) and extends the snare 10 out from the distal end of the snare-extension tube 512. FIGS. 66 to 69 show the snare-extender slide 292 (and, therefore, the rack 586) extended distally to the fullest extent to, thereby, move the non-illustrated snare 10 out from the distal face of the shuttle 580. With the gearing shown, an approximately 25 mm (about 1") movement of the rack 586 causes approximately 62.5 mm (about 2.5") of snare 10 extension out from the distal end. Thus, the overall length of the shuttle 580 can be reduced significantly.

As indicated above, it is desirable to prevent the shuttle body 581 from movement when the shuttle 580 is in a position where the snare 10 is to be moved. Various retaining features can be provided. One example of this retaining feature is a body interlock 590. In this example, the body interlock 590 is a leaf spring with an extension 593 that rides along the bottom surface of the guide rod 570 as the shuttle 580 moves and, when the shuttle 580 is in a position where snare 10 movement is permitted, a port 592 in the guide rod 590 is located to catch the extension 593 of the body interlock 590 therein and substantially prevent longitudinal movement of the shuttle 580 on the outer tube 270. Once the leaf spring of the body interlock 590 is allowed to move into the port 592, the free end 591 of the body interlock 590 moves out of the way of the extender slide 292, allowing the extender slide 292 to move distally. It is noted that the wrap-around extender slide 292 embodiment of FIGS. 58, 59, 66, and 70 to 74 entirely wraps around the shuttle body 581. In this configuration, the free end 591, is able to positively engage the extender slide 292 and prevent movement. In contrast, the exemplary embodiment of the short extender slide 292 in FIGS. 60 to 65 and 67 to 69 does not wrap around to the bottom surface of the shuttle body 581. Thus, the configuration of the body interlock 590 would not engage the short extender slide 292. For the short extender slide 292 in FIGS. 60 to 65 and 67 to 69, the body interlock 590 would be positioned behind the shaft 270, 570 in the figures and, therefore, would not be visible in these figures. Accordingly, the body interlock 590 is left at the lower surface of the shuttle body 581 for purposes of clarity only.

Once the extender slide 292 has moved any distance distally, it forcibly holds the leaf spring of the body interlock 590 in the port 592 thereby locking the shuttle 580 into the shuttle's distal-most position. When the extender slide 292 is returned to its proximal position (e.g., FIG. 60), the body interlock 590 remains engaged in the port 592. As the body interlock 590 is a leaf spring with ramps on either side of the extension 593, a sufficient force by the user to move the shuttle 580 proximally, overcomes the interlock and slides the extension 593 out from the port 592. In action, the body interlock 590 acts as a removable detent that provides sufficient force to retain the shuttle 580 in position when snare functions occur but that is insufficient to prevent retraction movement of the shuttle 580 by a force imposed by the user.

Figure 74:
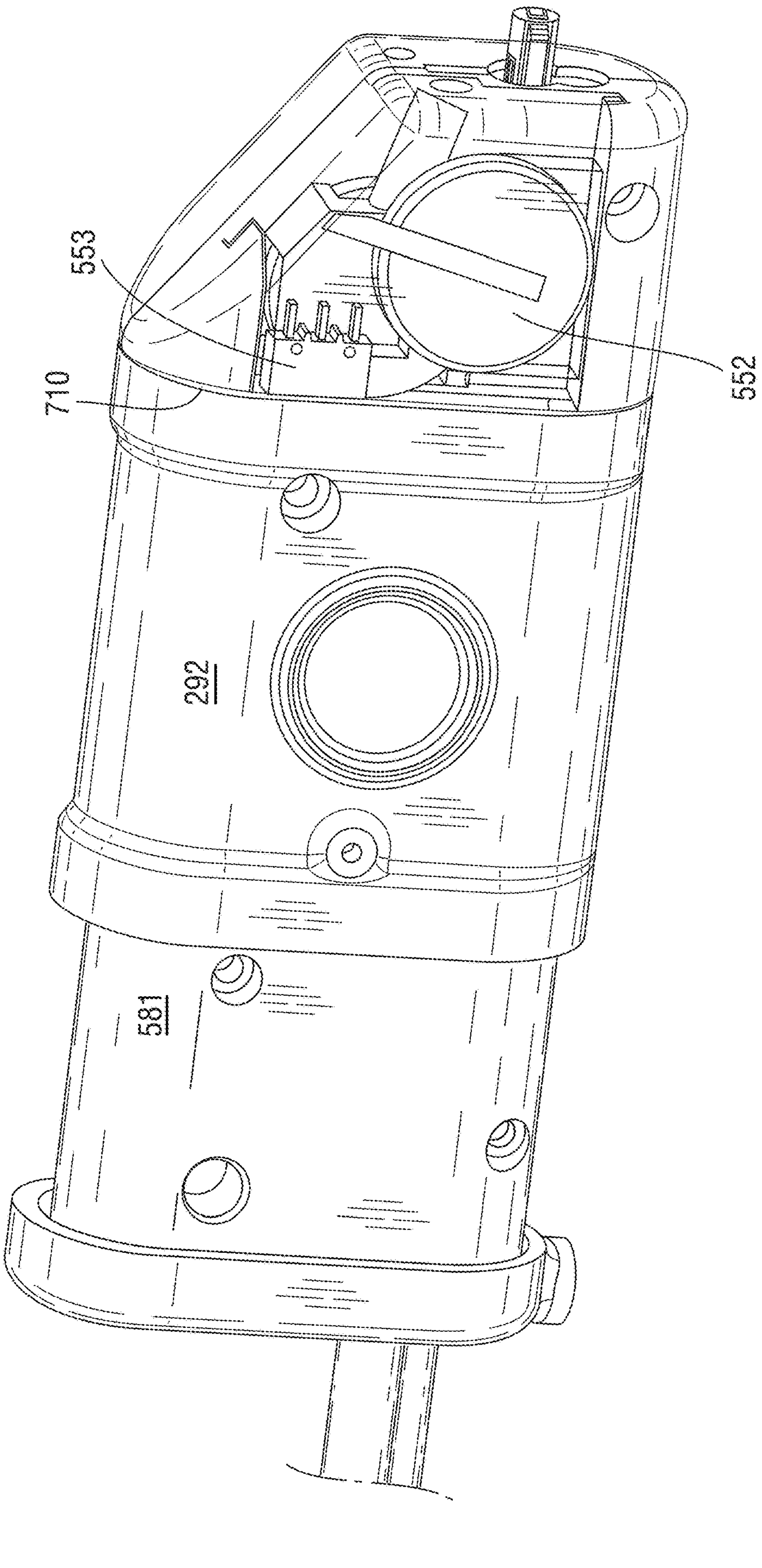
FIG. 74 is a fragmentary, partially transparent, perspective view of the multiple-firing crimp device of FIG. 70 with the shuttle in the snare-extended position.

When the devices described and/or shown herein are used in surgery, the location where the snare 10 is to capture cords 2 (e.g., sutures), is typically within a surgical site. Even though there is light from the surgical environment, many obstacles present shadows where the snare 10 is located during use. The color and size of the snare 10 also can make it difficult for a surgeon to see the snare 10 within the background of the surgical site. To alleviate this issue, the shuttle body 581 is provided with a distal headlight assembly 550. One or both of the sides of the shuttle body 581 is hollowed out and provided with a cover 551 to contain parts of the headlight assembly 550, as shown in FIGS. 70 to 74. The cover 551 is made transparent in FIG. 71 to show thereunder a power supply 552 (in the form of one or more coin cells) and a headlamp switch 553, which is, in this exemplary embodiment, a micro-switch having the switch on a proximal side thereof with the body of the micro-switch positioned flush with an end-of-travel surface 710 of the shuttle body 581 for the snare-extender slide 292 and with the switch plunger projecting distally from the end-of-travel surface 710. In such a configuration, when the snare-extender slide 292 reaches a point where the snare 10 is extended for snaring one or more cords (as shown in FIG. 74), the switch automatically depresses, thereby turning on the headlamp 554, which can take the form of one or more LEDs, for example. In this configuration, the headlamp 554 remains on until the snare-extender slide 292 is retracted proximally, in which case the snare 10 is within the shuttle 580 and has captured the one or more cords 2.

Figure 76:
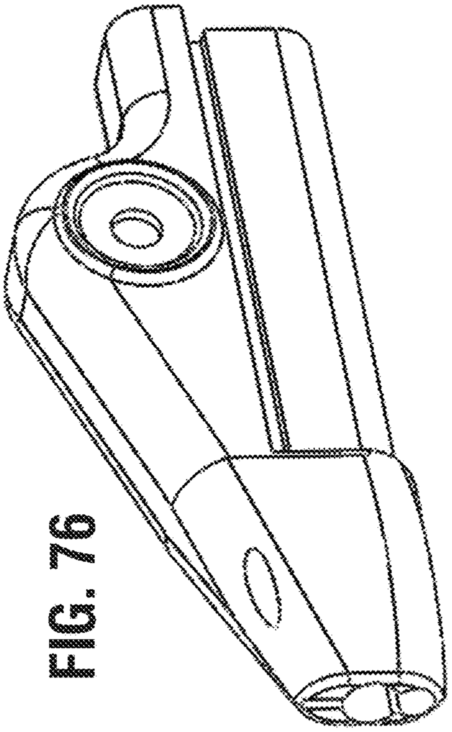
FIG. 76 is a perspective view of a left side of an alternative exemplary embodiment of a shuttle body with snare-extender slide removed.
Figure 77:
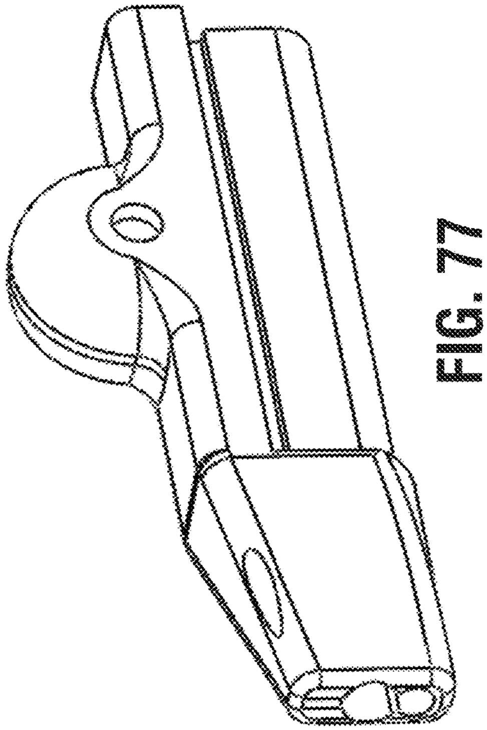
FIG. 77 is a perspective view of a left side of a left half of an alternative exemplary embodiment of a shuttle body with snare-extender slide removed.
Figure 75:
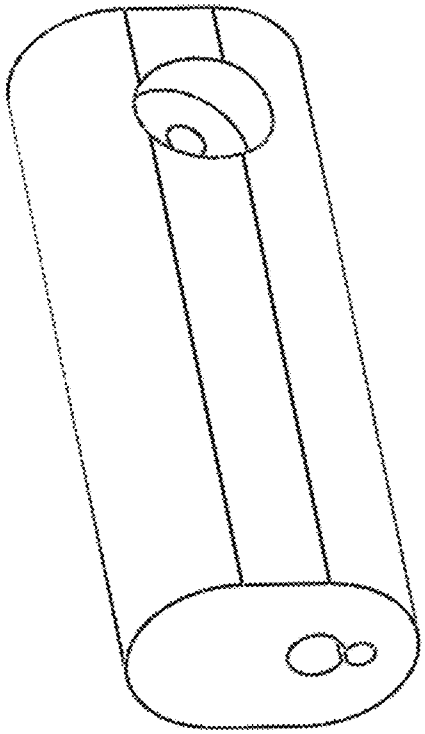
FIG. 75 is a perspective view of a left side of an alternative exemplary embodiment of a shuttle body.
Figure 78:
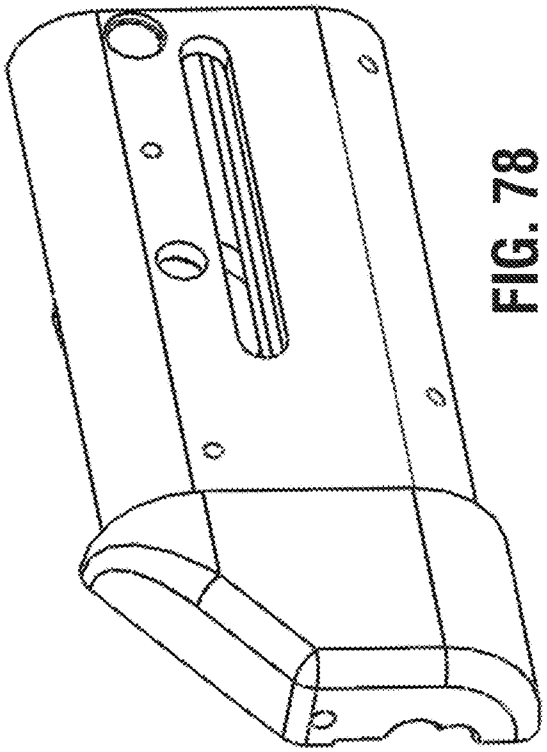
FIG. 78 is a perspective view of a left side of an alternative exemplary embodiment of a shuttle body with snare-extender slide removed.
Figure 76A:
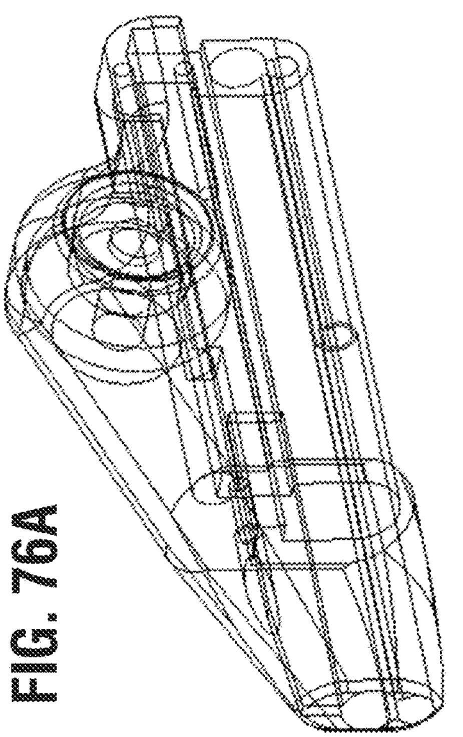
FIG. 76A is a transparent, perspective view of the shuttle body of FIG. 76.
Figure 77A:
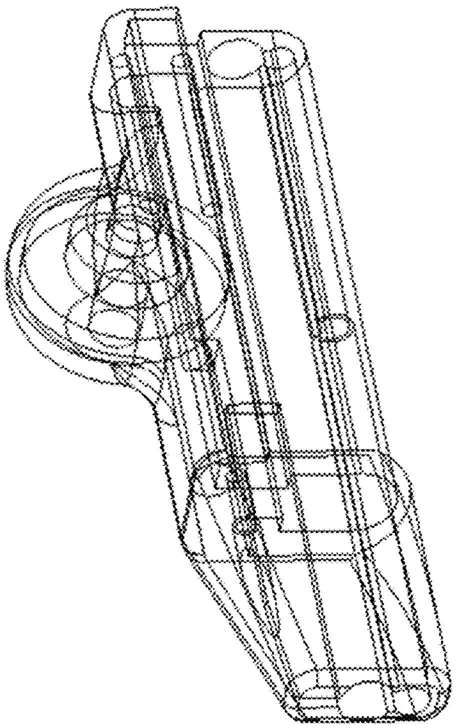
FIG. 77A is a transparent, perspective view of the shuttle body half of FIG. 77.
Figure 75A:
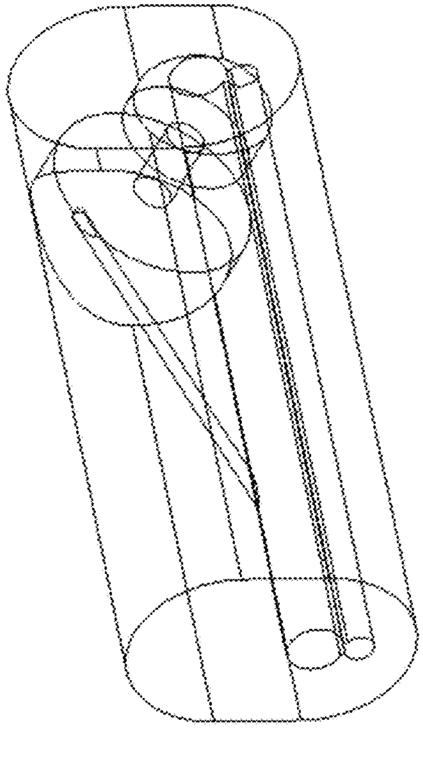
FIG. 75A is a transparent, perspective view of the shuttle body of FIG. 75.
Figure 78A:
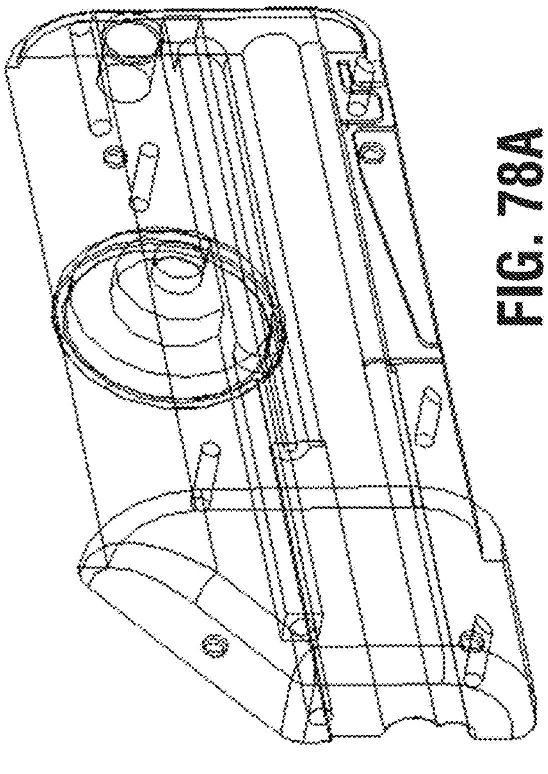
FIG. 78A is a transparent, perspective view of the shuttle body of FIG. 78.
Figure 75B:
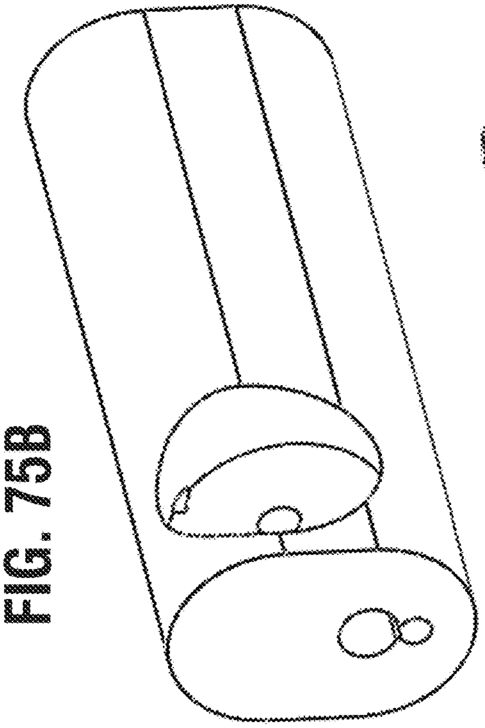
FIG. 75B is a perspective view of a right side of the shuttle body of FIG. 75.
Figure 78B:
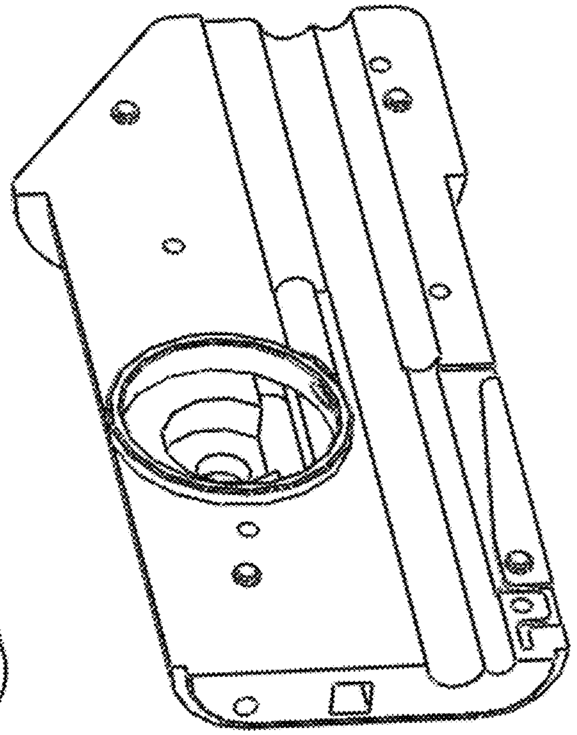
FIG. 78B is a perspective view of a right side of the shuttle body of FIG. 78.
Figure 76B:
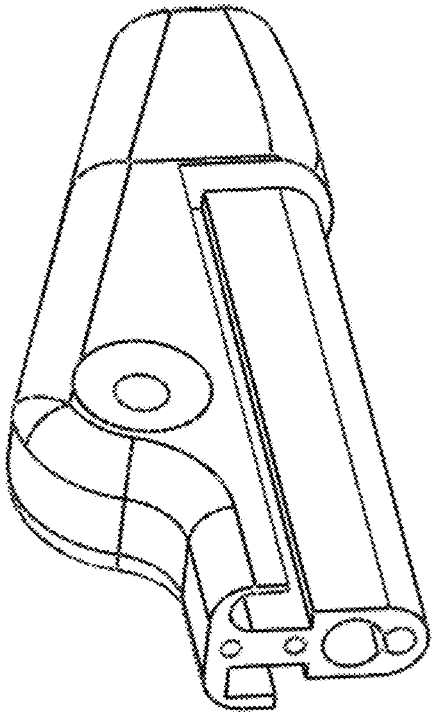
FIG. 76B is a perspective view of a right side of the shuttle body of FIG. 76.
Figure 77B:
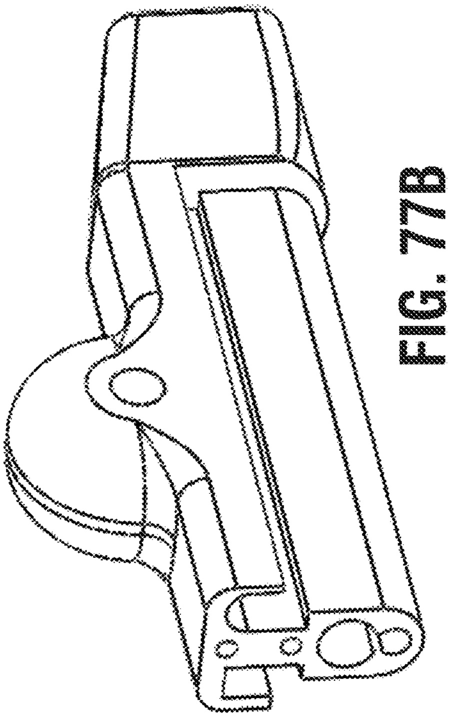
FIG. 77B is a perspective view of a right side of the shuttle body half of FIG. 77.

The shuttle body 581 is not limited to the shapes shown hereinabove. There are other configurations in which various characteristics are maximized or minimized. FIGS. 75, 75A, and 75B illustrate an exemplary embodiment of a shuttle body that allows the snare-extender tube to be relatively straight and positions the snare's exit from the snare spool from above the snare spool instead of below. FIGS. 76, 76A, and 76B illustrate an exemplary embodiment of a shuttle body configuration that removes some of the body material to lighten the shuttle and places the snare-extender slide only on the bottom half of the shuttle. A headlight assembly is also provided. The exemplary configuration in FIGS. 77, 77A, and 77B removes even more material from the shuttle body to further lighten the shuttle. The exemplary configuration of the left half of the shuttle body in FIGS. 78, 78A, and 78B is similar to the shuttle body embodiment of FIGS. 58 to 74 and shows differences in configuration, size, and material from the other shuttle bodies.

Figure 79:
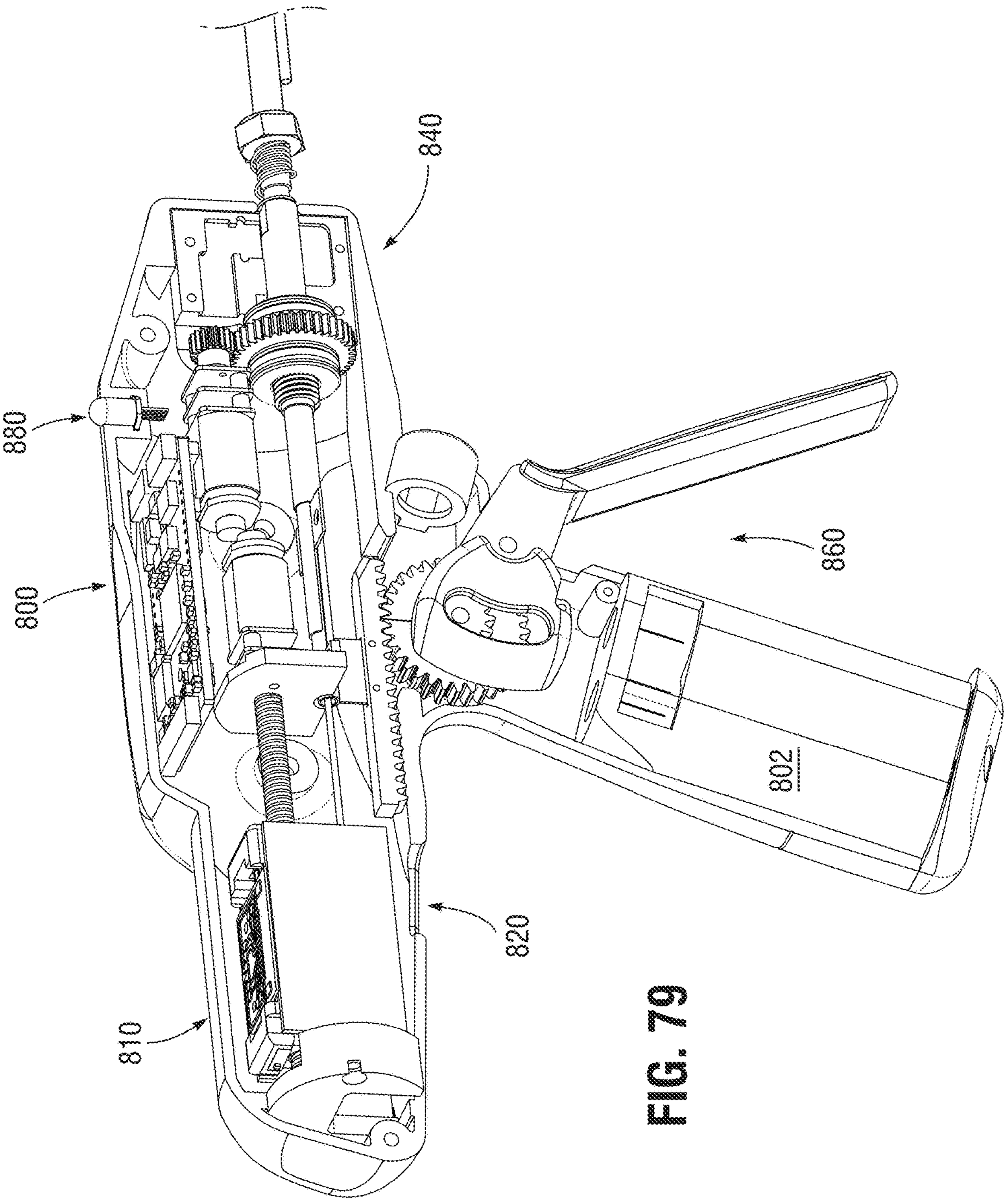
FIG. 79 is a fragmentary, perspective view of a right side of an exemplary embodiment of a handle for a multiple-firing crimp device with the right half of the handle body removed.
Figure 80:
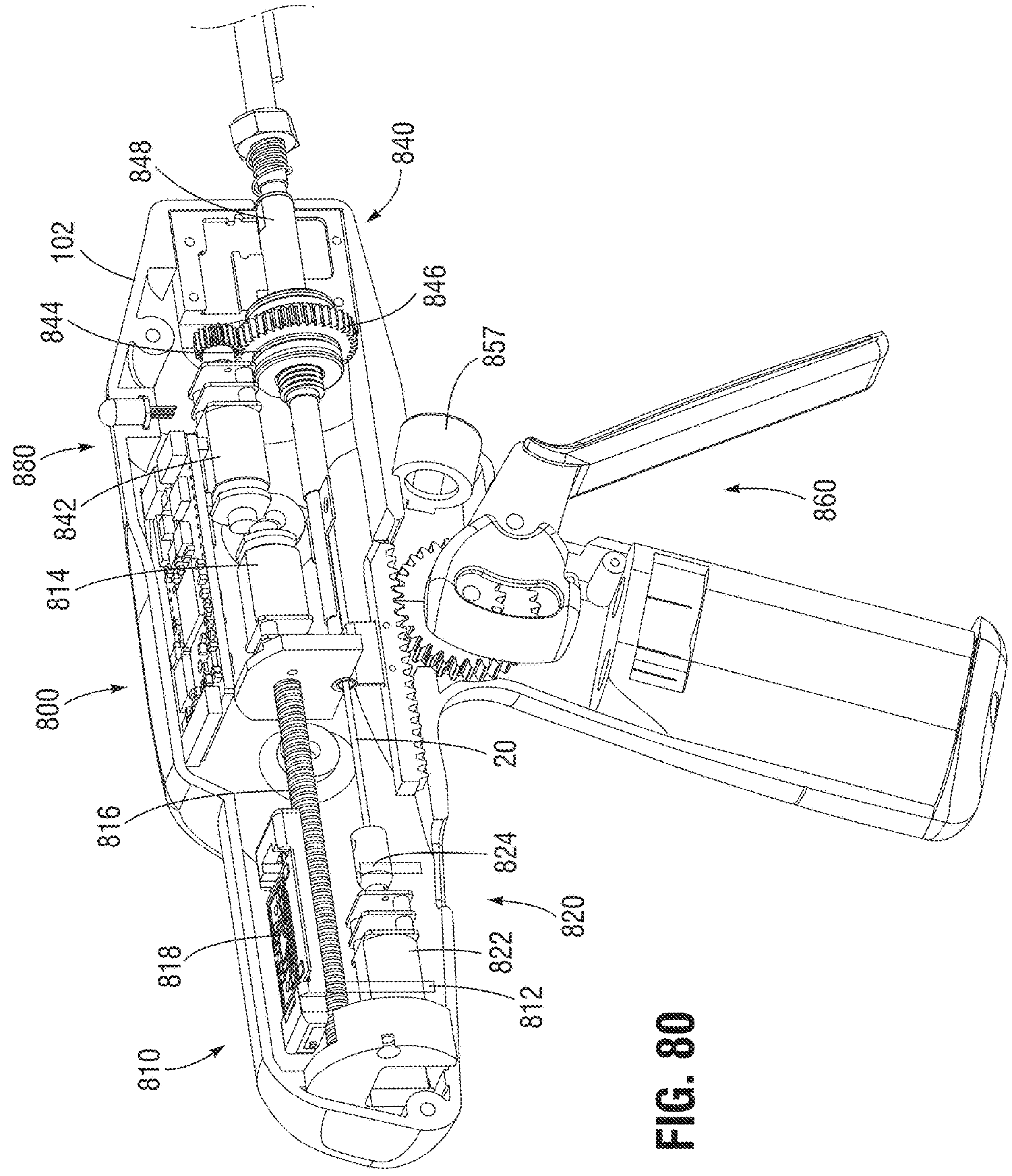
FIG. 80 is a fragmentary, perspective view of the handle of FIG. 79 with a cover of a carriage movement assembly transparent.
Figure 81:
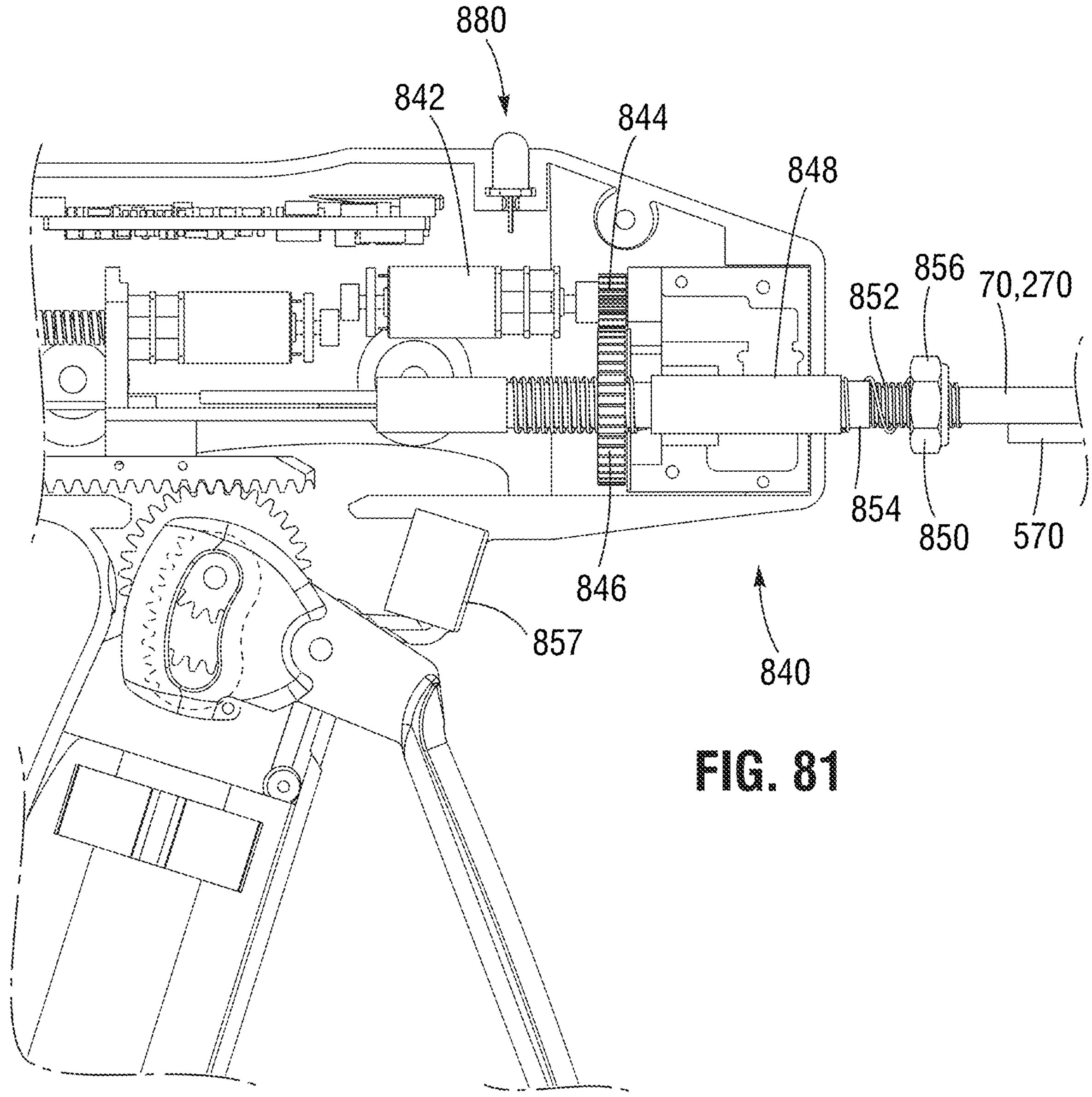
FIG. 81 is a fragmentary, side elevational view of a right side of the handle of FIG. 79 in a crimp-retracted state.

An exemplary embodiment of a handle 100 for the multiple-firing crimp device is illustrated in FIGS. 79 and 80, in FIG. 80, the carriage movement assembly is transparent to illustrate the structures therein. Within the handle 100 are various movement assemblies. Some of the movement assemblies are manual and some are automatic. As set forth herein, any of the automatic movement assemblies shown and described can be manual and any of the manual movement assemblies shown and described can be automatic. In this handle embodiment, the movement assemblies include a system control assembly 800, a carriage movement assembly 810, a carriage rotation assembly 820, a crimping assembly 840, a cutting assembly 860, a display assembly 880, and a force-measuring and indicating assembly 900.

The system control assembly 800 includes all circuitry sufficient to power and control all electronics on the multiple-firing crimp device. The system control assembly 800 is electrically connected to a power supply 802, which can be, for example, a pack of batteries, such as one or more CR2 or CR123 batteries. The power supply 802 can be powered by any electricity delivery measures including a supply mains.

The carriage movement assembly 810 includes a carriage conveyor 812 with a transparent cover that is best shown in FIG. 80. Also included in the carriage movement assembly 810 is a carriage motor 814 fixed to the handle 100 and rotating a conveyor spindle 816 that, when rotated, either moves the carriage conveyor 812 proximally or distally with respect to the handle body 102. The carriage conveyor 812 has a rotation sub-assembly 820 that, at its distal end, includes a coupler 824 that is rotationally and longitudinally fixed to the crimp carriage 20. As such, when the carriage conveyor spindle 816 rotates and causes the conveyor 812 to move proximally or distally, the crimp carriage 20 moves correspondingly with the coupler 824. In this regard, the carriage motor 814 is the device that positions the crimp(s) 30 towards and away from the crimp orifice 42 as well as positions the crimp 30' within the crimp orifice 42. Two non-illustrated limit switches are present in the carriage movement assembly 810 to define the extension and retraction limits of carriage conveyor 812 and, thereby, the crimp carriage 20.

The carriage rotation assembly 820 is part of the carriage movement assembly 810 and resides inside the carriage conveyor 812. The carriage rotation assembly 820 comprises a carriage rotation motor 822 and the coupler 824, which is rotationally fixed to the output of the carriage rotation motor 822. As such, when the carriage rotation motor 822 rotates, the crimp carriage 20 rotates to shuttle the crimps 30 and to withdraw from the crimp 30' within the crimp orifice 42. Electrical signals/power are supplied to the carriage rotation assembly 820 through a movable wiring harness 818 that is electrically connected to the main circuit board of the system control assembly 800.

Figure 82:
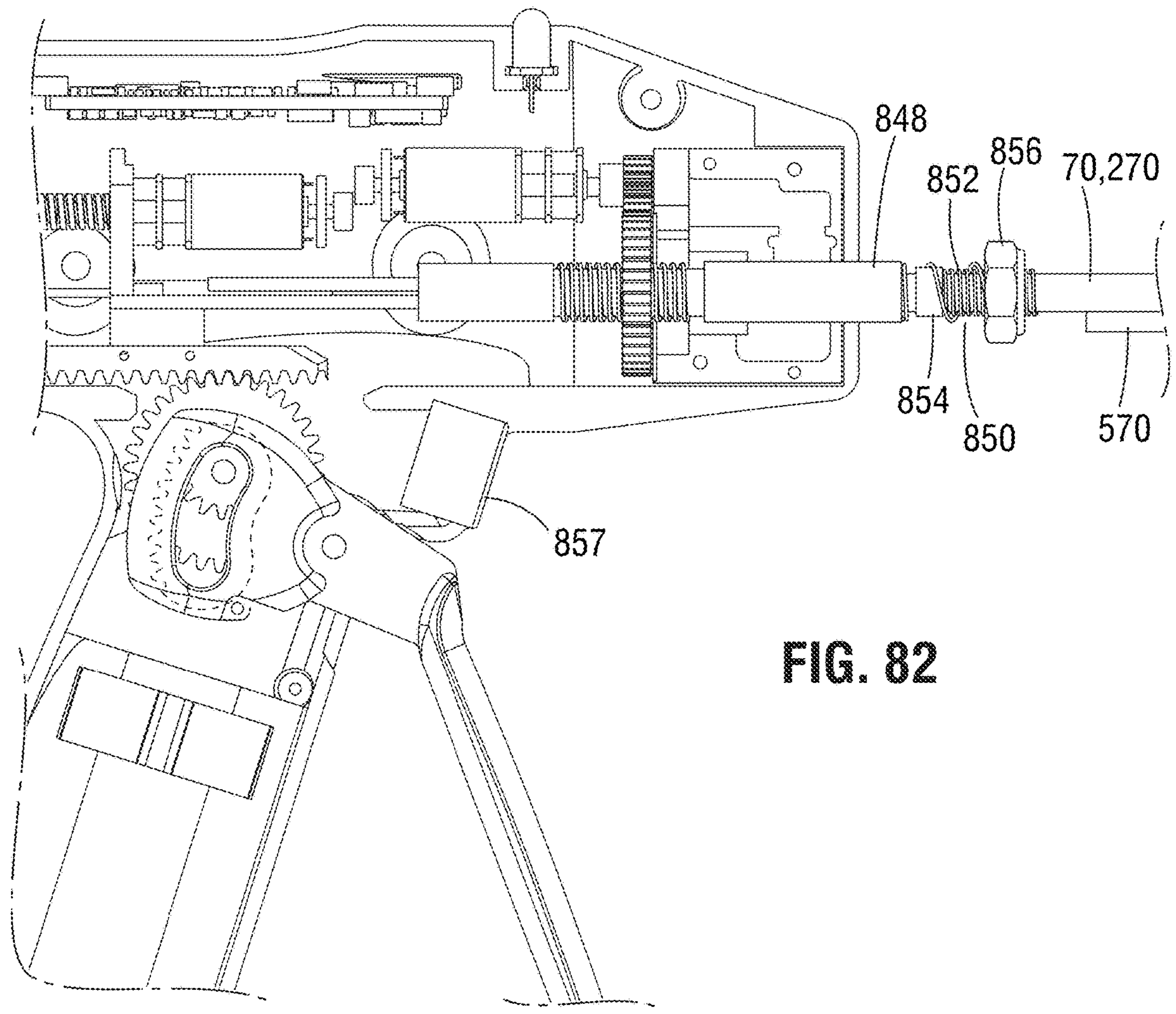
FIG. 82 is a fragmentary, side elevational view of the right side of the handle of FIG. 79 in a crimp-holding state.
Figure 83:
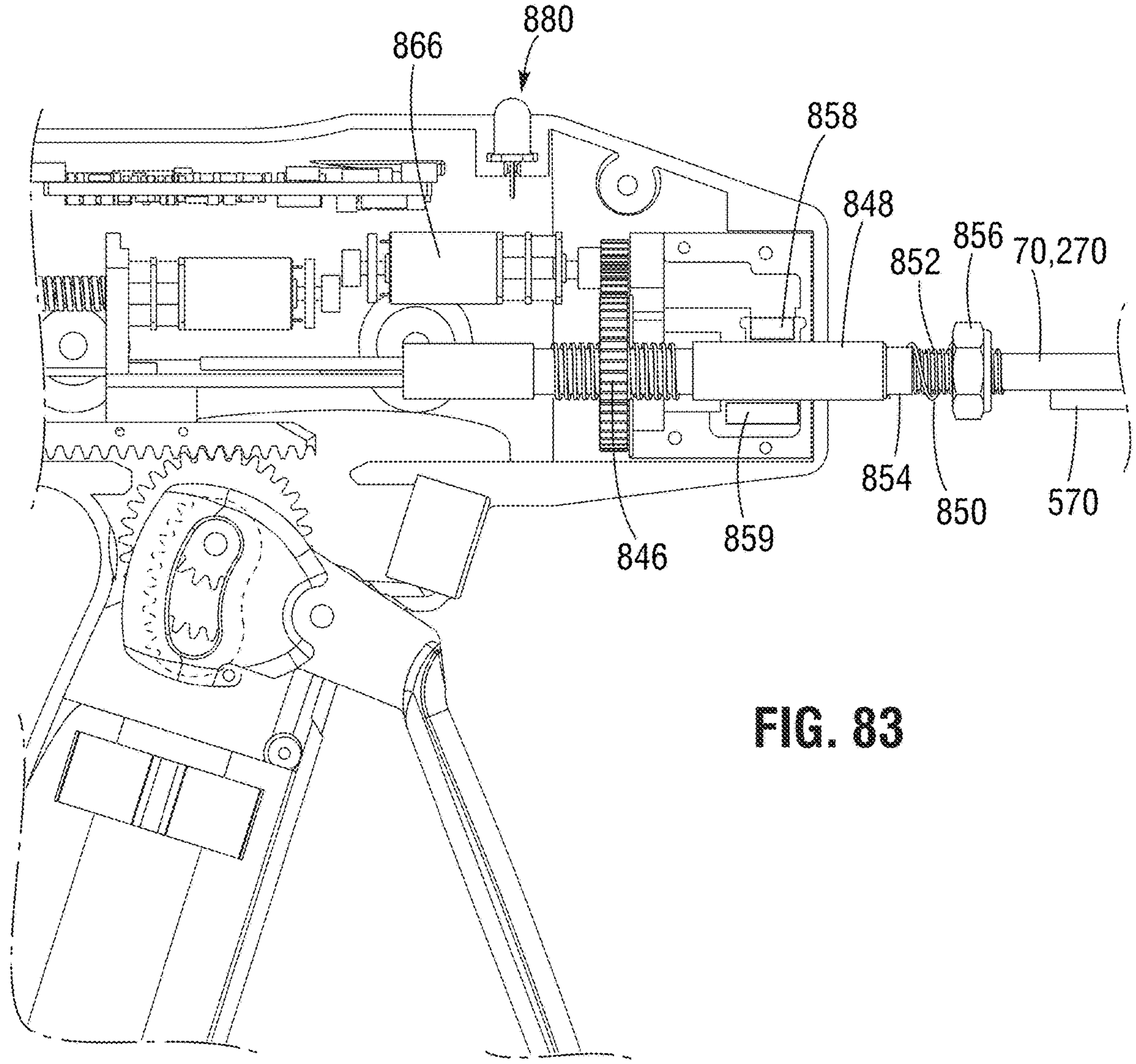
FIG. 83 is a fragmentary, side elevational view of the right side of the handle of FIG. 79 in a clutched state.

The crimping assembly 840 includes a crimping motor 842 fixed to the handle body 102 and rotationally connected a crimping pinion 844. The teeth of the crimping pinion 844 mesh with teeth of a flying gear 846. The flying gear 846 has a central bore with an interior thread corresponding to an exterior thread of a crimping clutch 848. Movement and functionality of the crimping clutch 848 is described with regard to FIGS. 81 to 84. In particular, there are two states in which the outer tube 70, 270, 570 is to be moved. The first is slightly forward so that the hammer 54 is gently pressed against the crimp 30' to hold it within the crimp orifice 42 and to not deform the crimp 30', and the second is forward to have the hammer 54 actively deform and fully crush the crimp 30'. To provide the first function of gently pressing the crimp 30', a clutch bias 850 (in the exemplary form of a spring) is disposed between a distal end of the crimping clutch 848 and a point on the outer tube 70, 270 a distance away from the distal end of the crimping clutch 848. This point is defined by a clutch stop 852 that has a proximal vertical surface 854 intended to contact the distal vertical surface of the crimping clutch 848 and prevent it, after such contact, from moving independent of the outer tube 70, 270. The clutch stop 852 can be simply a radial extension from the outer surface of the outer tube 70, 270, such as an integral collar, which is not adjustable, or it can be an adjustable clutch stop 852, 854, 856 that is formed on or is integral with the outer tube 70, 270 and has, for example, exterior threads 852 and a nut 856 threaded thereon as shown in FIGS. 81 to 84. With the clutch bias 850 disposed between the distal vertical surface of the crimping clutch 848 and the proximal vertical surface of the nut 856, the crimping clutch 848 is able to move asymmetrically with respect to the outer tube 70, 270 as it compresses the clutch bias 850. In this regard, with the clutch stop 852 disposed just distal of the distal end of the crimping clutch 848 to define a clutch distance therebetween and the clutch bias 850 therearound this intermediate portion, as the crimping clutch 848 starts to move distally (as shown in the transition from FIG. 81 to FIG. 82), the clutch bias 850 starts to compress and only moves the outer tube 70, 270 with a force that is proportional to the clutch bias 850. This force is set to be lower than the point at which the hammer 54 actually compresses the crimp 30'. In FIG. 82, for example, the crimping clutch 848 moves distally slightly (as compared to FIG. 81), compresses the clutch bias 850 and, thereby, moves the outer tube 70, 270, 570 distally but only with the force that compressed the spring. In the transition from FIG. 82 to FIG. 83, the crimping clutch 848 closed the distance and contacted the proximal vertical surface of the clutch stop 852. Because the spring of the clutch bias 850 has a coefficient less than a force able to compress the crimp 30', the spring is compressed without further movement of the outer tube 70, 270, 570 in this transition. However, after the crimping clutch 848 contacts the proximal vertical surface of the clutch stop 852, any further movement of the crimping clutch 848 corresponds to a 1:1 movement of the outer tube 70, 270, 570 and, thereby, causes movement of the outer tube 70, 270, 570 and crimping of the crimp 30'

A limit switch 858 is present adjacent the crimping clutch 848 to determine when the crimping clutch 848 has reached it furthest distance from the flying gear 846 and indicates to the system control assembly 800 that the crimping motor 842 should be stopped and prevent further turning of the flying gear 846. Also, to prevent the crimping clutch 848 from rotating with respect to the handle body 102, a keying assembly 859 is provided. This keying assembly can take the form of a pin and slotted block, a tongue-and-groove, or any similar rotation-preventing device.

As is indicated, the crimping assembly 840 is automated with the various motors and gears. The crimping process is started by depressing a non-illustrated trigger button disposed in a button orifice 857 of the handle 100. When this button is pressed, crimping of the crimp 30' occurs. The crimping assembly 840 holds the crimp 30' down and waits to reset the next crimp 30" until there is confirmation that the cords 2 have been cut, at which time a new crimp 30' is transitioned to the crimp orifice 42. Associated with the cutting assembly 860 is a non-illustrated limit switch that indicates a position at which the cutting blade is known to be or past a point where the cords 2 could be or the cutting blade pushrod is known to be or past the cutting tip of a fixed blade. When this limit switch is triggered, the crimping assembly 840 retracts to the crimp-ready position. An exemplary embodiment of an end effector portion of the cutting assembly 860 having a moving pushrod and a fixed blade is explained below with regard to FIGS. 85 to 91.

Figure 84:
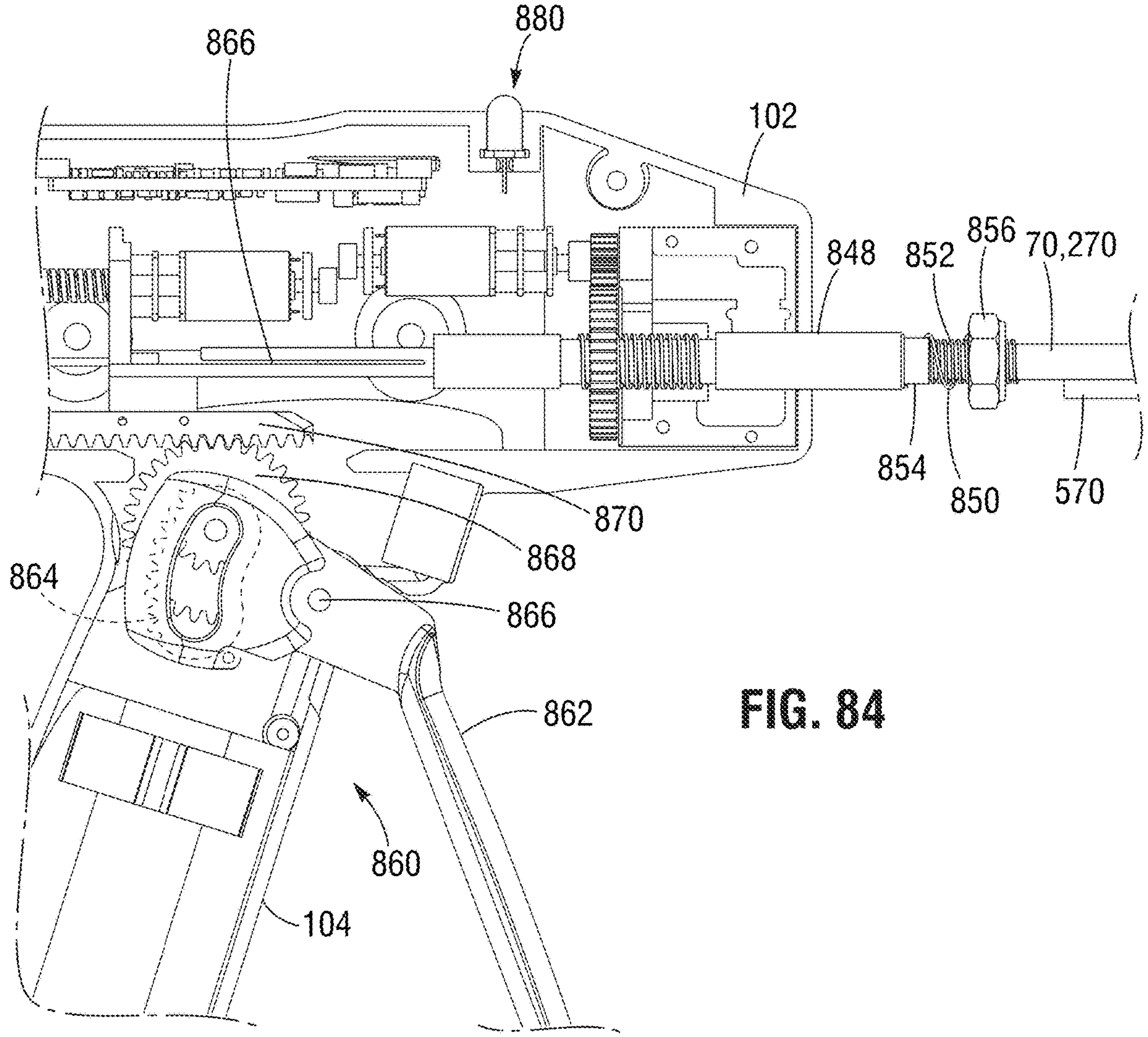
FIG. 84 is a fragmentary, side elevational view of the right side of the handle of FIG. 79 in a crimp-extended state.

Exemplary embodiments of a handle portion of the cutting assembly 860 are shown in FIGS. 81 to 84. With particular reference to FIG. 84, the handle portion of the cutting assembly includes a lever 862 with a kidney-shaped slot having, at a distal surface thereof, teeth 864 that are each disposed on a fixed radius from a pivot point 866 of the lever 862. Centrally fixed but rotatably disposed with respect to handle body 102 is a gear assembly 868 having a smaller gear interfacing with the teeth 864 and a larger gear interfacing with a rack 870. In this configuration with the smaller and larger gears of the gear assembly 868, closing the lever 862 onto the handgrip 104 of the handle 100 causes a distance-multiplied linear translation of the rack 870. The rack 870 is fixedly connected to the cutter push rod 64, thereby effecting a distal displacement of the cutter push rod 64 when the lever 862 is closed.

Figure 85:
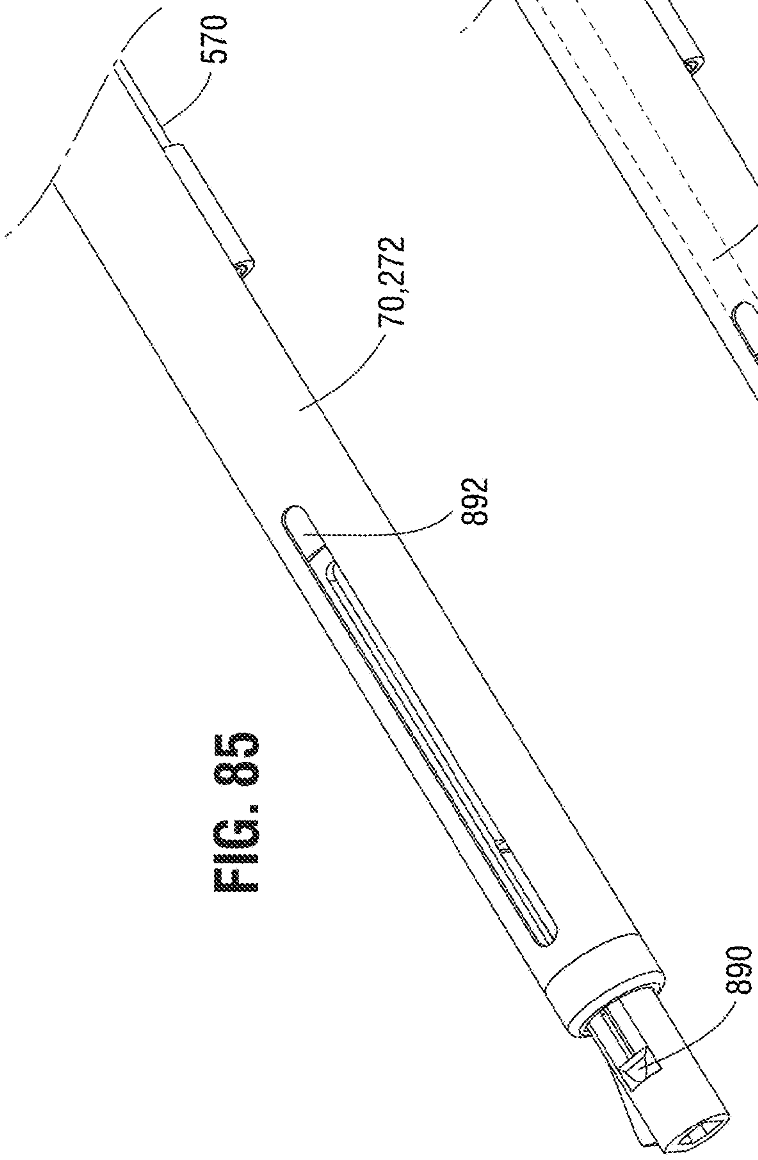
FIG. 85 is a fragmentary, perspective view of an exemplary embodiment of an end effector of a multiple-firing crimp device with a fixed blade and a blade pushrod in a fully retracted position and a crimping assembly in a non-crimping state.
Figure 86:
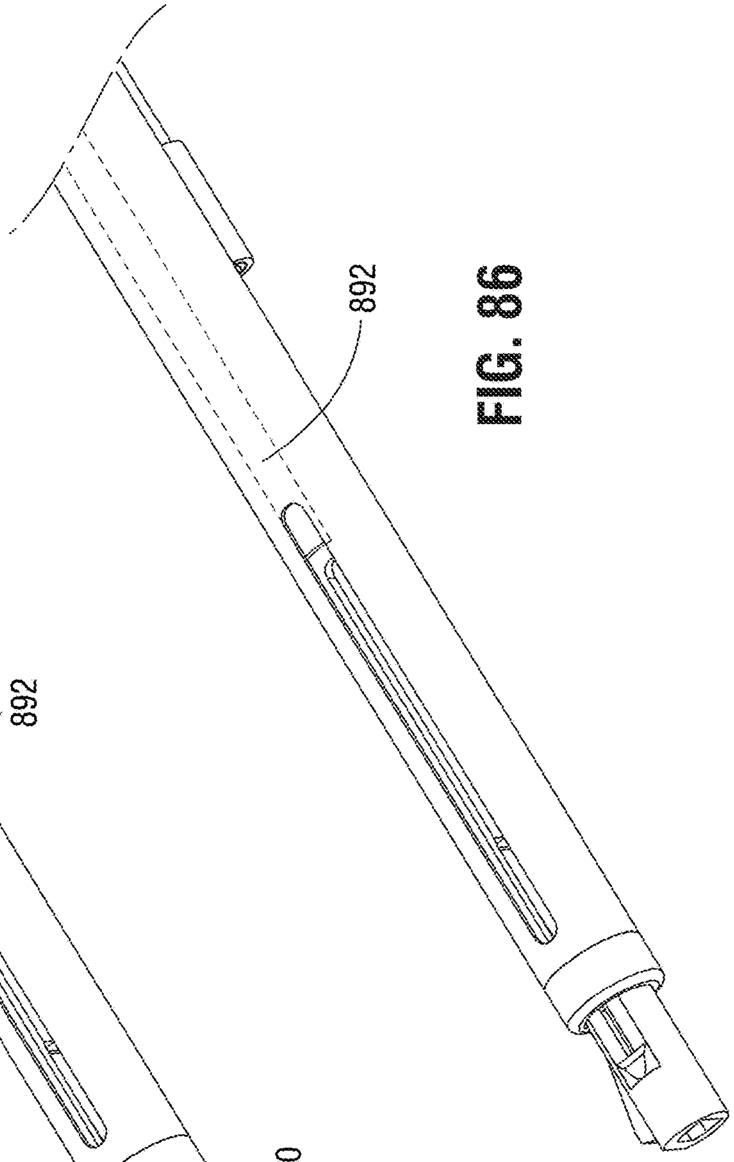
FIG. 86 is a fragmentary, perspective view of the end effector of FIG. 85 with the outer tube transparent.
Figure 88:
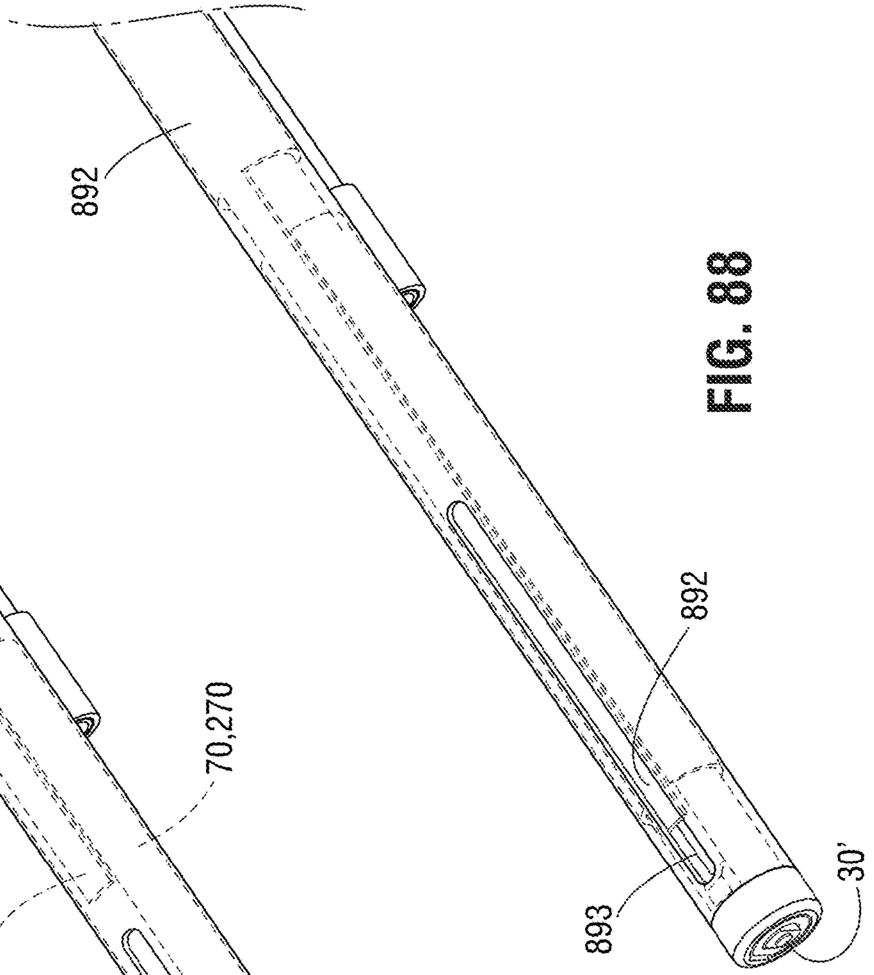
FIG. 88 is a fragmentary, perspective view of the end effector of FIG. 87 with the blade pushrod in a partially actuated state before cutting.
Figure 87:
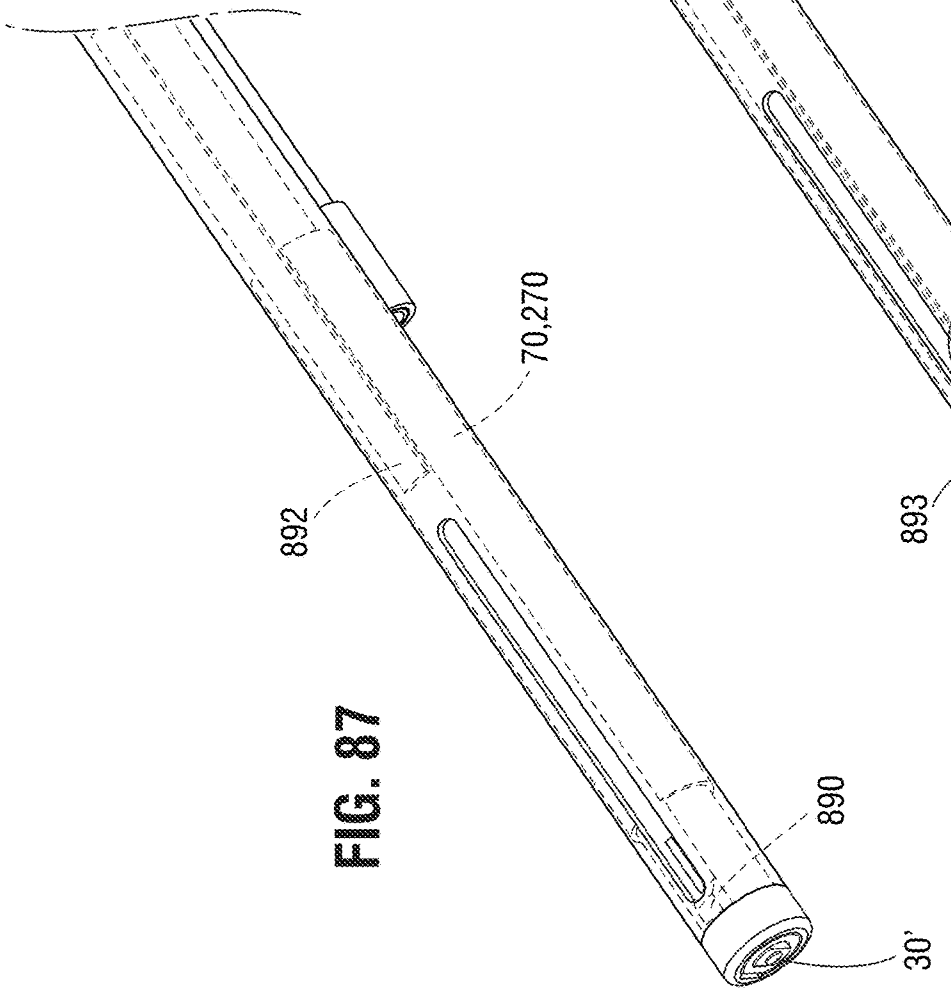
FIG. 87 is a fragmentary, perspective view of the end effector of FIG. 86 with the crimping assembly in a crimped state.
Figure 89:
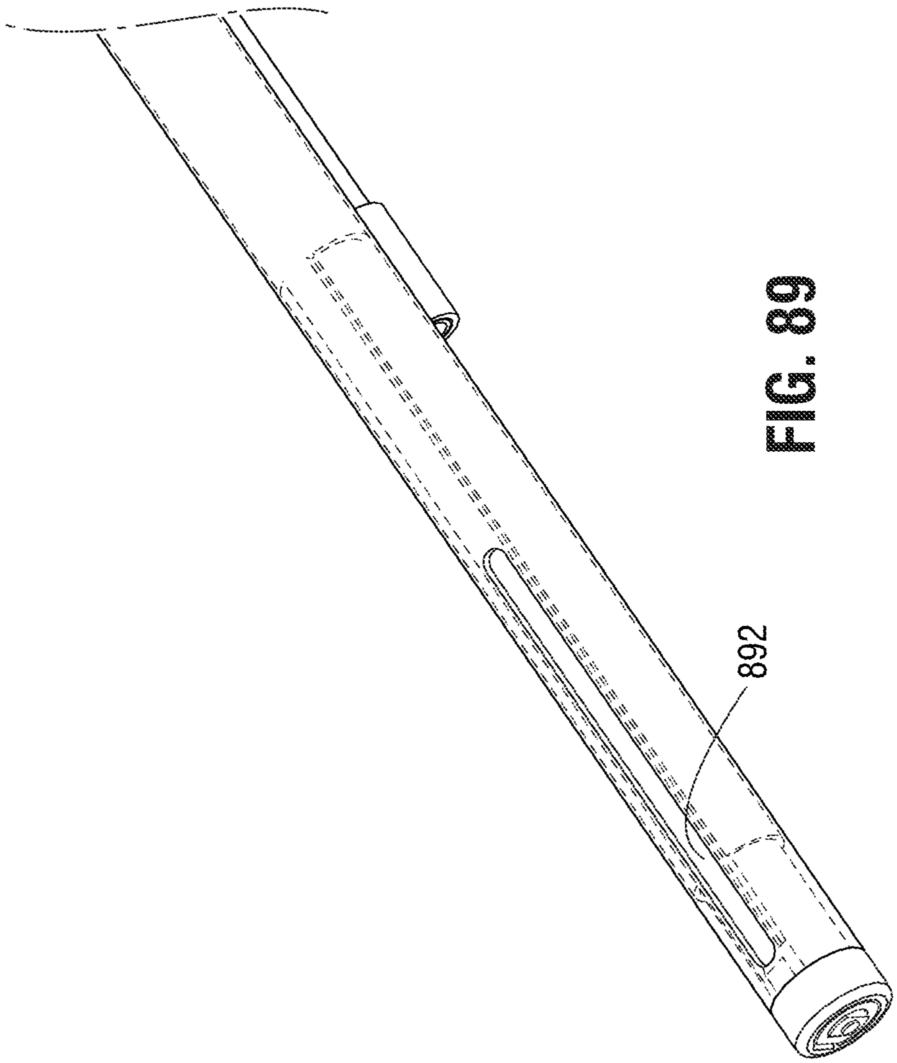
FIG. 89 is a fragmentary, perspective view of the end effector of FIG. 88 with the blade pushrod in a fully actuated state after cutting.
Figure 90:
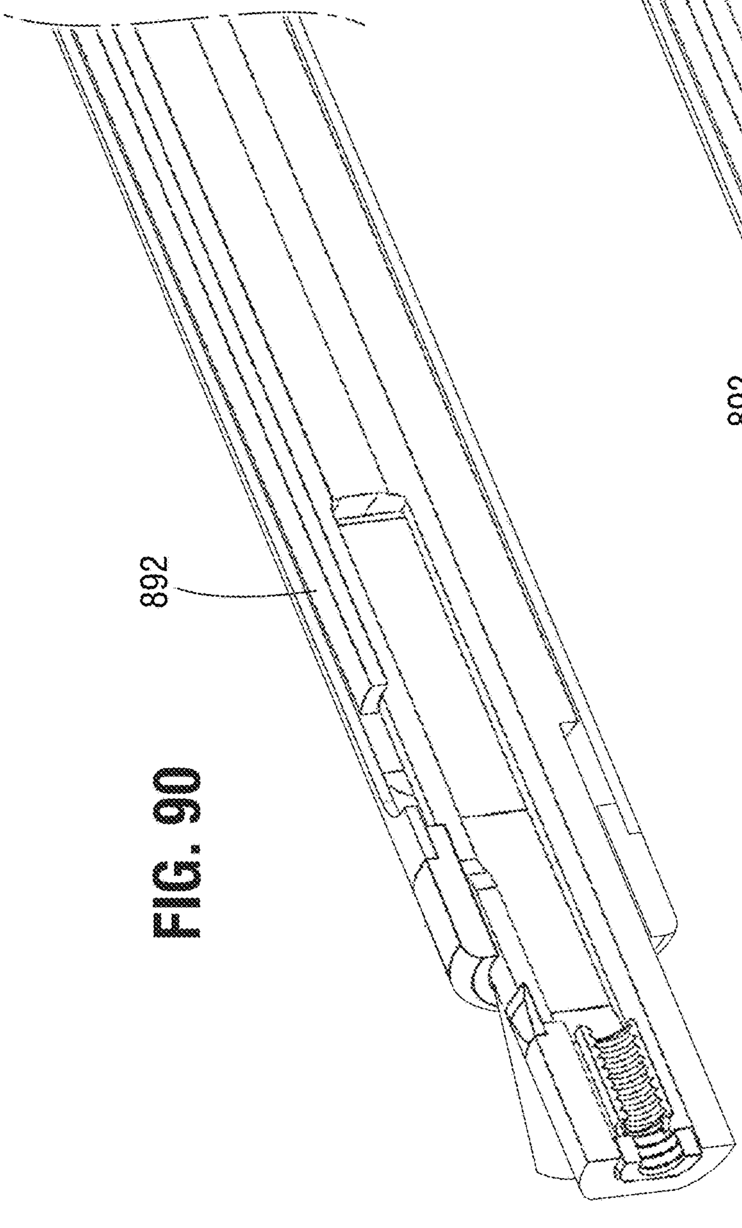
FIG. 90 is a fragmentary, longitudinally cross-sectional, perspective view of a distal end of the end effector of FIG. 85.
Figure 91:
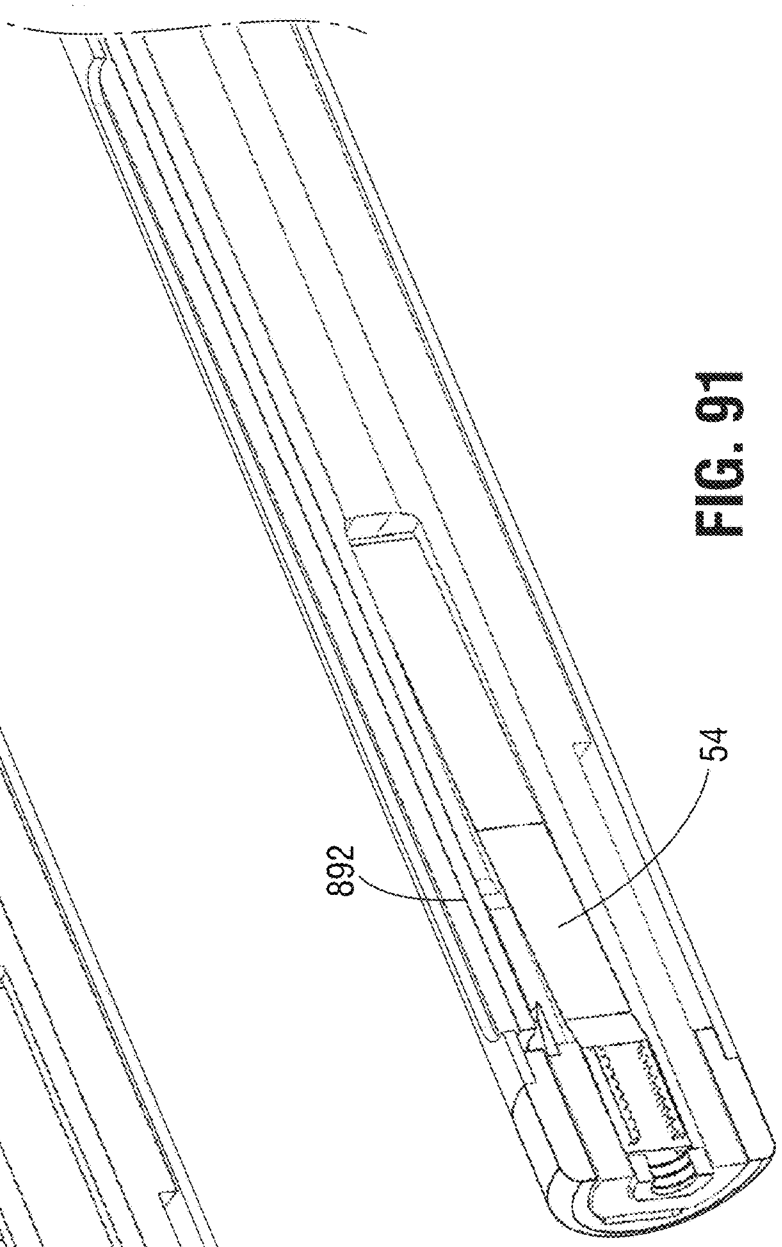
FIG. 91 is a fragmentary, longitudinally cross-sectional, perspective view of a distal end of the end effector of FIG. 89.

An alternative embodiment to the rotating cutter described above is a linear cutter shown in FIGS. 85 to 91. FIGS. 85, 86, and 90 illustrate an end effector of a multiple-firing crimp device with a fixed blade 890 and a blade pushrod 892 in a fully retracted position and with the crimping assembly 840 in a non-crimping state, in other words, the outer tube 70, 270 is retracted. FIG. 87 shows the crimping assembly 840 in a crimped state with the outer tube 70, 270 extended to crimp the crimp 30'. FIG. 88 shows the blade pushrod 892 in a partially actuated state before cutting occurs. It is noted from the right side of FIG. 88 that the blade pushrod 892 is a tube that rides inside the outer tube 70, 270. To ensure that the cords 2 are pressed against the fixed blade 890, the slot in which the cords 2 extend out the side of the outer tube 70, 270 narrows at a distal end 893 and terminates at the tip of the blade 890. FIGS. 89 and 91 show the blade pushrod 982 in a fully actuated state after cutting has occurred. (Due to limitations of the graphics software, the inwardly compressed hammer 54 in FIG. 91 is shown within the crimp 30'.)

The display assembly 880 is connected to the system control assembly 800 and, in this exemplary embodiment, is shown as an LED, which can be, for example, an RGB LED that can produce light in various colors; each distinct color (or even a flashing pattern) is able to indicate a particular function or status. The display assembly 880, in an alternative embodiment, can be an LCD or LED or OLED display panel that can produce any colors, text, video, or pictures indicating status or any other characteristic of the multiple-firing crimp device.

FIG. 92 shows a flow chart of a process for completing a crimping procedure with a multiple-firing crimp device described herein. In order to initialize the device, the outer tube and the crimp carriage are retracted. It is assumed that the crimps come preloaded on the crimp carriage before it is passed to a user. Of course, there can be a pre-initialization requirement that has the user load the crimp carriages with the crimps. Once initialized, the first crimp (the distal-most one) is advanced to the crimp loading orifice. The first crimp is secured at the crimp loading orifice by advancing the outer tube to gently press the hammer against the first crimp and hold it in the orifice. The crimp carriage is then rotated out from the first crimp (e.g., by a predefined number of turns) and further rotated to put the second crimp into a first crimp position at the distal end of the crimp carriage. The crimp carriage is moved proximally away from the end effector sufficiently far to prevent any interference with the crimping procedure into an idle position. The second crimp alignment can occur before, during, or after movement of the crimp carriage. As one crimp is no longer on the crimp carriage, the system can decrement a counter to keep track of the number of remaining crimps. At this point, the device is ready to use.

Figure 95:
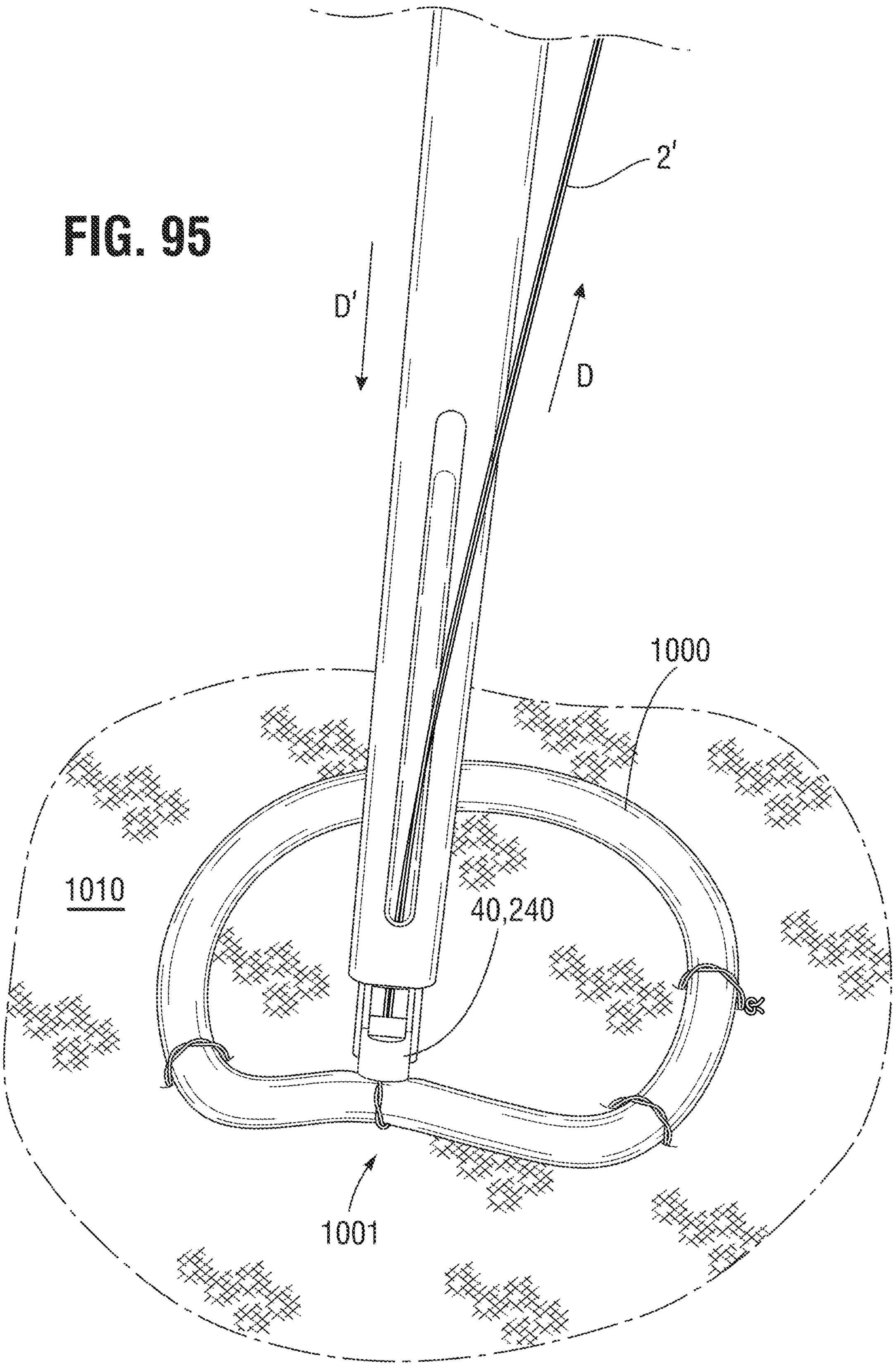
FIG. 95 is a photograph of a fragmentary, perspective view of the distal end of the multiple-crimp firing device of FIG. 93 with the suture and the distal end lifted from the surgical site.
Figure 96:
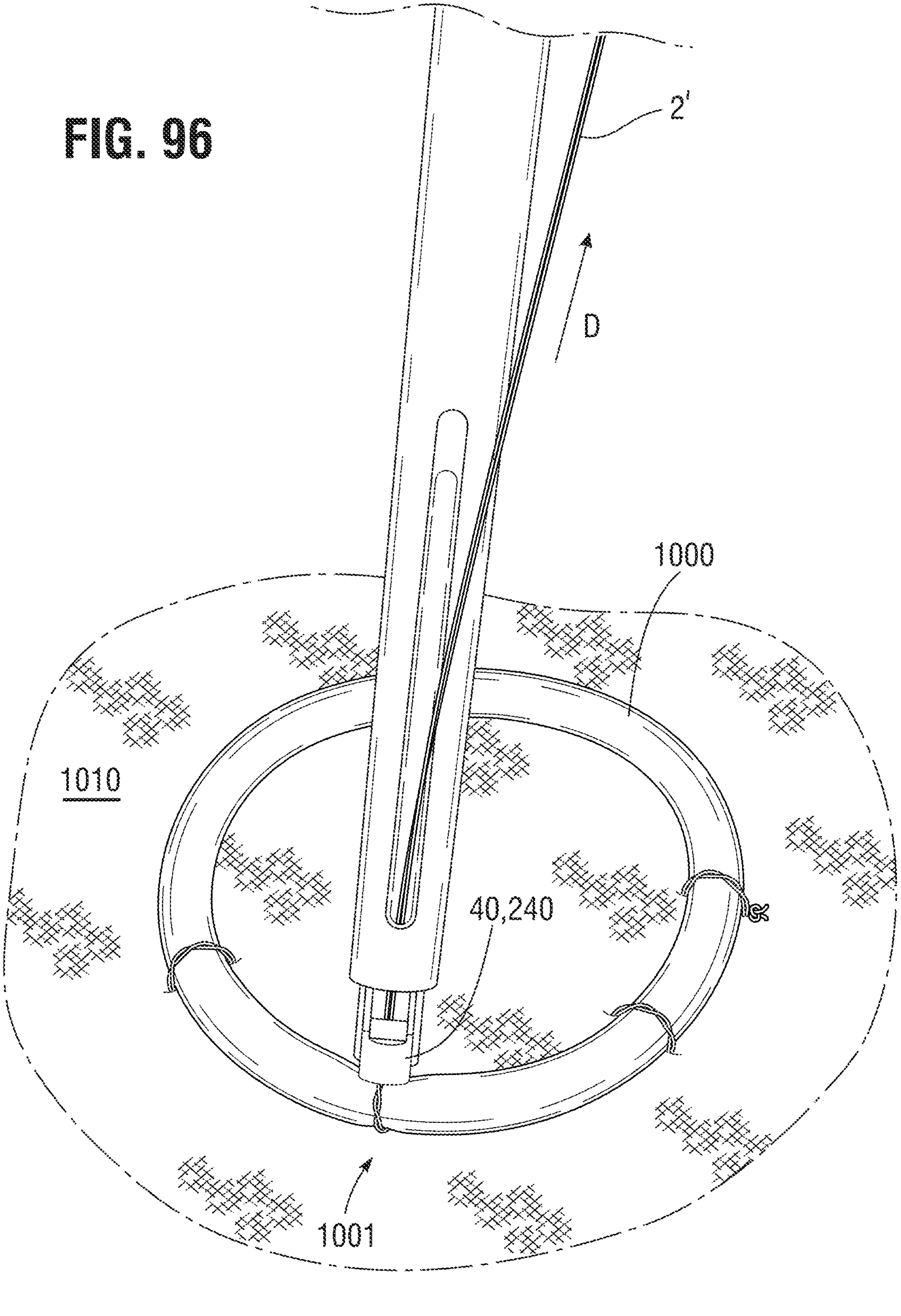
FIG. 96 is a photograph of a fragmentary, perspective view of the distal end of the multiple-crimp firing device of FIG. 93 with the suture cinched at the surgical site before a tying force is reached.
Figure 97:
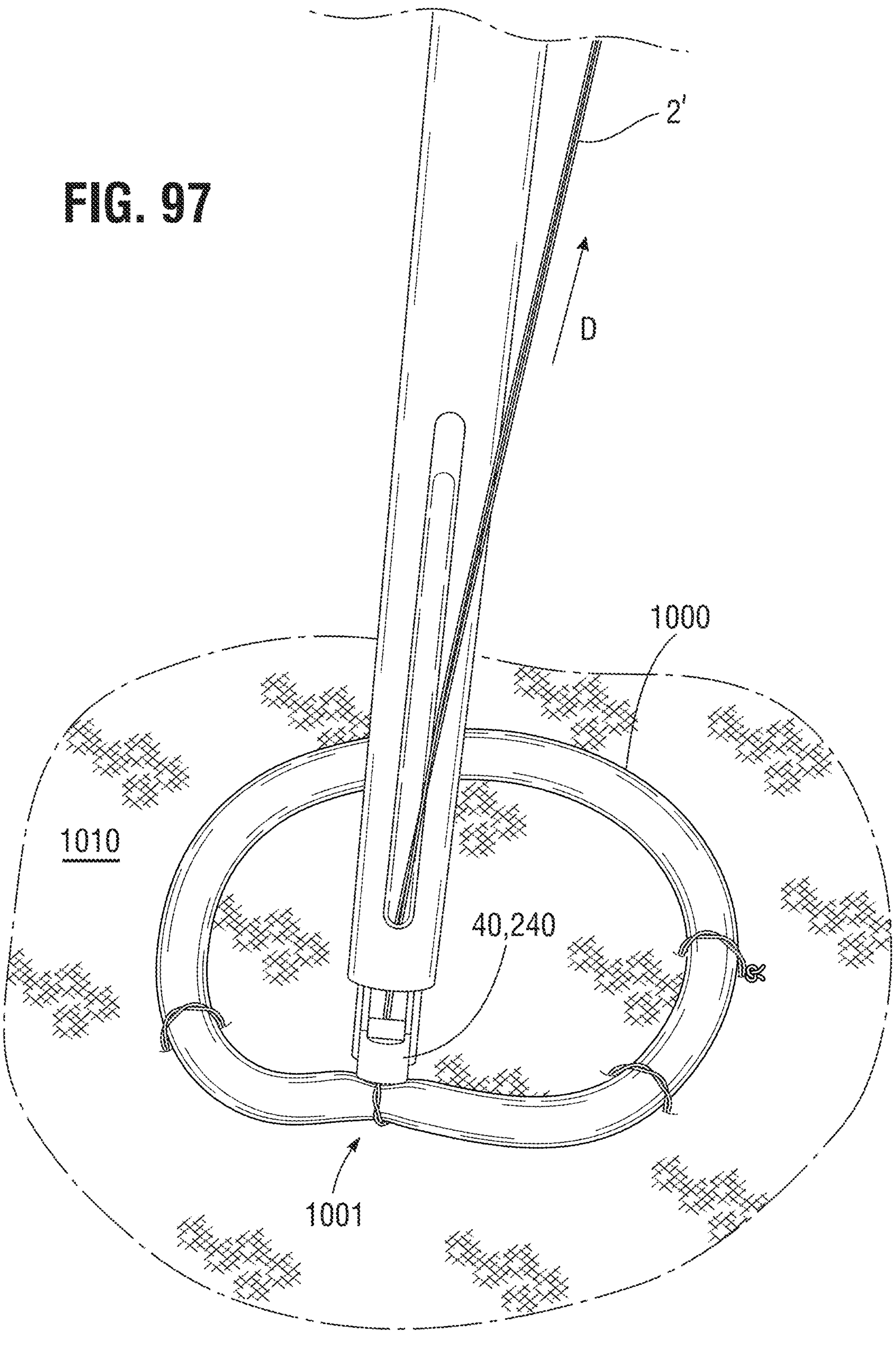
FIG. 97 is a photograph of a fragmentary, perspective view of the distal end of the multiple-crimp firing device of FIG. 93 with the suture cinched at the surgical site when the tying force is reached.

The user then carries out the manual steps of extending the snare, capturing the cord(s) within the snare, retracting the snare back to hold the cord(s), and then lifting the cord lifter or moving the shuttle proximally to present the end of the cord(s) outside the shaft of the device. The user grasps the exposed free end(s) of the cord(s) and pulls it/them taut. The end effector is then moved distally along the cord(s) to the place where the user desires to set the crimp. For example, where the cord is a surgical suture, the crimp is desired at the surgical site with no length of the suture between the crimp and the tissue. In such a case, the user will move the end effector up against the tissue to make the crimp ready to be fixed, such as shown in FIGS. 95 to 97.

The automatic crimping can now occur. The user presses the crimp-start button (for example) and the outer tube is advanced to the distal position where the hammer crushes the crimp. The tube is held there in place distally until the cutting assembly is actuated to cut the free ends of the cord/suture at the proximal side of the fixed crimp. When the system indicates that cutting has completed (e.g., when the cutting stroke is sufficient to insure that cords have been cut), the cutting assembly retracts to its idle position and the outer tube also retracts to its idle position, during which the now-crimped first crimp is released from the end effector. Now, the device is in its state for the next crimping process to begin, which starts with advancing the crimp conveyor to load the next crimp.

The process for crimping a cord in the exemplary embodiment of a heart valve replacement surgery is described with regard to FIGS. 93 to 97. This process and the devices described and/or shown are not limited to such a surgery. This surgery, in contrast, provides a good example for explaining the methods and systems. A ring 1000 is used as a surrogate for an actual replacement heart valve in this exemplary embodiment. The surgical site, e.g., the aortic valve seat in a heart, is indicated with a surface 1010, for example, made of neoprene. In this example, three sutures 1020 have been employed to secure the ring 100 at the surgical site 1010 by the multiple-firing crimp device 1 and a fourth suture 1022 is in the process of being secured at a surgical site 1001 (for illustrative purposes, the suture 1022 does not penetrate the surface 1010). An illustrative example of an installed crimp 30 can be seen on one of the sutures 1020 to the right of FIG. 93.

Figure 93:
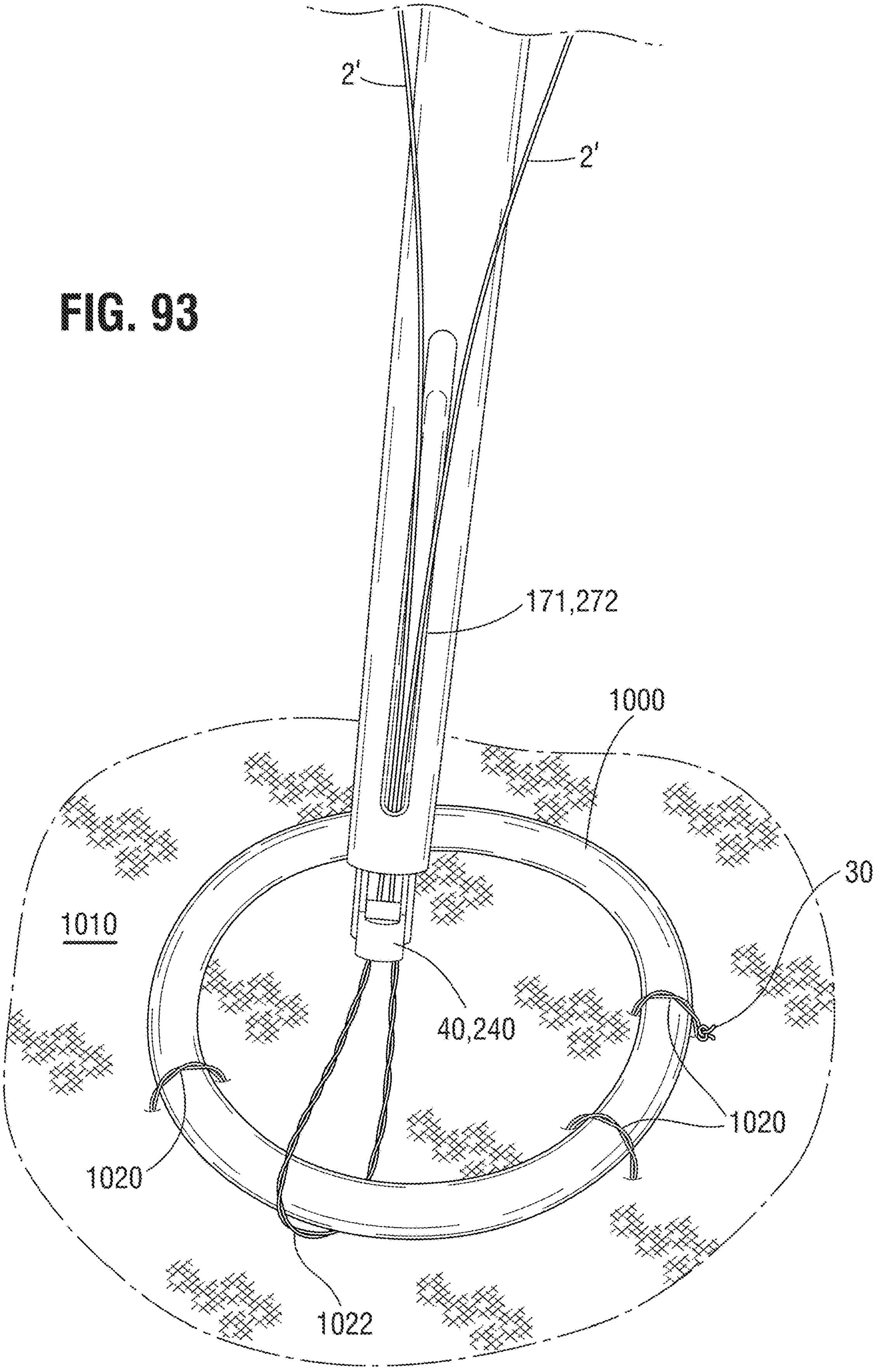
FIG. 93 is a photograph of a fragmentary, perspective view of an exemplary embodiment of the distal end of the multiple-crimp firing device with a suture wrapped around but not cinched at an illustration of a surgical site.
Figure 94:
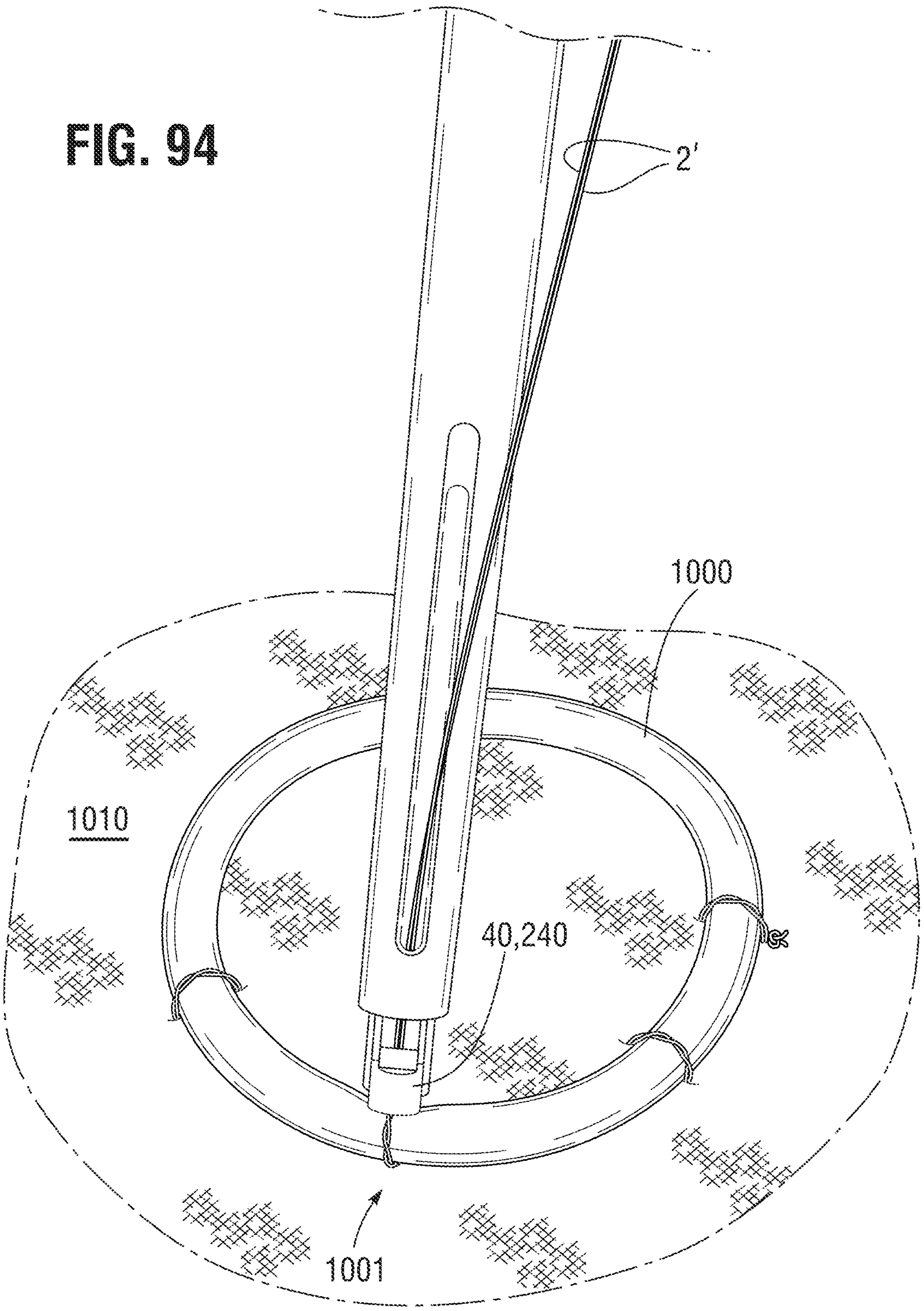
FIG. 94 is a photograph of a fragmentary, perspective view of the distal end of the multiple-crimp firing device of FIG. 93 with the suture closed at the surgical site.

In the view of FIG. 93, the suture 1022 to be crimped is wrapped around the ring 1000 and has already been threaded: through the crimp 30' that is loaded in the orifice 42; through the end effector body 40, 240; through a portion of the outer tube 70; and out the lateral opening 171, 272 of the outer tube 70. The ends 2' of the suture are distal of the end effector body 240 and are being held by the surgeon (see FIG. 97). To secure the suture 1022 for crimping, the suture ends 2' are pulled taut and the multiple-firing crimp device 1 is slid down the suture 2 until the end effector body 40, 240 along with the crimp 30' (not shown) rests against the position where crimping is to take place, which state is shown in FIG. 94. At this point, if the suture ends 2' are held in place with respect to the multiple-firing crimp device 1, both the suture ends 2' and the multiple-firing crimp device 1 can be raised or lowered without putting force on the surgical site 1001. Raising of the suture ends 2' and the multiple-firing crimp device 1 is shown in FIG. 95. In this state where the two items are moved together, any force imposed on the surgical site by pulling of the suture ends 2' in direction D is being counteracted by and is equal to the force D' in the opposite direction, thereby resulting in a net zero force on both the multiple-firing crimp device 1 and on the surgical site 1001. What is desired to be known is the force in which the suture 1022 is being knotted at the surgical site 1001, in other words, the tying force. The tying force can be determined because any force D that is imparted on the suture ends 2' is imparted directly upon the end effector body 40, 240, which force is transmitted directly to the handle 100 being held by the surgeon. Thus, if the distal end of the multiple-firing crimp device 1 is made to be movable with respect to the handle 100, then the exact amount of force D imposed by the surgeon on the suture ends 2' can be measured by placing the force-measuring and indicating assembly 900 between the distal end of the multiple-firing crimp device 1 and the handle 100.

Figure 97A:
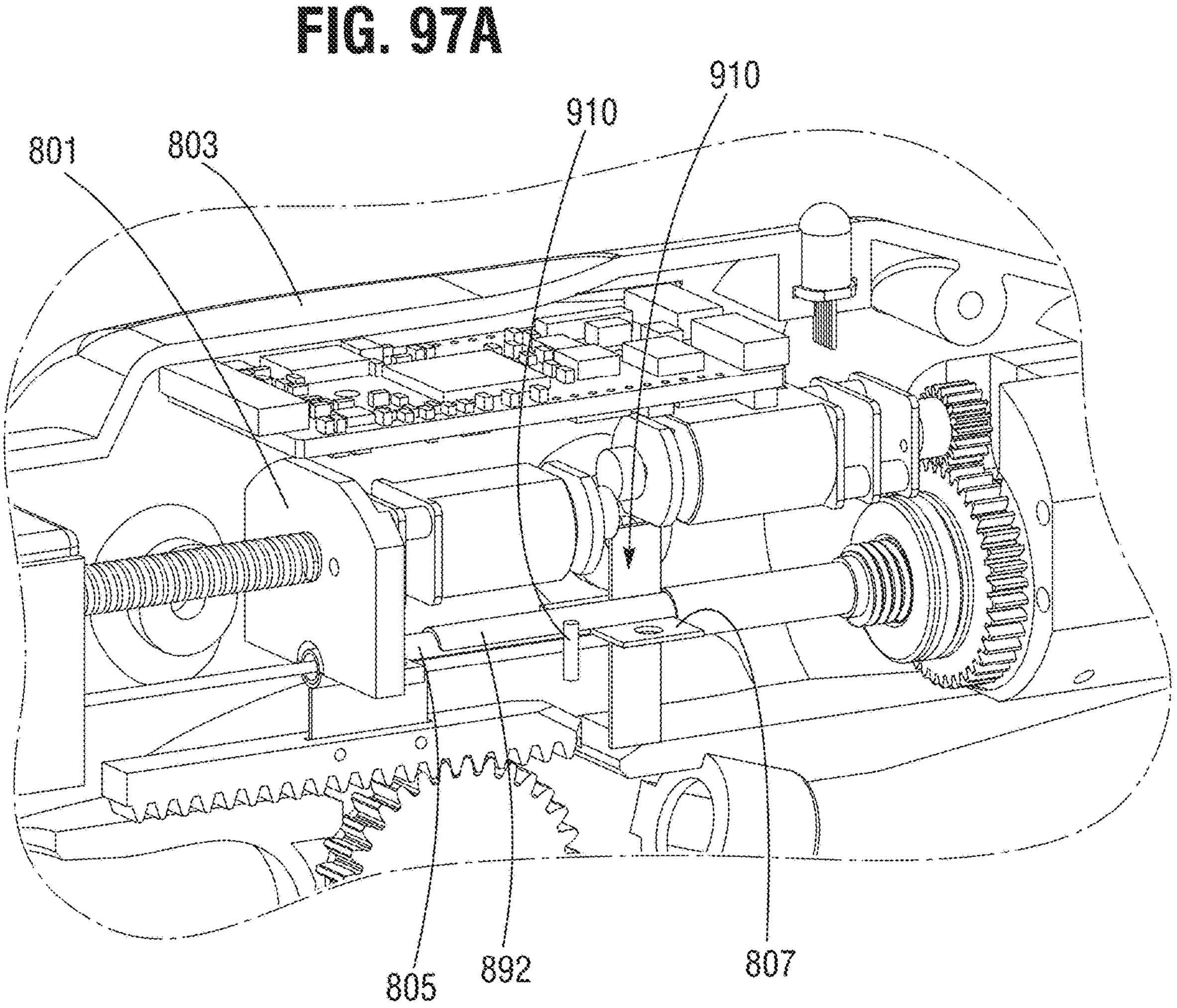
FIG. 97A is a fragmentary, enlarged, perspective view of the right side of the handle of FIG. 79 with a load sensor for detecting and measuring an amount of force being imparted on the cords at the surgical site before being secured.

In the exemplary embodiments described above and/or shown, the end effector body 40, 240 is grounded to the handle 100. The view of FIGS. 79 and 80 is suitable for understanding how the end effector body 40, 240 is grounded and the enlarged view of FIG. 97A is especially suitable for this purpose. Initially, it is noted that all of the internal components within the handle 100 are not individually connected to the handle 100. They are connected to a chassis 801 that actually is transparent in FIGS. 79 to 84 and 97 but is visible at least by its exterior lines. All of the components are connected to the chassis 801 and the chassis 801 is fixed to the interior surface of the handle body 803. If the handle body 803 is of a clam-shell configuration, the chassis 801 can be secured to one side and the second side can be secured to one or both of the one side and the chassis 801. To ground the end effector body 40, 240 to the chassis 801 (and thereby the handle 100), the end effector body 40, 240 is fixed to a grounding shaft 805 that runs proximally back and into the handle 100. The grounding shaft 805 is, then, fixed to the chassis 801. In this state, any force acting upon the end effector body 40, 240 is transmitted to the chassis 801 and handle 100. Grounding can be accomplished in a variety of ways, one exemplary configuration being shown by a wing 807 that is fixed/integral with the grounding shaft 805. By providing the handle 100 or the chassis 801 with a non-illustrated slot corresponding to the exterior dimensions of the wing 807, the grounding shaft 805 can be secured to the handle 100 and/or to the chassis 801. With a transverse through bore in the wing 807 and a corresponding through bore in the slot, a screw or other fastener can fix the wing 807 to the handle 100 or the chassis 801. In such a configuration, any force D imposed by the surgeon pulling upon the suture ends 2' will be counteracted by the grounding supplied by the handle 100.

This configuration, therefore, provides an appropriate location for determining how much force is being applied by the surgeon when the tying force is being applied and, thereby, received at the end effector body 40, 240. To allow such a force to be measured, the wing 807 is decoupled from the chassis 801/handle 100 and the grounding shaft 805 is connected indirectly to the chassis 801/handle 100 through the force-measuring and indicating assembly 900, which permits the grounding shaft 805 to move just enough with respect to the chassis 801/handle 100 to allow measurement of the tying force imposed on the end effector body 40, 240. To permit this movement, the proximal-most end of the blade pushrod 892 (in which the grounding shaft 805 resides) is provided with a longitudinal slot through which projects the wing 807. The force-measuring and indicating assembly 900 is disposed between the chassis 801 (or the handle 100) and the wing 805 and allows the grounding shaft 805 to move far enough to receive and measure the tying force imposed on end effector body 40, 240. In particular with regard to FIG. 97A, a load cell 910 (diagrammatically indicated) is fixed with respect to the chassis 801 (or handle 100) to receive any proximally directed force from the grounding shaft 805 (which is longitudinally connected to the end effector body 40, 240). The load cell 910 detects and measures the amount of tying force that is being imparted by the surgeon to the suture ends 2' when cinching the suture 1022 at the surgical site 1001. The load cell 910 supplies information corresponding to the tying force to the system control assembly 800 and/or the display assembly 880. Communication connectivity between the load cell 910 and the system control assembly 800 and/or the display assembly 880 is not illustrated for reasons of clarity. The amount of the tying force can be indicated in any way, for example, with a level indicator, with a dial, or with simple binary or tertiary indicators (e.g., yes/no or yes/no/too much). If a pre-set limit of the tying force is desired, an input function of the control assembly 800 can be used by the surgeon or the staff to set that force. Then, when in use, an indicator showing whether or not the amount of tying force is equal to or greater to the pre-set limit can be displayed. The display can take any form including those already described, for example, an LCD display with graphics, an LED with yellow, green, and red display colors, or simple yes/no mechanical and/or electrical indicators that show when sufficient tying force is being applied. Both audio and haptic feedback can be employed in addition to or instead of the visual indicators. A sound can be increasing in staccato until the desired tying force is imparted, at which time the sound is constant. Likewise, the handle can be still until the tying force is reached, at which time, the handle 100 vibrates. In this way, the user can maintain an exact and desired pressure (without putting too much force) against the surgical site 1001 by the suture 1022 until the crimp 30' is secured on the suture 2. When the indicator tells the surgeon that the tying force is within the desired range or at the desired level, the user can effect the crimping process to secure the crimp 30' to the suture 2.

With such a force-measurement assembly, reference is made to FIG. 96. Here, the surgeon can secure the suture 1022 as desired. First, the end effector body 40, 240 is pressed against the surgical site 1001 and the surgeon starts pulling on the suture ends 2' in direction D. During this process, the surgeon is looking at the indicator at the handle 100 and/or waiting for audio/haptic feedback. When the desired or pre-set tying force is reached, for example, as shown in the view FIG. 97, the surgeon actuates the crimping process and the crimp 30' is secured at the surgical site 1001. Alternatively, the device and method can have the crimping occur automatically once the desired/pre-set tying force is met and, thereafter, cutting can also occur, either automatically or manually. As a corollary to this, the crimping can be entirely prevented and locked out unless and until a desired or pre-set tying force is detected/measured by the force-measuring and indicating assembly 900. With the various forms of feedback that can be communicated to the surgeon, the tying force can be indicated to the user that there is not enough force being imparted upon the suture ends 2' or too much force is being imparted. The systems and methods are not limited to the various electrical embodiments described for supplying force level feedback. Mechanical systems and processes can also be incorporated. For example, a dial or needle on a scale can be provided to show the tying force being imparted. Regardless of the way that the tying force is measured, the system can record all of the data that is experienced by the various sensors and provide it as output for later read out or analysis.

In the above text, a load cell 910 is indicated as the device that measures the tying force. Any similar and/or equivalent structure or device can be substituted for the load cell 910 to measure the force imparted onto the distal end of the multiple-firing crimp device 1 by pulling on the suture ends 2'.

Figure 99:
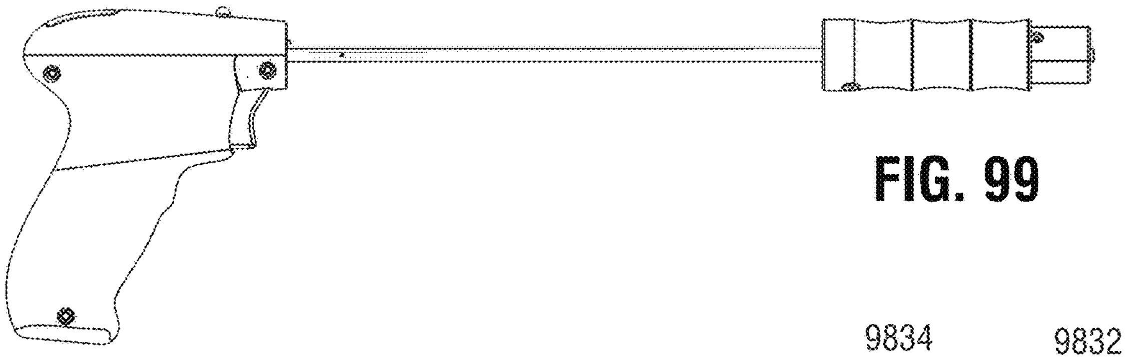
FIG. 99 is a right side elevational view of the multiple-clip securing device of FIG. 98 in a shuttle-extended state with the snare still contained within the snare assembly.
Figure 100:
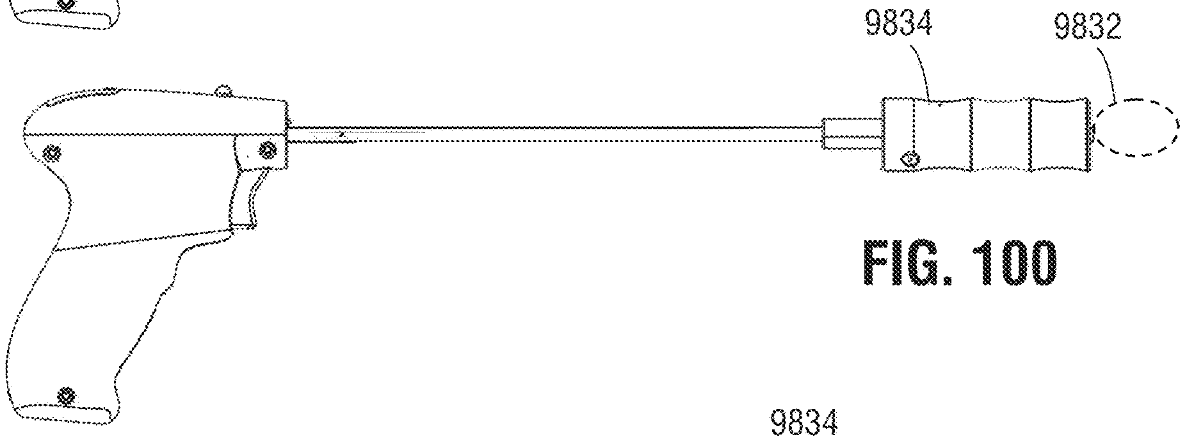
FIG. 100 is a right side elevational view of the multiple-clip securing device of FIG. 98 in a snare-extended state with the snare, indicated by dashed lines, extended out from the snare assembly and the snare assembly locked in the shuttle-extended position while the snare is extended.
Figure 101:
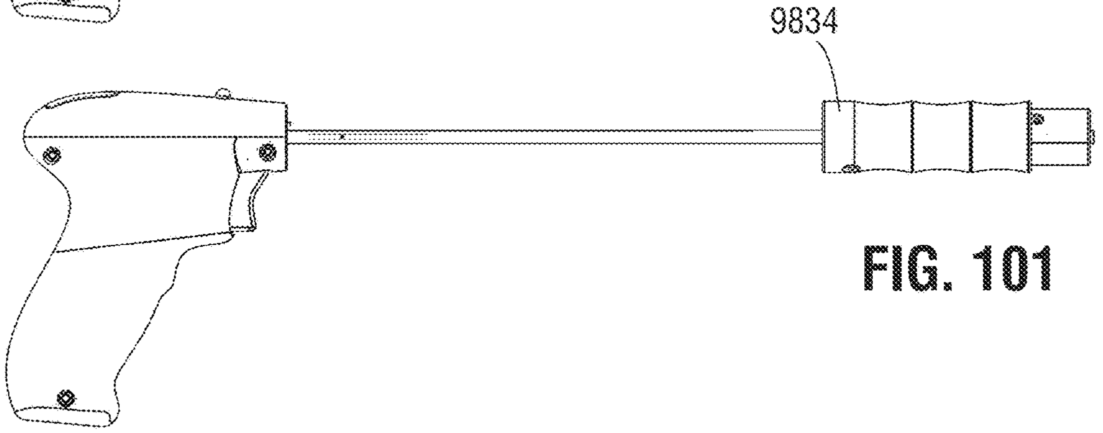
FIG. 101 is a right side elevational view of the multiple-clip securing device of FIG. 100 in the shuttle-extended state with the snare retracted back into the snare assembly and the snare assembly unlocked to permit retraction of the snare assembly.

The multi-securing devices described and/or shown herein are not limited to securing with crimps. Other exemplary embodiments include securing devices that are clips. One exemplary embodiment for a multiple-clip securing device 9800 is shown in FIGS. 98 to 102. A user handle 9810 includes a shaft 9820 in which resides a plurality of cord-securing clips described in detail below. Slidably disposed on the shaft 9820 is a snare assembly 9830. As in the other exemplary embodiments herein, the securing process includes moving the snare assembly 9830 to the distal end of the shaft 9820, as shown in FIG. 99. When the cords are ready to be snared, the snare 9832 is extended by moving a snare-extender slide 9834 distally, as shown in FIG. 100, the snare 9832 being represented diagrammatically with dashed lines. Moving the snare-extender slide 9834 proximally, as shown in FIG. 101, withdraws the snare 9832 and captures the cords 2 within the snare assembly 9830 for movement through a securing clip and out the side of the shaft 9820 for manipulation by the user. Sliding the snare assembly 9830 proximally, as shown in FIG. 102, pulls the ends of the cords 2 through the clip and out a snare-access window 9822 of the shaft 9820 to an orientation that allows a user to manipulate the free ends 2' of the cords 2. In this exemplary embodiment, the snare-access window 9822 is at the top of the shaft 9820 but it can be at another orientation along the circumference of the shaft 9820. When the cords 2 are ready to be secured by the clip, a clip-securing trigger 9812 of the handle 9810 is depressed to install the clip and activate a cord-cutting assembly within the handle 9810 and the shaft 9820 as described in further detail below. Finally, a reload trigger 9814 is pressed to automatically reload a clip for a further clip-securing procedure.

FIG. 103 shows a flow chart of a process for completing a cord-securing procedure with a multiple clip-securing device 9800. In order to initialize the device 9800, the snare assembly 9830 is in its retracted home position at the handle 9810. It is assumed that the clips come preloaded within the shaft 9820 before it is passed to a user, the clips being loaded, for example, at the manufacturer. Of course, there can be a pre-initialization requirement that has the user load the shaft 9820 with the clips. Once initialized, if the first clip (the distal-most one) is not already at a cord-securing location, it is advanced to the cord-securing location, examples of which are shown in FIGS. 104, 119, 121, 122, and 133. At this point, the device is ready to use.

One exemplary embodiment of a distal end of the multiple clip-securing device 9800 is depicted in FIGS. 104 to 111. As can be seen through a side window 10422 of an exemplary embodiment of the shaft 9820, a set of clips 10400 are installed on a guide rail 10410 for use in subsequent clip-securing operations. It is desirable to provide the outer surface of the shaft 9820 with the side window 10422 to allow a user to count the number of clips 10400 remaining in the multiple-clip securing device 9800. As can be seen, for example, in FIGS. 104, 107, 109 and, in particular, in FIG. 121, the inner and outer tubes of the shaft 9820 are flush at the distal end of the multiple-clip securing device 9800. This is desirable to allow a positioning of the clip 10400 flush to the inner and outer tube ends to aid in tensioning the device on cords 2 to be secured with the clip 10400 and to present the most blunt edge possible to the sewing cuff or tissue that is being affixed.

Figure 104:
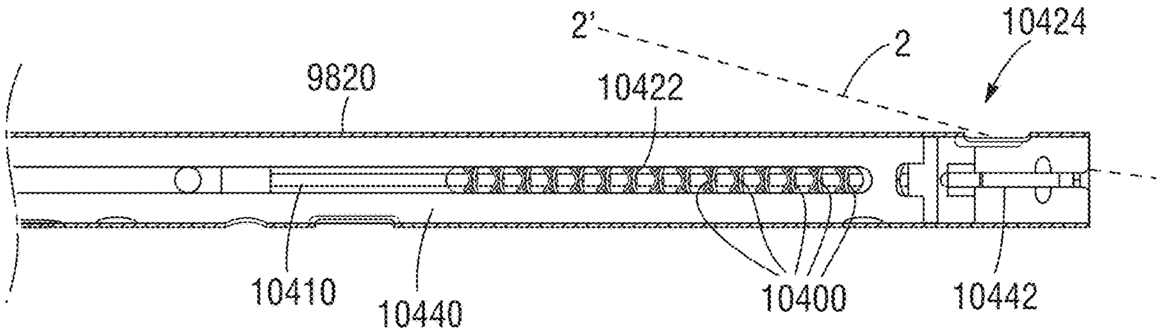
FIG. 104 is a fragmentary, partially transparent, side elevational view of a distal end of an exemplary embodiment of a distal end of the multiple-clip securing device of FIG. 98 with a clip loaded at the distal end in a ready-to-clip state.

The distal-most clip 10400 in the clip-securing position is not visible in the view of FIG. 104 because the clip 10400 is behind clip-movement arms 10442 and the body of a cutting/reloading assembly 10440. The user then carries out the manual steps for capturing the cords. In summary, first, the user distally extends the snare assembly 9830 from a proximal position at the handle 9810. During this movement, a snare-guiding tube 14140 will lower from the snare assembly 9830, enter a snare access window 10424, 11228 of the shaft 9820, and extend distally to place a distal exit 14142 of the snare-guiding tube 14140 just proximal of the distal-most clip 10400 to be used in the present clip-securing operation. In such an orientation, the distal exit 14142 is aligned with the opening within the clip 10400. Therefore, when the user distally extends the snare 9832 after the snare assembly 9830 reaches its distal end stop on the shaft 9820, the snare 9832 passes through the opening of the clip 10400 and opens up to receive cords 2 therein to be secured. The user manually captures the cord(s) 2 within the snare 9832 by, for example, threading sutures through the central opening of the snare 9832. Capturing is completed when the user retracts the snare 9832 proximally to hold the cord(s) 2 at the distal end of the snare assembly 9830. Assuming the user is satisfied with the way that the cords 2 are captured in the snare 9832, the user will, then, return the snare assembly 9830 proximally back to its proximal position at the handle 9810 to present the free ends 2' of the cord(s) 2 outside the shaft 9820. If the snaring is not acceptable, the snare 9832 is extended again for acceptable recapture. An orientation of the distal end of the shaft 9820 when the snare has moved proximally back to the handle 9810 and has threaded the cords 2 through the clip 10400 in this ready-to-secure state is depicted in FIG. 104. The cords 2 are depicted as being pulled taut by the user.

Figure 105:
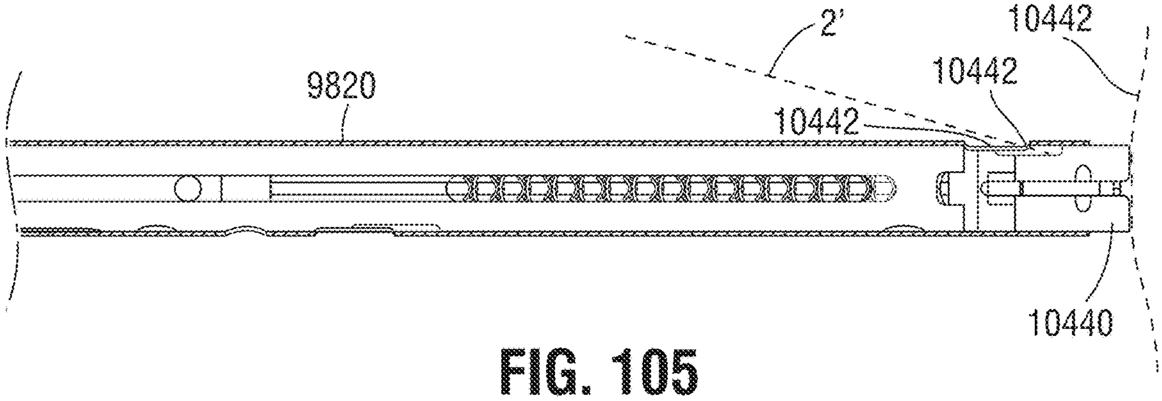
FIG. 105 is a fragmentary, partially transparent, side elevational view of the distal end of the multiple-clip securing device of FIG. 104 with a clip extended off a clip-holding rail and clipped to one or more cords but the cords not yet cut.
Figure 106:
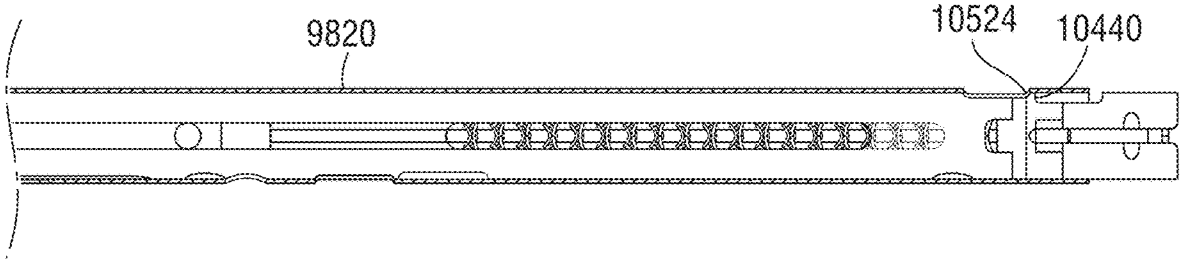
FIG. 106 is a fragmentary, partially transparent, side elevational view of the distal end of the multiple-clip securing device of FIG. 104 with a clip extended off a clip-holding rail and clipped to one or more cords after the cords are cut.
Figure 107:
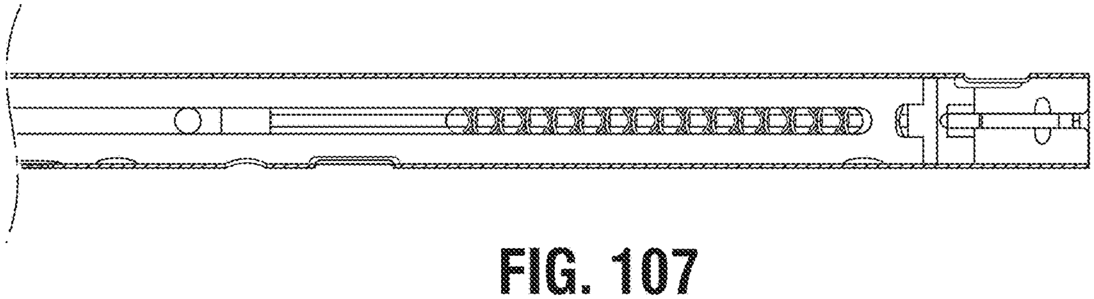
FIG. 107 is a fragmentary, partially transparent, side elevational view of the distal end of the multiple-clip securing device of FIG. 104 after a clip has been clipped to one or more cords and is ready to cut again or to reload another clip into a clip-ready location.

The distal end of the shaft 9820 is then slid distally along the cord(s) 2 to a place where the user desires to set the clip 10400 housed inside the distal end of the shaft 9820. For example, where the cord 2 is a surgical suture, a securing point of the clip 10400 is as close to the surgical site as possible with no length of the suture between the clip and the tissue. In such a case, the user moves the distal end of the shaft 9820 up against the tissue, diagrammatically depicted with reference numeral 10510, to place the clip 10400 in a ready to be fixed location, shown for example, in FIG. 105. Automatic clip securement can now occur. The user presses the clip-securing trigger 9812 and, in doing so, two actions occur. First, the clip 10400 is fixed to the cords 2 and, second, the cord(s) 2 is/are cut. FIG. 105 depicts the cutting/reloading assembly 10440 in an intermediate cutting position where the moving portion 10442 of the two cutting surfaces has moved distally towards the fixed portion 10524 of the two cutting surfaces. With further distal movement of the cutting/reloading assembly 10440, as shown in FIG. 106, cutting of the cords 2 is completed by placing the moving portion 10442 of the two cutting surfaces distally past the fixed portion 10524, thereby creating a scissor effect on the cords 2 with the two surfaces 10524, 10442 while, at the same time, sliding the clip 10400 off of the guide rail 10410 and entirely unsecuring it from the multiple clip-securing device 9800. Movement of the multiple clip-securing device 9800 away from the securing site 10510 reveals to the user that the clip 10400 is secured on the cords 2 and the cords 2 are cut on the side of the clip 10400 facing away from the site 10510. The multiple clip-securing device 9800 indicates (by visual, audible, tactile measures) that a cutting action has completed but a user can actuate the clip-securing trigger 9812 again, if desired, and the cutting action will repeat. FIG. 107 illustrates the device 9800 in state that is ready for recutting or reloading.

Figure 108:
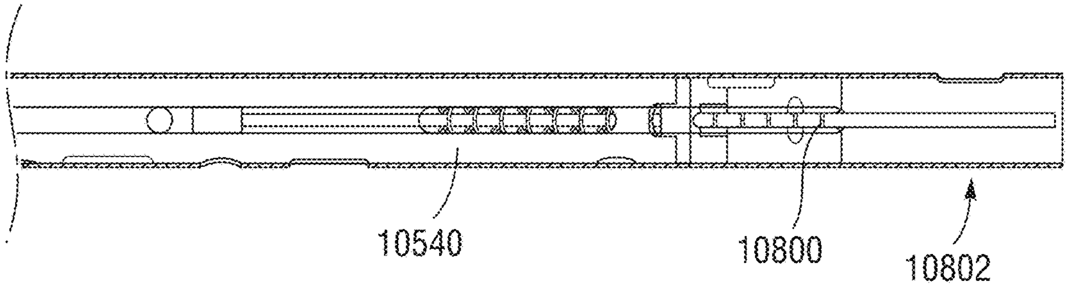
FIG. 108 is a fragmentary, partially transparent, side elevational view of the distal end of the multiple-clip securing device of FIG. 104 with a clip pusher moved proximally towards a clip-reloading position and with one of the clip-holding fingers removed for clarity.
Figure 109:
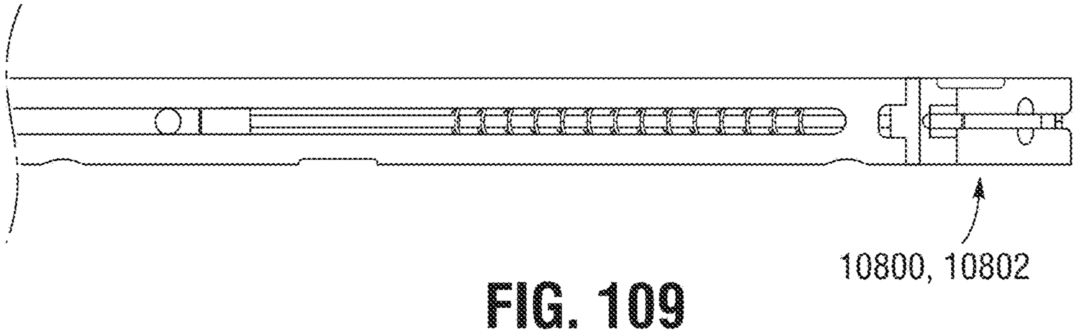
Figure 110:
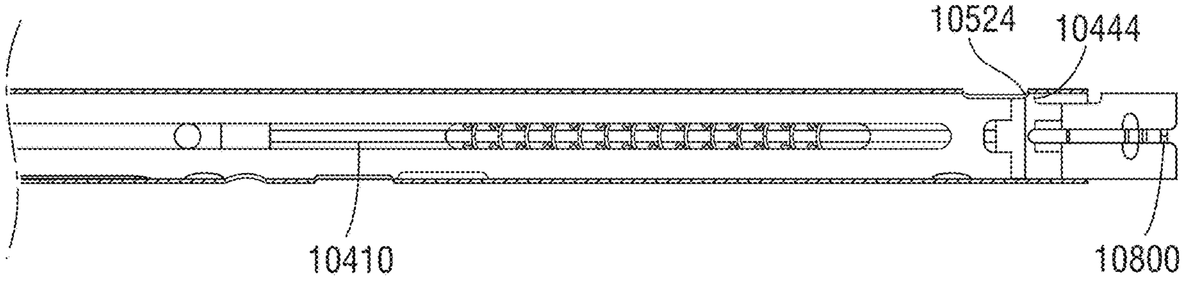
Figure 111:
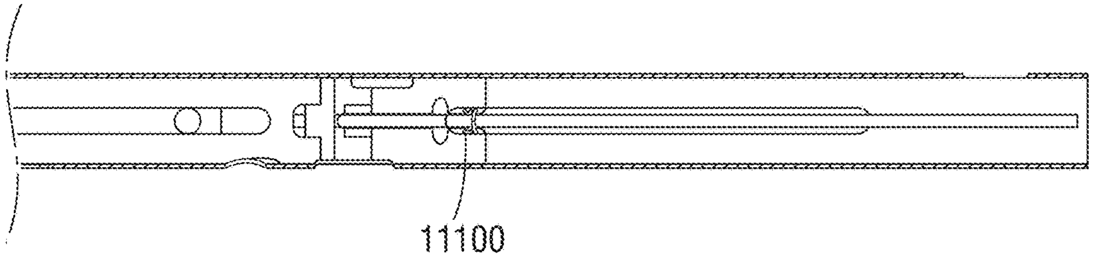

In order to reload the device 9800, the user presses the reload trigger 9814 and a procedure for placing a now distal-most clip 10800 at a cord-securing location 10802 at the distal end of the shaft 9820 can begin. The clip 10800 is visible because the clip-movement arms 10442 are not shown in this figure. The device 9800 automatically moves the cutting/reloading assembly 10440 rearward to a position where the clip-movement arms 10442 catch the clip 10800, which position is shown in FIG. 108. Then, the cutting/reloading assembly 10440 extends distally to place the clip 10800 at the cord-securing location 10802, which is hidden by the clip-movement arms 10442 in FIG. 109. The securing and cutting operations are repeated as before to secure the second clip 10800 on new cords 2 and move the clip 10800 off of the guide rail 10410, which orientation is depicted in FIG. 110. The clip-securing processes are repeated for as many times as needed in a given procedure. In the exemplary embodiment of FIGS. 108 to 111, there are fourteen clips illustrated. FIG. 111 illustrates the cutting/reloading assembly 10440 in a reloading position for the last clip 11100 after the other thirteen clips have been used. As can be understood, the cutting/reloading assembly 10440 moves a distance proximally that increases for each new clip that is being reloaded. The movement algorithm is set within the device 9800 as described in further detail below.

Another exemplary embodiment of a distal end of the multiple clip-securing device 11200 is depicted in FIGS. 112 to 137. Many of the features in this embodiment are similar or even the same as previous embodiments of the device. Even though such features may be referenced with a different numeral, that designation, alone, does not mean that the feature is different and can be the same. Likewise, where features are referenced with the numeral, that designation, alone, does not mean that the feature is the same and can be different.

Figure 116:
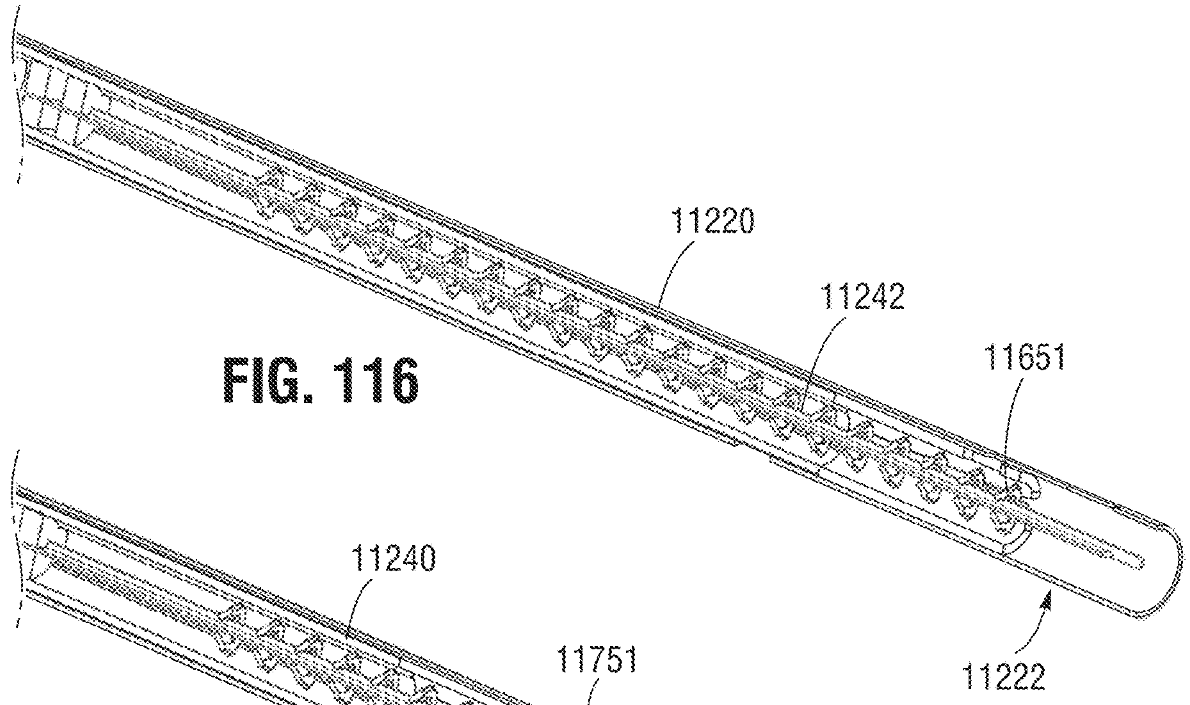
Figure 117:
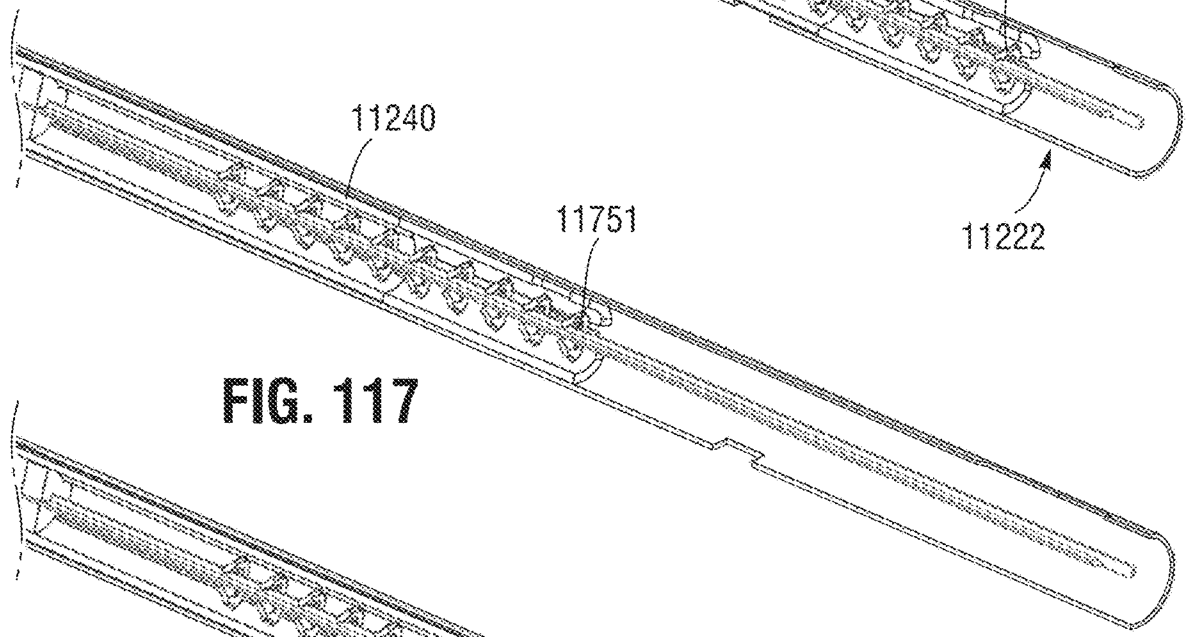
Figure 118:
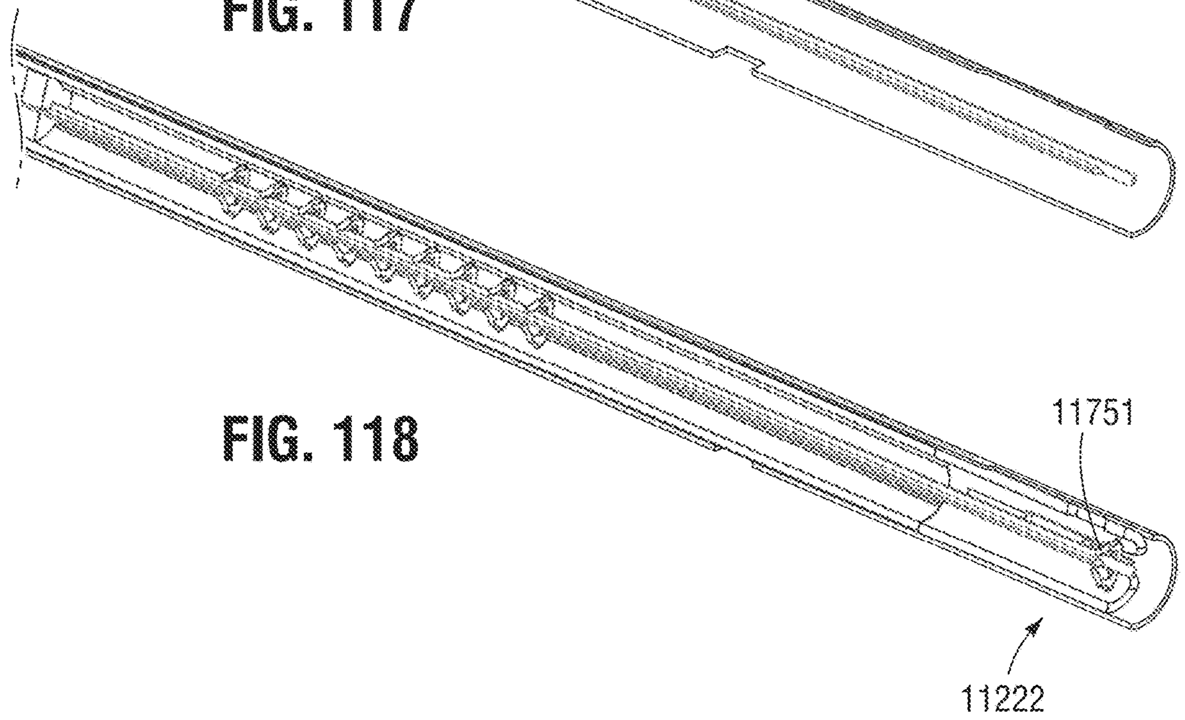

Depicted in FIGS. 112 to 118 is an exemplary embodiment of a distal end of the shaft 11220 in which is disposed a set of clips 11250 loaded on a guide rail 11210 that is fixedly secured within the shaft 11220 through a rail block 11212. Also disposed within the shaft 11220 is a distal portion of a cutting/reloading assembly 11240, which is slidably disposed within the shaft 11220. FIGS. 112 and 118 show the device 11200 a ready-to-secure state, the former showing an example where the device 11200 is full with clips 11250 and the latter showing the device 11200 having nine clips 11250 in addition to the one in the ready-to-secure state. In this state, the cutting/reloading assembly 11240 has delivered a distal-most clip 11251 to a distal cord-securing location 11222 within the shaft 11220. At this point, the user then carries out the manual steps for capturing the cords. In summary, first, the user distally extends the snare assembly 9830 from a proximal position at the handle 9810. During this movement, a snare-guiding tube 14140 will lower from the snare assembly 9830, enter a snare access window 10424, 11228 of the shaft 11220, and extend distally to place a distal exit 14142 of the snare-guiding tube 14140 just proximal of the distal-most clip 11251 to be used in the present clip-securing operation. In such an orientation, the distal exit 14142 is aligned with the opening within the clip 11251, as can be seen in FIG. 152, for example. Therefore, when the user distally extends the snare 9832 after the snare assembly 9830 reaches its distal end stop on the shaft 11220, the snare 9832 passes through the opening of the clip 11251 and opens up to receive cords 2 therein to be secured. The user manually captures the cord(s) 2 within the snare 9832 by, for example, threading sutures through the central opening of the snare 9832. Capturing is completed when the user retracts the snare 9832 proximally to hold the cord(s) 2 at the distal end of the snare assembly 9830. Assuming the user is satisfied with the way that the cords 2 are captured in the snare 9832, the user will, then, return the snare assembly 9830 proximally back to its proximal position at the handle 9810 to present the free ends 2' of the cord(s) 2 outside the shaft 11220. If the snaring is not acceptable, the snare 9832 is extended again for acceptable recapture. An orientation of the distal end of the shaft 11220 when the snare has moved proximally back to the handle 9810 and has threaded the cords 2 through the clip 10400 in this ready-to-secure state is depicted in FIGS. 122 and 123. The cords 2 are depicted as being pulled taut by the user.

The distal end of the shaft 11220 is then slid distally along the cord(s) 2 to a place where the user desires to set the clip 11251 housed inside the distal end of the shaft 11220. For example, where the cord 2 is a surgical suture, a securing point of the clip 11251 is as close to the surgical site as possible with no length of the suture between the clip and the tissue. In such a case, the user moves the distal end of the shaft 11220 up against the tissue, diagrammatically depicted in FIG. 123 with reference numeral 12310, to place the clip 11251 in a ready to be fixed location. Automatic clip securement can now occur. The user presses the clip-securing trigger 9812 and, in doing so, two actions occur. First, the clip 11251 is fixed to the cords 2 and, second, the cord(s) 2 is/are cut. With distal movement of the cutting/reloading assembly 11240, as shown in FIG. 127, cutting of the cords 2 is completed by placing the moving portion 11242 of the two cutting surfaces distally past the fixed portion 11224, thereby creating a scissor effect on the cords 2 with the two surfaces 11224, 11242 while, at the same time, sliding the clip 11251 off of the distal end of the guide rail 11210 and entirely unsecuring it from the multiple clip-securing device 11200. Movement of the multiple clip-securing device 11200 away from the securing site 12310 reveals to the user that the clip 11251 is secured on the cords 2 and the cords 2 are cut on the side of the clip 11251 facing away from the site 12310. The multiple clip-securing device 11200 indicates (by visual, audible, tactile measures) that a cutting action has completed but a user can actuate the clip-securing trigger 9812 again, if desired, and the cutting action will repeat. FIG. 116 illustrates the device 11200 in state that is ready for recutting and FIG. 115 illustrates the device 11200 in state that is ready for reloading.

To reload the device 11200, the user presses the reload trigger 9814 and a procedure for placing a now distal-most clip 11651 at the cord-securing location 11222 at the distal end of the shaft 11220 can begin. The device 11200 automatically moves the cutting/reloading assembly 11240 rearward to a position where the clip-movement arms 11242 (only one is shown in FIGS. 113 to 116) catch the clip 11651. Then, the cutting/reloading assembly 11240 extends distally to place the clip 11651 at the cord-securing location 11222. The securing and cutting operations are repeated as before to secure the second clip 11651 on new cords 2 and move the clip 11651 off of the guide rail 11210. The clip-securing processes are repeated for as many times as needed in a given procedure. In the exemplary embodiment of FIGS. 117 and 118, the procedure has been carried out until there are only ten clips left on the guide rail 11210. FIG. 117 illustrates the cutting/reloading assembly 11240 in a reloading position for a tenth-to-last clip 11751 after the preceding clips have been used. Likewise, FIG. 118 illustrates the cutting/reloading assembly 11240 reloading the tenth-to-last clip 11751 into the cord-securing location 11222. As can be understood, the cutting/reloading assembly 11240 moves a distance proximally that increases for each new clip that is being reloaded. The movement algorithm is set within the device 11200 as described in further detail below.

FIGS. 119 to 134 are various views of enlarged portions of the distal end of the device 11200 in various stages of the clip-securing process. Each will be described in turn.

FIGS. 119 to 123 illustrate the ready-to-secure state shown in FIGS. 121 and 122. Particularly in FIG. 120, it can be seen that the clip-movement arms 11242 have characteristic curves and thickenings, which will be described in further detail below. When the body of the cutting/reloading assembly 11240 is in this state, the moving portion 11244 of the cord-cutting surfaces is set away from the fixed portion

Figure 119:
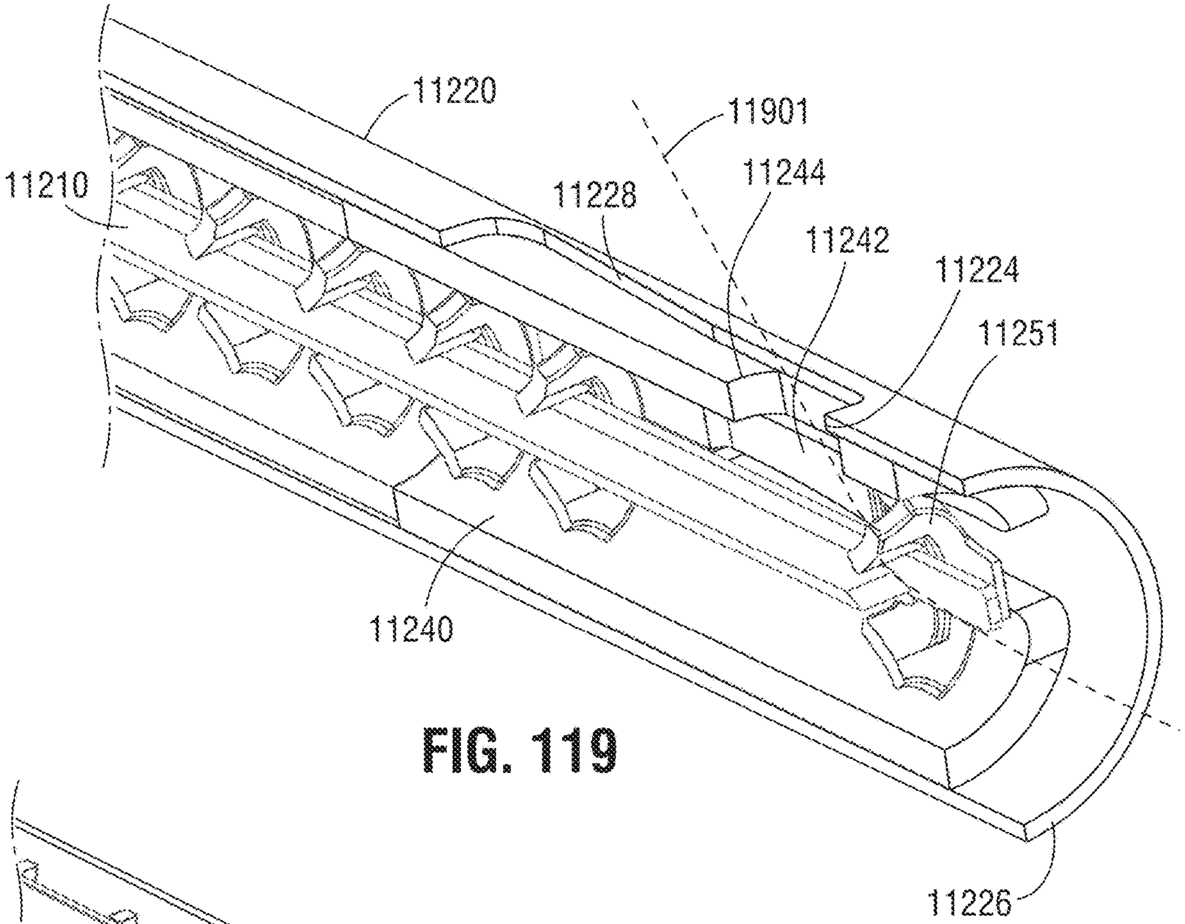
Figure 120:
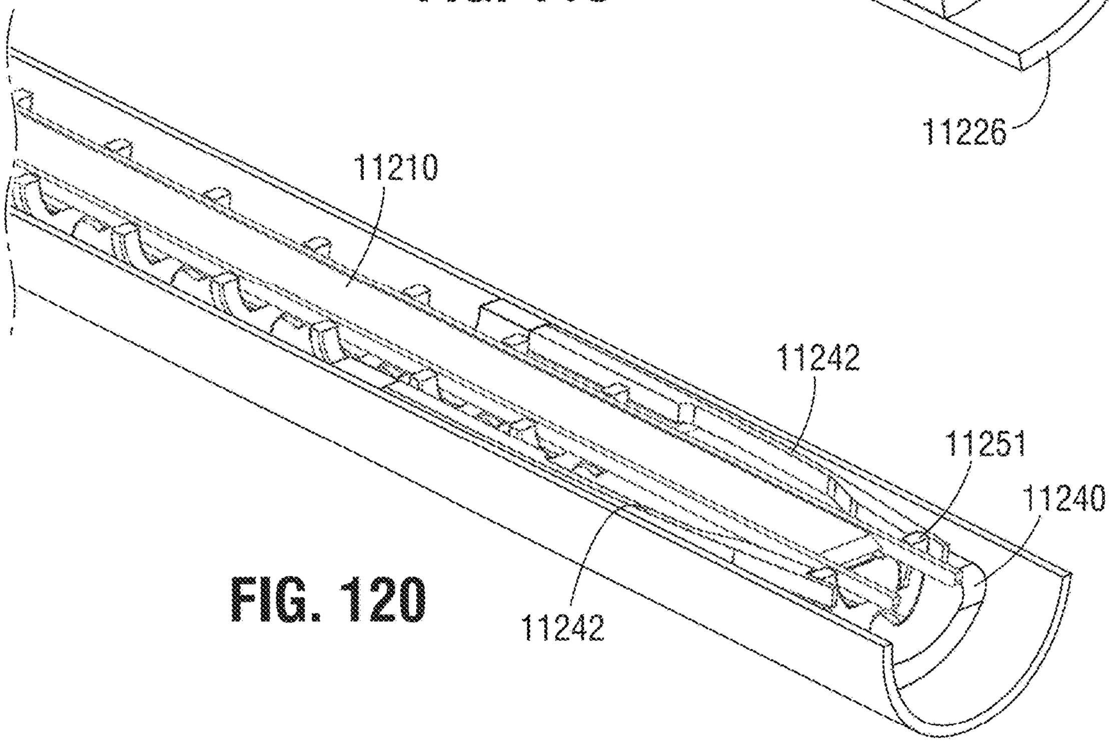

11224 of the cord-cutting surfaces. In the exemplary embodiment of FIGS. 119 and 120, the cord-securing location 11222 for the clip 11251 is set back proximally from the extreme distal end 11226 of the shaft 11220. Also illustrated in FIGS. 119 and 120 are various features of the guide rail 11210, which features will be described in further detail below. A diagrammatic illustration of the path 11901 of cords 2 is shown in FIG. 119 after they have been snared and pulled through the clip 11251, through the snare access window 11228, and out the side of the shaft 11220 for manipulation by a user. The cords 2, therefore, pivot or curve around the lower surface of the upper interior bending plate of the clip 11251. Similar views of the distal end of the shaft 11220 are shown in FIGS. 121 and 122, but these are not in cross-section. The path 11901 of the cords 2 can be seen well in both of these figures as well as in FIG. 123, and the fixed portion 11224 of the cutting surfaces can be seen especially well in FIG. 122 to be protected by the outer surface 11246 of the body of the cutting/reloading assembly 11240.

FIG. 124 illustrates an exemplary embodiment of how the guide rail 11210 is secured to the rail block 11212. In this embodiment, a port 12420 in the shaft 11220 allows a set screw 12422 to fix the proximal end of the guide rail 11210 to the rail block 11212. In turn, the rail block 11212 is fixed (e.g., by welding, soldering, press-fitting, threading) to an internal shaft 12424 that is fixed to the handle 9810 and, therefore, that does not move with respect to the shaft 11220. Alternatively, this can be made as a subassembly that is all welded or otherwise fixed together by any measures.

In comparison to FIGS. 119 to 123, FIGS. 125 to 128 illustrate the clip 11251 in a cord-secured state, in which the cords 2 are clamped or clipped between the upper and lower surfaces of the respective upper and lower interior bending plates of the clip 11251. In the view of FIGS. 125, the body of the cutting/reloading assembly 11240 has moved the clip 11251 distally from the cord-securing location on the guide rail 11210 to a position where the cords 2 are cut and the clip 11251 is free from the guide rail 11210. The cutting of the cords 2 is accomplished by distally moving the moving portion 11244 of the cord-cutting surfaces past the fixed portion 11224 of the cord-cutting surfaces. In this view, only the clip-movement arms 12560 are holding the clip 11251 and, with any proximal movement of the shaft 11220 by the user, that gripping force will be overcome to release the clip 11251 at the site where it has been clipped. FIG. 126 illustrates how the distal fingers 12563 of the clip-movement arms 12560 hold the clip 11251 in this manner before release. FIGS. 127 and 128 are views approximately of FIGS. 125 and 126 without the cross-section. FIG. 127 depicts the end of the device 11200 after the clipping has occurred but before cutting of the cords 2 have occurred. Here, the body of the cutting/reloading assembly 11240 has moved the clip 11251 distally from the cord-securing location on the guide rail 11210 to a position where the clip 11251 is free from the guide rail 11210. However, the moving portion 11244 of the cord-cutting surfaces is still proximal of the fixed portion 11224 of the cord-cutting surfaces before cutting occurs. In contrast, FIG. 128 depicts the end of the device 11200 after both clipping and cutting of the cords 2 have occurred. As in FIG. 127, the body of the cutting/reloading assembly 11240 has moved the clip 11251 distally from the cord-securing location on the guide rail 11210 to a position where the clip 11251 is free from the guide rail 11210. Additionally, the moving portion 11244 of the cord-cutting surfaces is distal of the fixed portion 11224 of the cord-cutting surfaces to effect cutting of the cords 2.

The snare access window 11228 that allows the cords 2 to be passed from distal of the device through the clip 11250 proximally and outside the shaft 11220 is placed to provide various desirable features. As can be seen in FIGS. 121 to 128, the two edges 11224, 11244 forming the scissor for cutting cords 2 are protected when not in use. First, as shown in FIGS. 121 and 123, the upper cutting edge 11244 of the movable inner tube 11240 is protected by offsetting the proximal edge of the window 11228 distally with respect to the upper cutting edge 11244 when in the ready-to-fire position. Second, the lower cutting edge 11224 of the outer shaft 11220 is covered and, thereby, protected when the inner tube 11240 is in the non-cutting state as shown in FIGS. 122 and 123. Particularly with respect to FIG. 123, the portion of the inner tube 11240 that protects the lower cutting edge can be formed from a short-length tubular section 12540 that is very precise in its diameter to lower the drag of the inner tube 11240 within the outer shaft 11220 while providing the best edge for improved cutting. This short-length, precision-diameter section 12540 can be integral with the inner tube 122542 or it can be a separate piece that is attached to the inner tube. See, for example, FIGS. 119 and 125.

With regard to the connection between the cutting/reloading assembly 10440, 11240 and the securing devices, e.g., the clip 10400, 10800, 11250, 11251, various exemplary embodiments include a tube that slides back and forth within the shaft 9820, 11220, a body . . . of that tube having, at its distal end, two clip-movement arms 10442, 11242, 12560. FIGS. 129 to 134 illustrate the details of the clip-movement arms 10442, 11242, 12560 and how they interact with the clip 10400, 10800, 11250, 11251 in order to carry out the cord-securing processes of the device 9800, 11200. For ease of understanding, only clip-movement arms 12560 will be referred to but this single reference applies to all embodiments of the clip-movement arms, including arms 10442 and 11242. Likewise, only clip 11251 will be referred to but this single reference applies to all embodiments of the clip, including clips 10400, 10800, and 11250.

As can be seen in FIGS. 125 and 126, an exemplary embodiment of the arm-carrying tube of the cutting/reloading assembly 12540 can be made from two parts, a proximal portion 12542 and a distal portion 12544. The proximal portion 12542, because of its long length within a narrow shaft 9820, 11220, is made of a material having strong torque and flexion features, for example, it is of stainless steel 304 or 316 that can be easily drawn into tubing. The distal portion 12544 carries the two clip-movement arms 12560. To secure the clip-movement arms 12560 thereto, the distal portion 12544 is made of a material, for example, able to bond through welding such as Stainless 17-7 but is substantially harder to make for an improved cutting edge. The clip-movement arms 12560 can be made of a similarly hard material, such as SS17-7 or 17-4, which can be hardened to a spring temper to allow the arms 12560 to flex and return to their original position.

In the exemplary embodiment, the clip-movement arms 12560 have three portions, a proximal base 12561, an intermediate flex spring 12562, and a distal finger 12563. The proximal base 12561 is shaped and configured to fixedly attach to the distal portion 12544. It can be press-fit, bonded, welded, or secured in any way so that, when so secured, it moves with the distal portion 12544 within the shaft 9820, 11220. The intermediate flex spring 12562 is, in this exemplary embodiment, in the form of a flexible, rectangular plate spring that is thinner (in the radial direction of the shaft 9820, 11220) than the proximal base 12561. This radial thickness difference from the proximal base 12561 is not a requirement. Finally, the distal finger 12563 has a number of features that is best described with reference to FIGS. 129 to 134 and, in particular, to FIG. 133.

When the clip-movement arms 12560 are in the orientation of FIG. 115, they flex radially inwards, due to the pre-set form of the flex spring 12562, and the fingers 12563 are in a radial position further inwards than that shown in FIGS. 112 to 114, e.g., when a clip 11251 is being held between the opposing fingers 12563. In such a state, a new, distal-most clip 11251 is desired to be loaded into the cord-securing location 11222. As described and/or shown herein, the cutting/reloading assembly 10440, 11240 retracts proximally for this action to occur. For a distance, the arms 12560 are still distal of the clip 11251 and do not touch any of the clips 12560. At a point illustrated in FIG. 129, an inside angled cam surface 12564 of each arm 12560 makes contact with the distal-most clip 11251. This cam surface 12564 is angled to form a guide rail that gradually moves each of the fingers 12563 radially outward, one of which is shown in FIG. 129. The distal end of the cam surface 12564 terminates at a clip step 12565, which, along with a distally extending fingernail 12566 at the outer end of the clip step 12565, forms a pocket or ledge that grasps and is used to move the clip 11251 from its pre-loaded position to the cord-securing location 10802, 11222 and, then, off of the guide rail 10410, 11210. In other words, the fingernail 12566 of each of the arms covers a side of the clip 11251 and the clip step 12565 acts as a pushing face that moves the clip 11251 distally by pressing against a proximal side of the clip 11251. The fingernail 12566 keeps the clip step 12565 engaged evenly at the edges of the clip 11251 to make sure that the clip 11251 is pushed straight and true. The fingernail 12566 also keeps the flexible arm 12560 straight to apply its forces in straight column loading. To pick up and move the distal-most clip 11251, the clip step 12565 must be on the proximal side of that clip 11251. But, if the clip step 12565 is moved too far proximally, there is a danger that the arms 12560 may pass the distal-most clip 11251 and the nose 12567 of the fingernail 12566 will fall proximally behind the distal-most clip 11251 and, thereafter, be unable to pick up that clip 11251. This situation is to be avoided. To ensure that such an event does not occur, the longitudinal length of the cam surface 12564 and the width of the arm 12560 are selected so that proximal movement of the arms 12560 allows the cam surface 12564 to touch the second distal-most clip 11252 as shown in FIG. 130 and, therefore, if the nose 12567 does happen to move proximal of the rear plane of the clip 11251, the nose 12567 will, nevertheless, still be positioned to the outside of the clip 11251 and will not be trapped behind the clip 11251. In other words, the cam surface 12564 has a length such that its radial thickness engages the next (e.g., second distal-most) clip 11252 before the fingernail 12566 disengages from the first clip 11251 to be loaded.

The clips 11251 are spaced apart from one another at known, pre-set distances 13000. By having the length of the cam surface 12564 be long enough to contact the second distal-most clip 11252, longitudinal control of the cutting/reloading assembly is provided with play to insure that the clip step 12565 will be moved proximally behind the distal-most clip 11251 every time a reloading procedure is undertaken and will fall radially inwardly to place the distal surface of the clip step 12565 against the proximal side of the clip 11251 and the inner surface of the fingernail 12566 against the outer side if the clip 11251-*a* position shown in FIG. 131. This position insures positive control of the clip 11251 from its pre-installed position (shown in FIG. 131), distally along the guide rail 10410, 11210 to an intermediate position 12200 before the cord-securing location (shown in FIG. 132), to the cord-securing location 10802, 11222 (shown in FIG. 133), and then off the distal end of the guide rail 10410, 11210 (shown in FIG. 134). An enlarged separated view of a distal portion of the arms 12560 is shown in FIG. 135.

Each of the arms 12560 flexes outwards to provide a positive bias against the clip 11251 that aids in holding the clip 11251 during all relevant steps where forces could act against the clip 11251. The fingernail features (12565, 12566) aid in stabilizing the arms 12560 so that they can be biased inward to a greater extent than needed. This forces the pushing faces to be held even with the outside edges of the clip 11251 and still have a biasing force against the clip 11251. For research and development purposes, a hold-open feature 12800 is provided (as shown in FIG. 128) to allow a field-reloadable magazine (e.g., with a funnel on its end to hold open the fingers) to reload a set of clips or for reprocessing the multiple-clip securing device. As can be seen in FIG. 129, a non-illustrated tool can be inserted into the feature 12800 to apply a force that moves the arms 10442, 11242 radially outward to, thereby, provide room for reloading clips 11251 onto the guide rail 10410, 11210.

The guide rail 10410, 11210 also possesses features that enhance the clip-securing processes of the exemplary systems 9800, 11200, exemplary embodiments of which are illustrated in FIGS. 136 and 137. For ease of understanding, only guide rail 11210 will be referred to but this single reference applies to all embodiments of the guide rail, including guide rail 10410. In the exemplary embodiment of FIG. 136, the clip-holding guide rail 11210 is H-shaped (in cross-section) with an intermediate bridge 11214 between opposing walls 11216. Here, the bridge 11214 is offset from center, but it can be centered in an alternative embodiment. The H-shape allows the clips 11251 to be held open with a minimal amount of contact area between the clip 11251 and the upper and lower edges of the walls 11216. This configuration can prevent damage to the clip 11251 as it is being slid over the length of the guide rail 11210. Polishing and surface treatments can further reduce any friction and/or wear that occurs during the sliding movement of the clips 11251. Other advantages of having an H-shape cross-section is that is provides an open space through which the cord-capturing snare 9832 can be passed to slide along the upper surface of the bridge 11214 and pass through the proximal face of the open clip 11251. To aid in guiding the snare through the internal opening of the clip 11251, the distal end of the intermediate bridge 11214 has a tapered slope 11218. This configuration allows for more precise and accurate movement of the snare 9832 out from its guiding tube, through the clip 11251, and out to a user. The angle of the slope 11218 can be set at any value, however, one beneficial angle is a value that is approximately equal to the angle that the lower internal flexing wall 13300 of the clip 11251 makes with respect to the bridge 11214. In this way, if the snare 9832 slides against the upper surface of the bridge 11214 and then down the slope 11218, having the lower surface of the wall 13300 match the slope 11218 permits travel of the snare 9832 substantially without friction or snagging. This is especially true if the central edge of the wall 13300 is just below the distal end of the slope 11218.

During manufacture of the multiple-clip securing device 9800, 11200, it is desirable to preload all of the clips 11251 onto the guide rail 11210 before the guide rail 11210 is installed in the handle 9810. To assist with this preloading, the proximal ends 11217 of the walls 11216 are ramped or chamfered. The ramp can start from a point or from almost a point and can taper outwards (up/down) until reaching a wall height that is desirable for extending the snare 9832 through the opening within the clip 11251. This means that the walls 11216 can have a variable height over a length of the guide rail 11210 that starts small to place a lower load on the internal features of the clip 11251, for example, for storage purposes, and only place the higher load on the internal features when the clip 11251 is at the distal end of the guide rail 11210 ready to be used. The walls 11216 at the distal end of the guide rail 11210 extend past the slope 11218 to create a fork that provides a larger opening in the available space through which the snare 9832 and cords 2 can be maneuvered. For manufacturing ease, one or more retainer holes 11219 can be made in the intermediate bridge 11214, as shown in FIG. 137, which holes 11219 do not interfere with the clean polished surfaces on which the clips 11251 slide. These holes 11219 can also be used to support the guide rail 11210 as the clips 11251 are loaded thereon. Shapes other than an H-shaped cross-section of the guide rail 11210 can be used to hold the clips 11251 open and ready for use. For example, a square bar that transitions to an H-shape, two independent square/round rods, a W-rail, a double U-shaped rail, a C-channel, or a rectangular cross-section bar.

The guide rail 11210 can be fabricated using various production methods including grinding, milling, wire EDM, stamping, laser cut and welding, extrusion with hardcoat, roll-formed, wire spool and welding, from ceramic, MIM, and/or DMLS. Some of the materials that can be used to form the guide rail 11210 include, but are not limited to, stainless steel, nickel and nickel alloys (e.g., MP5N), titanium, CoCr, aluminum with hardcoat, carbide, tool steel, and sapphire. Exemplary surface finish processes for the guide rail 11210 include, but are not limited to, materials that make the surface smooth, polishing (e.g., abrasive/mirror/electro), and grain orientation.

The handle of the multiple-clip securing devices contains various novel features. An exemplary embodiment of circuitry and proximal portions of the cutting/reloading assembly are contained in and attached to a single, drop-in, circuit board 13820, all of which is housed within a handle 13810 shown in FIG. 138.

All of the switches, including the clip-securing trigger 13830, the clip-reload button 13840, and the parking switch 13900 are side-mounted onto the circuit board 13820 to decrease the footprint within the handle 13810. The clip-securing trigger 13830 is, in this exemplary embodiment, pivoted about a pivot pin 13832. Actuation of the clip-securing 13830 is carried out by depressing a micro-switch or tact-switch 13834 that is surface-mounted on the circuit board 13820. In an alternative embodiment shown, for example in FIG. 155, the pivoting trigger 13830 is replaced by a sliding trigger 15512. A trigger that slides provides a longer stroke than the pivoting trigger 13830 and, by including a relatively heavier spring, the sliding trigger 15512 gives the user time to decide if firing should be cancelled, which makes the device less sensitive to inadvertent clip firing.

An exemplary embodiment of proximal portions of the cutting/reloading assembly is depicted in FIGS. 138 to 140. Included in the cutting/reloading assembly is a motor 13850 having a pinion 13852 that is operably connected to a proximal portion of a rack 13854. The exemplary embodiment of the motor 13850 shown has an internal gear box that terminates with the external pinion 13852. The distal portion of the rack 13854 is fixed longitudinally to the tube 12540 carrying the clip-movement arms 11242, 12560. Because it is desirable for the outer tube of the shaft 9820, 11220 to have an outer diameter that is no greater than 5 mm, to improve control of the device, a torque stiffening tube 14000 (which is free from interruptions and/or slots) is connected between the rack 13854 and the tube 12540. This functions to prevent torsional bending or twisting of the shaft 9820, 11220 in use. Another exemplary configuration for stiffening the two nested tubes 9820, 11220, 12540 in torque includes non-illustrated cross-pins at either end.

A power supply 13860, such as a battery, can be electrically connected to the circuit board 13820 by a wired connector as shown in FIG. 138 or by board-mounting. For various reasons, easy battery disposal is desirable. To provide such a feature, the handle 13810 in FIG. 138 shows the left-side clamshell 13812 but the right side clam-shell is removed. This right-side clamshell can be in two parts, which are delimited by the dashed breakaway line 13801. One part will be fixed to the left-side clamshell 13812 and will cover the circuit board and all of the components in the upper section above line 13801 and the second part will be a non-illustrated breakaway section that is the structure on the right side below the line 13801 in FIG. 138. This breakaway section, when pried away by a hemostat or other object inserted within a seam or a pocket below the line 13801 will expose the battery 13860 and allow it to be removed with ease. The battery 13860 is shown as being clipped into a standard 9V press-fit connection. In an alternative non-illustrated exemplary embodiment, the battery 13860 is pressed upwards, e.g., by a lower spring, to merely physically connect to two contacts that are on the top surface of the battery compartment 13862 adjacent the circuit board 13820. The ability to remove the battery 13860 can be accomplished in many other ways, such as a structure similar to a gun magazine, which can be released and slid out of the bottom of the grip portion or the entire grip portion containing the battery can be separated from the device to remove the battery and render the device unusable. This is of concern for a circumstance where separation is necessary for disposal of the battery for recycling purposes.

FIGS. 98 to 102 illustrates one exemplary embodiment of a movable snare assembly 9830. Another exemplary embodiment of a snare assembly 14100 is depicted in FIGS. 141 to 153 The snare assembly 14100 provides various complex functions. First, it is disposed on the shaft 11220 so that it can move longitudinally thereon from a retracted proximal position at the handle 13810 to an extended distal position in which the snare is extended through the snare access window 9822, 10424, 11228 and through the clip 10400, 11250 to a position distal of the shaft 11220 for capture of the cords 2. Second, the snare assembly 14100 provides various lockouts during this movement along the shaft 11220, for example, to prevent extension of the snare at all times except when the snare delivery tube is correctly positioned just proximal of the clip 10400, 11250. Third, the snare assembly 14100 extends the snare to a distal position that is maximized for easy cord snaring by a user but, at the same time, is to be as physically compact as possible for good human ergonomics.

FIGS. 141 and 142 illustrate the third feature, how the snare assembly 14100 extends the snare to a distance while the actual snare assembly 14100 is relatively small. To start, the snare assembly 14100 comprises three main parts, including an outer snare-extending sleeve 14110 that freely rotates about an interior body 14120 that is connected to a snare-movement body 14130. The ability of the snare-extending sleeve 14110 to rotate freely about the interior body 14120 allows the user to not be concerned about how his/her hand is placed on the sleeve 14110 as the device is being rotated constantly during a surgical procedure. Free rotation also prevents torque from being imparted to the snare assembly 14100, which torque would cause additional drag during longitudinal translation on the shaft 11220.

These three parts provide a mechanism that allows the snare (not illustrated here but appearing in further figures) to extend out from the distal end of the snare assembly to a distance that is a multiple of the distance that the snare-movement body 14130 moves with respect to the interior body 14120. This feature is best shown in FIGS. 141 and 142, in which a snare, for example with the shape shown in FIGS. 8, 12, 36, and 37 but not illustrated in FIGS. 141 and 142, is grounded at its proximal end at a grounding area 14132 within the movement body 14130. In this exemplary embodiment, the grounding area 14132 is a proximal end of a first tube 14134 that is fixed to the movement body 14130 and in which the proximal end of the snare is fixed, e.g., crimped. The snare progresses proximally in a first extent through the first tube 14134 and then through a 180-degree first bend 14122 within the interior body 14120. After the first bend 14122, the snare continues through a second tube 14136 that is slidably received through a portion of the movement body 14130. The snare then continues through a 180-degree second bend 14138, which terminates at the proximal end of a snare-guiding tube 14140 that, in this exemplary embodiment is substantially in a J-shape. The distal snaring portion of the snare is collapsed within the snare-guiding tube 14140 while in the non-extended state of the snare—the state shown in FIG. 141—with a terminal snare end (e.g., loop 12) extending slightly out of the distal end of the snare-guiding tube 14140. This configuration is referred to as a double trombone shape because it has two 180-degree U-turn bends (trombones). In essence, this configuration has three lengths traversing a total snare movement area. Therefore, motion of the snare by moving the movement body 14130 towards the interior body 14120 is amplified by a factor of three-thus, a 2 cm displacement of the movement body 14130 distally results in a 6 cm movement of the snare from its captured position within the snare-guiding tube 14140 to its final extended orientation outside the distal end of the snare assembly 14100. If the first tube 14134 is removed to form a single trombone, then two lengths will cross the intermediate movement area and the ratio of snare movement to movement body displacement is 2:1. An alternative to this relatively planar trombone configuration is a non-illustrated three-dimensional spiral cork-screw track, which also provides an increase in snare end movement as compared to the travel distance of the movement body 14130. FIG. 142 illustrates the snare assembly 14100 in the snare-extended state with the sleeve 14110 displacing the movement body 14130 distally to touch the proximal side of the interior body 14120 and, thereby, extend the snare distally out through a clip to its fullest extent.

Another feature of the snare assembly 14100 is that it provides various lockouts during movement along the shaft 11220. The many different lockouts are provided by a single device having a complex shape, which device interacts with other features within the snare assembly 14100 and the shaft 11220. This exemplary embodiment of the multi-function lockout 14300 has a shape similar to a silhouette of a helicopter. Depending on the state of the snare assembly and/or on the state of the movement body 14130, the lockout 14300 provides a different lockout function.

In a first lockout state, it is desired to retain the snare in its fully retracted position and prevent it from extending. This first state exists while the snare assembly 14100 is proximal of its distal-most position. FIGS. 143, 147, and 151 show the multi-function lockout 14300 in this first lockout state in which the snare assembly 14100 is able to translate along the shaft 11220 from the handle to the distal end of the shaft 11200. To fix the interior body 14120 in a single circumferential position about the shaft 11220, a canopy 14302 of the lockout 14300 rides in a groove 11221 of the shaft 11220 to act as a key within the keyway of the groove 11221. This groove 11221 is especially visible in FIG. 151. The blade feature of the canopy 14302 that is positively engaged in the groove 11221 on the shaft 11220 can selectively become disengaged from the keyway at the distal-most position while the tail 14304 keeps the snare assembly 14100 in position and clocking. Alternatively, the blade feature of the canopy 14302 can be made to stay continuously engaged in the groove 11221. In an alternative embodiment, there can be a separate key continuously engages the groove 11221. Other embodiments for clocking the interior body 14120 can include a keyway that is internal or external to the shaft 11220. Another exemplary embodiment for keeping the interior body 14120 clocked with respect to the shaft 11220 includes placing a secondary tube along the outside surface of the shaft 11220 to form a "snowman" cross-section. Likewise, that secondary tube can be replaced with an external blade or square wire or a hexagonal or other polygonal rod. The exterior shape of the shaft 11220 can also be altered to provide the keying feature. Other external configurations include a comb and slot or an integral stop such as a cross-pin, a horseshoe, or a fin on the shaft 11220. In another exemplary embodiment, the entire snare assembly 14100 can be freely rotating proximal to a given point on the shaft 11220 but, after passing a set distal location, the interior body 14120 is forced to clock into a given orientation. This can be accomplished, for example, with a funnel and pin assembly. All of these various features together define a method for keeping the snare assembly 14100 clocked onto the shaft 11220.

The lockout 14300 pivots about a pin 14301 that is oriented transverse to the shaft 11200. The rotational orientation of the lockout 14300 shown in FIGS. 143 and 147 keeps the tail 14304 below the shaft 11220 because the tail 14304 has a width greater than the width of the groove and, therefore, it is also wider than the canopy 14302. The cross-sectional views of FIGS. 143 and 144 do not allow the thickness of the tail 14304 or the sides of the lockout 14300 to be seen. Those features can be seen, however, in FIG. 147 and, especially in FIG. 151, in which the width of the tail 14304 and the canopy 14302 are apparent and it can also be seen that one or more side pontoons 14303 of the lockout 14300 extend laterally from the side of the lockout 14300. In this orientation, the pontoon 14303 opposes a blocking surface 14131 of the movement body 14130 to prevent the movement body 14130 from moving towards the interior body 14120, thereby keeping the movement body 14130 in its proximal position in which the snare is retained in its retracted position and cannot extend.

FIGS. 145 and 149 illustrate how the pontoon(s) 14303 is (are) moved out of the way of the blocking surface 14131 by various other features of the snare assembly 14100. First, the shaft 11220 defines a tail orifice 11223 just distal of a distal end 11225 of the groove 11221. The tail 14304 cannot move into the tail orifice 11223 by itself because it is biased with a clockwise force (in the view of FIGS. 143 to 149) by a non-illustrated bias device (e.g., a spring). What causes the desired tail-raising movement (e.g., counter-clockwise rotation of the lockout 14300) is a cam action that occurs when the sloped rear canopy edge 14305 comes into contact with and continues to contact the distal end 11225 of the groove 11221. Further distal movement of the interior body 14120 on the shaft 11220 causes the distal end 11225 of the groove 11221 to force the canopy 14302 downwards to thereby, move the tail 14304 into the tail orifice and, thereby, prevent any further distal movement of the interior body 14120—because the distal edge of the tail orifice 11223 forcibly contacts the distal face of the tail 14304. When this occurs, as shown in FIGS. 149 and, especially, FIG. 150, the lockout 14300 has pivoted to such an extent to move the pontoon(s) 14303 radially downwards sufficiently far to move out of the way of the blocking surface 14131, thereby freeing the movement body 14130 from its fixed state with respect to the interior body 14120. Simultaneously, the distal exit 14142 of the snare-guiding tube 14140 is at a position in which it can enter a snare access window 11228 in the shaft 11220.

The snare-guiding tube 14140 is grounded at its proximal end to provide support to the snare while being able to flex. As shown in FIGS. 143 to 153, the snare-guiding tube 14140 has a double bend 14144, 14146 to provide clearance so that the distal exit 14142 can flex upwards (with regard to the views of the drawings) when the distal end of the snare-guiding tube 14140 is not present at the snare-access window 10424, 11228 as shown in the difference between FIGS. 152 and 153. The flexing movement of the distal end of the snare-guiding tube 14140 is illustrated in FIG. 152 with the double-headed arrow. An alternative to this exemplary shape is a recurve or S-tube that can align the exit opening more in line with the top surface of the bridge of the guide rail so that the snare is presented with less ricochet into the opening of the clip. The S-tube can provide features to vertically position its exit relative to the guide rail, relative to the shaft, and/or, relative to the snare assembly. Another alternative embodiment of the snare-guiding tube includes an open cut scoop or similar shape that deflects the snare and directs it toward the clip opening.

Because a distal extent of the snare-guiding tube 14140 is pre-bent with a bias towards the shaft 11220, when the distal exit 14142 is not within the snare-access window 11228, the distal exit 14142 rides along the top exterior surface of the shaft 11220, as shown in FIG. 153. The tube 14140 remains in that radially outward flexed state until the distal exit 14142 of the snare-guiding tube 14140 enters the snare access window 11228 (as shown in FIGS. 145, 146, 149, 150, and 152), at which time, a radially extending cavity 14126 in which the distal extent of the snare-guiding tube 14140 resides allows that distal extent to spring radially inwards into the snare access window 11228 to an orientation in which the distal exit 14142 is aligned with the central opening of the clip that is loaded in the cord-securing location 10802, 11222 ready to secure cords 2, which orientation is especially visible in FIG. 152. At the point when the pontoon 14303 lowers, no lock of the lockout 14300 prevent the movement body 14130 from translating distally all the way until its distal surface meets a proximal side 14124 of the interior body 14120 (as shown in FIGS. 146, 150, and 152) at which time, the snare 14600 has extended out through the distal exit 14142 and, because the guide rail 10410, 11210 is disposed within the shaft 11220 (not shown in FIGS. 143 to 150 but shown in FIG. 152), the snare 14600 slides along the bridge 11214 of the guide rail 10410, 11210 and exits through the central opening of the clip 11251 to open and be ready to capture cords 2 within the snare opening. It is noted that the snare 14600 is prevented from being exposed to the environment outside the interior body 14120 when in the middle of reloading due to the length of the snare access window 11228, as shown in FIG. 153.

When the snare assembly 14100 is at its distal-most position, the lockout 14300 releases forward movement of the snare 14600 but also locks the snare assembly at its distal-most position—the tail 14304 prevents both distal and proximal movement of the movement body 14130 when the snare 14600 is extended. This means that, when at this distal-most position, the snare assembly 14100 is locked on the shaft 11220 at all times when the snare is being extended or retracted. Only after the snare 14600 is fully retracted into the snare assembly 15100 (e.g., where a small eyelet remains outside the snare-guiding tube 14140 as shown in FIG. 153), the lockout 14300 disengages the snare assembly 14100 from the end of the shaft 11220 but reengages fixation of the snare extension parts to prevent any movement of the snare when the snare assembly 14100 is not present at its distal-most, clip-snaring position on the shaft 11220. Leaving a small eyelet of the snare 14600 exposed allows the cords 2 to slide freely as the snare assembly 14100 is moved proximally along the shaft 11220. A mechanism such as a ramp or cam can be used to further forcibly flex the tip of the snare-guiding tube 14140 away from the outside of the shaft 11200 to enable freer movement of the cords. This action can be increased to a point where the cords 2 are separated far enough from the shaft 11220 to assist the operator in being able to grasp the cords 2.

The snare can be of different shapes and diameters, some of which are shown in FIGS. 8, 12, 36, and 37. In an exemplary embodiment, the area of the oval/circle encapsulated by the snare is between approximately 5 and 15 $cm^2$, in particular, between approximately 8 and 10 $cm^2$. Preferably, the distal end of the snare defines a small catch that positively places the cord(s) to be secured at the distal-most end of the snare. An example of such a catch or loop is shown in FIGS. 8, 12, 36, and 37. This distal-most end always remains partially extended to prevent binding of the suture cords as shown in FIGS. 57 and 153.

In operation of the snare, the snare-guiding tube houses the operative end of the snare and guides it through the tube opening of the shaft, along the upper surface of the guide rail, through the clip in the cord-securing location, and out the distal end of the multiple-clip securing device to be presented to the user for receiving one or more cords therein. The movement body ejects the snare out from the snare-guiding tube with enough force against guide rail to cause snare deflection along the top surface of the bridge of the guide rail (e.g., ricochet) and through the center of the securing device (e.g., the clip). In an exemplary embodiment, such as that shown in FIG. 152, the distal exit of the snare-guiding tube is cut at an angle to assist with snare positioning to ensure that it passes through the clip. As described and/or shown herein, it is beneficial for the snare tip to be exposed out from the snare-guiding tube at all times to ensure that it passes through the clip each time the snare is extended.

The snare access window 10424, 11228 can be of various shapes. FIGS. 104 to 111, 121 to 123, 127, 128 show the window with a curve-cornered rectangular shape and FIGS. 112, 119, 125 show the window having a funnel shape. The window having a proximal funnel shape that decreases in width in the distal direction provides the snare-guiding tube with easier access into the window.

It is desirable to retain the snare assembly adjacent the handle as shown in FIG. 139. One exemplary low-footprint embodiment for retaining this placement provides opposing magnets at both the distal end of the handle and the proximal end of the snare assembly. This retaining structure keeps the snare assembly parked in its most-proximal position. Locations 15400 for magnets forming the retaining structure can be found, for example, in FIGS. 139 and 154. A switch that detects when the snare assembly is parked, e.g., parking switch 13900, can be a Hall-effect sensor that detects when the snare assembly is in its most-proximal position and the magnets at the locations 15400 can be used to trigger this Hall-effect sensor. The sensor can be used to determine if the snare assembly 14100, 15530 has been advanced away from the handle 13810, 15510 when there is no clip in the ready-to-thread position. In this case, the drive system (e.g., 13850, 13852, 13854) can move the inner tube 12540, 15650 proximally by a small distance, which movement will make the openings 11223, 15523 that are normally aligned for receiving the stop 14304, 15664 to be closed by the inner tube 12540, 15650, thus entirely preventing extension of the snare.

Another exemplary embodiment for a multiple-clip securing device 15500 is shown in FIGS. 155 to 166. Many of the features in this embodiment are similar or even the same as previous embodiments of the device. Even though such features may be referenced with a different numeral, that designation, alone, does not mean that the feature is different and can be the same. Likewise, where features are referenced with the numeral, that designation, alone, does not mean that the feature is the same and can be different.

In the multiple-clip securing device 15500, a user handle 15510 includes a shaft 15520 in which resides a plurality of cord-securing clips described in detail below. Slidably disposed on the shaft 15520 is a snare assembly 15530. As in the other exemplary embodiments herein, the securing process includes moving the snare assembly 15530 to the distal end of the shaft 15520, as shown in FIGS. 157 and 160. When the cords are ready to be snared, the snare 15532 is extended by moving a snare-extender sleeve 15534 distally, as shown in FIG. 161, the snare 15532 being represented diagrammatically with dashed lines. Moving the snare-extender sleeve 15534 proximally, as shown in FIG. 158, withdraws the snare 15532 and captures the cords 2 within the snare assembly 15530 for movement through a securing clip 15550 and out the side of the shaft 15520 for manipulation by the user. Sliding the snare assembly 15530 proximally, as shown in FIGS. 162 and 163, pulls the ends of the cords 2 through the clip 15550 and out a snare-access window 15522 of the shaft 15520 to an orientation that allows a user to manipulate the free ends 2' of the cords 2. In this exemplary embodiment, the snare-access window 15522 is at the bottom of the shaft 15520 but it can be at another orientation along the circumference of the shaft 15520. Having the opening on the bottom allows the cords 2 to drape due to gravity and preferentially opening a loop that is easier for an operator to grasp. When the cords 2 are ready to be secured by the clip 15500, a clip-securing trigger 15512 of the handle 15510 is depressed to install the clip 15500 and activate a cord-cutting assembly within the handle 15510 and the shaft 15520 as described in further detail below. Finally, a reload trigger 15514 is pressed to automatically reload a clip 15550 for a further clip-securing procedure.

The flow chart of FIG. 103 describes an exemplary process for completing a cord-securing procedure with the multiple clip-securing device 15500. In order to initialize the device 15500, the snare assembly 15530 is in its retracted home position at the handle 15510. It is assumed that the clips 15550 come preloaded within the shaft 15520 before it is passed to a user, the clips 15550 being loaded, for example, at the manufacturer. Of course, there can be a pre-initialization requirement that has the user load the shaft 15520 with the clips 15550. Once initialized, if the first clip 15550 (the distal-most one) is not already at a cord-securing location 15622, it is advanced to the cord-securing location 15622, examples of which are shown in FIGS. 156 and 158. At this point, the device is ready to use.

An exemplary embodiment of a distal end of the shaft 15520 is depicted in FIGS. 155 to 163. As can be seen, a set of clips 15550' are installed on a guide rail 15540 for use in subsequent clip-securing operations. The guide rail 15540 is fixedly secured within the shaft 15520 through a rail block 15560. Also disposed within the shaft 15520 is a distal portion of a cutting/reloading shaft 15650, which is slidably disposed within the shaft 11220. It is desirable to provide the outer surface of the shaft 15520 with the side window to allow a user to count the number of clips 15550' remaining in the multiple-clip securing device 15500, but that side window is not illustrated in the cross-sections of FIG. 155 et seq, and an example can be seen in FIGS. 104 to 111.

To carry out the manual steps for capturing the cords 2, the user distally extends the snare assembly 15530 from a proximal position at the handle 15510 (seen in FIG. 155). During this movement, a snare-guiding tube 15610 will move from a position where the distal exit 15612 is sliding along the outer surface of the shaft 15520 to a radial-inward position in which it enters a snare access window 15522 of the shaft 15520, to place the distal exit 15612 of the snare-guiding tube 15610 just proximal of the distal-most clip 15550 to be used in the present clip-securing operation. In such an orientation, the distal exit 15612 is aligned with the opening within the clip 15550. Therefore, when the user distally extends the snare 15532 after the snare assembly 15530 reaches its distal end stop on the shaft 15520, the snare 15532 passes through the opening of the clip 15550 and opens up to receive cords 2 therein to be secured. The user manually captures the cord(s) 2 within the snare 15532 by, for example, threading sutures through the central opening of the snare 15532. Capturing is completed when the user retracts the snare 15532 proximally to hold the cord(s) 2 at the distal end of the snare assembly 15530. Assuming the user is satisfied with the way that the cords 2 are captured in the snare 15532, the user will, then, return the snare assembly 15530 proximally back to its proximal position at the handle 15510 to present the free ends 2' of the cord(s) 2 outside the shaft 15520. If the snaring is not acceptable, the snare 15532 is extended again for acceptable recapture. An orientation when the snare assembly 15530 has moved proximally back to the handle 15510 and has threaded the cords 2 through the clip 15550 in this ready-to-secure state is depicted in FIG. 162.

The distal end of the shaft 15520 is then slid distally along the cord(s) 2 to a place where the user desires to set the clip 15550 housed inside the distal end of the shaft 15520. For example, where the cord 2 is a surgical suture, a securing point of the clip 15550 is as close to the surgical site as possible with no length of the suture between the clip and the tissue. In such a case, the user moves the distal end of the shaft 15520 up against the tissue to place the clip 15550 in a ready to be fixed location. Automatic clip securement can now occur. The user presses the clip-securing trigger 15512 and, in doing so, two actions occur. First, the clip 15550 is fixed to the cords 2 and, second, the cord(s) 2 is/are cut, the latter of which is depicted in FIG. 163. Movement of the multiple clip-securing device 15500 away from the securing site reveals to the user that the clip 15550 is secured on the cords 2 and the cords 2 are cut on the side of the clip 15550 facing away from the site. The multiple clip-securing device 15500 indicates (by visual, audible, tactile measures) that a cutting action has completed but a user can actuate the clip-securing trigger 15512 again, if desired, and the cutting action will repeat.

To reload the device 15500, the user presses the reload trigger 15514 and a procedure for placing a now distal-most clip 15550' at a cord-securing location 15622 at the distal end of the shaft 15520 can begin. The device 15500 automatically moves the cutting/reloading shaft 15650 rearward to a position where the clip-movement arms catch the clip 15550'. Then, the cutting/reloading shaft 15650 extends distally to place the clip 15550' at the cord-securing location 15622. The securing and cutting operations are repeated as before to secure the second clip 15550 on new cords 2 and move the clip 15550 off of the guide rail 15540. The clip-securing processes are repeated for as many times as needed in a given procedure. In the exemplary embodiment of FIGS. 155 to 163, there is one clip 15550 and twenty reload clips 15550' illustrated. As can be understood, the cutting/reloading shaft 15650 moves a distance proximally that increases for each new clip that is being reloaded. The clips are loaded with a known and fixed separation distance between each clip. In this example, they are disposed about 1.3 mm (about 0.05") apart. The drive mechanism includes a position sensor so that the device knows precisely its position along the central axis, which can include, for example, a linear encoder or a rotary encoder on the motor or drive pinion. In such a case, the control system would know exactly how to move the clip positioning mechanism a distance incremented by the spacing (about 1.3 mm (about 0.05") in this example) with each subsequent clip that it is picking up. The movement algorithm is set within the device 9800, 11200, 15500 and starts in a ready position by holding a clip with the cutting/reloading shaft (e.g., the reloader) at the distal end of the shaft. This position aligns the shaft and the cutting/reloading shaft in a way that allows for snare access and securing of a cord or cords. When the user triggers the device to dispense the clip (e.g., by pulling in the clip-securing trigger), the cutting/reloading shaft is moved distally until the clip falls free from the guide rail and the two cord cutting edges closed. This movement is determined by a fixed displacement. The cutting/reloading shaft returns to a ready position upon release of the clip-securing trigger and waits for further user input. Upon triggering a reload (e.g., by depressing the reloading trigger), the reloader retracts proximally by a predetermined amount to a location of the next distal-most clip in the stack, which amount is incremented each time another distal-most clip is moved distally and dispensed. The reloader completes the movement sequence by moving distally and returning to the ready position.

With regard to the connection between the cutting/reloading assembly and the securing devices, e.g., the clip 10400, 10800, 11250, 11251, 15550, various exemplary embodiments include a cutting/reloading shaft 15650 that slides back and forth within the shaft 9820, 11220, 15520, a body of that cutting/reloading shaft 15650 having, at its distal end, two non-illustrated clip-movement arms. Exemplary embodiments of the clip-movement arms 10442, 11242, 12560 and how they interact with the clip 10400, 10800, 11250, 11251, 15550 in order to carry out the cord-securing processes of the device 9800, 11200, 15500 are illustrated FIGS. 129 to 134. The cutting/reloading shaft 15650 has all of the features of the arm-carrying tube of the cutting/reloading assemblies described above and/or shown and is, therefore, not repeated here.

The guide rail 15540 is similar to the other exemplary embodiments of the guide rail 10410, 11210. The guide rail 15540 also possesses features that enhance the clip-securing processes of the exemplary systems 9800, 11200, 15500. For ease of understanding, only guide rail 15540 will be referred to but this single reference applies to all embodiments of the guide rail.

In contrast to the exemplary embodiment of FIG. 136, the clip-holding guide rail 15540 is rectangular in cross-section with no intermediate bridge or opposing walls. The rectangular shape allows the clips 15550 to be held open with a virtually complete contact area between the two opposing, interior clipping surfaces of the clip 15550 and the upper and lower surfaces of the guide rail 15540. This configuration can prevent damage to the clip 15550 as it is being slid over the length of the guide rail 15540. Polishing and surface treatments can further reduce any friction and/or wear that occurs during the sliding movement of the clips 15550. The open space through which the cord-capturing snare 15532 is to be passed to slide along the upper surface of the guide rail 15540 and pass through the proximal face of the open clip 15550 is defined by a tapered slope 15542. The angle of the slope 15542 can be set at any value, however, one beneficial angle is a value that is approximately equal to the angle that the lower internal flexing wall 13300 of the clip 15550 makes with respect to the upper/lower surface of the guide rail 15540. In this way, if the snare 15532 slides against the upper surface of the guide rail 15540 and then down the slope 15542, having the surface of the lower internal flexing wall 13300 match the slope 15542 permits travel of the snare 15532 substantially without friction or snagging. This is especially true if the central edge of the wall 13300 is just below the distal end of the slope 15542.

During manufacture of the multiple-clip securing device 15500, it is desirable to preload all of the clips 15550 onto the guide rail 15540 before the guide rail 15540 is installed in the handle 15510. To assist with this preloading, the proximal end 15544 of the guide rail 15540 is ramped or chamfered. The ramp can start from a point or from almost a point and can taper outwards (up/down) until reaching a height that is desirable for extending the snare 15532 through the opening within the clip 15550. This means that the thickness of the guide rail 15540 (top/bottom) can be variable over the longitudinal length of the guide rail 15540 that starts small to place a lower load on the internal features of the clip 15550, for example, for storage purposes, and only place the higher load on the internal features when the clip 15550 is at the distal end of the guide rail 15540 ready to be used. For manufacturing ease, one or more retainer holes 15546 can be bored in the guide rail 15540. These holes 15546 can also be used to support the guide rail 15540 as the clips 15550 are loaded thereon. Shapes other than a rectangular cross-section of the guide rail 15540 can be used to hold the clips 15550 as mentioned herein.

The guide rail 15540 can be fabricated in the various production methods described and/or shown with respect to guide rail 11210, with the materials that can be used to form the guide rail 15540 and the surface finishing being selected from the same variations as well.

The handle 15510 of the multiple-clip securing device 15500 can be configured to contain the various features described with regard to other exemplary embodiment described and/or shown herein, including, for example, the single, drop-in, circuit board 13820, the power supply 13860, the motor 13850, pinion 13852 and rack 13854, and the side-mounted switches. As opposed to the clip-securing trigger 13830 which pivots about a pivot pin 13832, in this exemplary embodiment, the clip-securing trigger 15512 is a sliding trigger to provide a longer stroke than the pivoting trigger 13830 and to give the user time to decide if firing should be cancelled, which makes the device less sensitive to inadvertent clip firing.

FIGS. 98 to 102 and 141 to 153 illustrate exemplary embodiments of a movable snare assembly 9830, 14100. FIGS. 155 to 165 depict another exemplary embodiment of the snare assembly 15530. The snare assembly 15530 provides various complex functions. First, it is disposed on the shaft 15520 so that it can move longitudinally thereon from a retracted proximal position at the handle 15510 to an extended distal position in which the snare is extended through the snare access window 9822, 10424, 11228, 15522 and through the clip 10400, 11250, 15550 to a position distal of the shaft 15520 for capture of the cords 2. Second, the snare assembly 15530 provides various lockouts during this movement along the shaft 15520, for example, to prevent extension of the snare at all times except when the snare-guiding tube 15610 is correctly positioned just proximal of the clip 10400, 11250, 15550. Third, the snare assembly 15530 extends the snare 15532 to a distal position that is maximized for easy cord snaring by a user but, at the same time, is to be as physically compact as possible for good human ergonomics.

How the snare assembly 15530 extends the snare 15532 to a distance while the actual snare assembly 15530 is relatively small is explained with respect to other embodiments and is not repeated herein.

The snare assembly 15530 comprises three main parts, including the outer snare-extending sleeve 15534 that freely rotates about an interior body 15620, which is connected to a snare-movement body 15630. The ability of the snare-extending sleeve 15534 to rotate freely about the interior body 15620 allows the user to not be concerned about how his/her hand is placed on the sleeve 15620 as the device is being rotated constantly during a surgical procedure. Free rotation also prevents torque from being imparted to the snare assembly 15530, which torque would cause additional drag during longitudinal translation on the shaft 15520.

These three parts provide a mechanism that allows the non-illustrated snare to extend out from the distal end of the snare assembly 15530 to a distance that is a multiple of the distance that the snare-movement body 15630 moves with respect to the interior body 15620. As in the previous embodiments, motion of the snare 15532 occurs by moving the snare-movement body 15630 towards the interior body 15620 resulting in a movement of the snare 15532 from its captured position within the snare-guiding tube 15610 to its final extended orientation outside the distal end of the snare assembly 15530. The snare 15532 progresses through the distance multiplication features and terminates at the proximal end of the snare-guiding tube 15610 that, in this exemplary embodiment is substantially in a J-shape. The distal snaring portion of the snare 15532 is collapsed within the snare-guiding tube 15610 while in the non-extended state of the snare 15532—the state shown in FIGS. 155 to 159—with a terminal snare end (e.g., loop 12) extending slightly out of the distal end of the snare-guiding tube 15610.

In FIG. 159, the lockout 15660 is in a position that exists during sliding of the snare assembly 15530 along the shaft 15520. In this position, the anti-rotation fin 15662 acting as a key is engaged in the groove 15521 along the length of the shaft 15520. As the snare assembly 15530 reaches the distal end of the shaft 15520, the sloped distal fin edge 15668 hits the terminal wall of the groove 15521 and forces the lockout 15660 to pivot, thereby moving the stop 15664 into the stop orifice 15523 to halt motion of the snare assembly 15530 along the shaft 15520. FIGS. 160 and 161 illustrate the snare assembly 15530 in the snare-extended state with movement of the sleeve 15534 displacing the snare-movement body 15630 distally to touch the proximal side of the interior body 15520 and, thereby, extend the snare 15532 distally out through a clip to its fullest extent.

Grounding of the snare 15532 is illustrated in FIG. 164. The snare 15532 is grounded at its proximal end at a grounding area 15624 within the interior body 15620. In this exemplary embodiment, the grounding area 15624 is a crevice having a Z-shape that corresponds to an outer shape of a grounding end 16412 of a snare-grounding tube 16410. The grounding end 16412 is fixed to the interior body 15620 (e.g., with a screw 16420) and in which the proximal end of the snare 15532 is fixed, e.g., crimped. Also with respect to FIG. 164 and FIG. 165 as well, it can be seen that the outer tube of the shaft 15520 and the inner tube of the cutting/reloading shaft 15650 are flush at the distal end of the multiple-clip securing device 15500. This is desirable to allow a positioning of the clip 15550 flush to the inner and outer tube ends to aid in tensioning the device on cords 2 to be secured with the clip 15550 and to present the most blunt edge possible to the sewing cuff or tissue that is being affixed.

Another feature of the snare assembly 15530 is that it provides various lockouts during movement along the shaft 15520. The many different lockouts are provided by a single device having a complex shape, which device interacts with other features within the snare assembly 15530 and the shaft 15520. This exemplary embodiment of the multi-function lockout 15660 is a rocker pivoting about a pivot 15626 on the interior body 15620 and having fins and varying surface features and heights. Depending on the state of the snare assembly 15530 and/or on the state of the snare-movement body 15630, the lockout 15660 provides a different lockout function.

In a first lockout state, it is desired to retain the snare 15532 in its fully retracted position and prevent it from extending. This first state exists while the snare assembly 15530 is proximal of its distal-most position. FIGS. 155 to 159 show the multi-function lockout 15660 in this first lockout state in which the snare assembly 15530 is able to translate along the shaft 15520 from the handle 15510 to the distal end of the shaft 15520. To fix the interior body 15620 in a single circumferential position about the shaft 15520, an anti-rotation fin 15662 of the lockout 15660 rides in a groove 15521 of the shaft 15520 to act as a key within the keyway of the groove 15521. The blade feature of the fin 15662 that is positively engaged in the groove 15521 on the shaft 15520 is selected to have a length that remains within the groove 15521 at all times. In an alternative embodiment, the fin 15662 can selectively become disengaged from the keyway at the distal-most position while another portion of the lockout 15660 (e.g., the stop 15664) keeps the snare assembly 15530 in position and clocking. In a further alternative embodiment, there can be a separate key on parts of the snare assembly 15530 that continuously engages the groove 15521. Other embodiments for clocking the interior body 15620 can include a keyway that is internal or external to the shaft 15520. Another exemplary embodiment for keeping the internal body 15620 clocked with respect to the shaft 15520 includes placing a secondary tube along the outside surface of the shaft 15520 to form a "snowman" cross-section. Likewise, that secondary tube can be replaced with an external blade or square wire or a hexagonal or other polygonal rod. The exterior shape of the shaft 15520 can also be altered to provide the keying feature. Other external configurations include a comb and slot or an integral stop such as a cross-pin, a horseshoe, or a fin on the shaft 15520. In a further exemplary embodiment, the entire snare assembly 15530 can be freely rotating proximal to a given point on the shaft 15520 but, after passing a set distal location, the internal body 15620 is forced to clock into a given orientation. This can be accomplished, for example, with a funnel and pin assembly. All of these various features together define a method for keeping the snare assembly 15530 clocked onto the shaft 15520.

The lockout 15660 pivots about the pivot 15626 that is oriented transverse to the shaft 15520. The rotational orientation of the lockout 15660 shown in FIGS. 143 and 147 keeps the stop 15664 below the shaft 15520 because the stop 15664 has a width greater than the width of the groove 15521 and, therefore, it is also wider than the fin 15662. The cross-sectional views of FIGS. 155 to 165 do not allow the thickness of the stop 15664 or the sides of the lockout 15660 to be seen. Nonetheless, the width of the stop 15664 is greater than the fin 15662 so that the stop 15664 remains in the position shown in FIGS. 155 to 159 until the lockout 15660 moves distally to align the stop 15664 with a stop orifice 15523 of the shaft 15520. Also seen in FIGS. 155, 156, 159, and 161 is a side boss 15666 extending laterally from at least one side of the lockout 15660. In the orientation shown in these figures, the side boss 15666 rests within a slot 15634 of the snare-movement body 15630 to prevent the snare-movement body 15630 from moving either towards or away from the interior body 15620, thereby keeping the snare-movement body 15630 in its proximal position in which the snare 15532 is retained in its retracted position and cannot extend.

FIGS. 157 and 158 illustrate how the side boss 15666 is moved out of the slot 15634 by various other features of the snare assembly 15530. First, the shaft 15520 defines the stop orifice 15523 just distal of a distal end of the groove 15521. The stop 15664 slides along the outside surface of the shaft 15520 and, because the stop 15664 is wider than the groove 15521, a non-illustrated bias device (e.g., a spring) keeps the lockout 15660 biased in a counter-clockwise position (in the view of FIGS. 155 to 163) until it comes to the stop orifice 15523. What causes the desired fin-raising movement (e.g., clockwise rotation of the lockout 15660) is a cam action that occurs when the sloped distal fin edge 15668 comes into contact with and continues to contact the distal end of the groove 15521, which is depicted in FIG. 159. Further distal movement of the interior body 15620 on the shaft 15520 causes the distal end of the groove 15521 to force the fin 15662 upwards and, thereby, move the stop 15664 into the stop orifice 15223, which prevents any further distal movement of the interior body 15620—because the distal edge of the stop orifice 15523 forcibly contacts the distal face of the stop 15664. When this occurs, as shown in FIGS. 158 and 161, the lockout 15660 has pivoted to such an extent to move the side boss 15666 radially upwards sufficiently far to move out of the slot 15634, thereby freeing the snare-movement body 15630 from its fixed state with respect to the interior body 15620. Simultaneously, the distal exit 15612 of the snare-guiding tube 15610 is at a position in which it can enter a tube opening 15522 in the shaft 15620.

The snare-guiding tube 15610 is grounded near its distal end by a pivot supporting tube guide block 15810, which allows the snare-guiding tube 15610 to move freely up and down through an arc similar to that accomplished by the previously proximally grounded tube but with and advantage of a much shorter length, because the area of flexing of the tube is also part of the length of the trombone tube that is used to extend the snare. As shown in FIGS. 155 to 161, the snare-guiding tube 15610 has a bend 15614 to provide clearance so that the distal exit 15612 can flex downwards (with regard to the views of the drawings) when the distal exit 15612 of the snare-guiding tube 15610 is not present at the snare-access window 15522 as shown in the difference between FIGS. 158 and 158. The flexing movement of the distal end of the snare-guiding tube 15610 is illustrated in FIG. 158 with the double-headed arrow, a corresponding movement being carried out with the tube guide block 15810 that slides within a block cavity 15628 of the interior body 15620. An alternative to this exemplary shape is a double-bend or a recurve or S-tube that can align the opening of the distal exit 15612 more in line with the top surface of the guide rail 15540 so that the snare 15532 is presented with less ricochet into the opening of the clip 15550. Such an S-tube can provide features to vertically position its exit relative to the guide rail 15540, relative to the shaft 15510, and/or, relative to the snare assembly 15530. Another alternative embodiment of the snare-guiding tube 15610 includes an open cut scoop or similar shape that deflects the snare 15532 and directs it toward the clip opening.

Because a distal extent of the snare-guiding tube 15610 is pre-bent with a bias towards the shaft 15620, when the distal exit 15612 is not within the snare-access window 15522, the distal exit 15612 rides along the top exterior surface of the shaft 15620, as shown in FIG. 156. The snare-guiding tube 15610 remains in that radially outward flexed state until the distal exit 15612 of the snare-guiding tube 15610 enters the snare-access window 15522 (as shown in FIGS. 157, 158, 160, and 161), at which time, a radially extending cavity 15629 in which the distal extent of the snare-guiding tube 15610 resides allows that distal extent to spring radially inwards into the snare-access window 15522 to an orientation in which the distal exit 15612 is aligned with the central opening of the clip 15550 that is loaded in the cord-securing location 10802, 11222, 15622 ready to secure cords 2, which orientation is especially visible in FIG. 158. At a point when the side boss 15666 raises, no lock of the lockout 15660 prevents the snare-movement body 15630 from translating distally all the way until its distal surface meets a proximal side of the interior body 15620 (as shown in FIGS. 160 and 161) at which time, the snare 15532 has extended out through the distal exit 15612 and, because the guide rail 15540, is disposed within the shaft 15620, the snare 15532 slides along the surface of the guide rail 15540 and exits through the central opening of the clip 15550 to open and be ready to capture cords 2 within the snare opening. It is noted that the snare 15532 is prevented from being exposed to the environment outside the interior body 15620 when in the middle of reloading due to the length of the snare-access window 15522, as shown in FIG. 159.

Also shown in FIG. 159 is a secondary lock that prevents the lockout 15660 from rotating clockwise during the reloading operation. In particular, when the cutting/reloading shaft 15650 moves proximally, which it must do during any reloading operation, the opening in the cutting-reloading shaft 15650 that is aligned with the snare-access window 15522, is no longer aligned and, therefore, completely covers the stop orifice 15523 to prevent the stop 15664 from entering the stop orifice 15523. This, in turn, completely prevents the user from attempting to move the snare-movement body 15630 distally and deploy the snare 15532 while reloading.

To summarize the movement, when the snare assembly 15530 is at its distal-most position, the lockout 15660 releases forward movement of the snare-movement body 15630 (e.g., the snare 15532) but also locks the snare assembly 15530 at its distal-most position—the stop 15664 prevents both distal and proximal movement of the snare-movement body 15630 when the snare 15532 is extended. This means that, when at this distal-most position, the snare assembly 15530 is locked on the shaft 15520 at all times when the snare 15532 is being extended or retracted. Only after the snare 15532 is fully retracted into the snare assembly 15530 (e.g., where only the small eyelet remains outside the snare-guiding tube 15610 as shown in FIG. 153), the lockout 15660 disengages the snare assembly 15530 from the end of the shaft 15520 but reengages fixation of the snare extension parts to prevent any movement of the snare 15532 when the snare assembly 15530 is not present at its distal-most, clip-snaring position on the shaft 15520.

In operation of the snare 15532, the snare-guiding tube 15610 houses the operative end of the snare 15532 and guides it through the snare-access window 15522, along the upper surface of the guide rail 15540, through the clip 15550 in the cord-securing location 15622, and out the distal end of the multiple-clip securing device 15500 to be presented to the user for receiving one or more cords 2 therein. The snare-movement body 15630 ejects the snare 15532 out from the snare-guiding tube 15610 with enough force against guide rail 15540 to cause snare deflection along the top surface thereof (e.g., ricochet) and through the center of the securing device (e.g., the clip).

In this exemplary embodiment, the snare 15532 can be of different shapes and diameters as explained herein. These features are not repeated. Likewise, the snare access window 10424, 11228, 15522 can be of various shapes. FIGS. 156 and 161 show the window 15522 with a curve-cornered rectangular shape but the window 10424, 11228, 15522 can be of any desired shape including those described and/or shown herein.

It is desirable to retain the snare assembly 15530 adjacent the handle 15510 as shown in FIGS. 155, 162, and 163. One exemplary low-footprint embodiment for retaining this placement provides opposing magnets at both the distal end of the handle 15510 and the proximal end of the snare assembly 15530. This retaining structure keeps the snare assembly parked in its most-proximal position. Locations 15632 for magnets forming the retaining structure can be found, for example, in FIGS. 156 and 158. A switch that detects when the snare shuttle is parked, e.g., parking switch, can be a Hall-effect sensor that detects when the snare assembly is in its most-proximal position and the magnets at the locations 156320 can be used to trigger this Hall-effect sensor.

All together, the various features of the handle 13810, 15510 provide ways to minimize the so-called footprint of the multiple-clip securing device. An alternative embodiment to the pistol-shaped handle of FIGS. 98 to 102, 138, and 155 is a pear-shaped ball (similar to a conductor's wand) that can be rotated within a user's hand in all pitch, roll, and yaw axes.

With regard to the securing devices themselves, in general, they are stored-energy devices that use the stored energy to secure the cords. The clips have no stored energy before being forced onto the guide rail. However, when forced thereon and opened before firing, the energy for clipping is stored in the clip. The entire amount of energy can be stored right as the clip is slid onto the guide rail, or a variable amount can be store depending on where the clip is placed on the H-rail. Also envisioned is an E-shaped clip that uses a rail different from the H-rail.

Various clips have been mentioned herein and exemplary embodiments of the clip have been shown. One exemplary embodiment of the clip 11251, 15550 shown within other parts in various figures is shown by itself in FIGS. 171 and 172. For ease of understanding, reference numeral 17100 will be used to describe the clip 17100, which is in its rest or steady state in FIG. 171. Portions of this clip 17100 include a base 17110 having a cutout shape 17112 that defines an upper internal flexing wall 17120 and a lower internal flexing wall 17130. Here, the cutout shape 17112 has variations, the shape of which creating teeth 17122, 17132 on the opposing cord-securing surfaces 17124, 17134. As shown in FIG. 172, when the clip 17100 is installed on a guide rail, for example, the upper and lower internal flexing walls 17120, 17130 flex outward to define an opening 17140 and create a securing location between the opposing cord-securing surfaces 17124, 17134 and imparting cord-securing energy for future use of the clip 17100. The body 17110 of the clip 17100 can also be formed with handling surfaces 17114 for loading the clip 17100 onto a guide rail. Alternative exemplary embodiments of the cutout shape in a clip 17100 are depicted in FIGS. 173, 174, and 175. FIG. 173 illustrates ports 17300 and does not include teeth. FIG. 174 includes variations 17400 in the cord-securing surfaces. Finally, FIG. 175 shows a variation of a tooth 17500 formed by the cord-securing surfaces.

Motion of the securing devices (e.g., the clips) can be accomplished in various ways. Exemplary embodiments of a rack-and-pinion drive are shown in FIGS. 138 to 140 and 155 to 163. In another exemplary embodiment shown in FIGS. 167 to 169, linear-motion of the clips can be imparted by a screw drive and/or a variable pitch screw within the handle for high speed on exchange and high force for firing/cutting. Only the screw drive components are shown in FIGS. 167 to 169 for clarity but these components are envisioned to replace other drive components described and/or shown herein. In particular, an exemplary embodiment of a screw drive 16700 contains a motor 16710 (which can have an internal gear box 16712) having an output shaft 16714. A screw assembly 16720 includes a drive connector 16722 connected to the output shaft to receive the rotational movement thereof. The drive connector 16722 is fixedly connected or connected through a non-illustrated clutch to a screw 16724, which can have a constant or variable pitched thread 16726 depending on the circumstances of use. The outer shaft 9820, 11220, 15520 of the device is held immovable with respect to the motor 16710 and the screw 16724 by a frame 16730 that longitudinally holds the drive connector 16722 in place while allowing the drive connector 16722 to freely rotate along with the output shaft 16714. The cutting/reloading assembly/shaft 10440, 11240, 12424, 15650 has an internal guide with a correspondingly pitched internal thread (not illustrated) to the exterior threads 16726 of the screw 16724. In this way, rotation of the screw 16724 in a first direction will move the cutting/reloading assembly/shaft 10440, 11240, 12424, 15650 distally, as shown in the transition from FIG. 167 to FIG. 168, or proximally if rotated in the opposite direction. One advantage of a screw drive is the compactness of the long stroke because it submerges the screw into shaft.

To track motion of the any drives described and/or shown herein, an encoder can be mounted on the motor. Alternatively or additionally, a linear encoder can be mounted on the rack to determine absolute position independent of the motor. With a drive screw directly mounted to the motor, as shown in FIGS. 167 to 169, an encoder can be associated with the drive screw. A screw/nut drive also can be used. One drawback to this particular configuration is that two-times the stroke is needed or the screw needs to be buried inside the shaft. It is possible to have the nut small enough to be embedded within the shaft to shorten the handle length. An encoder can also be mounted on the main circuit board. For calibration of the drive, in an exemplary embodiment, position can be calibrated based on a sacrificial clip.

FIG. 170 illustrates an exemplary embodiment of an electro-mechanical way to deploy securing devices and to only use the gearbox for reloading and positioning the next securing device. This has the advantage of possibly improving the tactile feel by the user of deploying the securing device. This exemplary embodiment of a multiple-firing securement device 17000 has a motor-controlled screw mechanism 17010 that turns a screw 17012 to move the inner cutting/reloading assembly/shaft 10440, 11240, 12424, 15650 to thereby grasp various securing devices (e.g., clips) installed on the guide rail 17020 retainer at successively further distances on the guide rail 17020 from the securement-installing location 17022 and a mechanical lever 17030 that moves the entire cutting/reloading assembly/shaft 10440, 11240, 12424, 15650 distally to perform cutting of the cords 2.

Software of the control circuit of any of the exemplary embodiments can perform various functions for operating the multiple-clip securing device. First, error checking can be done based on the draw of current, which measures the torque that the motor is experiencing. Also, a distal detent position can be sensed using either or both of torque and current. Sensing of high current can be used to indicate that the device has picked up more than one or multiple clips. Sensing of low current can be used to indicate that the clip has been missed and not picked up by the reloading process. A self-clearing function can be added to the knife action based on a measurement of drag. Counting the number of securing devices can be done with a program that determines movement of the snare assembly before enabling the ability to fire the device and install the securing device. Based on a position of the parking switch, the device can lock out any reloading or firing if the snare assembly is not parked in the distal position. An alarm can be included to indicate motion of the snare assembly before a reload occurs. The LED on the circuit board as a user-interface can indicate (by color, flashing, patterns, etc.) various and many different states of the device. Also, voltage can be sensed on the battery to determine various operating conditions. These are only a few examples of how software can be used to monitor, report, display, and otherwise control use of the multiple-clip securing device.

With regard to powering on any of the multiple-clip securing devices, the multiple-clip securing device can be placed in packaging that, when the multiple-clip securing device is removed, a grenade pin is pulled or remains with the packaging to enable and, thereby power-on, the device. A battery-drain feature can also be provided to prevent multiple uses after a set amount of time occurs when the multiple-clip securing device has been removed from the packaging. When any motors are described and/or shown herein, they also include, where desirable, any gearing or transmissions that are necessary to reduce the motor turns rate to affect the function of that motor. These transmissions are not described herein in further detail.

The foregoing embodiments are described in U.S. Pat. No. 10,624,630, issued Apr. 21, 2020, which is incorporated by reference herein.

Embodiments with Suture Tensioning Systems

FIGS. 176-183 illustrate deployment devices that include a suture tensioning system to provide more precise and consistent tensioning to the sutures when securement devices are applied to the sutures. More precise and consistent tensioning leads to better securement of implanted prosthetic devices or other sutured objects, and reduces risk of suture failure due to excess tension or excess slack.

FIGS. 176 and 177 are side views of an exemplary suture clip deployment device 17610 that includes a suture tensioning system. FIG. 178 is a top view of the device 17610. The device 17610 comprises a proximal handle portion 17612, and distal shaft portion 17614. FIG. 179 is a perspective view of the proximal handle portion 17612, and FIG. 180 shows part of the outer housing cut away to illustrate internal components of the handle portion. The distal shaft portion 17614 has a distal end 17616 and is configured to contain one or more suture clips (also referred to as suture securement devices) located near the distal end, similar to other devices described herein. The device 17610 can also comprise other components similar to other embodiments described herein, such as a rail on which the suture clips are mounted, an outer shaft, a snare or snare assembly for loading the suture through the clips, a sliding carriage/reloader assembly 17660 that translates axially to assist with loading and reloading the suture clips, moving the clips into the deployment location, threading the suture through the clips and out the side of the shaft, and/or other functionalities described herein. The device 17610 receives at least one suture (e.g., two strands of one suture) 17650 through the distal end 17616 of the shaft portion and through the distal-most suture clip inside the shaft portion, and the suture then extends radially out through a lateral opening in the shaft wall, similar to other devices described herein.

Instead of (or in addition to) manually grasping and pulling the end portion of the suture 17650 extending out from the shaft to apply a desired amount of tension before pulling the trigger 17618 to deploy the distal-most suture clip, the device 17610 comprises a tensioning system that includes a peg 17620 on one side of the handle and a suture tensioning mechanism 17622 on the other side of the handle. The end portion of the suture 17650 is wrapped around the peg 17620, then across the trigger 17618, and then is coupled to the tensioning mechanism 17622. The tensioning mechanism can comprise a knob or spool that rotates to gradually wind the suture around it, thereby increasing tension in the suture. The tensioning mechanism can include notches, slots, slits, or other features for coupling the suture to it. As illustrated, the tensioning mechanism 17622 includes six tapered notches 17624 into which the suture can be inserted and held via a pinch fit. Once the suture is secured, the mechanism 17622 can be rotated to cause the suture to spool around a neck portion, as shown in FIG. 178, and also similarly shown in the embodiment of FIG. 183 (see neck portion 17644). As the tension in the suture increases, the suture applies increased force on the trigger 17618, which force tends to depress the trigger. The trigger can be configured such that when a predetermined amount of force is applied to it, it causes the device to deploy a suture clip onto the suture. Thus, actuating the tensioning mechanism 17622 eventually actuates the trigger 17618 to deploy a suture clip when a desired amount of tension is reached in the suture.

With reference to FIG. 180, the trigger 17618 can be coupled to an electrical switch (or sensor) 17632 within the handle portion, such that depression of the trigger activates the switch to signal a controller 17634 to initiate deployment of the suture clip onto the suture. The trigger 17618 can include a spring 17630 or other biasing mechanism having a spring constant and/or length that is selected to control the amount of force and/or travel distance that is needed to fully depress the trigger and activate the switch. For example, as the suture 17650 is tightened with the tensioning mechanism 17622, the part of the suture that runs across the trigger 17618 applies more and more proximally directed force on the trigger, which compresses the spring 17630 more and more until the amount of tension is sufficient to compress the spring enough to activate the switch 17632. Activation of the switch 17632 can be accomplished by the trigger physically moving proximally (e.g., depressing) a certain distance and contacting the switch, which corresponds to the spring compressing a certain distance. The trigger need not actually touch the switch, as a proximity sensor or other type of non-contact sensing can be employed. Alternatively, activation of the switch 17632 can be accomplished by force from the spring 17630 pressing on the switch, where the force from the spring increases with compression of the spring based on the length and spring constant. In any case, the amount of trigger depression force required to activate the switch can be calibrated to correspond to a desired amount of tension in the suture. In addition, the trigger can be mounted to the handle in such a way that only one degree of motion is permitted, e.g. a generally proximal direction, such that pressure from the suture is transferred to linear motion of the trigger. In other embodiments, the trigger can be mounted in a pivoting manner relative to the handle portion, such that the trigger travels in an arcuate path under pressure from the suture.

When the switch 17632 is activated, the controller 17634 can cause a motor (e.g., an electrical motor powered by battery 17636) to actuate an axial shaft 17638 that causes deployment of the distal-most suture clip. The components and movements that deploy the suture clips can be similar to that of other embodiments described herein.

In some embodiments, the device 17610 can include a torque sensor or other type of force/tension sensor that is coupled to the suture tension mechanism that determines the amount of tension that is being applied to the suture at a given instant, and provides that data to the controller and/or causes an output display to indicate to a user the current tension value in the suture.

The device 17610 can also include an indicator 17626 (e.g., an LED, other visual indicator, audio indicator, etc.) that can convey the state of the device to the user. For example, the indicator 17626 being green can indicate the device is ready to use, or that it is ready for the user to begin actuating the suture tensioning mechanism. The indicator being red can, for example, indicate a malfunction in the device or some other warning. Other colors can indicate other statuses, such as there being no suture clips remaining, a temporary error or jam that needs to be corrected, etc. The device 17610 can also include a clip-reload button 17628, similar to the button 13840, and/or various other buttons, switches, inputs and outputs, as described elsewhere herein.

In some embodiments, the peg 17620 can comprise a rivet, a hook, a T-bar, a lip, and/or other features that can help keep the suture from slipping off the peg. The peg can have a smooth surface or coating to minimize friction and allow the suture to smoothly slide around it. For example, in FIGS. 178 and 179 the peg is shown having a lateral lip that keeps the suture from slipping laterally off the peg. In some embodiments, the peg can rotate, and/or can comprise a pulley, to minimize friction. Similarly, the trigger 17618 can include a recess, slot, notch, ridge, lip, or other feature to help keep the suture located on the trigger in a desired position, while allowing the suture to slide lengthwise across the trigger as tension changes. For example, in FIGS. 176 and 177, the suture is shown positioned in a recess of the trigger so that the suture does not slip down off the trigger.

FIGS. 181-183 illustrate an alternative suture tensioning mechanism 17640 that is similar in function to the suture tensioning mechanism 17622. The mechanism 17640 includes four diametrically extending slots 17642 that can receive and secure the suture 17650. The mechanism 17640 can also include a narrow neck portion 17644 around which the suture can spool as the mechanism is rotated to increase the tension in the suture. For example, a user can manually tighten the suture to some degree first, then insert the suture into any of the diametrically extending slots 17642, and then wind the suture around the neck portion 17644.

In some embodiments, the suture tensioning mechanism can include a ratcheting system that allows the mechanism to be rotated only in one direction to increase the tension in the suture. The ratcheting system can feature small rotation increments that allow a user to finely increase tension in small increments. The ratcheting system can also maintain the tension in the suture at a fixed value when the user lets go of the tensioning mechanism and/or to allow the user to pause the tensioning process for a period of time.

In some embodiments, any one or more of the trigger, spring, switch, controller, tensioning mechanism, and/or other components can be adjustable to change the amount of tension in the suture that is required to depress the trigger and activate the switch to deploy the suture clip onto the suture. For example, some suture may require more tension that others for proper functionality, and the deployment device can be adjustable to apply suture clip to sutures at different tension levels. In some embodiments, the handle portion can have a user input that allows the user to select and change the predetermined tension level that triggers clip deployment. Such adjustment can be performed via movement or realignment of the switch, spring, and/or trigger, such that different amounts of force from the suture are needed to activate the switch.

In some embodiments, the deployment device 17610 can comprise a motor or other automated driver that rotates the suture tensioning mechanism in a desired manner to increase the tension in the suture.

In some embodiments, the deployment device 17610 can include a blade or other cutting device located at the distal end portion of the shaft portion and configured to cut the sutures just proximal to the suture clip just after the suture clip is deployed onto the sutures. The cutting mechanism can include a shearing motion between two components, a scissor-like aperture, a rotating blade, a pinching mechanism, or other mechanisms disclosed herein. The cutting mechanism can be configured to cut the free ends of the sutures to a predetermined length from the suture clip.

The deployment device 17610 can eliminate the guesswork in how much to tension the suture that exists in other conventional suture knotting/fixation devices. This can avoid the user having to manually guestimate how much tension that are applying to the sutures when deploying knots/fixation devices, which can help prevent under-tensioning (which can result in air knots and leakage between the fastener and the tissue at normal physiological pressures) and can help prevent over-tensioning (which can result in tearing of the tissue and improper fastener deployment).

Any of the components, methods, or other features described herein can be combined with or applied to the deployment device 17610 to provide a fully functioning device and method of use. Likewise, any of the components, methods, or other features of the deployment device 17610 can be combined with or applied to the other embodiments disclosed herein. In addition, the suture tensioning systems and constituent components and methods of use disclosed herein in for providing more precise and consistent suture tensioning can be applied to wide variety devices for various different applications that rely on properly tensioned sutures or other cords or strands, such as securing prosthetic implants (e.g., heart valves, annuloplasty rings, stents, etc.), laparoscopy procedures, closing wounds, and the like.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

In view of the many possible embodiments to which the principles of the disclosed technology may be applied, it should be recognized that the illustrated embodiments are only preferred examples of the technology and should not be taken as limiting the scope of the invention(s). Rather, the scope of the invention(s) is at least as broad as the full scope of the appended claims. We therefore claim as our invention(s) all that comes within the scope of the claims and their equivalents.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A device for deploying securement devices onto sutures, the apparatus comprising: a handle portion having a trigger and a suture tensioning mechanism; a shaft portion extending distally from the handle portion; and at least one suture securement device positioned at a distal end portion of the shaft portion; wherein the apparatus is configured to receive a suture extending through the suture securement device, across the trigger, and to the suture tensioning mechanism; wherein actuation of the suture tensioning mechanism adjusts tension in the received suture; wherein the trigger is actuated by the suture when a predetermined amount of tension is reached in the suture; and wherein actuation of the trigger causes the suture securement device to be deployed from the shaft portion onto the received suture.

Example 2. The device of any example herein, particularly example 1, wherein the suture tensioning mechanism comprises a spool, wherein rotating the spool winds the suture around the spool and increases tension in the suture.

Example 3. The device of any example herein, particularly any one of examples 1-2, wherein the suture tensioning mechanism comprises a suture fixation feature that secures the suture to the suture tensioning mechanism.

Example 4. The device of any example herein, particularly any one of examples 1-3, wherein the suture fixation feature comprises a slot in the suture tensioning mechanism, wherein the suture is fixed to the suture tensioning mechanism by inserting the suture into the slot.

Example 5. The device of any example herein, particularly any one of examples 1-4, wherein the handle portion further comprises a peg positioned on a first side of the trigger, wherein the suture tensioning mechanism is positioned on a second side of the trigger opposite the peg, and wherein the suture extends from the suture securement device around the peg, and the suture extends from the peg across the trigger to the suture tensioning mechanism.

Example 6. The device of any example herein, particularly any one of examples 1-5, wherein the peg has a flared end that retains the suture on the peg.

Example 7. The device of any example herein, particularly any one of examples 1-6, wherein trigger faces distally, and the peg and the suture tensioning mechanism are positioned proximally relative to the trigger, such that tension in the suture applies proximally directed pressure on the trigger.

Example 8. The device of any example herein, particularly any one of examples 1-7, wherein the trigger comprises a spring having a spring constant that is selected allow the trigger to be depressed to an activation depth by the suture once a predetermined amount of force is applied to the trigger by the suture, and wherein the predetermined amount of tension in the suture corresponds to the predetermined amount of force needed to depress the trigger to the activation depth.

Example 9. The device of any example herein, particularly any one of examples 1-8, wherein the handle portion further comprises: a motor that actuates the shaft portion to cause the suture securement device to be deployed from the shaft portion onto the received suture; and a switch electrically coupled to the motor, wherein the switch is activated by the trigger when the trigger is depressed to the activation depth.

Example 10. The device of any example herein, particularly any one of examples 1-9, wherein the trigger includes a notch that receives the suture and retains the suture at a fixed location on the trigger as the tension in the suture is adjusted.

Example 11. The device of any example herein, particularly any one of examples 1-10, wherein the at least one suture securement device comprises a plurality of suture securement devices positioned at a distal end portion of the shaft portion.

Example 12. The device of any example herein, particularly any one of examples 1-11, wherein the device is configured to deploy each of the plurality of suture securement devices successively onto different sutures.

Example 13. The device of any example herein, particularly any one of examples 1-12, wherein the at least one suture securement device comprises an annular outer body with an H-shaped inner securing orifice within the annular outer body.

Example 14. The device of any example herein, particularly any one of examples 1-13, wherein the shaft portion comprises an outer shaft and a rail positioned within the outer shaft, wherein the suture securement devices are mounted on the rail within the outer shaft.

Example 15. The device of any example herein, particularly any one of examples 1-14, further comprising a reloader axially movable along the shaft portion and having a distal portion shaped to temporarily contact the suture securement devices.

Example 16. The device of any example herein, particularly any one of examples 1-15, further comprising a reloader movement assembly configured to: move the reloader distally to deliver a first of the suture securement devices to an installing location from a first proximal location; and move the reloader proximally away from the installing location without the first suture securement device to a position in which the distal portion of the reloader temporarily contacts a second of the suture securement devices.

Example 17. The device of any example herein, particularly any one of examples 1-16, further comprising a snare assembly: having a snare shaped to pass distally through the first suture securement device at the installing location and shaped to receive the suture; configured to place the snare through the first suture securement device to a snaring position in which the suture is passed through the snare; and configured to pull the suture through the first suture securement device by moving the snare proximally through the first suture securement device.

Example 18. The device of any example herein, particularly any one of examples 1-17, wherein the shaft portion comprises a radial opening proximal to the at least one suture securement device, wherein the suture extends proximally through the at least one suture securement device within the shaft portion and radially out through the radial opening.

Example 19. The device of any example herein, particularly any one of examples 1-18, wherein the handle portion further comprises a tension sensor coupled to the suture tensioning mechanism, the tension sensor configured to determine an amount of tension in the suture based on a sensed amount of torque or force the suture applies to the suture tensioning mechanism.

Example 20. The device of any example herein, particularly any one of examples 1-19, wherein the handle portion further comprises a reload button.

Example 21. A method comprising: positioning a suture through a suture securement device that is positioned at a distal portion of a deployment device, the suture extending from a surgical location; positioning the suture across a trigger of the deployment device; coupling the suture to a suture tensioning mechanism of the deployment device; and actuating the suture tensioning mechanism to increase tension in the suture until the tension reaches a predetermined tension value, wherein the predetermined tension value is sufficient to cause the suture to actuate the trigger, wherein actuating the trigger causes the suture securement device to be deployed from the distal portion of a deployment device onto the suture with the predetermined tension value in the suture.

Example 22. The method of any example herein, particularly example 21, wherein actuating the suture tensioning mechanism comprises rotating the suture tensioning mechanism to wind the suture around the suture tensioning mechanism.

Example 23. The method of any example herein, particularly any one of examples 21-22, wherein coupling the suture to the suture tensioning mechanism comprises inserting the suture into a slot in the suture tensioning mechanism.

Example 24. The method of any example herein, particularly any one of examples 21-23, further comprising manually pre-tensioning the suture prior to coupling the suture to the suture tensioning mechanism.

Example 25. The method of any example herein, particularly any one of examples 21-24, further comprising positioning the suture around a peg, wherein the trigger is positioned between the peg and the suture tensioning mechanism, such that the suture extends from the peg, around the trigger, to the suture tensioning mechanism.

Example 26. The method of any example herein, particularly any one of examples 21-25, wherein the trigger is positioned distal to the peg and the suture tensioning mechanism, such that tension in the suture applies a proximal force on the trigger.

Example 27. The method of any example herein, particularly any one of examples 21-26, wherein the suture securement device is one of a plurality of suture securement devices positioned at the distal portion of a deployment device.

Example 28. The method of any example herein, particularly any one of examples 21-27, wherein the method comprises deploying each of the plurality of suture securement devices successively onto different sutures using the method of example 21.

Example 29. The method of any example herein, particularly any one of examples 21-28, wherein the distal portion comprises an outer shaft and a rail positioned within the outer shaft, wherein the suture securement devices are mounted on the rail within the outer shaft.

Example 30. The method of any example herein, particularly any one of examples 21-29, further comprising: moving a reloader distally along the distal portion to move a first of the suture securement devices to an installing location from a first proximal location; and moving the reloader proximally away from the installing location without the first suture securement device to a position in which the reloader temporarily contacts a second of the suture securement devices.

Example 31. The method of any example herein, particularly any one of examples 21-30, further comprising actuating a snare assembly of the deployment device to: move a snare through the first suture securement device to a snaring position; and with the suture passed through the snare, pull the suture through the first suture securement device by moving the snare proximally through the first suture securement device.

Example 32. The method of any example herein, particularly any one of examples 21-31, further comprising extending the suture through a radial opening in the distal portion of the deployment device, such that the suture extends through the radial opening between the suture securement device and the trigger.

Example 33. The method of any example herein, particularly any one of examples 21-32, wherein actuating the suture tensioning mechanism comprises turning a knob until a tension sensor indicates that the predetermined tension value is reached.

Example 34. The method of any example herein, particularly any one of examples 21-33, further comprising pressing a reload button on the deployment device after the suture securement device is deployed to prepare another suture securement device for deployment.

Example 35. The method of any example herein, particularly any one of examples 21-34, wherein the suture comprises a plurality of parallel sutures portions.

Example 36. The method of any example herein, particularly any one of examples 21-35, further comprising cutting the suture with the deployment device proximal to the suture securement device after the suture securement device is deployed onto the suture.

What is claimed is:

1. A device for deploying securement devices onto sutures, the apparatus comprising:
- a handle portion having a trigger and a suture tensioning mechanism
- a shaft portion extending distally from the handle portion; and
- at least one suture securement device positioned at a distal end portion of the shaft portion
- wherein the apparatus is configured to receive a suture extending through the suture securement device, across the trigger, and to the suture tensioning mechanism
- wherein actuation of the suture tensioning mechanism adjusts tension in the received suture
- wherein the trigger is actuated by the suture when a predetermined amount of tension is reached in the suture; and
- wherein actuation of the trigger causes the suture securement device to be deployed from the shaft portion onto the received suture; wherein the handle portion further comprises a peg positioned on a first side of the trigger, wherein the suture tensioning mechanism is positioned on a second side of the trigger opposite the peg, and wherein the suture extends from the suture securement device around the peg, and the suture extends from the peg across the trigger to the suture tensioning mechanism.

2. The device of claim 1, wherein the suture tensioning mechanism comprises a spool, wherein rotating the spool winds the suture around the spool and increases tension in the suture.

3. The device of claim 1, wherein the suture tensioning mechanism comprises a suture fixation feature that secures the suture to the suture tensioning mechanism.

4. The device of claim 3, wherein the suture fixation feature comprises a slot in the suture tensioning mechanism, wherein the suture is fixed to the suture tensioning mechanism by inserting the suture into the slot.

5. The device of claim 1, wherein the peg has a flared end that retains the suture on the peg.

6. The device of claim 1, wherein trigger faces distally, and the peg and the suture tensioning mechanism are positioned proximally relative to the trigger, such that tension in the suture applies proximally directed pressure on the trigger.

7. The device of claim 1, wherein the trigger comprises a spring having a spring constant that is selected allow the trigger to be depressed to an activation depth by the suture once a predetermined amount of force is applied to the trigger by the suture, and wherein the predetermined amount of tension in the suture corresponds to the predetermined amount of force needed to depress the trigger to the activation depth.

8. The device of claim 7, wherein the handle portion further comprises:
- a motor that actuates the shaft portion to cause the suture securement device to be deployed from the shaft portion onto the received suture; and
- a switch electrically coupled to the motor, wherein the switch is activated by the trigger when the trigger is depressed to the activation depth.

9. The device of claim 1, wherein the trigger includes a notch that receives the suture and retains the suture at a fixed location on the trigger as the tension in the suture is adjusted.

10. The device of claim 1, wherein the at least one suture securement device comprises a plurality of suture securement devices positioned at a distal end portion of the shaft portion.

11. The device of claim 10, wherein the device is configured to deploy each of the plurality of suture securement devices successively onto different sutures.

12. The device of claim 10, wherein the shaft portion comprises an outer shaft and a rail positioned within the outer shaft, wherein the suture securement devices are mounted on the rail within the outer shaft.

13. The device of claim 1, wherein the at least one suture securement device comprises an annular outer body with an H-shaped inner securing orifice within the annular outer body.

14. The device of claim 1, further comprising a reloader axially movable along the shaft portion and having a distal portion shaped to temporarily contact the suture securement devices.

15. The device of claim 14, further comprising a reloader movement assembly configured to:
- move the reloader distally to deliver a first of the suture securement devices to an installing location from a first proximal location; and
- move the reloader proximally away from the installing location without the first suture securement device to a position in which the distal portion of the reloader temporarily contacts a second of the suture securement devices.

16. The device of claim 15, further comprising a snare assembly:
- having a snare shaped to pass distally through the first suture securement device at the installing location and shaped to receive the suture
- configured to place the snare through the first suture securement device to a snaring position in which the suture is passed through the snare; and
- configured to pull the suture through the first suture securement device by moving the snare proximally through the first suture securement device.

17. The device of claim 1, wherein the shaft portion comprises a radial opening proximal to the at least one suture securement device, wherein the suture extends proximally through the at least one suture securement device within the shaft portion and radially out through the radial opening.

18. The device of claim 1, wherein the handle portion further comprises a tension sensor coupled to the suture tensioning mechanism, the tension sensor configured to determine an amount of tension in the suture based on a sensed amount of torque or force the suture applies to the suture tensioning mechanism.

19. The device of claim 1, wherein the handle portion further comprises a reload button.

* * * * *